(12) United States Patent
Armour et al.

(10) Patent No.: US 6,586,430 B1
(45) Date of Patent: Jul. 1, 2003

(54) CCR5 MODULATORS

(75) Inventors: Duncan Robert Armour, Kent (GB); David Anthony Price, Kent (GB); Blanda Luzia Christa Stammen, Kent (GB); Anthony Wood, Kent (GB); Manoussos Perros, Kent (GB); Martin Paul Edwards, Kent (GB)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/452,578

(22) Filed: Dec. 1, 1999

(30) Foreign Application Priority Data

Dec. 23, 1998 (GB) .............................. 9828420
Sep. 10, 1999 (GB) .............................. 9921375

(51) Int. Cl.[7] ...................... C07D 45/04; A61K 31/445; A61K 31/46; A61P 31/18
(52) U.S. Cl. .................... 514/235.2; 514/253; 514/256; 514/258; 514/266; 514/299; 514/303; 514/304; 514/307; 514/311; 544/127; 544/238; 544/242; 544/262; 544/263; 544/277; 544/295; 544/335; 544/336; 544/408; 546/112; 546/118; 546/119; 546/124; 546/125; 546/126; 546/139; 546/146; 546/152; 546/175; 546/176
(58) Field of Search ................................. 514/299, 253, 514/256, 235.2, 311, 307, 304, 303; 544/238, 242, 127, 262, 263, 277, 295, 335, 336, 406, 408; 546/112, 118, 119, 139, 146, 124, 125, 126

(56) References Cited

U.S. PATENT DOCUMENTS 5,824,650 A 10/1998 De Lacharriere et al. ..... 514/15
5,972,892 A 10/1999 De Lacharriere et al. ..... 514/15

FOREIGN PATENT DOCUMENTS

| EP | 0567767 | 3/1999 |
|---|---|---|
| WO | 9311122 | 6/1993 |
| WO | 9825604 | 6/1998 |
| WO | 9825605 | 6/1998 |
| WO | 9825617 | 6/1998 |
| WO | 9831364 | 7/1998 |
| WO | 9904794 | 2/1999 |
| WO | 9909984 | 3/1999 |

OTHER PUBLICATIONS

Cihlar, T. et al, Ann. Rep. Med. Chem., 35, 2000, 177–189.*
Wu, Lijun, et al, J. Exp. Med., 186(8), 1997, pp. 1373–1381.*
Aarons, Emma J. et al, Virology, 287, 2001, 382–290.*
Woodman, Richard. Pfizer says CCR5 Receptor Blocker Against HIV is a Top Priority, AIDSMEDs.COM May 30, 2002 [online], [retrived Feb. 21, 2003]. Retrieved from the Interner: <http://www.aidsmeds.com/news/20020530drdg-002.html>.*

* cited by examiner

*Primary Examiner*—Richard L. Raymond
*Assistant Examiner*—Thomas C. McKenzie

(57) ABSTRACT

Compounds of Formula 1

$$[R_{egion}\ \alpha]\text{-}[R_{egion}\ \beta]\text{-}[R_{egion}\ \gamma]\text{-}[R_{egion}\ \delta] \qquad (I)$$

which are useful as modulators of chemokine activity. The invention also provides pharmaceutical formulations and methods of treatment using these compounds.

21 Claims, No Drawings

CCR5 MODULATORS

This application claims priority under 35 U.S.C. §119 of Great Britain applications 9828420.1 and 9921375.3, filed respectively on Dec. 23, 1998 and Sep. 10, 1999, the texts of which are hereby incorporated by reference herein in their entireties.

This invention relates to new chemical compounds. These compounds find particular not exclusive use as pharmaceuticals, especially as CCR5 modulators.

This invention also relates to formulations or dosage forms including these compounds, to use of these compounds in manufacture of pharmaceutical formulations or dosage forms and methods of treatment, especially treatment of ant-inflammatory diseases and conditions and in the treatment and prevention of HIV-1 and genetically related retroviral infections.

The compounds of the present invention may be modulators, especially antagonists, of the activity of chemokine CCR5 receptors, particularly those which occur on the surfaces of certain cells within the human body. Modulators of CCR5 receptor may be useful in the treatment and prevention of various inflammatory diseases and conditions, and in the treatment and prevention of infection by HIV-1 and genetically related retroviruses.

The name "chemokine", is a contraction of "chemotactic cytokines". The chemokines comprise a large family of proteins which have in common important structural features and which have the ability to attract leukocytes. As leukocyte chemotactic factors, chemokines play an indispensable role in the attraction of leukocytes to various tissues of the body, a process which is essential for both inflammation and the body's response to infection. Because chemokines and their receptors are central to the pathophysiology of inflammatory and infectious diseases, agents which are active in modulating, preferably antagonizing, the activity of chemokines and their receptors, are useful in the therapeutic treatment of such inflammatory and infectious diseases.

The chemokine receptor CCR5 is of particular importance in the context of treating inflammatory and infectious diseases. CCR5 is a receptor for chemokines, especially for the macrophage inflammatory proteins (MIP) designated MIP-1α and MIP-1β, and for a protein which is regulated upon activation and is normal T-cell expressed and secreted (RANTES). The relationship between modulators, especially antagonists of CCR5 activity and therapeutic usefulness in treating inflammation and HIV infection, and the manner in which such a relationship may be demonstrated, is explained in more detail further below.

There is ongoing in the art a substantial investigation of different classes of modulators of chemokine receptor activity, especially that of the CCR5 chemokine receptor. A representative disclosure is Mills et al. WO 98/25617 relating to substituted aryl piperazines as modulators of chemokine receptor activity. However, the compositions described therein are not the same as, nor suggestive of those of the present invention. Further disclosures are: WO 98/025605; WO 98/025604; WO 98/002151; WO 98/004554; and WO 97/024325.

The present invention relates to compounds which may be conveniently considered to have four independently variable regions, reading from the left-hand side to right-hand side of said compound: $R_{egion}\ \alpha$, $R_{egion}\ \beta$, $R_{egion}\ \gamma$, and $R_{egion}\ \delta$, of Formula (I):

$$[R_{egion}\ \alpha]\text{-}[R_{egion}\ \beta]\text{-}[R_{egion}\ \gamma]\text{-}[R_{egion}\ \delta] \qquad (I)$$

and pharmaceutically acceptable salts and prodrug derivatives thereof. The compounds of the present invention may be selective CCR5 receptor modulators and are non-peptidyl in structure.

The compounds as exemplified by Formula (I) may contain one or more stereogenic centers and the present invention includes the recited compounds in both their separated and their unseparated forms. The separated forms can be obtained by conventional means, e.g., by asymmetric synthesis, by using high performance liquid chromatography employing a chiral stationary phase, or by chemical resolution via the formation of suitable salts or derivatives. It will be understood that the separate optically active forms of the compositions of the present invention, as well as reacemic mixtures thereof, will usually vary with respect to their biological properties because of the chirality-dependent conformation of the active site of an enzyme, receptor, etc.

The description which follows provides details of the particular moieties which comprise each of said $R_{egions}$. In order to present said details in an orderly and space-saving fashion, each major group in each Region is set out with a single dash ("-"), and each successive subdivision within each said group is set out in turn with two, three, etc. dashes as required.

In this specification and claims a reference to a range or class of groups for example $(C_1\text{-}C_3)$alkyl is to be understood as an express disclosure and reference of each member of the range or class, including isomers.

According to the present invention there is provided a compound of Formula (I):

$$[R_{egion}\ \alpha]\text{-}[R_{egion}\ \beta]\text{-}[R_{egion}\ \gamma]\text{-}[R_{egion}\ \delta] \qquad (I)$$

wherein $[R_{egion}\ \alpha]$ is selected from the group consisting of:
A. Aryl heterocyclyl substituent components comprising:
  1. hetero-phenylmethylene moieties of partial Formula (1.0.0):

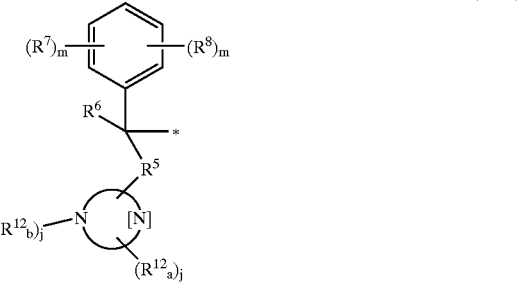

wherein: the symbol "*" indicates the point of attachment of the moiety of partial Formula (1.0.0) to $R_{egion}\ \beta$, as hereinafter defined;

$R^5$ is a member selected from the group consisting of a direct bond; —O—; —C(=O)—; —NR$^4$—; and —S(=O)$_p$—; where:

$R^4$ is hydrogen or $(C_1\text{-}C_2)$alkyl;

$R^6$ is a member selected from the group consisting of hydrogen; $(C_1\text{-}C_2)$alkyl; $(C_1\text{-}C_2)$alkoxy; —CN; —OH; and —C(=O)NH$_2$;

j is an integer selected from 0, 1, and 2;

m is an integer selected from 0, 1, and 2;

$R^7$ and $R^8$ are each a member selected from the group consisting of —F; —Cl; —CO$_2$R$^4$; —OH; —CN; —CONR$^4{}_aR^4{}_b$; —NR$^4{}_aR^4{}_b$—; —NR$^4{}_aC(=O)R^4{}_b$; —NR$^4{}_aC(=O)OR^4{}_b$; —NR$^4{}_aS(=O)_pR^4{}_b$; —S(=O)$_p$NR$^4{}_aR^4{}_b$; $(C_1\text{-}C_4)$alkyl, and $(C_1\text{-}C_4)$alkoxy wherein said alkyl and alkoxy are each substituted with 0 to 3 substituents independently selected from F and Cl; (C₁–C₂) alkoxycarbonyl; (C₁–C₂)alkylcarbonyl; and (C₁–C₂)alkylcarbonyloxy; where:
p is an integer selected from 0, 1, and 2;
R⁴$_a$ and R⁴$_b$ are each independently selected from hydrogen and (C₁–C₂)alkyl;

the moiety represented by partial Formula (1.0.1):

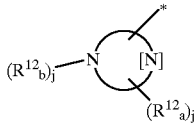

(1.0.1)

in partial Formula (1.0.0) represents a monocyclic heterocyclic group, or a bicyclic benzo-fused ring system containing said heterocyclic group wherein said heterocyclic group contains a total of 5- or 6-members of which one or two of said members is nitrogen, the presence of the optional second nitrogen atom being represented by: "[N]"; wherein said heterocyclic group or ring system are selected from the group consisting of pyrrolyl; pyrazolyl; imidazolyl; pyridinyl; pyrazinyl; pyrimidinyl; pyridazinyl; piperazinyl; indolyl; indazolinyl; benzimidazolyl; quinolinyl; iso-quinolinyl; and quinazolinyl; wherein:

R¹²$_a$ is a member selected from the group consisting of hydrogen; F; Cl; —CO₂R⁴; oxo; —OH; CN; NH₂; NH(C₁–C₂)alkyl; N(C₁–C₂)₂dialkyl; —CF₃; (C₁–C₄)alkyl; (C₂–C₄)alkenyl; (C₁–C₄)alkoxy; (C₃–C₇)cycloalkyl; and phenyl; wherein said alkyl, alkenyl, alkoxy, cycloalkyl and phenyl are substituted with 0 to 2 substituents R⁹ where:

R⁹ is a member independently selected from the group consisting of F; Cl; —CO₂R⁴; —OH; cyano; —CONR⁴$_a$R⁴$_b$; —NR⁴$_a$R⁴$_b$—; —NR⁴$_a$C(=O)R⁴$_b$; —NR⁴$_a$C(=O)OR⁴$_b$; —NR⁴$_a$S(=O)$_p$R⁴$_b$; —S(=O)$_p$NR⁴$_a$R⁴$_b$; (C₁–C₄)alkyl including dimethyl, and (C₁–C₄)alkoxy wherein said alkyl and alkoxy are each independently substituted with 0 to 3 substituents independently selected from F and Cl; (C₁–C₂)alkoxycarbonyl; (C₁–C₂)alkylcarbonyl; and (C₁–C₂)alkylcarbonyloxy; and R¹²$_b$ is absent or is a member selected from the group consisting of hydrogen; (C₁–C₄)alkyl; (C₂–C₄)alkenyl; (C₁–C₂)alkoxy; (C₃–C₇)cycloalkyl; and phenyl; wherein said alkyl, alkenyl, alkoxy, cycloalkyl and phenyl are substituted with 0 to 2 substituents R⁹ wherein R⁹ has the same meaning as above, except that it is selected independently selected therefrom; and 2. hetero-phenylmethylene moieties of partial Formula (1.1.0):

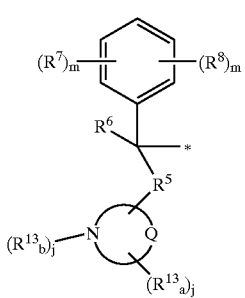

(1.1.0)

wherein: the symbol "*"; R⁵; R⁶; R⁷; R⁸; j and m are as defined further above, except that all of the above-recited substituents are selected independently of their selection above;

the moiety represented by partial Formula (1.1.1):

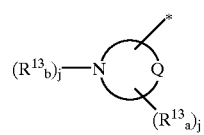

(1.1.1)

in partial Formula (1.1.0) represents:
a. a monocyclic heterocyclic group containing a total of 5 or 6 members of which one said member is nitrogen and Q is selected from O and S where said S may optionally be in the sulfonate form, —S(=O)₂; wherein said heterocyclic group is selected from the group consisting of oxazolyl; oxazolidinyl; isoxazolyl; thiazolyl; thiazolidinyl; iso-thiazolyl; morpholinyl; and thiomorpholinyl; or
b. a monocyclic heterocyclic group containing a total of 5- or 6-members of which two said members are nitrogen and a third or fourth said member is independently selected from N, O, and S where said S may optionally be in the sulfonate form, —S(=O)₂; wherein said heterocyclic group is selected from the group consisting of triazolyl; triazinyl; tetrazolyl; oxadiazolyl; thiadiazolyl; and R¹³$_a$ is selected from the group consisting of hydrogen; F; Cl; —CO₂R⁴; oxo; —OH; CN; NH₂; NH(C₁–C₂)alkyl; N(C₁–C₂)₂dialkyl; —CF₃; (C₁–C₄)alkyl; (C₂–C₄)alkenyl; (C₁–C₂)alkoxy; (C₃–C₇)cycloalkyl; and phenyl; wherein said alkyl, alkenyl, alkoxy, cycloalkyl and phenyl are substituted with 0 to 2 substituents R¹¹ where:

R¹¹ is a member selected from the group consisting of F; Cl; —CO₂R⁴; —OH; —CN; —CONR⁴$_a$R⁴$_b$; R⁴$_a$R⁴$_b$; —NR⁴$_a$C(=O)R⁴$_b$; —NR⁴$_a$C(=O)OR⁴$_b$; —NR⁴$_a$S(=O)$_p$R⁴$_b$; —S(=O)$_p$NR⁴$_a$R⁴$_b$; (C₁–C₄)alkyl including dimethyl, and (C₁–C₄) alkoxy wherein said alkyl and alkoxy are each independently substituted with 0 to 3 substituents independently selected from F and Cl; (C₁–C₂) alkoxycarbonyl; (C₁–C₂)alkylcarbonyl; and (C₁–C₂)alkylcarbonyloxy; and R¹³$_b$ is a member selected from the group consisting of hydrogen; (C₁–C₄)alkyl; (C₂–C₄)alkenyl; (C₁–C₂)alkoxy; (C₃–C₇)cycloalkyl; C(=O) (C₁–C₄)alkyl; S(=O)₂(C₁–C₄)alkyl; and phenyl; wherein said alkyl, alkenyl, alkoxy, cycloalkyl and phenyl are substituted with 0 to 2 substituents R¹¹ wherein R¹¹ has the same meaning as in above, except that it is selected independently;

B. a (substituted)-amido-aryl or -heterocyclyl moiety selected from the group consisting of
1. alkyl-, alkenyl-, and alkynyl-substituted-amido-aryl moieties of partial Formula (2.0.0):

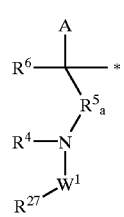

(2.0.0)

wherein: the symbol "*"; $R^4$ and $R^6$; are as defined above, except that all of the above-recited substituents are selected independently of their selection above;

A is a member selected from the group consisting of:
1. the moiety of partial Formula (2.0.3)

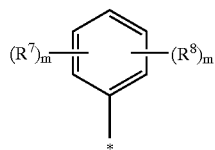

(2.0.3)

wherein: the symbol $R^7$; $R^8$ and m are as defined above, except that all of the above-recited substituents are selected independently of their selection above; and the symbol: "*" indicates the point of attachment of the moiety A to the, remaining portions of partial Formula (2.0.0);

2. the moiety of partial Formula (2.0.4)

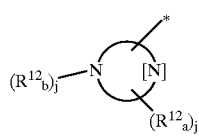

(2.0.4)

which represents a monocyclic heterocyclic group, selected from the group consisting of pyrrolyl; pyrazolyl; imidazolyl; pyridinyl; pyrazinyl; pyrimidinyl; wherein: the symbol $R^{12}{}_a$ and $R^{12}{}_b$ are as defined above, except that all of the above-recited substituents are selected independently of their selection above; and the symbol: "*" indicates the point of attachment of the moiety A to the other, remaining portions of partial Formula (2.0.0);

3. the moiety of partial Formula (2.0.5)

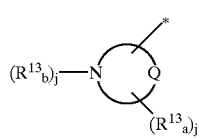

(2.0.5)

which represents
a. a monocyclic heteroaromatic group containing a total of 5-members of which one said member is nitrogen and Q is selected from O and S where said S may optionally be in the sulfonate form, —S(=O)$_2$; selected from the group consisting of oxazolyl; isoxazolyl; thiazolyl; and iso-thiazolyl; or
b. a monocyclic heterocyclic group containing a total of 5- or 6-members of which two said members are nitrogen and a third or fourth said member is independently selected from N, O, and S where said S may optionally be in the sulfonate form, —S(=O)$_2$; selected from the group consisting of triazolyl; triazinyl; tetrazotyl; oxadiazolyl; and thiadiazolyl; and wherein: the $R^{13}{}_a$, $R^{13}{}_b$ and j are as defined above, except that all of the above-recited substituents are selected independently of their selection above; and the symbol:

"*" indicates the point of attachment of the moiety A to the other, remaining portions of partial Formula (2.0.2);

$R^5{}_a$ is a member selected from the group consisting of a direct bond; —C(=O)—; and —S(=O)$_2$—;

$W^1$ is (1.) a direct bond; (2.) in the case where $R^5{}_a$ is —C(=O)— or —S(=O)$_2$, $W^1$ is a direct bond or —(C$_1$–C$_3$)alkylene- wherein any single carbon atom thereof is substituted by 0 to 2 substituents $R^{23}$ where $R^{23}$ is a member selected from the group consisting of —F; —Cl; —CO$_2$R$^4$; —OH; —CN; (C$_1$–C$_4$)alkoxy, (C$_3$–C$_7$)cycloalkyl; and phenyl; wherein said alkoxy, cycloalkyl, and phenyl are substituted with 0 to 2 substituents $R^{11}$, wherein said $R^{11}$ is as defined above, except that all of the above-recited substituents are selected independently of their selection above; or (3.) is a member independently selected from the group consisting of the moieties of partial Formulas (2.0.6) through (2.0.16), inclusive:

(2.0.6)

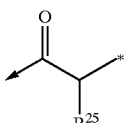

(2.0.7)

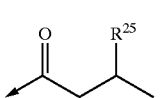

(2.0.8)

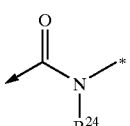

(2.0.9)

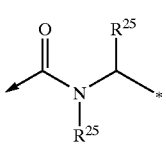

(2.0.10)

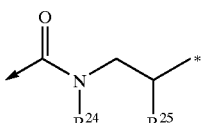

(2.0.11)

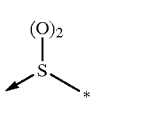

(2.0.12)

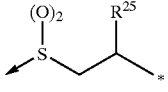

(2.0.13)

-continued (2.0.14)

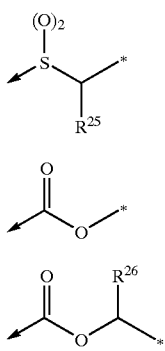

(2.0.15)

(2.0.16)

wherein: the symbol: "→" indicates the point of attachment of the moiety $W^1$ to the nitrogen atom in partial Formula (2.0.0), and the symbol: "*" indicates the point of attachment of the moiety $W^1$ to the other, remaining portions of partial Formula (2.0.0); and $R^4$ is as defined further above, but selected on an independent basis;

$R^{24}$ is selected from the group consisting of hydrogen and $(C_1-C_4)$alkyl; and $R^{25}$ and $R^{26}$ are each selected from the group consisting of —OH; $(C_1-C_2)$alkyl substituted by 0 to 3 substituents selected from F; and OH; and $(C_1-C_2)$alkoxy; and $R^{27}$ is selected from the group consisting of $(C_1-C_6)$alkyl; $(C_2-C_6)$alkenyl; and $(C_2-C_6)$alkynyl; wherein said alkyl, alkenyl, and alkynyl groups comprising $R^{27}$ are substituted with 0 to 3 substituents $R^{28}$ where:

$R^{28}$ is selected from the group consisting of phenyl; F or Cl; oxo; hydroxy, $(C_1-C_2)$alkyl; $(C_1-C_3)$alkoxy; —C(=O)OR$^{29}$; —C(=O)(C_1-C_4)alkyl; —S(=O)$_2$(C_1-C_4)alkyl; —C(=O)NR$^{29}$R$^{30}$; —NR$^{29}$R$^{30}$; —NR$^{29}$C(=O)R$^{30}$; —NR$^{29}$C(=O)OR$^{30}$; —NR$^{29}$S(=O)$_p$R$^{30}$; and —S(=O)$_2$NR$^{29}$R$^{30}$, where:

$R^{29}$ and $R^{30}$ are each a member independently selected from the group consisting of hydrogen and $(C_1-C_4)$alkyl substituted by 0 to 3 substituents selected from the group consisting of F and Cl;

2. cycloalkyl-substituted-amido-aryl moieties of partial Formula (2.1.0):

(2.1.0)

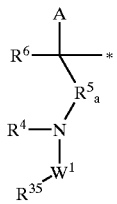

wherein: A; $W^1$; the symbol "*"; $R^4$; $R^5_a$; and $R^6$ have the same meaning as set out above, except that all of the above-recited substituents are selected independently of their selection above; and $R^{32}$ is a member selected from the group consisting of —(CH$_2$)$_n$—(C$_3$-C$_7$)cycloalkyl, where n is an integer selected from 0, 1, and 2; in the event n is 0, then the α-carbon atom of said (C$_3$-C$_7$)cycloalkyl is substituted by 0 or 1 (C$_1$-C$_4$)alkyl or phenyl, where said alkyl or phenyl are substituted by 0, 1, or 2 of CH$_3$, OCH$_3$, OH or NH$_2$; and in the event that n is 1 or 2, the resulting methylene or ethylene is substituted by 0 or 1 of F; NH$_2$; N(CH$_3$)$_2$; OH; OCH$_3$; (C$_1$-C$_4$)alkyl; or phenyl; where said alkyl and phenyl are substituted by 0, 1, or 2 of CH$_3$, OCH$_3$, OH, and NH$_2$; and further wherein said (C$_3$-C$_7$)cycloalkyl is substituted by 0 to 3 substituents $R^{28}$ where $R^{28}$ is as defined further above, but selected independently 3. aryl and heterocyclic-substituted-amido-aryl moieties of partial Formula (2.2.0):

(2.2.0)

wherein: A; $W^1$; the symbol: "*"; $R^4$; $R^5_a$; and $R^6$ have the same meaning as set out above, except that all of the above-recited substituents are selected independently of their selection above; and $R^{35}$ is selected from the group consisting of phenyl; furyl; tetrahydrofuranyl; tetrahydropyranyl; oxetanyl; thienyl; pyrrolyl; pyrrolidinyl; oxazolyl; isoxazolyl; thiazolyl; isothiazolyl; imidazolyl; pyrazolyl; oxadiazolyl; thiadiazolyl; triazolyl; pyridyl; pyrazinyl; pyridazinyl; piperazinyl; pyrimidinyl; pyranyl; azetidinyl; morpholinyl; parathiazinyl; indolyl; indolinyl; benzo[b]furanyl; 2;3-dihydrobenzofuranyl; benzothienyl; 1H-indazolyl; benzimidazolyl; benzoxazolyl; benzisoxazolyl; benzthiazolyl; quinolinyl; isoquinolinyl; phthalazinyl; quinazolinyl; and quinoxalinyl; wherein (1.) said group $R^{35}$ may be substituted upon any one or more carbon atoms thereof by 0 to 3 substituents $R^{28}$ where $R^{28}$ is as defined above, except that it is selected independently; (2.) said group $R^{35}$ is substituted with respect to any one or more nitrogen atoms thereof that is not a point of attachment of said aryl or heterocyclic moiety, by 0 to 3 substituents $R^{13}_b$ where $R^{13}_b$ is as defined above, except that it is selected independently; and (3.) said group $R^{35}$ with respect to any sulfur atom thereof that is not a point of attachment of said heterocyclic moiety, is substituted by 0 or 2 oxygen atoms;

[R$_{egion}$ β] is an alkyl bridging element of partial Formula (3.0.0):

(3.0.0)

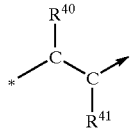

wherein:

"*" is a symbol which represents the point of attachment of the moiety of partial Formula (3.0.0) to R$_{egion}$ α;

"→" is a symbol which represents the point of attachment of the moiety of partial Formula (3.0.0) to R$_{egion}$ γ;

$R^{40}$ and $R^{41}$ are independently selected from the group consisting of hydrogen; $(C_1-C_2)$ alkyl including dimethyl; hydroxy; and $(C_1-C_3)$ alkoxy;

$[R_{egion} \gamma]$ is an aza-bicyclic moiety of partial Formula (4.2.0):

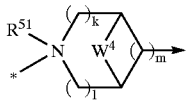

(4.2.0)

wherein

"*" is a symbol which represents the point of attachment of the moiety of partial Formula (4.2.0) to $R_{egion} \beta$;

"→" is a symbol representing a covalent bond from any of the carbon atoms of the moiety of partial Formula (4.2.0) to $R_{egion} \delta$;

$W^4$ is a direct bond; or is a member independently selected from the group consisting of partial Formulas (4.2.1) through (4.2.6):

(4.2.1)

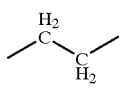

(4.2.2)

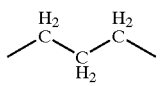

(4.2.3)

where:

$R^{52}$ is a member selected from the group consisting of hydrogen; phenyl; $(C_1-C_4)$alkyl substituted by 0 or 1 substituent independently selected from $(C_1-C_2)$alkoxy and $—CO_2R^4$; $(C_3-C_6)$cycloalkyl; $—CO_2R^4$; →O; $C(=O)(C_1-C_3)$alkyl; $—C(=O)NR^4{}_aR^4{}_b$; $—S(=O)(C_1-C_4)$alkyl; and $(C_1-C_2)$alkylcarbonyl; where $R^4$, $R^4{}_a$, and $R^4{}_b$; are as defined above, but selected on an independent basis;

$R^{51}$ is absent or is a member selected from the group consisting of $(C_1-C_4)$alkyl substituted by 0 or 1 substituent independently selected from $(C_1-C_2)$ alkoxy and $—CO_2R^4$ where $R^4$ is as defined above; and →O; it being understood that in the case where substituent $R^{51}$ is present, the nitrogen atom is in quaternary form; and k, l and m are each an integer selected from 0, 1, 2, and 3;

$[R_{egion} \delta]$ is a member selected from the group consisting of:

A. a two-nitrogen-atom-containing five-membered heterocyclic moiety of partial Formulas (5.0.0) through (5.0.10):

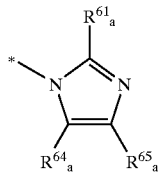

(5.0.0)

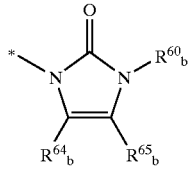

(5.0.1)

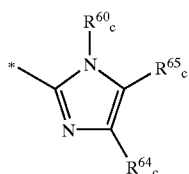

(5.0.2)

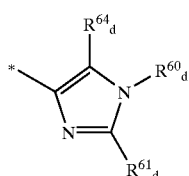

(5.0.3)

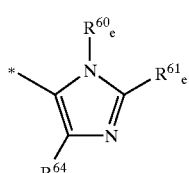

(5.0.4)

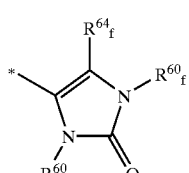

(5.0.5)

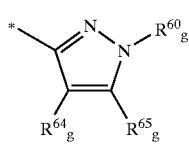

(5.0.6)

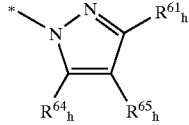

(5.0.7)

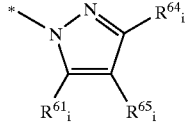

(5.0.8)

-continued

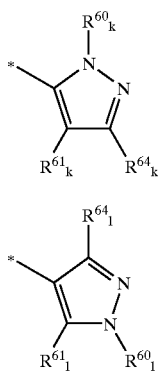

(5.0.9)

(5.0.10)

wherein: the symbol: "*" indicates the point of attachment of each of the moieties of partial Formulas (5.0.0) through (5.0.10), inclusive, to $R_{egion}$ γ;

$R^{60}{}_b$ through $R^{60}{}_g$, inclusive, $R^{60}{}_k$, and $R^{60}{}_l$ are each a member selected from the group consisting of hydrogen; —$CO_2R^4$; —C(=O)$NR^4{}_aR^4{}_b$; —S(=O)$_p$ $NR^4{}_aR^4{}_b$; where: $R^4$; $R^4{}_a$; and $R^4{}_b$ are as defined above but selected on an independent basis; →O; ($C_1$–$C_2$) alkylcarbonyl; —($C_1$–$C_4$)alkyl; —$(CH_2)_n$—($C_3$–$C_7$) cycloalkyl; —($C_2$–$C_3$)alkenyl; —$(CH_2)_n$—(phenyl); and —$(CH_2)_n$—($HET_1$), where n is an integer independently selected from 0, 1, and 2; wherein said ($C_1$–$C_4$) alkyl, alkenyl, cycloalkyl, phenyl, and heterocyclyl groups are independently substituted with 0 to 3 substituents $R^{66}$, where:

$HET_1$ is a heterocyclyl group selected from the group consisting of thienyl; oxazolyl; isoxazolyl; thiazolyl; isothiazolyl; pyrazolyl; oxadiazolyl; thiadiazolyl; triazolyl; pyridyl; pyrazinyl; pyridazinyl; pyrimidinyl; parathiazinyl; and morpholinyl; where:

$R^{66}$ is a member selected from the group consisting of —F; —Cl; —OH; cyano; —C(=O)$OR^{68}$; —C(=O)$NR^{68}R^{69}$; —$NR^{68}R^{69}$; —$NR^{68}$C(=O) $R^{69}$; —$NR^{68}$C(=O)$OR^{69}$; —$NR^{68}$S(=O)$_2R^{69}$; —S(=O)$_2NR^{68}R^{69}$; ($C_1$–$C_4$)alkyl including dimethyl, and ($C_1$–$C_4$)alkoxy wherein said alkyl and alkoxy are each independently substituted with 0 to 3 substituents independently selected from F and Cl; ($C_1$–$C_2$)alkoxycarbonyl; ($C_1$–$C_2$) alkylcarbonyl; and ($C_1$–$C_2$)alkylcarbonyloxy, where:

$R^{68}$ and $R^{69}$ are each a member selected from the group consisting of hydrogen; and ($C_1$–$C_2$) alkyl; and where said:

$R^{61}{}_a$; $R^{61}{}_d$; $R^{61}{}_e$; and $R^{61}{}_h$ through $R^{61}{}_l$ inclusive; $R^{64}{}_a$ through $R^{64}{}_i$ inclusive; $R^{65}{}_a$ through $R^{65}{}_c$ inclusive; and $R^{65}{}_g$ through $R^{65}{}_i$ inclusive are each a member selected from the group consisting of hydrogen; —OH; —$CF_3$; cyano; —($C_1$–$C_3$)alkoxy; —C(=O)$OR^4$; —C(=O)$NR^4{}_aR^4{}_b$; —$NR^4{}_aR^4{}_b$; —$NR^4{}_aC(=O)R^4{}_b$; —$NR^4{}_aC(=O)OR^4{}_b$; —$NR^4{}_aS(=O)_pR^4{}_b$; —S(=O)$_p$ $NR^4{}_aR^4{}_b$; where: $R^4$; $R^4{}_a$; and $R^4{}_b$ are as defined further above but selected on an independent basis; —($C_1$–$C_4$)alkyl; —$(CH_2)_n$—($C_3$–$C_7$)cycloalkyl; —($C_2$–$C_3$)alkenyl; —$(CH_2)_n$—(phenyl); and —$(CH_2)_n$—($HET_1$), where n is an integer selected from 0, 1, and 2; wherein said ($C_1$–$C_4$)alkyl, alkenyl, cycloalkyl, phenyl, and heterocyclyl groups where heterocyclyl groups is as defined above, are independently substituted with 0 to 3 substituents $R^{66}$ where:

$R^{66}$ is as defined above, or $R^{64}{}_a$ through $R^{64}{}_c$ inclusive; $R^{64}{}_g$ through $R^{64}{}_i$ inclusive; $R^{65}{}_a$ through $R^{65}{}_c$inclusive; and $R^{65}{}_g$ through $R^{65}{}_i$ inclusive may be taken together in their same subscript denominated pairs along with the remaining portions of the moieties of partial Formulas (5.0.0) through (5.0.2), and (5.0.6) through (5.0.8), to form a fused bicyclic ring system comprising a member independently selected from the group consisting of benzimidazolyl; purinyl, i.e., imidazopyrimidinyl; and imidazopyridinyl; wherein said fused bicyclic ring system is independently substituted with 0 to 3 substituents $R^{66}$, where $R^{66}$ has the same meaning as set out further above, except that it is independently selected therefrom;

B. a (substituted)-amide, carbamate, or urea moiety selected from the group consisting of:
1. alkyl-, cycloalkyl-, and alkenyl-(substituted)-amide, carbamate, or urea moieties of partial Formula (5.1.0):

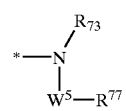

(5.1.0)

wherein: the symbol "*" is as defined above;

$R^{73}$ is a member selected from the group consisting of hydrogen and ($C_1$–$C_2$)alkyl;

$W^5$ is selected from the group consisting the moieties of partial Formulas (5.1.1) through (5.1.12):

(5.1.1)

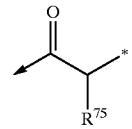

(5.1.2)

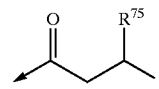

(5.1.3)

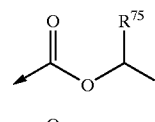

(5.1.4)

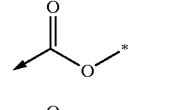

(5.1.5)

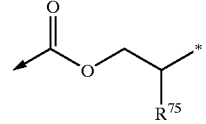

(5.1.6)

(5.1.7)

-continued

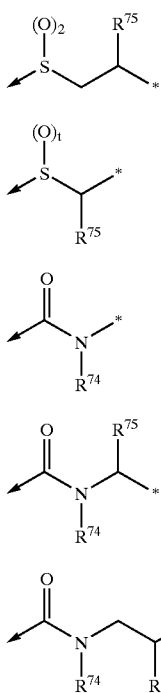

(5.1.8)

(5.1.9)

(5.1.10)

(5.1.11)

(5.1.12)

wherein: the symbol: "→" indicates the point of attachment of the moiety $W_5$ represented by partial Formulas (5.1.1) through (5.1.12), inclusive, to the nitrogen atom in partial Formula (5.1.0), and the symbol: "*" indicates the point of attachment of the moiety $W^5$ to $R^{77}$ as defined further below;

$R^{74}$ and $R^{75}$ are each selected from the group consisting of hydrogen; $(C_1-C_2)$alkyl substituted by 0 or 1 substituent independently selected from OH; and $(C_1-C_2)$alkoxy; and $R^{77}$ is a member selected from the group consisting of $(C_1-C_6)$alkyl; $(C_2-C_6)$alkenyl; and —$(CH_2)_n$—$(C_3-C_7)$cycloalkyl, where n is an integer selected from 0, 1, and 2; and wherein said alkyl, alkenyl, and cycloalkyl groups comprising $R^{77}$ are substituted with 0 to 3 substituents $R^{78}$, where:

$R^{78}$ is a member selected from the group consisting of oxo; —OH; —$(C_1-C_2)$alkyl; —$(C_1-C_3)$alkoxy; —$CF_3$; —$C(=O)OR^{79}$; —$C(=O)NR^{79}R^{80}$; —$NR^{79}R^{80}$; —$NR^{79}C(=O)R^{80}$; —$NR^{79}C(=O)OR^{80}$; —$NR^{79}S(=O)_2R^{80}$; and —$S(=O)_2NR^{79}R^{80}$, where:

$R^{79}$ and $R^{80}$ are each a member independently selected from the group consisting of hydrogen; and $(C_1-C_4)$alkyl; and 2. aryl and heterocyclyl(substituted)-amide, carbamate, or urea moieties of partial Formula (5.2.0):

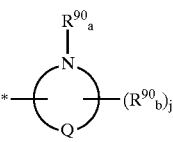

(5.2.0)

wherein: the symbol: "*"; $R^{73}$; and $W^5$ have the same meanings as under the definitions of partial Formula (5.1.0) above, except that they are independently selected therefrom; and under $W^5$ the symbols: "→" and "*", are as defined under partial Formula (5.1.0); and $R^{82}$ is a member selected from the group consisting of phenyl; cinnolinyl; furyl; thienyl; pyrrolyl; oxazolyl; isoxazolyl; thiazolyl; isothiazolyl; imidazolyl; imidazolinyl; pyrazolyl; pyrazolinyl; oxadiazolyl; thiadiazolyl; triazolyl; pyridyl; pyrazinyl; pyridazinyl; pyrimidinyl; parathiazinyl; indolyl; isoindolyl; indolinyl; benzo[b]furanyl; 2;3-dihydrobenzofuranyl; benzo[b]thiophenyl; 1H-indazolyl; benzimidazolyl; benzthiazolyl; quinolinyl; isoquinolinyl; phthalazinyl; quinazolinyl; quinoxalinyl; wherein:
the aryl or heterocyclyl moiety is substituted by 0 to 3 substituents $R^{78}$ where $R^{78}$ is as defined above, but selected on an independent basis; or C. a (substituted)-heterocyclyl moiety independently selected from the group consisting of:
1. a heterocyclyl moiety of partial Formula (5.3.0):

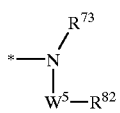

(5.3.0)

wherein: the symbol: "*" indicates the point of attachment of partial Formula (5.3.0) to $R_{egion}$ γ; Q is N, O or S and
partial Formula (5.3.0) represents:
a. a monocyclic heterocyclic group containing a total of 5-members of which one said member is nitrogen and a second said member is selected from O and S where said S may optionally be in the sulfonate form, wherein said heterocyclic group is selected from the group consisting of oxazolyl; isoxazolyl; thiazolyl; and iso-thiazolyl; or
b. a monocyclic heterocyclic group containing a total of 5-members of which two said members are nitrogen and a third or fourth said member is independently selected from N, O, and S where said S may optionally be in the sulfonate form, —$S(=O)_2$; wherein said heterocyclic group is independently selected from the group consisting of triazolyl; tetrazolyl; oxadiazolyl; and thiadiazolyl; and $R^{90}_a$ and $R^{90}_b$ are each a member independently selected from the group consisting of hydrogen, —$(C_1-C_2)$alkylcarbonyl; —$(C_1-C_4)$alkyl; —$(CH_2)_n$—$(C_3-C_7)$cycloalkyl; —$(C_2-C_3)$alkenyl; —$(CH_{2n}$—(phenyl); and —$(CH_2)_n$—(HET$_2$), where n is an integer independently selected from 0, 1, and 2; wherein said $(C_1-C_4)$ alkyl, alkenyl, cycloalkyl, phenyl, and HET$_2$ groups are independently substituted with 0 to 3 substituents $R^{91}$, where:
j has the same meaning as set forth above, but is selected on an independent basis therefrom;
HET$_2$ is a heterocyclyl group selected from the group consisting of thienyl; oxazolyl; isoxazolyl; thiazolyl; isothiazolyl; pyrazolyl; oxadiazolyl; thiadiazolyl; triazolyl; pyridyl; pyrazinyl; pyridazinyl; pyrimidinyl; parathiazinyl; and morpholinyl; where:
$R^{91}$ is selected from the group consisting of —F; —Cl; —$CO_2R^4$; —OH; —CN;

—CONR$^{93}$R$^{94}$; —NR$^{93}$R$^{94}$; C(=O)(C$_1$–C$_4$) alkyl; —NR$^{93}$C(=O)R$^{94}$; —NR$^{93}$C(=O)OR$^{94}$; —NR$^{93}$S(=O)R$^{94}$; —S(=O)NR$^{93}$R$^{94}$; (C$_1$–C$_4$)alkyl including dimethyl, and (C$_1$–C$_4$)alkoxy wherein said alkyl and alkoxy are each independently substituted with 0 to 3 substituents independently selected from F and Cl; (C$_1$–C$_2$)alkoxycarbonyl; (C$_1$–C$_2$)alkylcarbonyl; and (C$_1$–C$_2$)alkylcarbonyloxy, wherein:

R$^{93}$ and R$^{94}$ are each a member independently selected from the group consisting of hydrogen; and (C$_1$–C$_2$)alkyl; and 2. a heterocyclyl moiety of partial Formula (5.4.0):

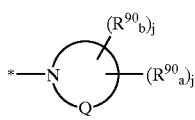

(5.4.0)

wherein: R$^{90a}$; R$^{90b}$; and j have the same meanings as set out above, but are selected independently.

Attention is drawn to our copending application nos P60190WO and P60191WO.

An important aspect of the present invention is the limitation to R$_{egion}$ γ. The copending case relates to alternative limitations of Formula (I).

This invention also provides pharmaceutical formulations and dosage forms including as an active ingredient a compound of Formula I. Use of a compound of Formula I in manufacture of a formulation or dosage form and methods of treatment are also provided.

[R$_{egion}$ α] is at the left-hand end of the CCR5 receptor modulator of the present invention. The region designated as R$_{egion}$ α may comprise a moiety selected from several different classes of substituent components, all of which may be and are preferably isosteres of each other.

The first class of R$_{egion}$ α substituent components (under A) are heterocyclyl phenylmethylene moieties as described further below. A preferred group of heterocyclyl phenylmethylene moiety embodiments (under A.1.) comprises the group consisting of hetero-phenylmethylene moieties of partial Formula (1.0.0),

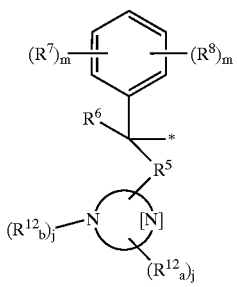

The substituent R$^5$ is a member independently selected from the group consisting of a direct bond; —O—; —C(=O)—; —NR$^4$—; and —S(=O)$_p$—; where R$^4$ is hydrogen or (C$_1$–C$_2$)alkyl.

The substituent R$^6$ is a member independently selected from the group consisting of hydrogen; (C$_1$–C$_2$)alkyl; (C$_1$–C$_2$)alkoxy; —C(=O)NH$_2$; —CN; and —OH. Most preferably R$^6$ is hydrogen and there is no substituent at this position.

Included within the partial Formula (1.0.0) are position isomer variations thereof that are not shown, but that arise where the optional substituents R$^7$ and R$^8$ are different. Substituents R$^7$ and R$^8$ are present once or twice or not at all, as indicated by their representation as: "(R$^7$)$_m$" and "(R$^8$)$_m$", where m is defined as being an integer selected from 0, 1, and 2. In the most preferred embodiments of the present invention, m is 0, although in alternative embodiments m is 1.

The substituents R$^7$ and R$^8$ comprise —F; —Cl; —CO$_2$R$^4$; —OH; —CN; —CONR$^4_a$R$^4_b$; —NR$^4_a$R$^4_b$; —NR$^4_a$C(=O)R$^4_b$; —NR$^4_a$C(=O)OR$^4_b$; —NR$^4_a$S(=O)$_p$R$^4_b$; —S(=O)$_p$NR$^4_a$R$^4_b$; (C$_1$–C$_4$)alkyl including dimethyl, and (C$_1$–C$_4$)alkoxy wherein said alkyl and alkoxy are each independently substituted with 0 to 3 substituents independently selected from —F and —Cl; (C$_1$–C$_2$)alkoxycarbonyl; (C$_1$–C$_2$)alkylcarbonyl; and (C$_1$–C$_2$)alkylcarbonyloxy. The substituents R$^4_a$ and R$^4_b$, in turn, are selected from hydrogen and (C$_1$–C$_2$)alkyl. With regard to the R$^7$ and R$^8$ substituent groups, it is preferred that they are absent (m=0); or that if they are present, that they be methyl; cyclopropyl, cyclobutyl; methoxy, —COOH; —OH; —F; —Cl; —COO(C$_1$–C$_2$)alkyl; or —CF$_3$. Of these choices, the more preferred substituent choices for R$^7$ and R$^8$ are that they are absent or that they are —F or Cl.

R$^5$ as defined by Formula (1.0.0) is preferably a direct bond. The moiety R$^5$ may alternatively be selected from —O—; —C(=O)—; —NR$^4$— where R$^4$ is hydrogen or (C$_1$–C$_2$)alkyl; and —S(=O)$_p$—.

In partial Formula (1.0.0), the presence of substituent R$^{12}_a$ is determined by the subscript "j", which is an integer independently selected from 0, 1, and 2. Where j is 0, accordingly, the substituent R$^{12}_a$ will be absent. Where j is 1 or 2, there may be one or two substituents R$^{12}_a$ present, and these may be attached to any available carbon atom in partial Formula (1.0.0).

R$^{12}_a$ is a member independently selected from the group consisting of hydrogen; —F; —Cl; —CO$_2$R$^4$ where R$^4$ is hydrogen or (C$_1$–C$_2$)alkyl as already defined above; -oxo; —OH; —CN; —NH$_2$; —NH(C$_1$–C$_2$)alkyl; —N(C$_1$–C$_2$)$_2$ dialkyl; —CF$_3$; (C$_1$–C$_4$)alkyl; (C$_2$–C$_4$)alkenyl; (C$_1$–C$_4$)alkoxy; (C$_3$–C$_7$)cycloalkyl; and phenyl; wherein said alkyl, alkenyl, alkoxy, cycloalkyl and phenyl groups are substituted with 0 to 2 substituents R$^9$ wherein R$^9$ is a member independently selected from the group consisting of —F; —Cl; —CO$_2$R$^4$ where R$^4$ is hydrogen or (C$_1$–C$_2$)alkyl; —OH; cyano; —CONR$^4_a$R$^4_b$; —NR$^4_a$R$^4_b$; —NR$^4_a$C(=O)R$^4_b$; —NR$^4_a$C(=O)OR$^4_b$; —NR$^4_a$S(=O)$_p$R$^4_b$; —S(=O)$_p$NR$^4_a$R$^4_b$; (C$_1$–C$_4$)alkyl including dimethyl, and (C$_1$–C$_4$)alkoxy wherein said alkyl and alkoxy are each independently substituted with 0 to 3 substituents independently selected from F and Cl; (C$_1$–C$_2$)alkoxycarbonyl; (C$_1$–C$_2$)alkylcarbonyl; and (C$_1$–C$_2$)alkylcarbonyloxy.

Where a R$^{12}_a$ substituent is present and consists of an alkyl, alkenyl, alkoxy, cycloalkyl or phenyl group, it may optionally be mono- or di-substituted in turn by a further substituent R$^9$, which is independently selected from the above-recited groups. This includes in particular (C$_1$–C$_4$) alkyl substituted with 1 to 3 substituents independently selected from F and Cl. Accordingly, the substituent —CF$_3$ is a preferred definition of R$^9$ in the compounds of partial Formula (1.0.0).

The R$^{12}_b$ substituent is attached directly to the nitrogen atom of the heterocyclic group depicted in partial Formula (1.0.0), and its presence is determined by the subscript "j", which is an integer independently selected from 0, 1, and 2. Where j is 0, accordingly, the substituent R$^{12}_b$ is absent. In that case that the nitrogen atom is attached by a covalent double bond to an adjacent atom in the heterocyclic group depicted in partial Formula (1.0.0). Where j is 1 or 2, there will be one or two substituents $R^{12}{}_b$ attached to the nitrogen atom of the heterocyclic group depicted in partial Formula (1.0.0). Where two such $R^{12}{}_b$ substituents are attached, the nitrogen atom is in quaternary form. The substituent $R^{12}{}_b$ is independently selected from the group consisting of hydrogen; $(C_1-C_4)$alkyl; $(C_2-C_4)$alkenyl; $(C_1-C_2)$alkoxy; $(C_3-C_7)$cycloalkyl; and phenyl; wherein said alkyl, alkenyl, alkoxy, cycloalkyl and phenyl are substituted with 0 to 2 substituents $R^9$ wherein $R^9$ has the same meaning as in $R^9$ defined above, except that it is selected independently therefrom.

The group represented by partial Formula (1.0.1):

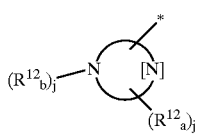

(1.0.1)

represents a monocyclic heterocyclic group, or a bicyclic benzo-fused ring system containing said heterocyclic group wherein said heterocyclic group contains a total of 5- or 6-members of which one or two of said members is nitrogen, the presence of the optional second nitrogen atom being represented by: "[N]"; wherein said heterocyclic group or ring system is selected from the group consisting of pyrrolyl; pyrazolyl; imidazolyl; pyridinyl; pyrazinyl; pyrimidinyl; pyridazinyl; piperazinyl; indolyl; indazolinyl; benzimidazolyl; quinolinyl; isoquinolinyl; and quinazolinyl.

N-containing heterocyclic moieties of partial Formula (1.0.0) result in some of the following preferred embodiments of $R_{egion}$ α, represented by partial Formulas (1.0.4) through (1.0.10), inclusive:

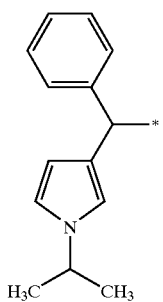

(1.0.4)

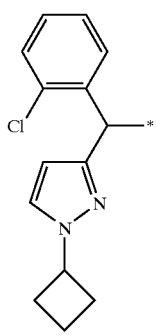

(1.0.5)

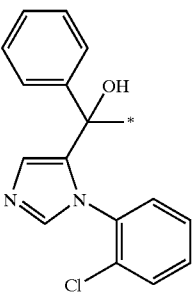

(1.0.6)

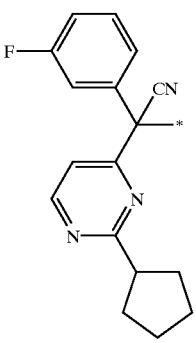

(1.0.7)

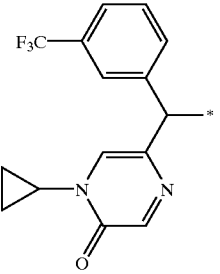

(1.0.8)

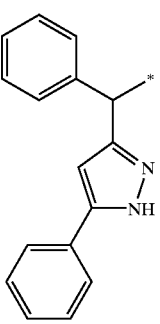

(1.0.9)

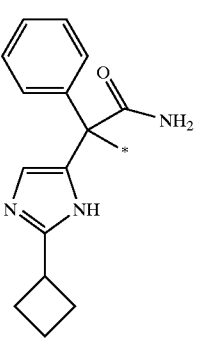

(1.0.10)

A further group of N-containing heterocyclic phenylmethylene moieties (under A.2 comprises several subgeneric groups within partial Formula (1.1.0):

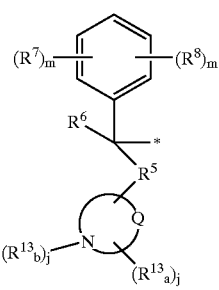

(1.1.0)

where the symbol "*" and $R^5$; $R^6$; $R^7$; $R^8$; j and m are as defined above;

and $R^{13}_a$ is a member selected from the group consisting of hydrogen; F; Cl; —$CO_2R^4$; oxo; —OH; CN; $NH_2$; $NH(C_1–C_2)$alkyl; $N(C_1–C_2)_2$dialkyl; —$CF_3$; $(C_1–C_4)$ alkyl; $(C_2–C_4)$alkenyl; $(C_1–C_2)$alkoxy; $(C_3–C_7)$ cycloalkyl; and phenyl; wherein said alkyl, alkenyl, alkoxy, cycloalkyl and phenyl are substituted with 0 to 2 substituents $R^{11}$ wherein $R^{11}$ is a member independently selected from the group consisting of F; Cl; —$CO_2R^4$; —OH; —CN; —$CONR^4_aR^4_b$; —$NR^4_aR^4_b$; —$NR^4_aC(=O)R^4_b$; —$NR^4_aC(=O)OR^4_b$; —$NR^4_aS(=O)_pR^4_b$; —$S(=O)_pNR^4_aR^4_b$; $(C_1–C_4)$alkyl including dimethyl, and $(C_1–C_4)$alkoxy wherein said alkyl and alkoxy are each independently substituted with 0 to 3 substituents independently selected from F and Cl; $(C_1–C_2)$alkoxycarbonyl; $(C_1–C_2)$alkylcarbonyl; and $(C_1–C_2)$alkylcarbonyloxy; and $R^{13}_b$ is selected from the group consisting of hydrogen; $(C_1–C_4)$alkyl; $(C_2–C_4)$alkenyl; $(C_1–C_2)$alkoxy; $(C_3–C_7)$cycloalkyl; $C(=O)(C_1–C_4)$alkyl; $S(=O)_2(C_1–C_4)$alkyl; and phenyl; wherein said alkyl, alkenyl, alkoxy, cycloalkyl and phenyl are substituted with 0 to 2 substituents $R^{11}$ wherein $R^{11}$ has the same meaning as in above, except that it is independently selected therefrom.

The moiety of partial Formula (1.1.1):

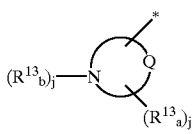

(1.1.1)

represents, inter alia, a monocyclic heterocyclic group containing a total of 5-members of which one said member is nitrogen and Q is selected from O and S The heterocyclic group may be selected from the group consisting of oxazolyl; oxazolidinyl; isoxazolyl; thiazolyl; thiazolidinyl; iso-thiazolyl: morpholinyl and thiamorpholinyl.

Moieties of partial Formula (1.1.0) containing the group of partial Formula (1.1.1) result in the following preferred embodiments of $R_{egion}$ α, represented by partial Formulas (1.1.3) through (1.1.9):

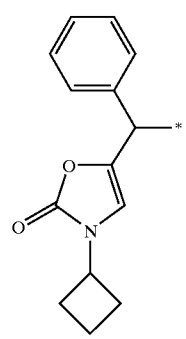

(1.1.3)

(1.1.4)

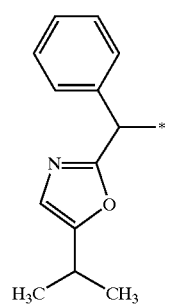

(1.1.5)

(1.1.6)

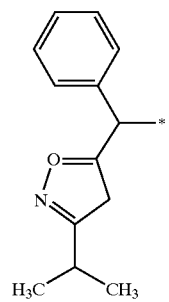

(1.1.7)

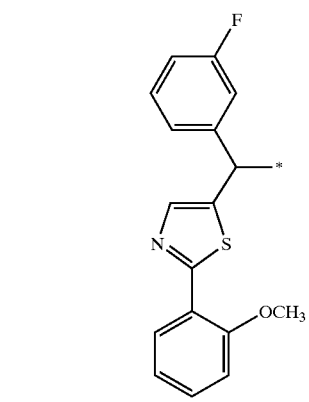

(1.1.8)

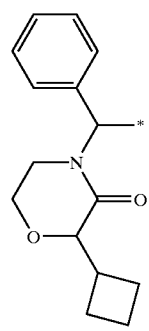

(1.1.9)

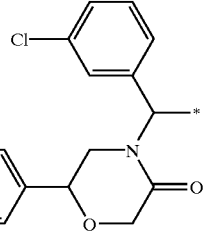

In alternative preferred embodiments the heterocyclic group may selected from the group consisting of triazolyl; triazinyl; tetrazolyl; oxadiazolyl; and thiadiazolyl.

Further preferred embodiments of $R_{egion}$ α, are represented by partial Formulas (1.1.20) through (1.1.24), inclusive:

(1.1.20)

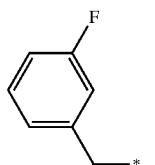

(1.1.21)

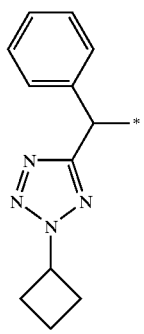

(1.1.22)

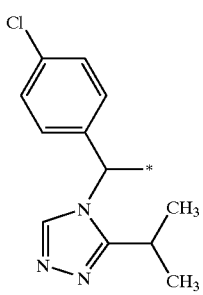

(1.1.23)

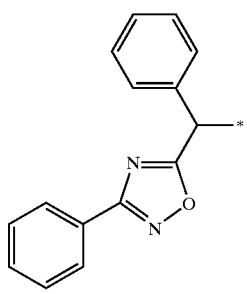

(1.1.24)

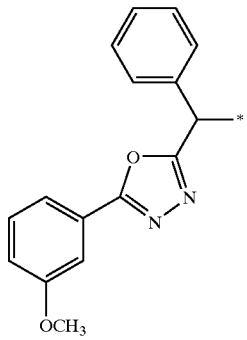

Another class of which $R_{egion}$ α a moeities (under B) are (substituted)-amido-aryl or -heterocyclyl moieties which may be independently selected from several groups, as described in more detail below.

The first such class of (substituted)-amido-aryl or -heterocyclyl moieties of $R_{egion}$ α are those in which the amido-aryl or -heterocyclyl portion of the group is substituted by alkyl-, alkenyl-, or alkynyl, as represented by partial Formula (2.0.0)

(2.0.0)

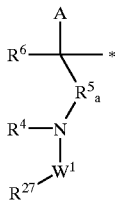

where the symbol "*" and $R^4$ and $R^6$; and m, $R^7$ and $R^8$ in the further definition of A; are as defined in the partial formulas above, except that all of the above-recited substituents are selected independently.

The moiety A in partial Formula (2.0.0) is a member independently selected from the group consisting of several different classes of moieties, as discussed below. The first class represented by partial Formula (2.0.3) is a preferred embodiment of this invention (2.0.3)

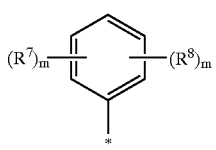

wherein the symbols $R^7$; $R^8$ and m are as defined in the partial formulas further above, except that all of the above-recited substituents are selected independently of their selection in said partial formulas further above; and the symbol: "*" indicates the point of attachment of the moiety A to the other, remaining portions of partial Formula (2.0.0).

Further embodiments of moiety A are depicted by partial Formulas (2.0.4) and (2.0.5). Partial Formula (2.0.4) is:

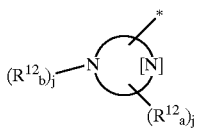

(2.0.4)

which represents a monocyclic heterocyclic group, selected from the group consisting of pyrrolyl; pyrazolyl; imidazolyl; pyridinyl; pyrazinyl; and pyrimidinyl. It is noted that in the moiety of partial Formula (2.0.3), the symbols $R^{12}{}_a$ and $R^{12}{}_b$, and the subscript "j" which determines their presence, are as defined in the partial formulas further above, except that "j" is 0 or 1 and all of the above-recited substituents are selected independently of their selection further above; and the symbol: "*" indicates the point of attachment of the moiety A to the other, remaining portions of partial Formula (2.0.0).

Further embodiments of moiety A are depicted by partial Formula (2.0.5)

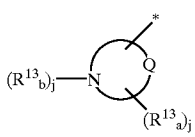

(2.0.5)

which represents a monocyclic heteroaromatic group containing a total of 5-members of which one said member is nitrogen and Q is selected from O and S where said S may optionally be in the sulfonate form, $—S(=O)_2$. Said heterocyclic group may be selected from the group consisting of oxazolyl; isoxazolyl; thiazolyl; and isothiazolyl; triazolyl; triazinyl; tetrazolyl; oxadiazolyl; and thiadiazolyl. It is noted that the symbols $R^{13}{}_a$ and $R^{13}{}_b$, and the subscript "j" which determines their presence, are as defined in the partial formulas further above, except that "j" is 0 or 1 and all of the above-recited substituents are selected independently of their selection in said partial formulas further above; and the symbol: "*" indicates the point of attachment of the moiety A to the other, remaining portions of partial Formula (2.0.0).

The group $R^5{}_a$ is selected from a direct bond; $—C(=O)—$; and $—S(=O)_2—$. In preferred embodiments of the present invention $R^5{}_a$ is a direct bond. It is provided, however, that where $R^5{}_a$ is $—CO—$ or $—SO_2—$, the divalent moiety $W^1$ is defined to additionally include the meaning of being a direct bond.

In partial Formula (2.0.0), $R^{27}$ is a member selected from the group consisting of $(C_1-C_6)$alkyl; $(C_2-C_6)$alkenyl; and $(C_2-C_6)$alkynyl; wherein said alkyl, alkenyl, and alkynyl groups comprising $R^{27}$ may be substituted with 0 to 3 substituents $R^{28}$ where $R^{28}$ is selected from the group consisting of F; Cl; oxo; hydroxy; $(C_1-C_2)$alkyl; $(C_1-C_3)$ alkoxy; $—C(=O)OR^{29}$; $C(=O)(C_1-C_4)$alkyl; $—S(=O)_2(C_1-C_4)$alkyl; $—C(=O)NR^{29}R^{30}$; $—NR^{29}R^{30}$; $—NR^{29}C(=O)R^{30}$; $—NR^{29}C(=O)OR^{30}$; $—NR^{29}S(=O)_2R^{30}$; and $—S(=O)_2NR^{29}R^{30}$, where $R^{29}$ and $R^{30}$ are independently selected from hydrogen and $(C_1-C_4)$alkyl.

The moiety $W^1$ is a member independently selected from the group consisting of divalent moieties of partial Formulas (2.0.6) through (2.0.16), inclusive:

(2.0.6)

(2.0.7)

(2.0.8)

(2.0.19)

(2.0.10)

(2.0.11)

(2.0.12)

(2.0.13)

(2.0.14)

(2.0.15)

(2.0.16)

where the symbol: "→" indicates the point of attachment of the moiety $W^1$ to the nitrogen atom in partial Formula (2.0.0), and the symbol: "*" indicates the point of attachment of the moiety $W^1$ to the moiety $R^{27}$ which represents the remaining portions of partial Formula (2.0.0); and $R^{25}$ and $R^{26}$ are each independently a member selected from the group consisting of hydrogen; $(C_1-C_2)$alkyl substituted by 0 or 1 substituent independently selected from F and OH; and $(C_1-C_2)$alkoxy.

The bridging element —N($R^4$)—$W^1$— may alternatively constitute or contain several different functionalities. The first and most preferred of these is an amide functionality, which may be represented as: —$NR^4$—C(=O)—. Other functionality types include sulfonamido and ureido moieties within the scope of partial Formulas (2.0.6) through (2.0.16).

Preferred alkyl and alkenyl groups $R^{27}$ include: methyl; ethyl; iso-propyl; t-butyl; and propenyl (allyl). These alkyl and alkenyl groups may be substituted by 0 to 3 substituents $R^{28}$. It is preferred that where a substituent is present that it be a single substituent independently selected from F; Cl; OH; $CF_3$; $CH_3$; $OCH_3$; CN; $NH_2$; $NHCH_3$; $N(CH_3)_2$; $NHCOCH_3$ and $NCH_3(COCH_3)$ Consequently, groups of partial Formula (2.0.0) which are preferred embodiments of the present invention constituting $R_{egion}$ α include the following moieties of partial Formulas (2.0.30) through (2.0.36), inclusive:

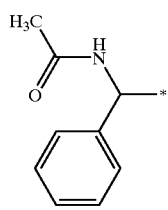
(2.0.30)

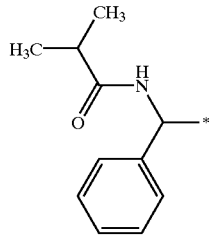
(2.0.31)

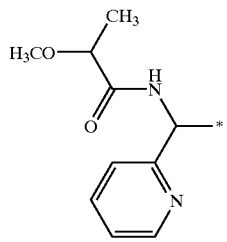
(2.0.32)

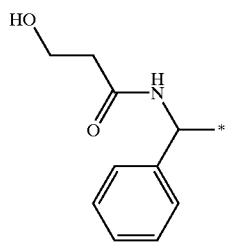
(2.0.33)

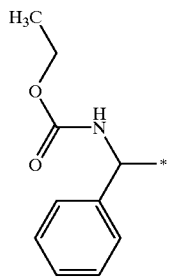
(2.0.34)

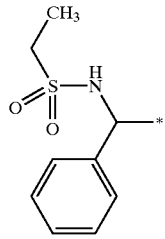
(2.0.35)

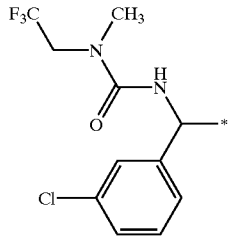
(2.0.36)

The second class of (substituted)-amido-aryl moieties comprising $R_{egion}$ α are those in which the amido-aryl portion of the group is substituted by cycloalkyl) or -alkyl (cycloalkyl), as represented by partial Formula (2.1.0).

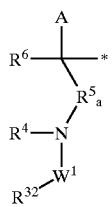
(2.1.0)

where; A; $W^1$; the symbol "*" and $R^4$; $R^5_a$; $R^6$; and m, $R^7$ and $R^8$ in the further definition of A; have the same meaning as set out in the partial formulas further above, except that all of the above-recited substituents are selected independently of their selection further above. $R^{32}$ is a member independently selected from the group consisting of —$(CH_2)_n$—$(C_3-C_7)$cycloalkyl, where n is an integer selected from 0, 1, and 2; in the event n is 0, then the α-carbon atom of said $(C_3-C_7)$cycloalkyl may be substituted by $(C_1-C_4)$alkyl or phenyl, where said alkyl or phenyl may be substituted by 1, or 2 of $CH_3$, $OCH_3$, OH or $NH_2$; and in the event that n is 1 or 2, the resulting methylene or ethylene group may be substituted by of F; Cl; CN; $NH_2$; $N(CH_3)_2$; OH; $OCH_3$; $(C_1-C_4)$alkyl; or phenyl. It will also be further noted that the basic $(C_3-C_7)$cycloalkyl group comprising $R^{32}$ may also be substituted by 0 to 3 substituents $R^{28}$ where $R^{28}$ has the same meaning as defined further above with respect to substituents for group $R^{27}$ under partial Formula (2.0.0), but independently selected therefrom.

Representative cycloalkyl and alkylcycloalkyl groups within the scope of $R^{32}$ include cyclopropyl, cyclobutyl, cyclopentyl, cyclohexyl; cyclopropylmethyl; cydobutyl-ethyl; cyclopentylpropmethyl; and cyclopentylmethyl. More preferred single substituents for these cycloalkyl and alkylcycloalkyl groups include F, Cl, and CN, especially OH; $OCH_3$; and $NH_2$. Accordingly, groups of partial Formula (2.1.0) which are preferred embodiments of $R_{egion}$ α include partial Formulas (2.1.3) through (2.1.10).

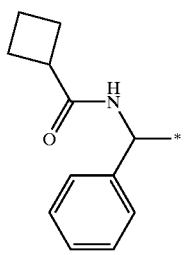
(2.1.3)

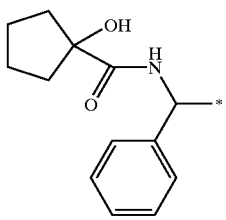
(2.1.4)

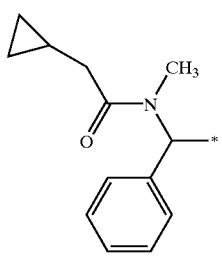
(2.1.5)

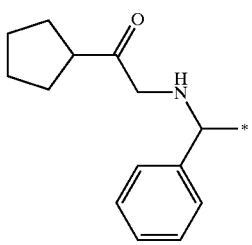
(2.1.6)

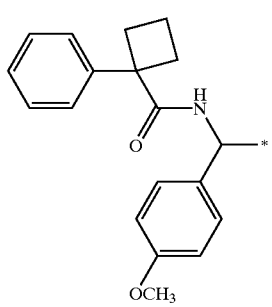
(2.1.7)

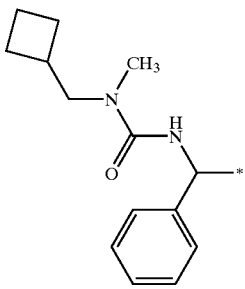
(2.1.8)

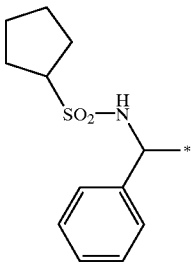
(2.1.9)

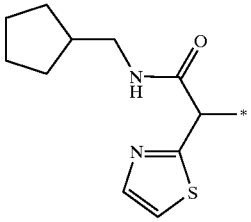
(2.1.10)

The third class of (substituted)-amido-aryl moieties of $R_{egion}$ α are those in which the amido-aryl portion of the group is substituted by aryl- and heterocyclyl-substituted-amido-aryl moieties of partial Formula (2.2.0).

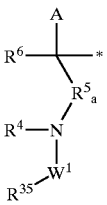
(2.2.0)

where A; $W^1$; the symbol "*" and $R^4$; $R^5_a$; $R^6$; and m, $R^7$ and $R^8$ in the definition of A; have the same meaning as set out above, except that all of the above-recited substituents are selected independently.

The moiety $R^{35}$ may be selected from the group consisting of phenyl; furyl; tetrahydropyranyl; tetrahydrofuranyl; oxetanyl; thienyl; pyrrolyl; pyrrolidinyl; oxazolyl; isoxazolyl; thiazolyl; isothiazolyl; imidazolyl; imidazolinyl; pyrazolyl; pyrazolinyl; oxadiazolyl; thiadiazolyl; triazolyl; pyridyl; pyrazinyl; pyridazinyl; piperazinyl; pyrimidinyl; pyranyl; azetidinyl; morpholinyl; parathiazinyl; indolyl; isoindolyl; 3H-indolyl; indolinyl; benzo[b]furanyl; 2;3-dihydrobenzofuranyl; benzothienyl; 1H-indazolyl; benzimidazolyl; benzoxazolyl; benzisoxazolyl; benzthiazolyl; benzoxdiazolyl; quinolinyl; isoquinolinyl; phthalazinyl; quinazolinyl; and quinoxalinyl.

Preferred meanings of $R^{35}$ are phenyl; pyrrolyl; oxazolyl; imidazolyl; pyridinyl; pyrimidinyl; triazolyl; indolyl; benzimidazolyl; benzotriazolyl; quinolinyl; thienyl; furfuryl; benzofuranyl; thiazolyl; oxazolyl; isoxazolyl; oxadiazolyl; and benzoxazolyl; and benzoxadiazolyl. Most preferred are tetrahydropyranyl; oxetanyl; azetidinyl and tetrahydrofuranyl. Group $R^{35}$ may be substituted by 3 substituents $R^{28}$ where $R^{28}$ has the same meaning as defined above but selected independently.

Alternative aryl and heterocyclyl groups falling within the scope of $R^{35}$ include phenyl; pyrrolyl; imidazolyl; pyridyl; oxazolyl; furyl; and benzofuranyl. Preferred single or double substituents for these groups include —CN; —F; —Cl; —CONH$_2$; —CH$_3$; —CF$_3$; and —OCH$_3$.

Accordingly, groups of partial Formula (2.2.0) which are preferred embodiments of $R_{egion}$ α include partial Formulas (2.2.3) through (2.2.14)

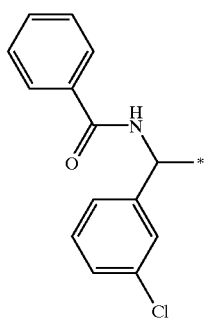

(2.2.3)

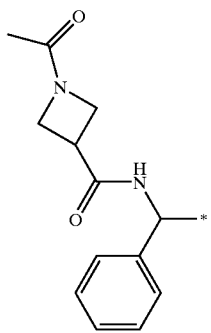

(2.2.4)

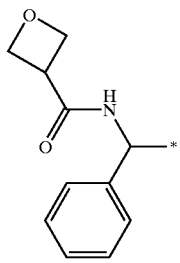

(2.2.5)

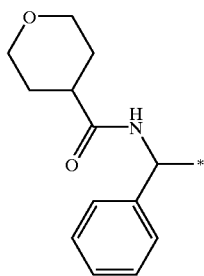

(2.2.6)

-continued

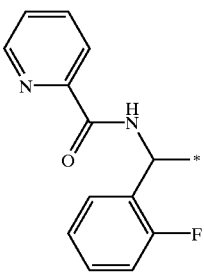

(2.2.7)

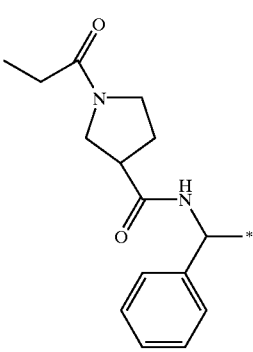

(2.2.8)

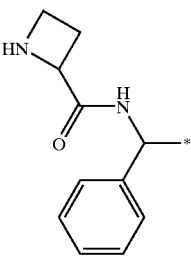

(2.2.9)

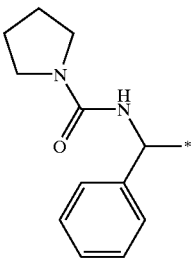

(2.2.10)

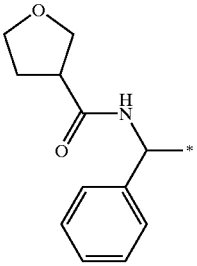

(2.2.11)

-continued (2.2.12)
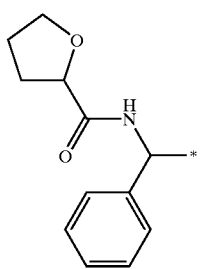

(2.2.13)
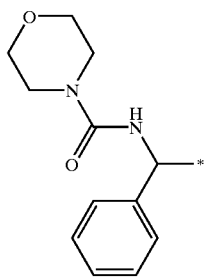

(2.2.14)
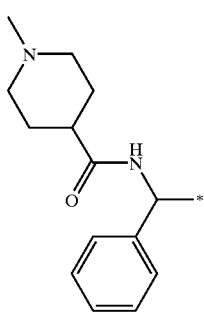

[$R_{egion}$ β] may be considered to be to the left-hand end of the molecule of the present invention as depicted, and comprises a bridging element between $R_{egion}$ α described above, and $R_{egion}$ γ described below.

The alkyl bridging element of $R_{egion}$ β comprises a moiety of partial Formula (3.0.0):

(3.0.0)
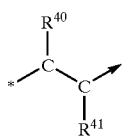

where the symbol "*" represents the point of attachment of the alkyl bridging element moiety of partial Formula (3.0.0) to $R_{egion}$ α of the modulator compound of Formula (I); and the symbol "→" represents the point of attachment of the alkyl bridging element moiety of partial Formula (3.0.0) to $R_{egion}$ γ of the modulator compound of Formula (I). Substituents $R^{40}$ and $R^{41}$ are both independently selected from the group consisting of hydrogen; ($C_1$–$C_2$) alkyl including dimethyl; hydroxy; and ($C_1$–$C_3$) alkoxy; provided that only one of $R^{40}$ and $R^{41}$ may be ($C_1$–$C_3$) alkoxy or hydroxy, the other one of $R^{40}$ or $R^{41}$ being selected from hydrogen and ($C_1$–$C_2$) alkyl including dimethyl.

Accordingly, $R^{40}$ and $R^{41}$ may be hydrogen; methyl; ethyl; dimethyl, i.e., two methyl groups joined to the single carbon atom to which $R^{40}$ or $R^{41}$ is attached; hydroxy; methoxy; ethoxy; or propoxy.

Some representative embodiments of the alkyl bridging element of partial Formula (3.0.0) include the following moieties of partial Formulas (3.0.1) through (3.0.7), inclusive:

(3.0.1)
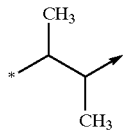

(3.0.2)
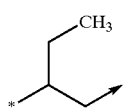

(3.0.3)
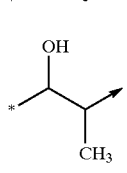

(3.0.4)
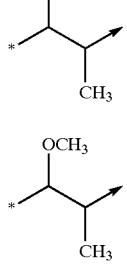

(3.0.5)
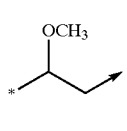

(3.0.6)
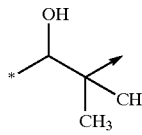

(3.0.7)
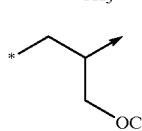

In the most preferred embodiments of the modulator compounds of the present invention, both $R^{40}$ and $R^{41}$ are hydrogen, and the alkyl bridging element of partial Formula (3.0.0) is unsubstituted ethylene. In preferred embodiments a single methyl, hydroxy, or methoxy substituent may be present, resulting in alkyl bridging elements such as those of partial Formulas (3.0.8) through (3.0.10):

(3.0.8)
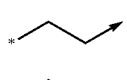

(3.0.9)
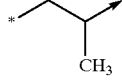

(3.0.10)
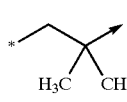

[$R_{egion}$ γ] comprises an aza-bicyclic moiety of partial Formula (4.2.0):

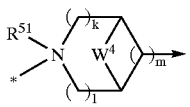
(4.2.0)

where "*" is a symbol which represents the point of attachment of the moiety of partial Formula (4.2.0) to $R_{egion}$ β of the compound of Formula (I); and "→" is a symbol representing the point of attachment to $R_{egion}$ δ. The substituent group $R^{51}$ is absent or is a member selected from the group consisting of; $(C_1-C_4)$alkyl substituted by 0 or 1 substituent independently selected from $(C_1-C_2)$alkoxy and $-CO_2R^4$ where $R^4$ is as defined above; and →O; it being understood that in the case where the substituent $R^{51}$ is present the nitrogen atom of partial Formula (4.2.0) is in quaternary form.

$W^4$ in the moiety of partial Formula (4.2.0) defines a bridging element and may be a direct bond, or selected from the group consisting of the moieties of partial Formulas (4.2.1) through (4.2.6):

(4.2.1)

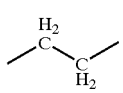
(4.2.2)

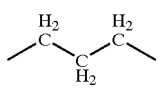
(4.2.3)

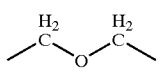
(4.2.4)

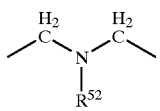
(4.2.5)

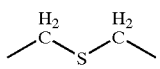
(4.2.6)

$R^{52}$ may be selected from hydrogen phenyl; $(C_1-C_4)$alkyl substituted by 0 or 1 substituent independently selected from $(C_1-C_2)$alkoxy and $-CO_2R^4$ where $R^4$ is as defined further above; $(C_3-C_6)$cycloalkyl; $-CO_2R^4$; $(C_1-C_2)$alkoxycarbonyl; →O; $-C(=O)NR^4_aR^4_b$; $-S(=O)_p$ $(C_1-C_4)$alkyl; and $(C_1-C_2)$alkylcarbonyl.

The subscripts "k", "l" and "m" are each an integer independently selected from 0, 1, 2, and 3.

In preferred embodiments of partial Formula (4.2.0), there are two carbon atoms between the point of attachment to $R_{egion}$ δ and the nitrogen atom point of attachment of the moiety of partial Formula (4.2.0) to $R_{egion}$ β. Preferably, this relationship is maintained, whatever the definitions of k, l, and m.

Included among preferred embodiments of partial Formula (4.2.0) are partial Formulas (4.2.16) through (4.2.27).

The dashed lines indicate the points of attachment. A number of conformers of partial Formula (4.2.0) are illustrated:

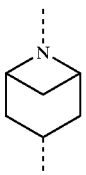
(4.2.16)

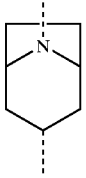
(4.2.17)

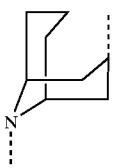
(4.2.18)

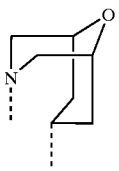
4.2.19)

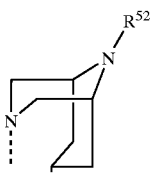
(4.2.20)

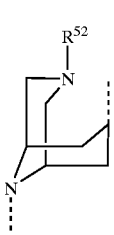
(4.2.21)

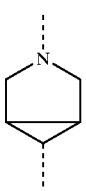
(4.2.22)

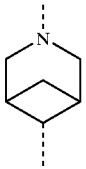
(4.2.23)

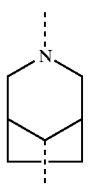 (4.2.24)

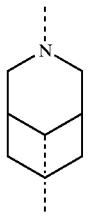 (4.2.25)

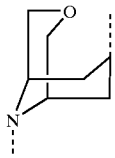 (4.2.26)

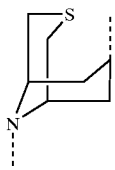 (4.2.27)

The group $R^{52}$ is selected from hydrogen; phenyl; $(C_1-C_4)$alkyl substituted by 0 or 1 substituent independently selected from $(C_1-C_2)$alkoxy and —$CO_2R^4$; $(C_3-C_6)$cycloalkyl; $C(=O)(C_1-C_4)$ alkyl; $S(=O)_2(C_1-C_4)$alkyl; →O; —$C(=O)NR^4_aR^4_b$; —$S(=O)_p(C_1-C_4)$alkyl; and $(C_1-C_2)$alkylcarbonyl; where $R^4$, $R^4_a$, and $R^4_b$ are as defined further above, but selected on an independent basis. It is generally more preferred that the nitrogen atom be unsubstituted, i.e., that $R^{52}$ is hydrogen, but other preferred embodiments include those where $R^{52}$ is methyl, methyl carboxylate, methylcarbonyl, or →O. Quaternary salts also may be provided.

The substituent group $R^{51}$ is preferably absent.

[$R_{egion}$ δ] constitutes the right-hand end of the compounds of Formula (I) and is attached directly to $R_{egion}$ γ described above. $R_{egion}$ δ comprises three different groups: bicyclic heterocycles; substituted amides and monocyclic heterocycles, all of which are described in detail below.

The first group of moieties (under A.) comprises two-nitrogen-atom-containing five membered heterocyclic moieties of partial Formulas (5.0.0) through (5.0.10):

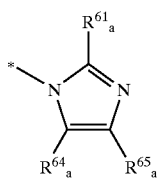 (5.0.0)

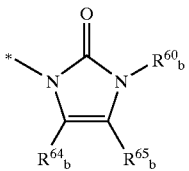 (5.0.1)

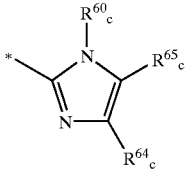 (5.0.2)

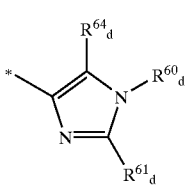 (5.0.3)

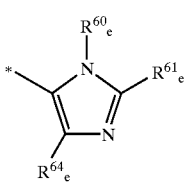 (5.0.4)

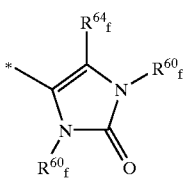 (5.0.5)

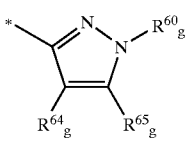 (5.0.6)

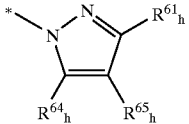 (5.0.7)

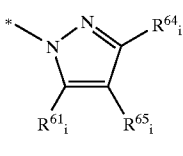 (5.0.8)

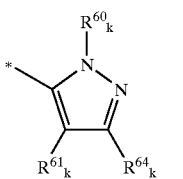 (5.0.9)

-continued

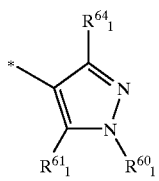
(5.0.10)

where the symbol: "*" indicates the point of attachment of each of the moieties of partial Formulas (5.0.0) through (5.0.10), inclusive, to $R_{egion}$ δ.

One of the two nitrogen atoms in the heterocyclic moieties of partial Formulas (5.0.0) through (5.0.10) is substituted by $R^{60}{}_b$ through $R^{60}{}_g$, $R^{60}{}_k$, and $R^{60}{}_l$, and these substituents are selected from hydrogen; —CO$_2$R$^4$; —C(=O)NR$^4{}_a$R$^4{}_a$; —S(=O)$_p$NR$^4{}_a$R$^4{}_b$; where: R$^4$; R$^4{}_a$; and R$^4{}_b$ are as defined further above but selected on an independent basis; →O; (C$_1$–C$_2$)alkylcarbonyl; —(C$_1$–C$_4$)alkyl; —(CH$_2$)$_n$—(C$_3$–C$_7$)cycloalkyl; —(C$_2$–C$_3$)alkenyl; —(CH$_2$)$_n$—(phenyl); and —(CH$_2$)$_n$—(HET$_1$), where n is an integer selected from 0, 1, and 2; wherein said (C$_1$–C$_4$)alkyl, alkenyl, cycloalkyl, phenyl, and HET$_1$ groups are independently substituted with 0 to 3 substituents R$^{66}$.

The symbol "HET$_1$" is intended to mean a heterocyclyl group selected from the group consisting of thienyl; oxazolyl; isoxazolyl; thiazolyl; isothiazolyl; pyrazolyl; oxadiazolyl; thiadiazolyl; triazolyl; pyridyl; pyrazinyl; pyridazinyl; pyrimidinyl; parathiazinyl; and morpholinyl. The heterocyclyl group HET$_1$ may be attached directly or through an alkylene bridge, which is encompassed within the scope of "—(CH$_2$)$_n$—", where n is an integer selected from 0, 1, and 2. Where this heterocyclyl group, or an alkyl, alkenyl, cycloalkyl or phenyl group defining one of the R$^{60}$ groups is present, it may be substituted in turn by a substituent group R$^{66}$. The group R$^{66}$ is selected from the group consisting of —F; —Cl; —OH; —CN; —C(=O)OR$^{68}$; —C(=O)NR$^{68}$R$^{69}$; —NR$^{68}$R$^{69}$; —NR$^{68}$C(=O)R$^{69}$; —NR$^{68}$C(=O)OR$^{69}$; —NR$^{68}$S(=O)$_2$R$^{69}$; —S(=O)$_2$NR$^{68}$R$^{69}$; (C$_1$–C$_4$) alkyl including dimethyl, and (C$_1$–C$_4$)alkoxy wherein said alkyl and alkoxy are each independently substituted with 3 substituents independently selected from F and Cl; (C$_1$–C$_2$) alkoxycarbonyl; (C$_1$–C$_2$)alkylcarbonyl; and (C$_1$–C$_2$) alkylcarbonyloxy. The substituents R$^{68}$ and R$^{69}$ are in turn selected from hydrogen and (C$_1$–C$_2$)alkyl. In the most preferred compounds of Formula (I), these nitrogen atoms will be substituted either with hydrogen or methyl.

The remaining substituents: $R^{61}{}_a$; $R^{61}{}_d$; $R^{61}{}_e$; $R^{61}{}_h$ through $R^{61}{}_j$, $R^{64}{}_a$ through $R^{64}{}_j$, $R^{65}{}_a$ through $R^{65}{}_c$ and $R^{65}{}_g$ through $R^{65}{}_j$, are each independently selected from the group consisting of hydrogen; OH; CF$_3$; —CN (C$_1$–C$_3$) alkoxy; —C(=O)OR$^4$; —C(=O)NR$^4{}_a$R$^4{}_b$; —NR$^4{}_a$R$^4{}_b$; —NR$^4{}_a$C(=O)R$^4{}_b$; —NR$^4{}_a$C(=O)OR$^4{}_b$; —NR$^4{}_a$S(=O)$_p$R$^4{}_b$; and —S(=O)$_p$NR$^4{}_a$R$^4{}_b$ where R$^4$; R$^4{}_a$; and R$^4{}_b$ are as defined further above; —(C$_1$–C$_4$)alkyl; —(CH$_2$)$_n$—(C$_3$–C$_7$) cycloalkyl; —(C$_2$–C$_3$)alkenyl; —(CH$_2$)$_n$—(phenyl); and —(CH$_2$)$_n$—(HET$_1$), where n is an integer selected from 0, 1, and 2 and HET$_1$, including possible substituents are as defined above.

Accordingly, preferred embodiments of monocyclic heterocyclic moieties of partial Formulas (5.0.0) through (5.0.10) optionally substituted as above-described include partial Formulas (5.0.15) through (5.0.30):

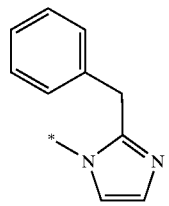
(5.0.15)

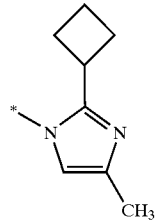
(5.0.16)

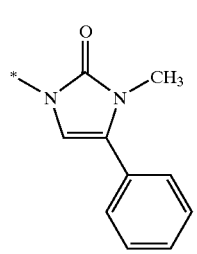
(5.0.17)

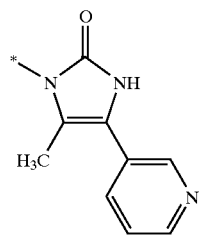
(5.0.18)

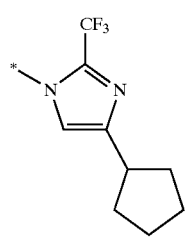
(5.0.19)

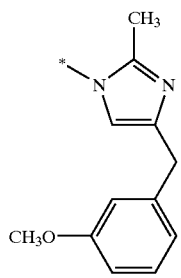
(5.0.20)

(5.0.21)

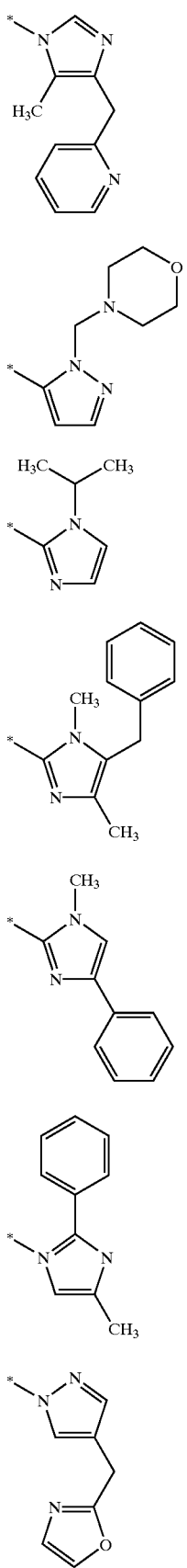

(5.0.22)

(5.0.23)

(5.0.24)

(5.0.25)

(5.0.26)

(5.0.27)

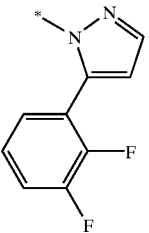

(5.0.28)

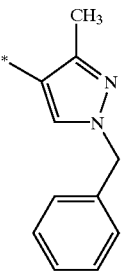

(5.0.29)

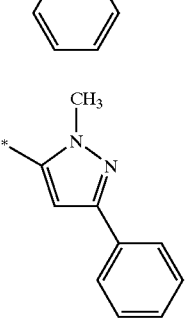

(5.0.30)

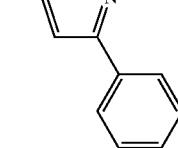

The preferred subclass of moieties under partial Formulas (5.0.0) through (5.0.10) are those wherein $R^{64}_a$ through $R^{64}_c$, $R^{64}_g$ through $R^{64}_i$, $R_{65a}$ through $R^{65}_c$, and $R^{65}_g$ through $R^{65}_i$, are taken together in their same subscript denominated pairs along with the remaining portions of the moieties of partial Formulas (5.0.0) through (5.0.10) to form a fused bicyclic ring system comprising benzimidazolyl; purinyl, i.e., imidazopyrimidinyl; or imidazopyridinyl. The above-mentioned fused bicyclic ring systems are also optionally substituted with up to 3 substituents $R^{66}$ selected from F; Cl; oxo; —OH; —CN; $(C_1-C_2)$alkyl; —CF$_3$; —C(=O)OR$^{68}$; —C(=O)NR$^{68}$R$^{69}$; —NR$^{68}$R$^{69}$; —NR$^{68}$C(=O)R$^{69}$; —NR$^{68}$C(=O)OR$^{69}$; —NR$^{68}$S(=O)$_2$R$^{69}$; and —S(=O)$_2$NR$^{68}$R$^{69}$ where $R^{68}$ and $R^{69}$ are each selected from hydrogen and $(C_1-C_2)$alkyl.

Preferred embodiments of this type of moiety under partial Formulas (5.0.0) through (5.0.10) are illustrated in the following partial Formulas (5.0.35) through (5.0.47)

(5.0.35)

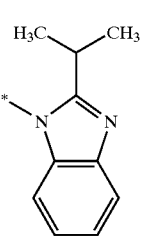

(5.0.36) 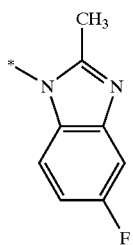

(5.0.37) 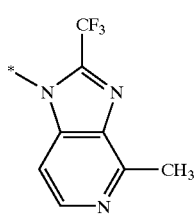

(5.0.38) 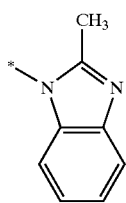

(5.0.39) 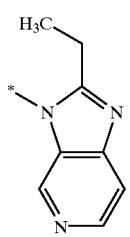

(5.0.40) 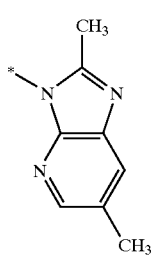

(5.0.41) 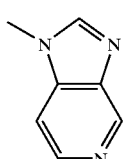

(5.0.42) 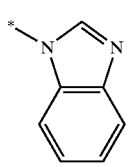

(5.0.43) 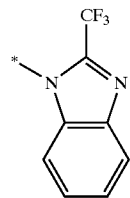

(5.0.44) 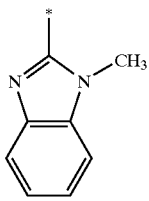

(5.0.45) 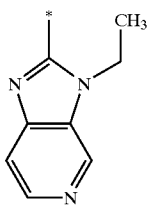

(5.0.46) 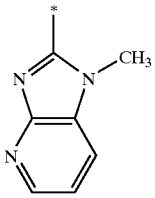

(5.0.47) 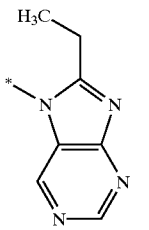

Another class of moieties (under B.) defining $R_{egion}$ δ of the compounds of Formula (I) are (substituted)-amides, carbamates or ureas which includes subclasses consisting of alkyl-, cycloalkyl-, and alkenyl substituents; and aryl and heterocyclyl substituents. The first subclass comprises moieties of partial Formula (5.1.0):

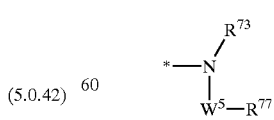

where the symbol "*" has the same meaning as defined further above; $R^{73}$ is hydrogen or $(C_1-C_2)$alkyl; and $W^5$ is selected from the moieties of partial Formulas (5.1.1) through (5.1.12), inclusive:

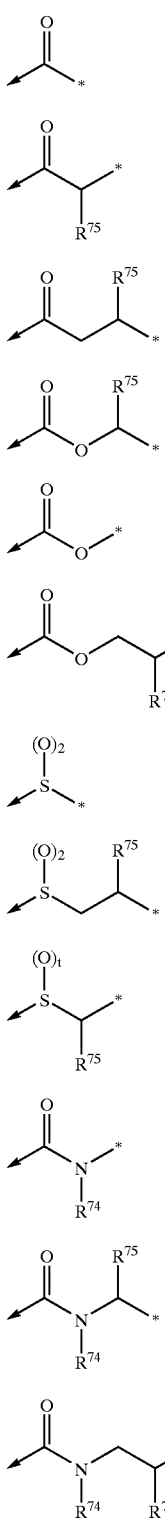

(5.1.1)
(5.1.2)
(5.1.3)
(5.1.4)
(5.1.5)
(5.1.6)
(5.1.7)
(5.1.8)
(5.1.9)
(5.1.10)
(5.1.11)
(5.1.12)

where the symbol: "→" indicates the point of attachment of the moiety $W^5$ represented by partial Formulas (5.1.1) through (5.1.12) to the nitrogen atom in partial Formula (5.1.0), and the symbol: "*" indicates the point of attachment of the moiety $W^5$ to $R^{77}$. The substituents $R^{74}$ and $R^{75}$ are independently selected from hydrogen; $(C_1-C_2)$alkyl substituted by 0 or 1 substituent independently selected from OH; and $(C_1-C_2)$alkoxy.

The group $R^{77}$ may be selected from $(C_1-C_6)$alkyl; $(C_2-C_6)$alkenyl; and —$(CH_2)_n$—$(C_3-C_7)$cycloalkyl, where n is 0, 1, or 2; and where said alkyl, alkenyl, alkynyl and cycloalkyl groups are substituted with 0 to 3 substituents $R^{78}$, where $R^{78}$ is selected from oxo; —OH; $(C_1-C_2)$alkyl; $(C_1-C_3)$alkoxy; —$CF_3$; —$C(=O)OR^{79}$; —$C(=O)NR^{79}R^{80}$; —$NR_{79}R_{80}$; —$NR^{79}C(=O)R^{80}$; —$NR^{79}C(=O)OR^{80}$; —$NR^{79}S(=O)_2R^{80}$; and —$S(=O)_2NR^{79}R^{80}$, where $R^{79}$ and $R^{80}$ are each hydrogen or $(C^1-C_4)$alkyl.

Preferred groups of Formula 5.1.0 include ureas and amides. Carbamates are most preferred.

The alkyl and alkenyl groups comprising the moiety $R^{77}$ preferably include such groups as methyl; ethyl; isopropyl; t-butyl; and propenyl (allyl). These alkyl and alkenyl groups are substituted by 0 to 3 substituents $R^{78}$ recited above. It is preferred that where a substituent is present that it be a single substituent selected from —OH; —$CF_3$; —$(CH_3$; —$OCH_3$; and —$NH_2$. Consequently, groups of partial Formula (5.1.0) which are preferred embodiments of $R_{egion}$ δ include partial Formulas (5.1.15) through (5.1.22):

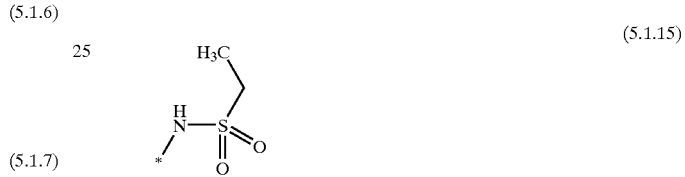
(5.1.15)

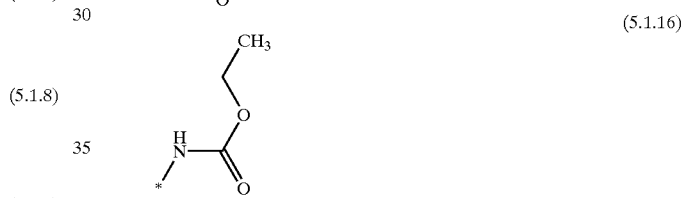
(5.1.16)

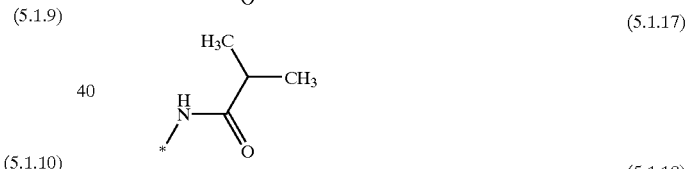
(5.1.17)

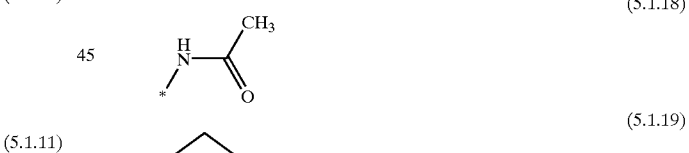
(5.1.18)

(5.1.19)

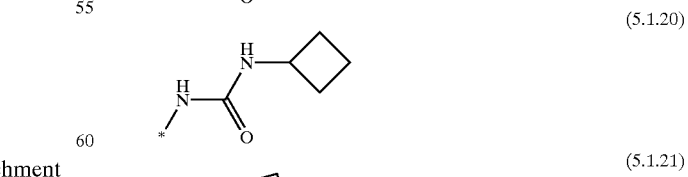
(5.1.20)

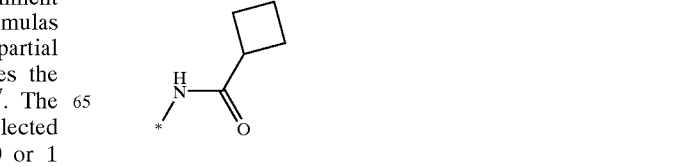
(5.1.21)

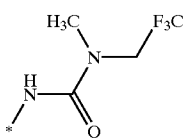 (5.1.22)

Another subclass of (substituted)-amide, carbamate, or urea moieties defining $R_{egion}$ δ includes aryl and heterocyclyl substituents. This second subclass comprises moieties of partial Formula (5.2.0):

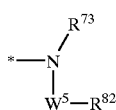 (5.2.0)

where the symbol: "*"; $R^{73}$ and $W^5$ have the same meanings as under the definition of partial Formula (5.1.0) above; and under $W^5$ the symbol: "*" is as defined under the Formula (5.1.0). The group $R^{82}$ is selected from phenyl; cinnolinyl; furyl; thienyl; pyrrolyl; oxazolyl; isoxazolyl; thiazolyl; isothiazolyl; imidazolyl; imidazolinyl; pyrazolyl; pyrazolinyl; oxadiazolyl; thiadiazolyl; triazolyl; pyridyl; pyrazinyl; pyridazinyl; pyrimidinyl; parathiazinyl; indolyl; isoindolyl; indolinyl; benzo[b]furanyl; 2;3-dihydrobenzofuranyl; benzo[b]thiophenyl; 1H-indazolyl; benzimidazolyl; benzthiazolyl; quinolinyl; isoquinolinyl; phthalazinyl; quinazolinyl; and quinoxalinyl. The aryl or heterocyclyl groups comprising $R^{82}$ may be substituted by 3 substituents $R^{78}$ where $R^{78}$ has the same meaning as defined above. Accordingly, preferred embodiments of the compounds of the present invention include partial Formulas (5.2.1) through (5.2.10):

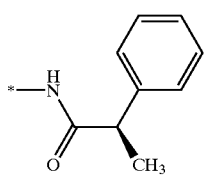 (5.2.1)

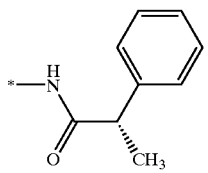 (5.2.2)

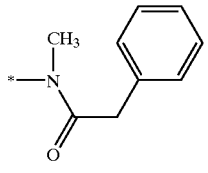 (5.2.3)

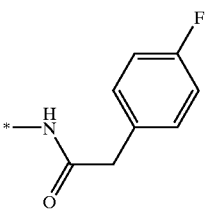 (5.2.4)

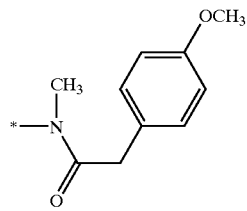 (5.2.5)

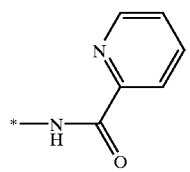 (5.2.6)

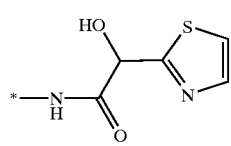 (5.2.7)

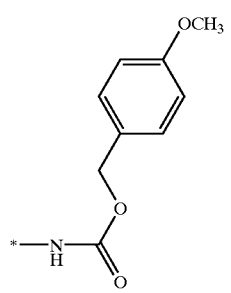 (5.2.8)

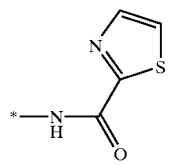 (5.2.9)

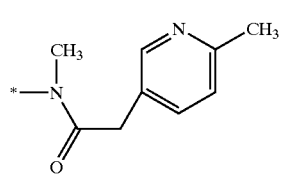 (5.2.10)

Another class of moieties (under C.) defining $R_{egion}$ δ of the compounds of Formula (I) comprises two subclasses of (substituted)-heterocyclyl moieties. The first subclass (under C.2.) of such heterocyclyl moieties is selected from those of partial Formula (5.3.0):

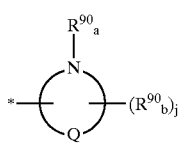

(5.3.0)

where the symbol: "*" indicates the point of attachment of partial Formula (5.3.0) to $R_{egion}$ δ; Q is N, O or S; and $R^{90}{}_a$ and $R^{90}{}_b$, are independently selected from the group consisting of hydrogen, —($C_1$-$C_2$)alkylcarbonyl; —($C_1$-$C_4$)alkyl; —($CH_2$)$_n$—($C_3$-$C_7$)cycloalkyl; —($C_2$-$C_3$)alkenyl; —($CH_2$)$_n$—(phenyl); and —($CH_2$)$_n$—($HET_2$), where n is an integer selected from 0, 1, and 2. Further, j has the same meaning as above, but is selected independently. It is more preferred that j is 0, in which case the $R^{90}{}_b$ substituent is absent. However, preferred embodiments of the present invention also include those wherein j is 1 and $R^{90}{}_b$ is methyl.

The heterocyclyl group $HET_2$ may be selected from the group consisting of thienyl; oxazolyl; isoxazolyl; thiazolyl; isothiazolyl; pyrazolyl; oxadiazolyl; thiadiazolyl; triazolyl; pyridyl; pyrazinyl; pyridazinyl; pyrimidinyl; parathiazinyl; morpholinyl.

The above-mentioned alkyl, alkenyl, cycloalkyl, phenyl, and heterocyclyl groups are optionally substituted with up to 3 substituents $R^{91}$ independently selected from the group consisting of F; Cl; —C(=O)$OR^{93}$; —OH; —CN; C(=O)($C_1$-$C_4$)alkyl; S(=O)$_2$($C_1$-$C_4$)alkyl; —CONR$^{93}$R$^{94}$; —NR$^{93}$R$^{94}$—; —NR$^{93}$C(=O)R$^{94}$; —NR$^{93}$C(=O)OR$^{94}$; —NR$^{93}$S(=O)$_2$R$^{94}$; —S(=O)$_2$NR$^{93}$R$^{94}$; ($C_1$-$C_4$)alkyl including dimethyl, and ($C_1$-$C_4$)alkoxy each substituted with 1 to 3 substituents independently selected from F and Cl; ($C_1$-$C_2$)alkoxycarbonyl; ($C_1$-$C_2$)alkylcarbonyl; and ($C_1$-$C_2$)alkylcarbonyloxy, where $R^{93}$ and $R^{94}$ are each a member independently selected from the group consisting of hydrogen; and ($C_1$-$C_2$)alkyl.

The heterocyclic group which constitutes a part of the moiety of partial Formula (5.3.0), may be a five membered monocyclic group containing two or more of N, O or S, for example oxazolyl; isoxazolyl; thiazolyl; iso-thiazolyl; triazolyl; triazinyl; tetrazolyl; oxadiazolyl; and thiadiazolyl.

Preferred embodiments include Formulas (5.3.5) through (5.3.9):

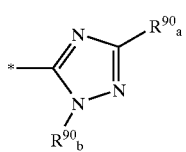

(5.3.5)

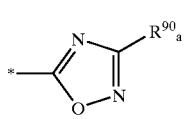

(5.3.6)

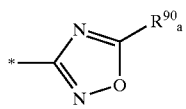

(5.3.7)

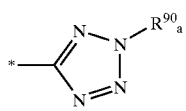

(5.3.8)

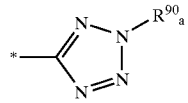

(5.3.9)

Accordingly, the following are preferred embodiments of the compounds of the present invention comprising moieties defining $R_{egion}$ δ in accordance with partial Formula (5.3.0), as represented by partial Formulas (5.3.15) through (5.3.26):

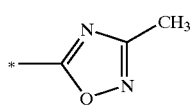

(5.3.15)

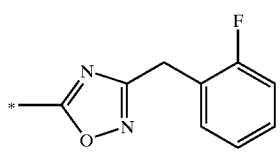

(5.3.16)

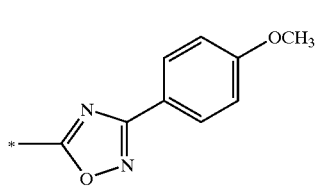

(5.3.17)

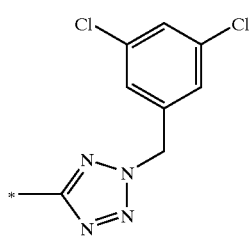

(5.3.18)

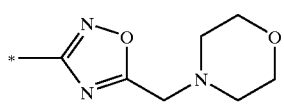

(5.3.19)

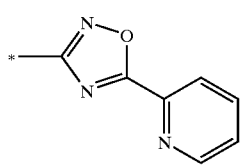

(5.3.20)

-continued

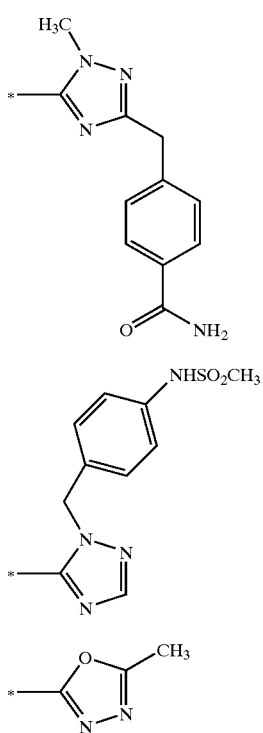

(5.3.21)

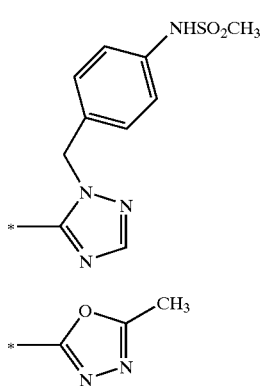

(5.3.22)

(5.3.23)

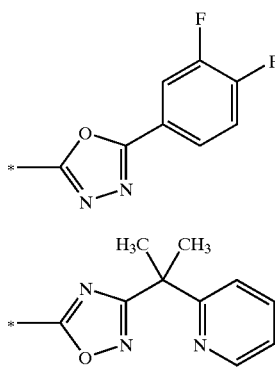

(5.3.24)

(5.3.25)

(5.3.26)

The second subclass of moieties (under C.2.) defining $R_{egion}$ δ may be selected from those of partial Formula (5.4.0):

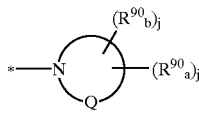

(5.4.0)

where Q, $R^{90}{}_a$ and $R^{90}{}_b$ have the same meaning as defined above, but are selected independently.

The heterocyclic group may be the same as in Formula 5.3.0 except that the nitrogen atom is the point of attachment. Accordingly, Formulas (5.4.5) through (5.4.8) result:

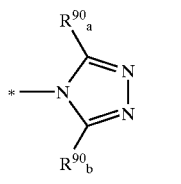

(5.4.5)

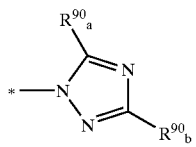

(5.4.6)

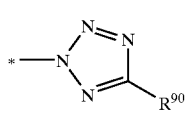

(5.4.7)

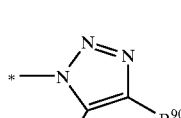

(5.4.8)

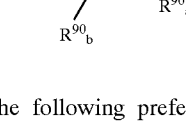

The following preferred embodiments of $R_{egion}$ δ are represented by partial Formulas (5.4.10) through (5.4.17):

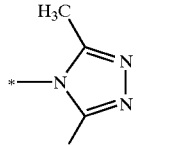

(5.4.10)

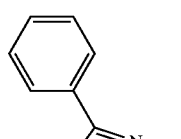

(5.4.11)

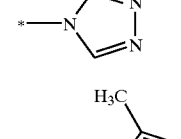

(5.4.12)

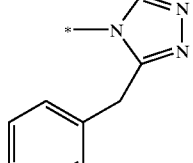

(5.4.13)

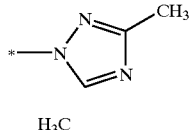

(5.4.14)

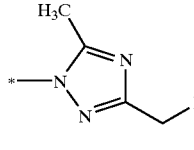

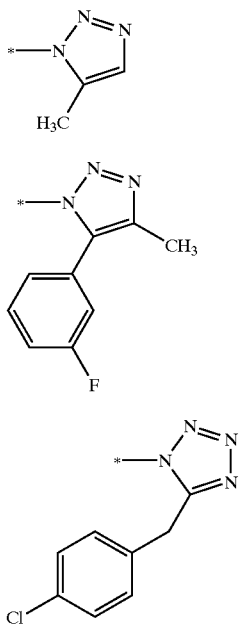

(5.4.15)

(5.4.16)

(5.4.17)

The compounds of the present invention may be utilized in the form of acids, esters, or other chemical derivatives. It is also within the scope of the present invention to utilize those compounds in the form of pharmaceutically acceptable salts derived from various organic and inorganic acids and bases in accordance with procedures well known in the art. The expression "pharmaceutically acceptable salt" as used herein is intended to mean an active ingredient comprising a compound of Formula (I) utilized in the form of a salt thereof, especially where said salt form confers on said active ingredient improved pharmacokinetic properties as compared to the free form of said active ingredient or other previously disclosed salt form.

A pharmaceutically acceptable salt form of said active ingredient may also initially confer a desirable pharmacokinetic property on said active ingredient which it did not previously possess, and may even positively affect the pharmacodynamics of said active ingredient with respect to its therapeutic activity in the body.

The pharmacokinetic properties of said active ingredient which may be favorably affected include, e.g., the manner in which said active ingredient is transported across cell membranes, which in turn may directly and positively affect the absorption, distribution, biotransformation or excretion of said active ingredient. While the route of administration of the pharmaceutical composition is important and various anatomical, physiological and pathological factors can critically affect bioavailability, the solubility of said active ingredient is usually dependent upon the character of the particular salt form thereof which it utilized. Further, an aqueous solution may provide the most rapid absorption of an active ingredient into the body of a patient being treated, while lipid solutions and suspensions, as well as solid dosage forms, may result in less rapid absorption. Oral ingestion of said active ingredient is the most preferred route of administration for reasons of safety, convenience, and economy, but absorption of such an oral dosage form can be adversely affected by physical characteristics such as polarity, emesis caused by irritation of the gastrointestinal mucosa, destruction by digestive enzymes and low pH, irregular absorption or propulsion in the presence of food or other drugs, and metabolism by enzymes of the mucosa, the intestinal flora, or the liver. Formulation of said active ingredient into different pharmaceutically acceptable salt forms may be effective in overcoming or alleviating one or more of the above-recited problems encountered with absorption of oral dosage forms.

Well-known pharmaceutically acceptable salts include, but are not limited to acetate, adipate, alginate, aspartate, benzoate, benzenesulfonate, besylate, bisulfate, butyrate, citrate, camphorate, camphorsulfonate, cyclopentanepropionate, digluconate, dodecysulfate, ethanesulfonate, fumarate, glucoheptanoate, gluconate, glycerophosphate, hemisuccinate, hemisulfate, heptanoate, hexanoate, hippurate, hydrochloride, hydrobromide, hydroiodide, 2-hydroxyethanesulfonate, isethionate, lactate, lactobionate, maleate, mandelate, methanesulfonate, 2-naphthalenesulfonate, nicotinate, nitrate, oxalate, oleate, pamoate, pectinate, persulfate, 3-phenylpropionate, phosphonate, picrate, pivalate, propionate, salicylate, sodium phosphate, stearate, succinate, sulfate, sulfosalicylate, tartrate, thiocyanate, thiomalate, tosylate, and undecanoate.

Base salts of the compounds of the present invention include, but are not limited to ammonium salts; alkali metal salts such as sodium and potassium; alkaline earth metal salts such as calcium and magnesium; salts with organic bases such as dicyclohexylamine, meglumine, N-methyl-D-glucamine, trishydroxymethyl)methylamine (tromethamine), and salts with amino acids such as arginine, lysine, etc. Compounds of the present invention which comprise basic nitrogen-containing groups may be quaternized with such agents as $(C_1C_4)$ alkyl halides, e.g., methyl, ethyl, iso-propyl and tert-butyl chlorides, bromides and iodides; di$(C_1-C_4)$ alkyl sulfate, e.g., dimethyl, diethyl and diamyl sulfates; $(C_{10}-C_{18})$ alkyl halides, e.g., decyl, dodecyl, lauryl, myristyl and stearyl chlorides, bromides and iodides; and aryl-$(C_1-C_4)$ alkyl halides, e.g., benzyl chloride and phenethyl bromide. Such salts permit the preparation of both water-soluble and oil-soluble compounds of the present invention.

Among the above-recited pharmaceutical salts those which are preferred include, but are not limited to acetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate, and tromethamine.

Multiple salts forms are included within the scope of the present invention where a compound of the present invention contains more than one group capable of forming such pharmaceutically acceptable salts. Examples of typical multiple salt forms include, but are not limited to bitartrate, diacetate, difumarate, dimeglumine, diphosphate, disodium, and trihydrochloride.

The compounds of this invention can be administered alone but will generally be administered in admixture with one or more suitable pharmaceutical excipients, diluents or carriers selected with regard to the intended route of administration and standard pharmaceutical practice.

For example, the compounds of the formula (I) can be administered orally or sublingually in the form of tablets, capsules, ovules, elixirs, solutions or suspensions, which may contain flavouring or colouring agents, for immediate or controlled release applications.

Such tablets may contain excipients such as microcrystalline cellulose, lactose, sodium citrate, calcium carbonate, dicalcium phosphate and glycine, disintegrants such as starch (preferably corn, potato or tapioca starch), alginic acid and certain complex silicates, and granulation binders such as polyvinylpyrrolidone, sucrose, gelatin and acacia. Additionally, lubricating agents such as magnesium stearate, sodium lauryl sulfate and talc may be included.

Solid compositions of a similar type may also be employed as fillers in gelatin capsules. Preferred excipients in this regard include lactose or milk sugar as well as high molecular weight polyethylene glycols. For aqueous suspensions and/or elixirs, the compounds of the formula (I) may be combined with various sweetening or flavouring agents, colouring matter or dyes, with emulsifying and/or suspending agents and with diluents such as water, ethanol, propylene glycol and glycerin, and combinations thereof.

The compounds of the formula (I) can also be injected parenterally, for example, intravenously, intraperitoneally, intrathecally, intraventricularly, intrasternally, intracranially, intramuscularly or subcutaneously, or they may be administered by infusion techniques. They are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

For oral and parenteral administration to human patients, the daily dosage level of the compounds of the formula (I) will usually be from 1 microgram/kg to 25 mg/kg (in single or divided doses).

Thus tablets or capsules of the compound of the formula (I) may contain from 0.05 mg to 1.0 g of active compound for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention.

The compounds of formula (I) can also be administered intranasally or by inhalation and are conveniently delivered in the form of a dry powder inhaler or an aerosol spray presentation from a pressurised container or a nebuliser with the use of a suitable propellant, eg dichlorodifluoromethane, trichlorofluoromethane, dichlorotetrafluoroethane, a hydrofluoroalkane such as 1,1,1,2-tetrafluorethane (HFA 134a), carbon dioxide or other suitable gas. In the case of a pressurised aerosol, the dosage unit may be determined by providing a valve to deliver a metered amount The pressurised container or nebuliser may contain a solution or suspension of the active compound, eg using a mixture of ethanol and the propellant as the solvent, which may additional contain a lubricant, eg sorbitan trioleate. Capsules and cartridges (made, for example, from gelatin) for use in an inhaler or insufflator may be formulated to contain a powder mix of a compound of the formula (I) and a suitable powder base such as lactose or starch.

Aerosol or dry powder formulations are preferably arranged so that each metered dose or "puff" contains from 20 μg to 20 mg of a compound of the formula (I) for delivery to the patient The overall daily dose with an aerosol will be in the range of from 20 μg to 20 mg which may be administered in a single dose or, more usually, in divided doses throughout the day.

Alternatively, the compounds of the formula (I) can be administered in the form of a suppository or pessary, or they may be applied topically in the form of a lotion, solution, cream, ointment or dusting powder. The compounds of the formula (I) may also be transdermally administered by the use of a skin patch. They may also be administered by the ocular route, particularly for treating neurological disorders of the eye.

For ophthalmic use, the compounds can be formulated as micronised suspensions in isotonic, pH adjusted, sterile saline, or, preferably, as solutions in isotonic, pH adjusted, sterile saline, optionally in combination with a preservative such as benzylalkonium chloride. Alternatively, they may be formulated in an ointment such as petrolatum.

For application topically to the skin, the compounds of the formula (I) can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benyl alcohol and water.

The compounds of Formula (I) are described herein as possessing biological activity such that they are able to modulate CCR5 chemokine receptor activity and consequent or associated pathogenic processes subsequently mediated by the CCR5 receptor and its ligands. The expression "modulate CCR5 chemokine receptor activity" as used herein is intended to refer to manipulation of the basic physiological processes and agencies which involve CCR5 chemokine receptors and their ligands. Included within the scope of this intended meaning are all types and subtypes of CCR5 receptors, in whatever tissues of a particular patient they are found, and in or on whatever components of the cells comprising those tissues they may be located. Most commonly, CCR5 receptors are situated on the cell membranes of particular cell types such as monocytes. CCR5 receptors participate in and define, along with various endogenous ligands to which they are naturally bound, signaling pathways which control important cellular and tissue functions by means of the influence which they exert on the movement of agents such as the chemokines, into and out of those cells and tissues.

The basic functioning of the CCR5 receptors and their ligands may be modulated in a number of ways, and the scope of the present invention is not limited in that regard to any particular existing or hypothesized pathway or process. Thus, included within the intended meaning of modulation of CCR5 chemokine receptor activity, is the use of synthetically derived modulators introduced into a patient being treated, such as the compounds of Formula (I) described herein. These exogenous agents may modulate CCR5 receptor activity by such well known mechanisms as competitive binding in which the natural ligands are displaced and their inherent functions disrupted. However, the present invention is not limited to any such specific mechanism or mode of action. Thus, "modulation" as used herein is intended to encompass preferably antagonism, but also agonism, partial antagonism and/or partial agonism. Correspondingly, the term therapeutically effective amount means the amount of the subject compound that will elicit the biological or medical response of a tissue, system, animal or human that is being sought.

The term "patient" in this specification refers particularly to humans. However the compounds, methods and pharmaceutical compositions of the present invention may be used in the treatment of animals.

Further included within the scope of the present invention are metabolites or residues of the compounds of Formula (I) which possess biological activity such that they are able to modulate CCR5 chemokine receptor activity and consequent or associated pathogenic processes subsequently mediated by the CCR5 receptor and its ligands. Once synthesized, the CCR5 chemokine receptor modulating activities and specificities of the compounds of Formula (I) according to the present invention may be determined using in vitro and in vivo assays which are described in detail further below.

The desirable biological activity of the compounds of Formula (I) may also be improved by appending thereto appropriate functionalities which enhance existing biological properties of the compound, improve the selectivity of the compound for the existing biological activities, or add to the existing biological activities further desirable biological activities. Such modifications are known in the art and include those which increase biological penetration into a given biological system, e.g., blood, the lymphatic system, and central nervous system; increase oral availability; increase solubility to allow administration by injection; alter metabolism; and alter the rate of excretion of the compound of Formula (I).

The dosage and dose rate of the compounds of Formula (I) effective for treating or preventing diseases and conditions in a patient which are mediated by or associated with modulation of CCR5 chemokine receptor activity as described herein, as well as for favorably affecting the outcome thereof in said patient, in accordance with the methods of treatment of the present invention comprising administering to said patient a therapeutically effective amount of a compound of Formula (I), will depend on a variety of factors such as the nature of the active ingredient, the size of the patient, the goal of the treatment, the nature of the pathology being treated, the specific pharmaceutical composition used, the concurrent treatments that the patient may be subject to, and the observations and conclusions of the treating physician.

Generally, however, the effective therapeutic dose of a compound of Formula (I) which will be administered to a patient will be between about 10 $\mu$g (0.01 mg)/kg and about 60.0 mg/kg of body weight per day, preferably between about 100 $\mu$g (0.1 mg)/kg and about 10 mg/kg of body weight per day, more preferably between about 1.0 mg/kg and about 6.0 mg/kg of body weight per day, and most preferably between about 2.0 mg/kg and about 4.0 mg/kg of body weight per day of the active ingredient of Formula (I).

Included within the scope of the present invention are embodiments comprising coadministration of, and compositions which contain, in addition to a compound of the present invention as active ingredient, additional therapeutic agents and active ingredients. Such multiple drug regimens, often referred to as combination therapy, may be used in the treatment and prevention of any of the diseases or conditions mediated by or associated with CCR5 chemokine receptor modulation, particularly infection by human immunodeficiency virus, HIV. The use of such combinations of therapeutic agents is especially pertinent with respect to the treatment and prevention of infection and multiplication within a patient in need of treatment or one at risk of becoming such a patient, of the human immunodeficiency virus, HIV, and related pathogenic retroviruses. The ability of such retroviral pathogens to evolve within a relatively short period of time into strains resistant to any monotherapy which has been administered to said patient is well known in the technical literature.

In addition to the requirement of therapeutic efficacy which may necessitate the use of active agents in addition to the CCR5 chemokine receptor modulating compounds of Formula (I), there may be additional rationales which compel or highly recommend the use of combinations of drugs involving active ingredients which represent adjunct therapy, i.e., which complement and supplement the function performed by the CCR5 chemokine receptor modulating compounds of the present invention. Such supplementary therapeutic agents used for the purpose of auxiliary treatment include drugs which, instead of directly treating or preventing a disease or condition mediated by or associated with CCR5 chemokine receptor modulation, treat diseases or conditions which directly result from or indirectly accompany the basic or underlying CCR5 chemokine receptor modulated disease or condition. For example, where the basic CCR5 chemokine receptor modulated disease or condition is HIV infection and multiplication, it may be necessary or at least desirable to treat opportunistic infections, neoplasms, and other conditions which occur as the result of the immune-compromised state of the patient being treated. Other active agents may be used with the compounds of Formula (I), e.g., in order to provide immune stimulation or to treat pain and inflammation which accompany the initial and fundamental HIV infection.

Thus, the methods of treatment and pharmaceutical compositions of the present invention may employ the compounds of Formula (I) in the form of monotherapy, but said methods and compositions may also be used in the form of multiple therapy in which one or more compounds of Formula (I) are coadministered in combination with one or more known therapeutic agents such as those described in detail further herein.

The present invention also provides methods of treatment in which said pharmaceutical compositions are administered to a patient Such methods relate to treating or preventing a disease or condition by modulating CCR5 chemokine receptor activity and consequent or associated pathogenic processes subsequently mediated by the CCR5 receptor and the active ligands with which it interacts or is bound. CCR5 and the other chemotactic cytokine, i.e., chemokine, receptors, play a key role in the control of a number of processes which take place in the bodies of animals. Chemokine receptors, of which more than forty different species divided into four families are presently known to exist, are proteins having a number of structural features in common, which act through chemical signaling. In the a family of chemokines, one amino acid (X) separates the first two cysteine residues, while in the $\beta$-chemokines the first two cysteine residues are adjacent to each other (C—C). Accordingly, these two families are identified as CXC and CC chemokines, respectively. The chemokines bind specific cell-surface receptors belonging to the family of G-protein-coupled seven-transmembrane-domain proteins called "chemokine receptors", named in accordance with the class of chemokines which they bind, followed by "R" and a number. Thus, "CCR5" is a C—C chemokine receptor. See Horuk, *Trends Pharm. Sci.*, 15,159–165 (1994) for further details. CCR5 thus belongs to the -chemokine receptor family, which is currently known to contain eight members, CCR1 through CCR8.

The CC type of chemokine receptor interacts with various signaling proteins, including the monocyte chemoattractant proteins, MCP-1, -2, -3, -4, and -5; eotaxin-1; macrophage inflammatory proteins MIP-1$\alpha$, and MIP-1$\beta$; and those regulated upon activation which are normal T-cell expressed and secreted, RANTES. The CCR5 type of chemokine receptor in particular is known to interact with MIP-1α, MIP-1β; and RANTES in monocytes, activated T cells, dendritic cells, and natural killer cells. These β-chemokines do not act on neutrophils but rather attract monocytes, eosinophils, basophils, and lymphocytes with varying degrees of selectivity.

The present invention relates to compounds of Formula (I) which are useful in treating or preventing HIV infection, and to methods of treatment and pharmaceutical compositions containing such compounds as the active ingredient. It will be understood that the term "HIV" as used herein refers to human immunodeficiency virus (HIV), which is the etiological agent of AIDS (acquired immune deficiency syndrome), a disease that results in progressive destruction of the immune system and degeneration of the central and peripheral nervous system. Several HIV replication inhibitors are currently used as therapeutic or prophylactic agents against AIDS, and numerous others are presently under investigation.

In addition to cell-surface CD4, it has recently been shown that for entry into target cells, human immunodeficiency viruses require a chemokine receptor, CCR5 and CXCR-4 among others, as well as the virus's primary receptor CD4. The principal cofactor for entry mediated by the envelope glycoproteins of primary macrophage-tropic strains of HIV-1 is CCR5, which as already mentioned, is a receptor for the β-chemokines RANTES, MIP-1α and MIP-1β. See Deng, et al., *Nature*, 381, 661–66 (1996) for a further description of CCR5 mediated HIV entry.

HIV attaches to the CD4 molecule on cells through a region of its envelope protein, gp120, and gp120 is part of a multi-subunit complex, most likely a trimer of gp160, i.e., gp120+gp41. It is believed that the CD4 binding site on the gp120 of HIV interacts with the CD4 molecule on the cell surface, triggering conformational changes across the trimer, which allow it to bind to another cell-surface receptor, such as CCR5. This in turn enables gp41 to induce fusion with the cell membrane, and entry of the viral core into the cell. In addition, macrophage-tropic HIV and SIV envelope proteins have been shown to induce a signal through CCR5 on CD4+ cells, which may enhance the replication of the virus. See Weissman, et al., *Nature*, 389, 981–985 (1997) for a description of this phenomenon. Further, it has been shown that a complex of gp120 and soluble CD4 interacts specifically with CCR5 and inhibits the binding of the natural CCR5 ligands, as described in Wu, et al., *Nature*, 384, 179–183 (1996); and Trkola, et al., *Nature*, 384, 184–187 (1996). It has further been demonstrated that β-chemokines and related molecules, e.g., (AOP)-RANTES, prevent HIV fusion to the cell membrane and subsequent infection, both in vito, as described in Dragic, et al., *Nature*, 381, 667–673 (1996), and in animal models. Finally, absence of CCR5 appears to confer protection from HIV-1 infection, as described in *Nature*, 382, 668–669 (1996). In particular, an inherited frame-shifting mutation in the CCR5 gene, β32, has been shown to abolish functional expression of the gene in vitro, and individuals homozygous for the mutation are apparently not susceptible to HIV infection, while at the same time they do not seem to be immuno-compromised by this variant. Furthermore, those heterozygote individuals that have been infected by HIV progress more slowly to full-blown clinical AIDS. In addition to validating the role of CCR5 in the infectious cycle of HIV, the above observations suggest that CCR5 is dispensable in the adult organism.

Although most HIV-1 isolates studied to date utilize CCR5 or CXCR-4, at least nine other chemokine receptors, or structurally related molecules, have also been described as supporting HIV-1 env-mediated membrane fusion or viral entry in vitro. These include CCR2b, CCR3, BOB/GPR15, Bonzo/STRL33/TYMSTR, GPR1, CCR8, US28, V28/CX3CR1, LTB-4, and APJ. There is good evidence that CCR3 can be used efficiently by a significant fraction of HIV-1 isolates in vito, provided that this protein is over-expressed in transfected cells. Nevertheless, consistent evidence indicates that anti-HIV drugs targeted to chemokine receptors may not be compromised by this variability. Indeed, the chemokines RANTES, MIP-1α, MIP-1β, SDF-1 have been shown to suppress replication of primary HIV isolates. A derivative of RANTES, (AOP)-RANTES, is a sub-nanomolar antagonist of CCR5 function in monocytes. Monoclonal antibodies to CCR5 have been reported to block infection of cells by HIV in vitro. A small molecule antagonist of CXCR4, identified as AMD3100, has been reported to inhibit infection of susceptible cultures by CXCR4 dependent primary and lab-adapted HIV viruses while another small molecule called TAK 779 blocks entry of CCR5-tropic strains (Baba, et al. *PNAS*, 96 (10), 5698–5703 (1999); In addition, the majority of primary strains from early and late disease stages utilize CCR5 exclusively or in addition to other chemokine receptors, indicating that CCR5 dependent infection may play an essential role in the initiation and maintenance of productive HIV infection in a host. Accordingly, an agent which blocks CCR5 in patients including mammals, and especially humans who possess normal chemokine receptors, can reasonably be expected to prevent infection in healthy individuals and slow or halt viral progression in infected patients.

Accordingly, the present invention is directed to the compounds of Formula (I) which inhibit the entry of human immunodeficiency virus into target cells and are therefore of value in the prevention and/or treatment of infection by HIV, as well as the prevention and/or treatment of the resulting acquired immune deficiency syndrome (AIDS). Evidence can be produced which is probative of the fact that the compounds of Formula (I) described herein inhibit viral entry through selective blockade of CCR5 dependent fusion. Consequently, the present invention also relates to pharmaceutical compositions containing the compounds of Formula (I) as an active ingredient, as well as to the corresponding method of use of the compounds of Formula (I) as stand-alone agents, or in conjunction with other agents for the prevention and treatment of infection by HIV and resulting AIDS.

The utility of the compounds of Formula (I) of the present invention as inhibitors of HIV infection may be demonstrated by any one or more methodologies known in the art, such as the HIV microculture assays described in Dimitrov et al., *J. Clin. Microbiol.* 28, 734–737 (1990)), and the pseudotyped HIV reporter assay described in Connor et al., *Virology* 206 (2) 935–44 (1995). In particular, specific compounds of Formula (I) disclosed herein as preferred embodiments are shown to inhibit p24 production following replication of laboratory-adapted and primary HIV strains in primary blood lymphocytes (PBLs) and clonal cell-lines known to support replication of both CCR5 and CXCR-4 tropic viruses, e.g., PM-1 and MOLT4-clone 8. It is also noted that only those viral strains known to use CCR5 are shown to be inhibited, whereas replication of CXCR-4 tropic viruses is shown to be unaffected, indicating that compounds of Formula (I) disclosed herein are able to prevent viral entry through selective blockade of CCR5 dependent fusion. Furthermore, compounds of Formula (I) are shown to inhibit entry of chimeric HIV reporter viruses pseudotyped with envelope from a CCR5 dependent strain (ADA). Finally, compounds of Formula (I) are shown to inhibit infection of primary cells by HIV isolated from infected patient blood. Further confirmation of this anti-HIV mechanism is provided by experiments outlined below.

The ability of the compounds of Formula (I) to modulate chemokine receptor activity is demonstrated by methodology known in the art, such as the assay for CCR5 binding following procedures disclosed in Combadiere et al., *J. Leukoc. Biol.* 60, 147–52 (1996); and/or intracellular calcium mobilisation assays as described by the same authors. Cell lines expressing the receptor of interest include those naturally expressing the receptor, such as PM-1, or IL-2 stimulated peripheral blood lymphocytes (PBL), or a cell engineered to express a recombinant receptor, such as CHO, 300.19, L1.2 or HEK-293. In particular, the compounds of Formula (I) disclosed herein are shown to have activity in preventing binding of all known chemokine ligands to CCR5 in the above-mentioned binding assays. In addition, the compounds of Formula (I) disclosed herein are shown to prevent intracellular calcium mobilization in response to endogenous agonists, which is consistent with their functioning as CCR5 antagonists. For the treatment of infection by HIV and the prevention and/or treatment of the resulting acquired immune deficiency syndrome (AIDS), compounds of Formula (I) which are shown to be antagonists are preferred to compounds of Formula (I) which are shown to be agonists.

The present invention in one of its preferred embodiments is directed to the use of the compounds of Formula (I) disclosed herein for the prevention or treatment of infection by a retrovirus, in particular, the human immunodeficiency virus (HIV) and the treatment and/or delaying of the onset of consequent pathological conditions, including but no limited to AIDS. The expressions "treating or preventing AIDS", and "preventing or treating infection by HIV" as used herein are intended to mean the treatment of a wide range of states of HIV infection: AIDS, ARC (AIDS related complex), both symptomatic and asymptomatic, and actual or potential exposure to HIV. The quoted expressions are not intended, however, to be limited to the recited treatments, but rather are contemplated to include all beneficial uses relating to conditions attributable to an AIDS causative agent For example, the compounds of Formula (I) are useful in treating infection by HIV after suspected past exposure to HIV by, e.g., blood transfusion, organ transplant, exchange of body fluids, sexual intercourse, bites, needle stick, or exposure to patent blood. In addition, a compound of Formula (I) may be used for the prevention of infection by HIV and the prevention of AIDS, such as in pre- or post-coital prophylaxis or in the prevention of maternal transmission of the HIV virus to a fetus or a child, whether at the time of birth, during the period of nursing, or in any other manner as above-described.

In a preferred embodiment of the present invention, a compound of Formula (I) may be used in a method of inhibiting the binding of human immunodeficiency virus to a chemokine receptor such as CCR5, which comprises contacting the target cell with a therapeutically effective amount of a compound of Formula (I) which is effective to inhibit the binding of the virus to the chemokine receptor. The subject treated by these preferred methods of the present invention is a mammal, preferably a human, male or female, in whom modulation of chemokine receptor activity is desired and contemplated to be efficacious. As already pointed out, the term "modulation" as used herein is intended to encompass preferably antagonism, but also agonism, partial antagonism and/or partial agonism. Also, the expression "therapeutically effective amount" as used herein is intended to mean the amount of a compound of Formula (I) as disclosed herein that will elicit the biological or medical response of a tissue, system, or animal, especially human that is being sought.

In another preferred embodiment of the present invention, a compound of Formula (I) may be used to evaluate putative retrovirus, especially HIV, mutants considered to be resistant to anti-HIV therapeutic agents, including the compounds of Formula (I) disclosed herein. Mutant viruses may be isolated from in vitro cultures by methods known in the art, but may also be isolated from in vivo animal infection models which have been disclosed in the art. More significantly, mutant viruses may be isolated from samples of patients undergoing treatment, whether optimal or sub-optimal, comprising administration of a compound of Formula (I), or any combination thereof with other known or to-be-discovered therapeutic agents. Such mutant viruses or their components, particularly their envelope proteins, may be used for several advantageous purposes, including but not limited to the following: (i) the evaluation and/or development of novel chemokine modulators or other agents having improved activity against such mutant viruses; and (ii) the development of diagnostics capable of assisting physicians or other clinicians in the choice of a therapeutic regimen and/or outcome prediction for a patient.

In a further preferred embodiment of the present invention, compounds of Formula (I) disclosed herein are used as tools for determining the co-receptor affinity of retroviruses including HIV and SIV, or their components, especially their envelope proteins. This affinity data can be used for several advantageous purposes, including but not limited to phenotyping a given viral population, e.g. prior to administration of anti-retroviral therapy. The affinity data may also be used to predict the progression and outcome of the infection by the virus population involved.

In another preferred embodiment of the present invention, a compound of Formula (I) is used in the preparation and execution of screening assays for compounds which modulate the activity of chemokine, especially CCR5 receptors. For example, compounds of Formula (I) as disclosed herein are useful for isolating receptor mutants, which can then be made into screening tools for the discovery of even more potent compounds, following procedures well known in the art. Furthermore, the compounds of Formula (I) are useful in establishing or characterizing the binding sites of other ligands, including compounds other than those of Formula (I) and viral envelope proteins, to chemokine receptors, e.g., by competitive inhibition. The compounds of Formula (I) are also useful for the evaluation of putative specific modulators of various chemokine receptors. As will be appreciated by the artisan, thorough evaluation of specific agonists and antagonists of the above-described chemokine receptors has been hampered by the lack of non-peptidyl, i.e., metabolically resistant compounds with high binding affinity for these receptors. Thus, the compounds of Formula (I) are useful as products which may be commercially exploited for these and other beneficial purposes.

Included within the scope of the present invention are combinations of the compounds of Formula (I) with one or more therapeutic agents useful in the prevention or treatment of AIDS. For example, the compounds of the present invention may be effectively administered, whether at periods of pre-exposure and/or post-exposure to HIV, in combination with therapeutically effective amounts of known AIDS antivirals, immunomodulators, anti-infectives, or vaccines familiar to those skilled in the art. It will be understood that the scope of such combinations which include the compounds of Formula (I) is not limited to the above-recited list, but includes as well any combination with another pharmaceutically active agent which is useful for the prevention or treatment of HIV and AIDS.

Preferred combinations of the present invention include simultaneous, or sequential treatments with a compound of Formula (I) and one or more inhibitors of HIV protease and/or inhibitors of HIV reverse transcriptase, preferably selected from the class of non-nucleoside reverse transcriptase inhibitors (NNRTI), including but not limited to nevirapine, delavirdine, and efavirenz; from among the nucleoside/nucleotide inhibitors, including but not limited to zidovudine, didanosine, zalcitabine, stavudine, lamivudine, abacavir, and adefovir dipivoxil; and from among the protease inhibitors, including but not limited to indinavir, ritonavir, saquinavir, nelfinavir, and amprenavir. Other agents useful in the above-described preferred embodiment combinations of the present invention include current and to-be-discovered investigational drugs from any of the above classes of inhibitors, including but not limited to FTC, PMPA, fozivudine tidoxil, talviraline, S-1153, MKG-442, MSC-204, MSH-372, DMP450, PNU-140690, ABT-378, and KNI-764. There is also included within the scope of the preferred embodiments of the present invention, combinations of a compound of Formula (I) together with a supplementary therapeutic agent used for the purpose of auxiliary treatment, wherein said supplementary therapeutic agent comprises one or more members independently selected from the group consisting of proliferation inhibitors, e.g., hydroxyurea; immunomodulators, e.g., sargramostim, and various forms of interferon or interferon derivatives; fusion inhibitors, e.g., AMD3100, T-20, PRO-542, AD-349, BB-10010 and other chemokine receptor agonists/antagonists; integrase inhibitors, e.g., AR177; RNaseH inhibitors; inhibitors of viral transcription and RNA replication; and other agents that inhibit viral infection or improve the condition or outcome of HIV-infected individuals through different mechanisms.

Preferred methods of treatment of the present invention for the prevention of HIV infection, or treatment of aviremic and asymptomatic subjects potentially or effectively infected with HIV, include but are not limited to administration of a member independently selected from the group consisting of: (i) a compound within the scope of Formula (I) as disclosed herein; (ii) one NNRTI in addition to a compound of (i); (iii) two NRTI in addition to a compound of (i); (iv) one NRTI in addition to the combination of (ii); and (v) a compound selected from the class of protease inhibitors used in place of an NRTI in combinations (iii) and (iv).

The preferred methods of the present invention for therapy of HIV-infected individuals with detectable viremia or abnormally low CD4 counts further include as a member to be selected: (vi) treatment according to (i) above in addition to the standard recommended initial regimens for the therapy of established HIV infections, e.g., as described in Bartett, J. G., "1998 Medical management of HIV infection", Johns Hopkins University publishers, ISBN 0-9244-28094-0. Such standard regimens include but are not limited to an agent from the class of protease inhibitors in combination with two NRTIs; and (vii) a standard recommended initial regimens for the therapy of established HIV infections, e.g., as described in Bartlett, J. G., "1998 Medical management of HIV infection", Johns Hopkins University publishers, ISBN 0-9244-2809-0), where either the protease inhibitor component, or one or both of the NRTIs is/are replaced by a compound within the scope of Formula (I) as disclosed herein.

The preferred methods of the present invention for therapy of HIV-infected individuals that have failed antiviral therapy further include as a member to be selected: (viii) treatment according to (i) above, in addition to the standard recommended regimens for the therapy of such patients, e.g., as described in Bartlett J. G., "1998 Medical management of HIV infection", Johns Hopkins University publishers, ISBN 0-9244-2809-0); and (ix) a standard recommended initial regimens for the therapy of patients who have failed antiretroviral therapy, e.g., as described in Bartlett. J. G., "1998 Medical management of HIV infection", Johns Hopkins University publishers, ISBN 0-9244-2809-0), where either one of the protease inhibitor components, or one or both of the NRTIs is/are replaced by a compound within the scope of Formula (I) as disclosed herein.

In the above-described preferred embodiment combinations of the present invention, the compound of Formula (I) and other therapeutic active agents may be administered in terms of dosage forms either separately or in conjunction with each other, and in terms of their time of administration, either serially or simultaneously. Thus, the administration of one component agent may be prior to, concurrent with, or subsequent to the administration of the other component agent(s).

The compounds of Formula (I) may be administered in accordance with a regimen of 1 to 4 times per day, preferably once or twice per day. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy. In particular, however, the treatment of retroviral infections, and more particularly HIV, may be guided by genotyping and phenotyping the virus in the course of or prior to the initiation of administration of the therapeutic agent. In this way, it is possible to optimise dosing regimens and efficacy when administering a compound of Formula (I) for the prevention or treatment of infection by a retrovirus, in particular, the human immunodeficiency virus (HIV).

The compounds of this invention may be used for treatment of respiratory disorders, including: adult respiratory distress syndrome (ARDS), bronchitis, chronic bronchitis, chronic obstructive pulmonary disease, cystic fibrosis, asthma, emphysema, rhinitis and chronic sinusitis.

The invention is further described by means of examples, but not in any limitative sense.

The following synthetic routes were employed.

Synthesis I

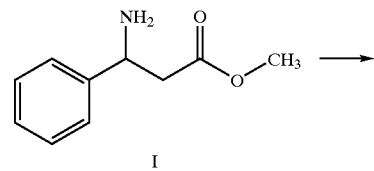

I

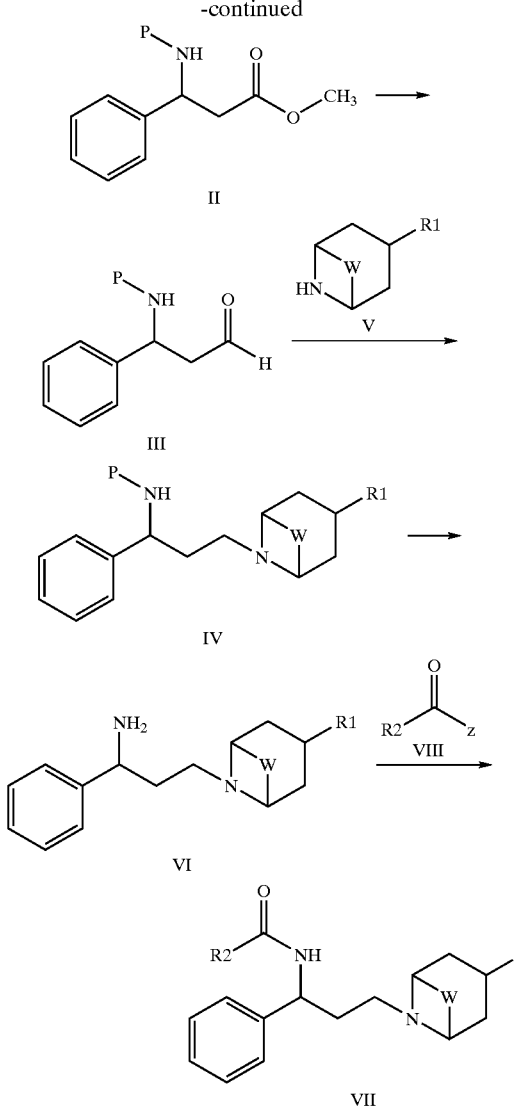

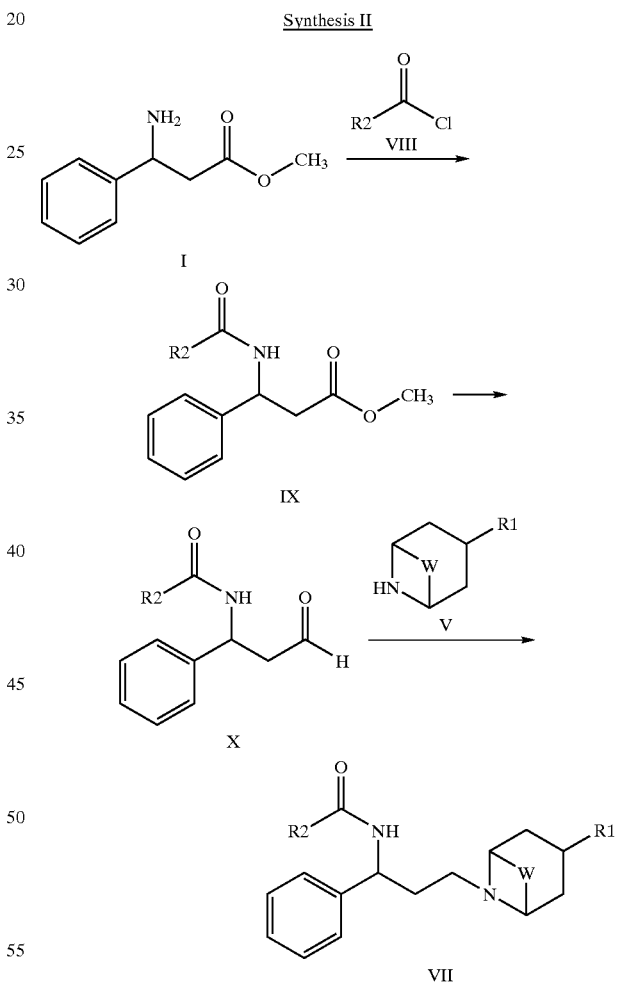

Preparation of the compounds of formula II from the amino acid derivative I where P is a suitable protecting group (preferably BOC), may be achieved for example, by reaction with di-tert-butyl dicarbonate in the presence of a base such as aqueous sodium hydroxide in a suitable solvent such as tetrahydrofuran.

Compounds of formula III may be prepared by reduction of compounds of formula II, using a suitable reducing agent. preferably diisobutylaluminium hydride in dichloromethane at −78° C.

Compounds of the general formula IV may be prepared by the reductive alkylation of an appropriate amine of formula V, with an aldehyde, of formula III. The reaction may be carried out in the presence of an excess of suitable reducing agent (eg. sodium triacetoxyborohydride) in a protic solvent system (acetic acid in dichloromethane or 1,1,1-trichloroethane), at room temperature.

Subsequent removal of the nitrogen protecting group may be achieved using trifluoroacetic acid or hydrochloric acid in a solvent such as dioxan or dichloromethane at room temperature for from 1 to 60 hours to provide the compound of formula VI. Compounds of general formula VII may be prepared by coupling the amine of formula VI with an acid (Z=OH) or acid derivative (eg, Z=Cl) of formula VIII using conventional amide bond forming techniques. For example, the acid VIII may be activated using a carbodiimide such as 3-(3-dimethylamino-1-propyl)-1-ethylcarbodiimide, optionally in the presence of 1-hydroxybenzotriazole hydrate. These reactions may be performed in a suitable solvent such as dichloromethane, optionally in the presence of a tertiary amine, such as triethylamine or N-ethyldiisopropylamine at about room temperature.

Alternatively an acyl chloride of formula VIII, may be reacted with an amine of formula VI in the presence of a tertiary amine, such as triethylamine or N-ethyldiisopropylamine in a suitable solvent such as dichloromethane at room temperature for about 3 hours.

In a further variation a compound of formula VII, may be formed in a "one-pot procedure" by deprotection of a compound of formula IV, and coupling the resultant amine of formula VI with the acid derivative of formula VIII, using methods previously described.

Synthesis II

Compounds of formula IX may be prepared by coupling the amino acid derivative of formula I with an acid chloride of formula VIII in the presence of a tertiary amine, such as triethylamine, in a suitable solvent, such as dichloromethane at between 0° C. and room temperature. Compounds of formula X may be prepared by reduction of compounds of formula IX, according to the method described in synthesis I. Reductive alkylation of the amine of formula V, with the aldehyde of formula X, according to the method described in synthesis I, may provide the compounds of formula VII.

Synthesis III

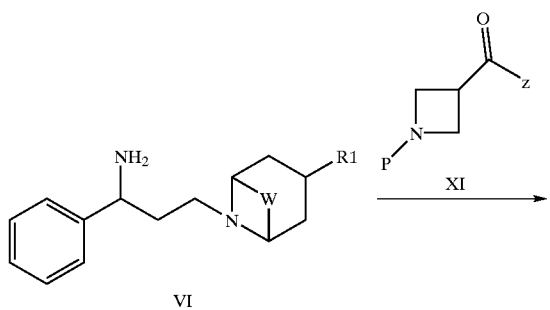

VI

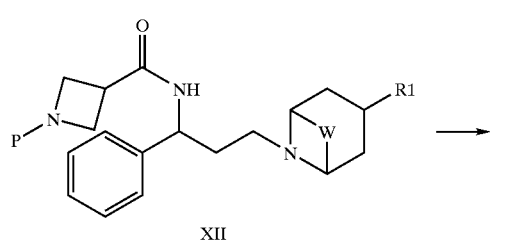

XII

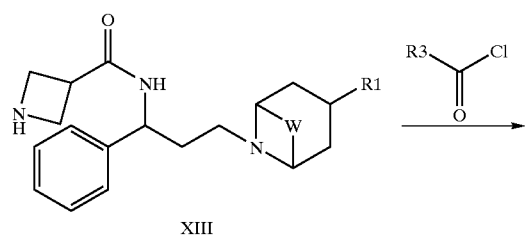

XIII

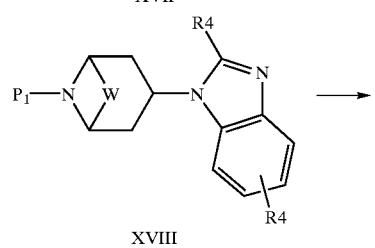

XIV

Compounds of the general formula XII may be prepared by coupling the amine of formula VI with the protected amino acid derivative of formula XI (where Z=Cl or OH and P is preferably BOC or benzyl), using methods previously described in synthesis I. Removal of the nitrogen protecting group, using standard methodology provides the compound of formula XIII. Typically, removal of a CBz protecting group may be achieved under catalytic hydrogenation conditions using a catalyst such as Pearlman's catalyst, in the presence of an excess of ammonium formate, in a suitable solvent such as ethanol under reflux conditions.

Compounds of formula XIV may be obtained by coupling the amine of formula XIII with an appropriate acyl chloride, using methods previously described in synthesis II.

Alternatively, a compound of formula XIV may be formed in a "one-pot procedure", by deprotection of the nitrogen group, and coupling the, resultant intermediate with an acyl chloride as described above.

Synthesis IV

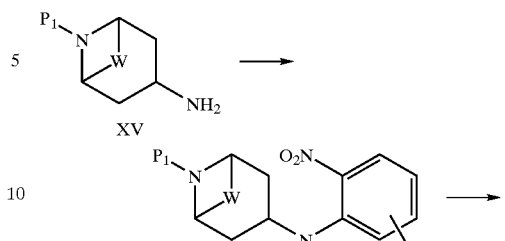

XV, XVI, XVII

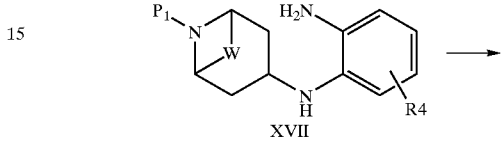

XVIII

V

Compounds of formula XVI may be prepared by the alkylation of amines of formula XV using a suitable alkylating agent, preferably 2-fluoronitrobenzene, in the presence of an excess of a suitable base, typically potassium carbonate, in a solvent such as N,N-dimethylformamide at between 100° C. and 140° C. for about 2 to 18 hours. Compounds of formula XVII may be prepared by reduction of the corresponding compounds of formula XVI. This reduction may be performed under a variety of reaction conditions, for example by catalytic hydrogenation (10% palladium on charcoal, in a solvent such as ethyl acetate, optionally in the presence of an alcohol, such as methanol, at 1 atm. $H_2$ pressure and room temperature) or by transition metal catalysed reduction (at reflux temperature in the presence of an excess of iron powder in acetic acid, or iron powder and calcium chloride in aqueous ethanol, or an excess of tin chloride dihydrate in ethanol, for about 2 hours). It will be appreciated by those skilled in the art, that when $P_1$ is acid labile (eg BOC) the conditions required for transition metal catalysed reduction may also result in the simultaneous deprotecton of the nitrogen group.

Compounds of formula XVIII may be prepared by the condensation of the amine of formula XVII and an appropriate orthoester under reflux conditions, optionally in the presence of acid catalysis, (eg hydrochloric acid or p-toluenesulphonic acid).

Deprotection of the nitrogen protecting group (when necessary) to yield the amine of formula V may be accomplished using the method of Genet et al (Tet. Lett. 36; 8; 1267, 1995) or by using methods as previously described above.

Synthesis V

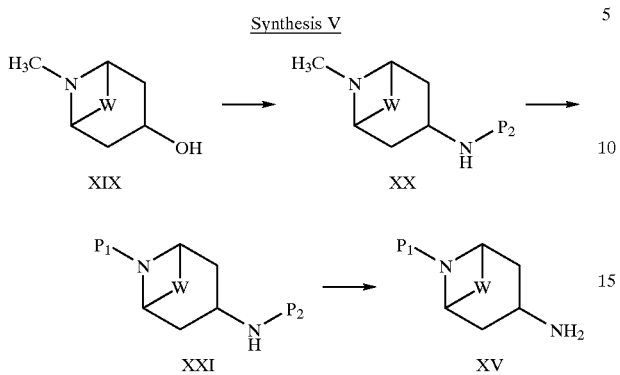

The amine of formula XX may be prepared from the alcohol of formula XIX by reaction with a protected amine, (P₂NH₂), for example phthalimide, according to the method of Mitsunobu (Org. React. 1992; 42; 335). The compound of formula XXI may be prepared by a concerted demethylation and protection of the amine of formula XX. Typically this is achieved using a large excess of ethyl choroformate, in a suitable solvent such as toluene, at about 90° C. Deprotection of the nitrogen (P₂) of the compound of formula XXI using for example, hydrazine hydrate, in a suitable solvent such as ethanol at reflux temperature provided the amine of formula XV.

Synthesis VI

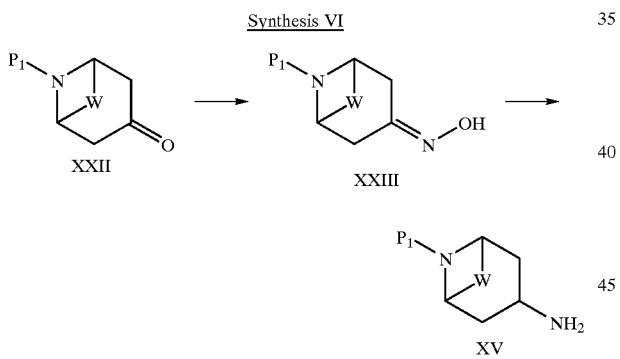

Oximes of general formula XXIII may be prepared by the condensation of compounds of general formula XII with hydroxylamine hydrochloride, in the presence of a base such as pyridine, and in a suitable solvent, typically ethanol, at reflux temperature for about 2 hours. Reduction of the compounds of formula XXIII may be achieved using sodium in the presence of an alcohol, typically pentanol, to provide the amine of formula XV.

Synthesis VII

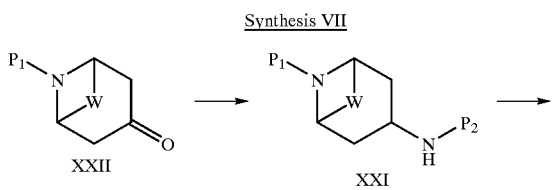

-continued

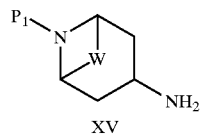

The nitrogen protected diamine of formula XXI may alternatively be prepared by reaction of the ketone of formula XXII with a protected amine (preferably benzyl) using reductive amination methodology, as previously described in synthesis I. Deprotection of this benzyl group typically using catalytic hydrogentaion conditions using palladium on charcoal as a catalyst in a suitable solvent such as ethyl acetate at 1 atm of H₂ pressure at between about room temperature and 50° C., provides the amine of formula XV.

Synthesis VIII

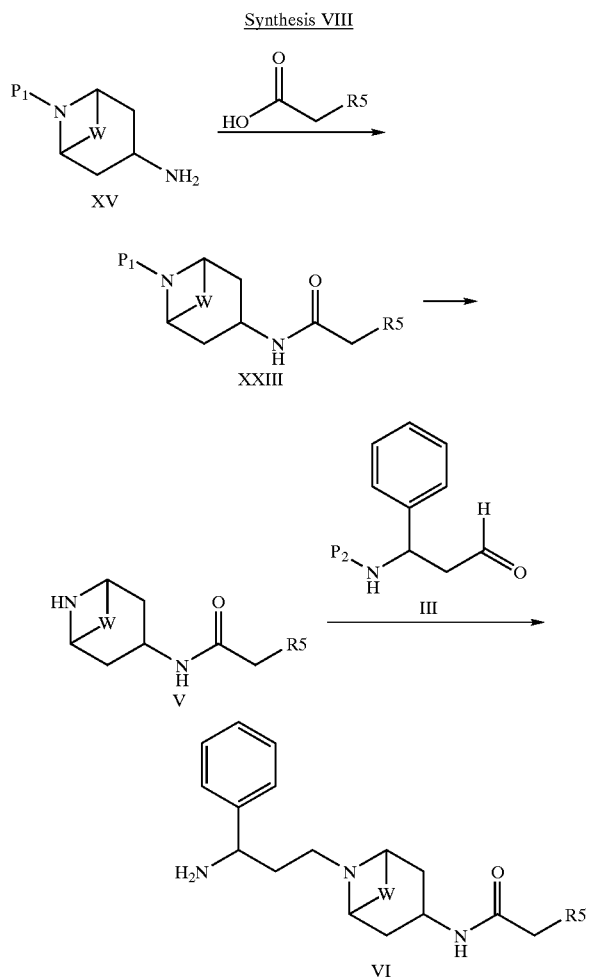

Compounds of the formula XXIII, may be prepared by coupling the protected amine of formula XV (P₁ is for example, BOC or Benzyl) with a carboxylic acid of formula (R₅CH₂COOH). The coupling may be achieved using conventional amide bond forming techniques, as described in synthesis I. For example the acid may be activated using a carbodiimide such as 1-(3-dimethylaminopropyl)-3-ethyl-carbodiimide in the presence of 1-hydroxybenzotriazole in a suitable solvent such as dichloromethane, in the presence of a tertiary amine such as diisopropylamine. Compounds of formula V may be prepared by nitrogen deprotection of compounds of formula XXIII, using techniques previously described above. Compounds of formula VI may be prepared by the reductive amination of amines of formula V with an appropriate aldehyde of formula III. The reaction may be carried out in the presence of a suitable reducing agent (eg sodium triacetoxyborohydride) in a protic solvent system (eg acetic acid, dichloromethane). Deprotection of the nitrogen using standard methodology as previously described, provides the compounds of general formula VI.

Synthesis IX

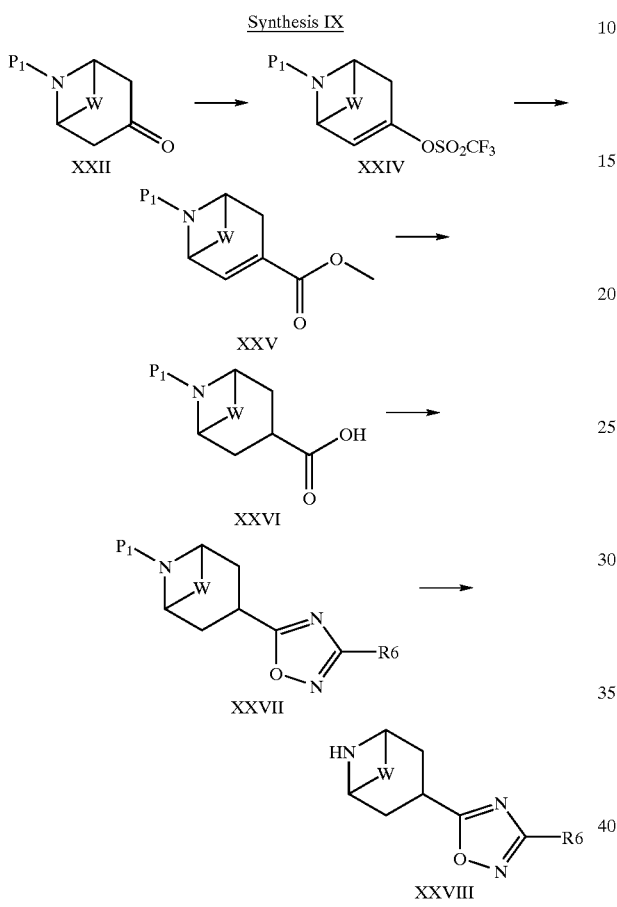

Compounds of formula XXIV may be prepared from the carbonyl compounds of formula XXII, by treatment initially with a suitable base such as lithium diisopropylamine at −78° C., and quenching the resultant anion with an appropriate electrophilic triflate, such as N-(5-chloro-2-pyridyl)triflimide, in a solvent, such as tetrahydrofuran, according to the method of Comins (Tet. Lett. 33; 6299; 1992).

Compounds of formula XXV may be prepared from compounds of formula XXIV, by palladium catalysed functionalisation of the vinyl triflate group. For example, treatment of compound XXIV with a palladium catalyst (prepared in-situ from palladium acetate and triphenylphosphine) in the presence of a suitable base such as triethylamine, in a mixture of DMF and methanol, under an atmosphere of carbon monoxide gives compounds of formula XXV.

Compounds of formula XXVI may be prepared in a "one-pot", two-step procedure from compounds of formula XXIV. Reduction of the double bond under hydrogenation conditions, typically using a catalyst such as Raney® Nickel, in an alcohol (eg methanol), at 60 psi of $H_2$ pressure and room temperature. Hydrolysis of the intermediate alkyl ester, according to the plethora of methods currently available yielded compounds of formula XXVI. For example, treatment with sodium hydroxide in a mixture of tetrahydrofuran and water at room temperature. Compounds of formula XXVII may be prepared by coupling the acid of formula XXVI with an appropriate oxime, followed by in-situ cyclocondensation. For example, the acid may be activated using a fluorinating agent, such as N,N,N',N'-bis(tetramethylene)fluoroformamidinium hexafluorophosphate (J.A.C.S. 1995; 117(19); 5401) in the presence of a base such as N-ethyldiisopropylamine in a suitable solvent such as dichloromethane at room temperature. Cyclocondensation of the resultant intermediate may subsequently be achieved by heating in an appropriate solvent such as dioxan at elevated temperature (eg 130° C.) for about 3 hours.

Deprotection of the nitrogen group (typically BOC) of compounds of formula XXVII using standard methodology such as protonolysis using hydrochloric acid, according to the methods previously described, affords compounds of formula XXVIII.

PREPARATION 1

Methyl 3-amino-3-phenylpropanoate Hydrochloride

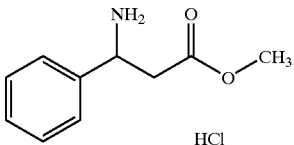

3-Phenyl-β-alanine (13.0 g, 78.8 mmol) was dissolved in methanolic hydrochloric acid (200 ml, 2.25M). The reaction was heated under reflux for 18 hours, then the cooled mixture was concentrated under reduced pressure to afford the tile compound as a yellow oil, 16.9 g.

$^1$H-NMR (400 MHz, CD$_3$OD): δ [ppm] 3.00–3.19 (2H, m), 3.72 (3H, s), 4.74 (1H, t), 7.48 (5H, s).

PREPARATION 2

Methyl 3-[(cyclobutylcarbonyl)amino]-3-phenylpropanoate

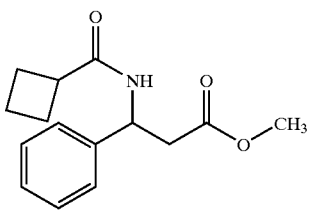

Cyclobutanecarbonyl chloride (6.91 ml, 86.7 mmol) was added dropwise to a solution of the title compound of preparation 1 (16.9 g, 78.8 mmol) and triethylamine (24.2 ml, 173.4 mmol) in dichloromethane (200 ml) at 0° C. The reaction mixture was stirred for 56 hours at room temperature after which time the mixture was washed with water, then brine, dried (MgSO$_4$), filtered and the solvent removed under reduced pressure to afford the title compound as a yellow oil, 20.8 g.

$^1$H-NMR (400 MHz, CDCl$_3$): δ [ppm] 2.00–2.10 (2H, m), 2.10–2.35 (4H, m), 2.80–3.00 (2H, m), 3.03 (1H, m), 3.62 (3H, s), 5.42 (1H, m), 6.50 (1H, d), 7.25–7.35 (5H, m). LRMS m/z 262 (MH$^+$).

PREPARATION 3

N-(3-oxo-1-phenylpropyl)cyclobutanecarboxamide

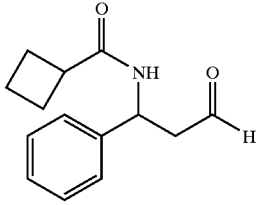

Diisobutylaluminium hydride (42.1 ml of a 1.0M solution in dichloromethane, 42.1 mmol) was added dropwise to a solution of the title compound of preparation 2 (5.0 g, 19.1 mmol) in dichloromethane (100 ml) at −78° C. The reaction mixture was stirred at this temperature for an hour, then methanol (5 ml) pre-cooled to −78° C. was added. The mixture was warmed to room temperature and washed with 2N hydrochloric acid, water, brine, dried (MgSO$_4$), filtered and the solvent evaporated under reduced pressure to afford the title compound as a yellow oil, 3.3 g.

$^1$H-NMR (400 MHz, CDCl$_3$): δ [ppm] 1.81–2.35 (6H, m), 2.90–3.10 (3H, m), 5.50 (1H, m), 6.00 (1H, bd), 7.23–7.39 (5H, m), 9.75 (1H, m). LRMS: m/z 232 (MH$^+$).

PREPARATION 4

Methyl (3S)-3-amino-3-phenylpropanoate

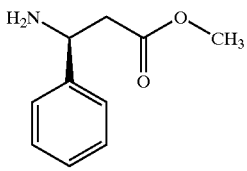

A solution of tert-butyl (3S)-3-amino-3-phenylpropanoate (5.04 g, 22.9 mmol) in 2.25M methanolic hydrochloric acid (100 ml) was heated under reflux for 2½ hours. The mixture was cooled to room temperature, basified with saturated sodium carbonate solution to pH 8 and the phases separated. The aqueous layer was extracted with dichloromethane (4×), the combined organic solutions were washed with brine, dried (MgSO$_4$), filtered and evaporated under reduced pressure to afford the title compound, 3.97 g.

$^1$H-NMR (400 MHz, CDCl$_3$): δ [ppm] 1.70 (2H, s), 2.66 (2H, d), 3.68 (3H, s), 4.43 (1H, t), 7.25–7.40 (5H, m). LRMS: m/z 180.3 (MH$^+$).

PREPARATION 5

Methyl (3S)-3-[(tert-butoxycarbonyl)amino]-3-phenylpropanoate

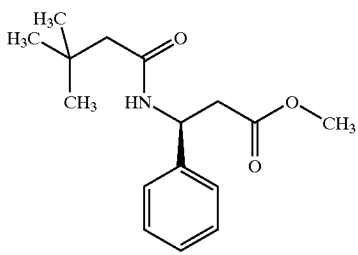

The title compound from preparation 4 (5.38 g, 30 mmol) and di-tertbutyl dicarbonate (8.72 g, 40 mmol) in tetrahydrofuran (50 ml) and 2N sodium hydroxide solution (25 ml) were stirred at room temperature for 2 hours. The reaction mixture was diluted with ethyl acetate, the layers separated and the aqueous phase extracted with ethyl acetate (2×). The combined organic solutions were washed with water, brine, dried (MgSO$_4$), filtered and evaporated under reduced pressure to afford the title compound as a white solid, 8.39 g.

$^1$H NMR (400 MHz, CDCl$_3$): δ [ppm] 1.41 (9H, s), 2.84 (2H, m), 3.61 (3H, s), 5.10 (1H, bs), 5.41 (1H, bs), 7.22–7.36 (5H, m). LRMS: m/z 279.7 (MH$^+$).

PREPARATION 6

Methyl (3S)-3-[(cyclobutylcarbonyl)amino]-3-phenylpropanoate

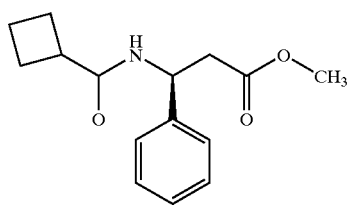

Obtained from the title compound of preparation 4 and cyclobutanecarbonyl chloride as a brown solid in 82% yield using a similar procedure to that in preparation 2.

$^1$H-NMR (300 MHz, CDCl$_3$): δ [ppm] 1.81–2.06 (2H, m), 2.10–2.40 (5H, m), 2.82–3.08 (2H, m), 3.62 (3H, s), 5.42 (1H, m), 6.42 (1H, d), 7.22–7.38 (5H, m).

PREPARATION 7 tert-Butyl (1S)-3-oxo-1-phenylpropylcarbamate

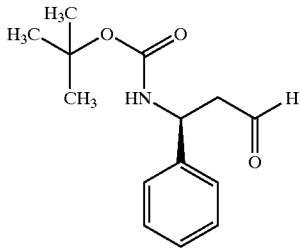

Diisobutylaluminium hydride (1M in dichloromethane, 60 ml, 60 mmol) was cooled to −78° C. and added dropwise to a solution of the title compound from preparation 5 (8.39 g, 30 mmol) in dichloromethane (150 ml) at −78° C. The reaction was stirred for 90 minutes, then methanol (precooled to −78° C.) (40 ml) was added. The mixture was allowed to warm to room temperature and poured into 2M hydrochloric acid (200 ml). The layers were separated and the aqueous phase extracted with dichloromethane (2×). The combined organic layers were dried (MgSO$_4$), filtered and evaporated under reduced pressure to afford the five compound as a white solid, 6.72 g.

$^1$H NMR (400 MHz, CDCl$_3$): δ [ppm] 1.42 (9H, s), 2.86–3.00 (2H, m), 5.06 (1H, bs), 5.20 (1H, bs), 7.22–7.38 (5H, m), 9.75 (1H, s). LRMS: m/z 250.1 (MH$^+$).

PREPARATION 8

N-[(1S)-3-oxo-1-phenylpropyl]cyclobutanecarboxamide

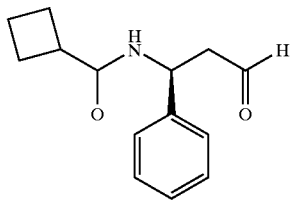

Obtained from the title compound of preparation 6 as a brown oil in 82% yield using a similar procedure to that in preparation 7.

$^1$H-NMR (300 MHz, CDCl$_3$): δ [ppm] 1.81–2.35 (6H, m), 2.90–3.10 (3H, m), 5.53 (1H, m), 5.98 (1H, bd), 7.23–7.39 (5H, m), 9.78 (1H, m).

PREPARATION 9 exo 2-(8-Methyl-8-azabicyclo[3.2.1]oct-3-yl)-1H-isoindole-1,3(2H)-dione

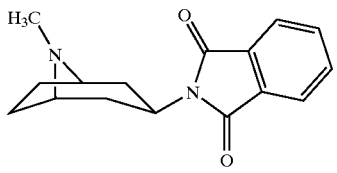

Diethyl azodicarboxylate (61.36 ml, 0.39 mol) was added dropwise over a period of 1 hour to a mixture of triphenylphosphine (102.2 g, 0.39 mol), phthalimide (52.04 g, 0.35 mol) and tropine (50 g, 0.35 mol) in tetrahydrofuran (400 ml) at 0° C. The reaction mixture was stirred for 20 hours at room temperature, and the solvent evaporated under reduced pressure. The residue was dissolved in dichloromethane, the solution extracted with hydrochloric acid (2×1N) and the combined aqueous extracts basified with potassium carbonate. This aqueous solution was then extracted with dichloromethane (×3), the combined organic extracts dried (MgSO$_4$), filtered and evaporated under reduced pressure. The crude product was triturated with ether and filtered, to afford the title compound (12 g). The filtrate was evaporated under reduced pressure and the residue purified by column chromatography on silica gel using an elution gradient of dichloromethane:methanol (95:5 to 90:10) to afford additional title compound (30 g total).

$^1$H-NMR (400 MHz, CDCl$_3$) δ [ppm] 1.40 (2H, m), 1.74 (2H, m), 2.12 (2H, m), 2.54 (3H, s), 2.63 (2H, m), 3.32 (2H, m), 4.52 (1H, m), 7.68 (2H, m), 7.80 (2H, m). LRMS: m/z 271 (MH$^+$).

PREPARATION 10

Ethyl exo 3-(1,3-dioxo-1,3-dihydro-2H-isoindol-2-yl)-8-azabicyclo[3.2.1]octane-8-carboxylate

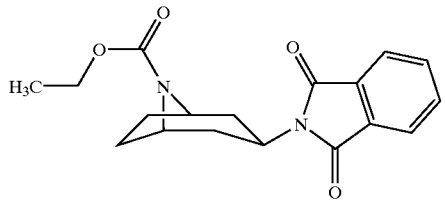

Ethyl chloroformate (22 ml, 0.2 mol) was added to a solution of the title compound from preparation 9 (20 g, 7.4 mmol) in toluene (200 ml). The solution was heated to 90° C. for 6 hours, then the mixture was cooled, and the solvent evaporated under reduced pressure to afford the title compound as a solid, 22.3 g.

$^1$H-NMR (400 MHz, CDCl$_3$): δ [ppm] 1.33 (3H, t), 1.62 (2H, m), 1.85 (2H, m), 2.06 (2H, m), 2.61 (2H, t), 4.21 (2H, m), 4.38 (2H, m), 4.68 (1H, m), 7.68 (2H, m), 7.80 (2H, m).

PREPARATION 11

Ethyl exo-3-Amino-8-azabicyclo[3.2.1]octane-8-carboxylate

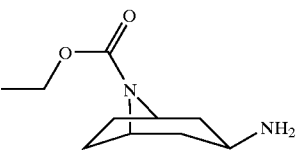

Hydrazine hydrate (3.73 g, 74.6 mmol) was added to a solution of the title compound of preparation 10 (22.4 g, 68.2 mmol) in ethanol (200 ml) and the reaction was heated under reflux for 1¾ hours. Water (500 ml) was added to the cooled mixture, this solution acidified using concentrated hydrochloric acid (100 ml), the precipitate was filtered off and the aqueous filtrate basified to pH 8 using sodium carbonate. This aqueous solution was extracted with dichloromethane (×3), the combined organic extracts dried (MgSO$_4$), filtered and evaporated under reduced pressure to afford the title compound as a yellow oil, 12.7 g.

$^1$H-NMR (300 MHz, CDCl$_3$): δ [ppm] 1.24 (3H, t), 1.40–1.60 (2H, m), 1.64 (2H, m), 1.85 (2H, m), 1.99 (2H, m), 2.41 (2H, bs), 3.20 (1H, m), 4.12 (2H, q), 4.28 (2H, bs). LRMS: m/z 199 (MH$^+$).

PREPARATION 12

8-Benzyl-8-azabicyclo[3.2.1]octan-3-one

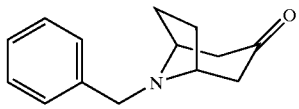

A solution of 2,5 dimethoxytetrahydrofuran (50 g, 378 mmol) in 0.025M hydrochloric acid (160 ml) was cooled to 0° C. for 16 hours. Benzylamine hydrochloride (65 g, 453 mmol), ketomalonic acid (55 g, 377 mmol) and an aqueous solution of sodium acetate (300 ml, 0.69M) were added and the reaction stirred at room temperature for 1 hour. The mixture was heated to 50° C. for a further 90 minutes and then cooled in an ice bath whilst basifying to pH12 with 2N sodium hydroxide solution. The layers were separated, and the aqueous phase extracted with ethyl acetate (3×). The combined organic solutions were washed with water, dried (MgSO$_4$), filtered and evaporated under reduced pressure. The residual brown oil was distilled under reduced pressure (126° C. @ 3 mm of Hg) to afford the title compound as an off-white solid, 37.81 g.

$^1$H NMR (400 MHz, CDCl$_3$): δ [ppm] 1.64 (2H, m), 2.06–2.14 (2H, m), 2.18 (1H, s), 2.23 (1H, s), 2.68 (1H, m), 2.72 (1H, m), 3.48 (2H, s), 3.73 (2H, s), 7.20–7.29 (1H, m), 7.32 (2H, m), 7.42 (2H, d). LRMS: m/z 216.3 (MH$^+$).

PREPARATION 13 tert-Butyl 3-oxo-8-Azabicyclo[3.2.1]octan-8-carboxylate

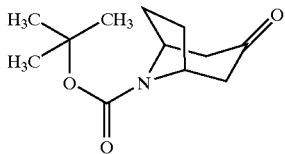

A mixture of the title compound from preparation 12 (15.0 g, 69.7 mmol) di-tert-butyl dicarbonate (18.2 g, 83.4 mmol) and 20% w/w palladium hydroxide on carbon (3.0 g) in ethyl acetate (165 ml) was stirred for 4 hours at room temperature under a 39 psi atmosphere of hydrogen. The mixture was filtered through Arbocel® and the solvent removed under reduced pressure. The residue was purified by column chromatography on silica gel using an elution gradient of hexane:ether (100:0 to 50:50) to afford the title compound as a colourless oil which crystallized on standing, 16.2 g.

$^1$H NMR (400 MHz, CDCl$_3$): δ [ppm] 1.48 (9H, s), 1.60–1.68 (2H, m), 2.00–2.11 (2H, m), 2.26–2.34 (2H, m), 2.48–2.82 (2H, m), 4.35 4.58 (2H, m).

PREPARATION 14

2-(2,2-Diethoxyethoxy)-1,1-diethoxyethane

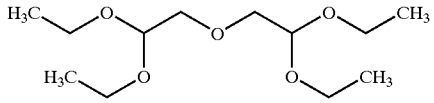

Glycolaldehyde diethyl acetal (45.4 g, 338 mmol) was added dropwise to a stirred solution of sodium hydride (14.3 g, 60% dispersion in mineral oil, 357 mmol) in xylene (100 ml), and the reaction heated under reflux for 1 hour. The reaction mixture was cooled to room temperature and bromoacetaldehyde diethyl acetal (100 g, 507 mmol) was added. The resulting solution was heated under reflux for 20 hours, then cooled to room temperature. The solvent was removed under reduced pressure, and the residual solution was distilled under reduced pressure (80° C. @ 6 mm Hg), to afford the title compound as a colourless oil, 60.8 g.

$^1$H NMR (400 MHz, CDCl$_3$): δ [ppm] 1.22 (12H, t), 3.55 (8H, m), 3.70 (4H, m), 4.60 (2H, t). LRMS: m/z 269 (MNH$_4^+$).

PREPARATION 15

9-Benzyl-3-oxa-9-azabicyclo[3.3.1]nonan-7-one

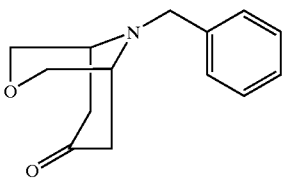

A solution of the title compound from preparation 14 (53.6 g, 214 mmol) in 0.025M hydrochloric acid (90 ml) was stirred at room temperature for 16 hours. Benzylamine hydrochloride (30.7 g, 213 mmol), ketomalonic acid (26 g, 178 mmol), and a solution of sodium acetate (8 g, 97 mmol) in water (180 ml) were added and the reaction was stirred at room temperature for 1 hour, then heated to 50° C. for 3 hours. The reaction mixture was cooled in an ice bath whilst basifying to pH12 using 1N sodium hydroxide solution. The layers were separated, and the aqueous phase extracted with ethyl acetate (2×). The combined organic solutions were washed with water, dried (MgSO$_4$), filtered and evaporated under reduced pressure. The residue was purified by column chromatography on silica gel, using ethyl acetate as eluant, to afford the title compound as a white solid, 41.5 g.

$^1$H NMR (400 MHz, CD$_3$OD): δ [ppm] 0.75 (2H, d), 1.38 (2H, m), 1.70 (2H, d), 2.19 (2H, d), 2.30 (2H, d), 2.45 (2H, s), 5.78 (1H, m), 5.83 (2H, t), 5.95 (2H, d). LRMS: m/z 232.1 (MH$^+$).

PREPARATION 16 tert-Butyl 7-oxo-3-oxa-9-Azabicyclo[3.3.1]nonane-9-carboxylate

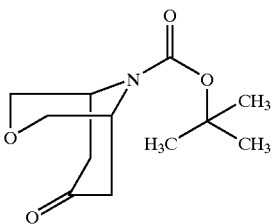

A mixture of the title compound from preparation 15 (10 g, 43.2 mmol), 20% palladium hydroxyde on carbon (2 g) and di-tert-butyl dicarbonate (11.32 g, 51.8 mmol) in ethyl acetate (100 ml) was hydrogenated under 40 psi of hydrogen for 16 hours at room temperature. The reaction was filtered through Arbocel® and the solvent removed under reduced pressure. The residue was purified by column chromatography on silica gel, using an elution gradient of dichloromethane:methanol (98:2 to 94:6) to afford the title compound as a white solid, 9.80 g.

¹H NMR (300 MHz, CDCl₃): δ [ppm] 1.25 (2H, m), 1.50 (9H, s), 2.50 (2H, m), 3.50 (2H, m), 3.75 (2H, m), 4.38 (1H, m), 4.45 (1H, m). LRMS: m/z 264.0 (MNa⁺).

PREPARATION 17

9-Allyl-3-thia-9-azabicyclo[3.3.1]nonan-7-one

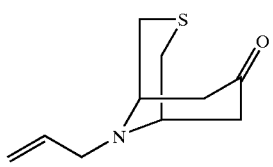

A solution of thiodiglycolaldehyde bis(diethyl acetal) (30 g 112.3 mmol) (Carbohydr. Res. 1981 90(2) 309) in 0.025M hydrochloric acid (90 ml) was stirred at 100° C. for 1 hour. The solution was cooled to room temperature and allylamine hydrochloride (13.65 g, 146 mmol), ketomalonic acid (16.4 g, 112.7 mmol) and sodium acetate (5.1 g, 62 mmol) in water (180 ml) were added. The reaction was stirred at room temperature for 16 hours, then heated to 50° C. for 2 hours. The reaction was cooled in an ice bath whilst basifying to pH12 with 1N sodium hydroxide solution. The layers were separated, and the aqueous phase was extracted with ethyl acetate (3×). The combined organic solutions were washed with water, dried (MgSO₄) filtered and evaporated under reduced pressure. The residue was purified by column chromatography on silica gel, using an eluant of dichloromethane:methanol (99:1) to afford the title compound as a pink solid, 6.41 g.

¹H NMR (400 MHz, CD₃Cl₃): δ [ppm] 2.15 (2H, d), 2.30 (2H, d), 2.55 (2H, m), 3.15 (2H, d), 3.30 (2H, d), 3.50 (2H, s), 5.20 (2H, m), 5.65 (1H, m).

PREPARATION 18 tert-Butyl 3-{[(trifluoromethyl)sulphonyl]oxy}8azabicyclo[3.2.1]oct-2-ene-8-carboxylate

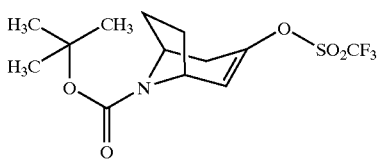

Lithium diisopropylamine (2M in hexanes) (36 ml, 71 mmol) was added to a stirred solution of the title compound from preparation 13 (13.41 g, 59 mmol) in tetrahydrofuran at −78° C., and the reaction stirred for 2 hours. A solution of N-(5-chloro-2-pyridyl)triflimide (25.71 g, 65.45 mmol) in tetrahydrofuran (60 ml) was added dropwise and the reaction was stirred for 2 hours at −78° C. then allowed to warm to room temperature. The solution was partitioned between dichloromethane and water, the layers separated and the organic phase was washed with brine, dried (MgSO₄) and evaporated under reduced pressure.

The residue was purified by column chromatography on basic activated aluminium oxide using an elution gradient of dichloromethane:methanol (100:0 to 98:2) to afford the title compound as a yellow oil, 14.1 g.

¹H NMR (400 MHz, CDCl₃): δ [ppm] 1.50 (9H, s), 1.70 (1H, bs), 1.90–2.10 (3H, bm), 2.25 (1H, bs), 3.00 (1H, m), 4.40 (2H, m), 6.10 (1H, s). LRMS: m/z 357 (MH⁺).

PREPARATION 19

8-(tert-Butyl) 3-methyl 8-azabicyclo[3.2.1]oct-2-ene-3,8-dicarboxylate

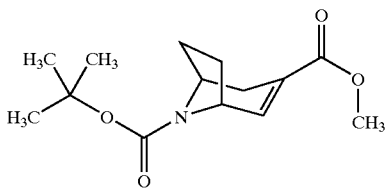

A mixture of the title compound from preparation 18 (14.1 g, 39.4 mmol), palladium acetate (270 mg), triphenylphosphine (620 mg, 2.37 mmol), triethylamine (11 ml, 78.9 mmol) and methanol (60 ml) was stirred in N,N-dimethylformamide (150 ml) at room temperature under a carbon monoxide atmosphere for 12 hours. The solution was partitioned between water and ethyl acetate, and the aqueous layer was extracted with ethyl acetate (3×). The combined organic solutions were washed with water, then brine, dried (MgSO₄), filtered and evaporated under reduced pressure. The oily residue was purified by column chromatography on silica gel, using an elution gradient of dichloromethane:methanol (100:0 to 95:5) to afford the title compound as a black oil, 10.4 g.

¹H NMR (400 MHz, CDCl₃): δ [ppm] 1.45 (9H, s), 1.6 (1H, m), 1.95 (2H, m), 2.10 (1H, d), 2.15 (1H, m), 2.90 (1H, bm), 3.70 (3H, s), 4.30–4.50 (2H, bm), 7.10 (1H, s). LRMS: m/z 535.2 (2MH⁺).

PREPARATION 20

8-(tert-Butoxycarbonyl)-8-azabicyclo[3.2.1]octane-3-exo-carboxylic Acid

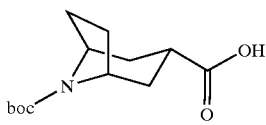

A mixture of the title compound from preparation 19 (10.4 g, 38.9 mmol) and Raney® nickel (4 g) in methanol (70 ml) was stirred under 60 psi of hydrogen for 7 hours at room temperature. The reaction was filtered through Celite® and the solvent removed under reduced pressure. The white solid obtained was stirred with sodium hydroxide (1.32 g, 33 mmol), water (10 ml) and tetrahydrofuran (70 ml) for hours at room temperature. The reaction mixture was partitioned between water and dichloromethane, the layers separated and the aqueous phase was extracted with dichloromethane (2×). The combined organic solutions were dried (MgSO₄), filtered and evaporated under reduced pressure.

The residue was purified by column chromatography on silica gel, using an eluant of dichloromethane:methanol (98:2) to afford the title compound as a colourless oil, 3.23 g ¹H NMR (400 MHz, CDCl₃): δ [ppm]: 1.45 (9H, s), 1.65 (2H, m), 1.59 (2H, m), 1.90 (2H, m), 2.00 (2H, m), 2.82 (1H, m), 4.25 (2H, bd). LRMS: m/z 279.0 (MNa⁺).

PREPARATION 21

8-Benzyl-8-azabicyclo[3.2.1]octan-3-one Oxime

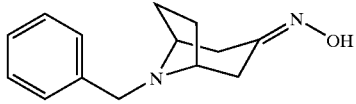

A mixture of the title compound from preparation 12 (17.72 g, 82 mmol), hydroxylamine hydrochloride (5.72 g, 82 mmol) and pyridine (7.2 ml, 89 mmol), were heated under reflux in ethanol (500 ml) for 20 hours. The reaction was allowed to cool to room temperature and diluted with saturated sodium carbonate solution. The mixture was filtered and the filtrate evaporated under reduced pressure. The residue was partitioned between dichloromethane and water, the layers separated and the aqueous layer extracted with dichloromethane (2×). The combined organic extracts were washed with brine, dried (MgSO₄), filtered and evaporated under reduced pressure to afford the title compound as a pale brown solid, 18.10 g.

¹H NMR (400 MHz, CDCl₃): δ [ppm] 1.45–1.56 (1H, m), 1.60–1.67 (1H, m), 1.96–2.07 (2H, bm), 2.12 (1H, m), 2.21 (1H, m), 2.57 (1H, m), 2.97 (1H, m), 3.32 (2H, m), 3.64 (2H, s), 7.06 (1H, s), 7.21–7.28 (1H, m), 7.32 (2H, m), 7.38 (2H, d). LRMS: m/z 231.2 (MH⁺).

PREPARATION 22 tert-Butyl 3-endo-(benzylamino)-8-azabicyclo[3.2.1]octane-8-carboxylate

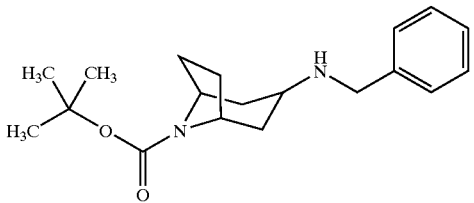

A solution of the title compound from preparation 13 (10.0 g, 44.4 mmol), benzylamine (4.85 ml, 49.7 mmol) and sodium triacetoxyborohydride (14.11 g, 66.6 mmol) was stirred for 16 hours at room temperature in a mixture of glacial acetic acid:dichloromethane (290 ml) (1:9). The solvents were evaporated under reduced pressure and the residue dissolved in ethyl acetate, washed with saturated sodium carbonate solution and then water. The organic solution was dried (MgSO₄), filtered and evaporated under reduced pressure. The residue was purified by column chromatography on silica gel using an eluant of dichloromethane:methanol:0.88 ammonia (98:2:0.25) to afford the title compound as a white solid, 7.00 g.

¹H NMR (400 MHz, CDCl₃): δ [ppm] 1.42–1.48 (11H, m), 1.52–1.61 (2H, m), 1.85–2.19 (5H, m), 2.95–3.03 (1H, m), 3.74 (2H, s), 4.03–4.23 (2H, m), 7.20–7.26 (1H, m), 7.26–7.32 (4H, m).

PREPARATION 23

9-Benzyl-3-oxa-9-azabicyclo[3.3.1]nonan-7-one Oxime

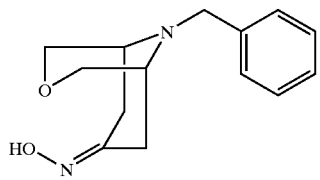

A solution of the title compound from preparation 15 (7 g, 30 mmol), hydroxylamine hydrochloride (2.31 g, 33 mmol) and pyridine (3 ml, 37 mmol) in ethanol (300 ml) was heated under reflux for 2 hours. The reaction was allowed to cool to room temperature and saturated aqueous sodium carbonate solution added. The mixture was filtered and the solvent removed under reduced pressure. The residue was partitioned between water and dichloromethane and the layers separated. The aqueous phase was extracted with further dichloromethane (2×). The combined organic solutions were washed with brine, dried (MgSO₄), filtered and evaporated under reduced pressure to afford the title compound as a pale brown solid, 6.6 g.

¹H NMR (400 MHz, CDCl₃): δ [ppm] 2.25 (1H, s), 2.32 (1H, s), 2.40 (2H, m), 2.70 (2H, m), 2.90 (4H, bs), 3.12 (1H, s), 3.18 (1H, s), 3.70 (2H, d), 3.78 (2H, d), 7.25–7.40 (10H, m). LRMS: m/z 247.1 (MH⁺).

PREPARATION 24 tert-Butyl 7-endo-(benzylamino)-3-oxa-9-azabicyclo[3.3.1]nonane-9-carboxylate

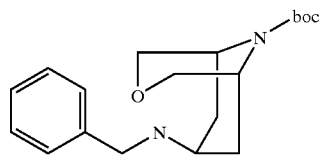

A mixture of the title compound from preparation 16 (9.80 g, 40.6 mmol), benzylamine (5.32 ml, 48.7 mmol), sodium triacetoxyborohydride (12.9 g, 60.9 mmol), and glacial acetic acid (2.5 ml) in dichloromethane (120 ml) was stirred at room temperature for 16 hours. The reaction mixture was basified to pH 8 using saturated aqueous sodium carbonate solution. The layers were separated and the aqueous phase was extracted with dichloromethane (2×). The combined organic solutions were washed with brine, dried (MgSO₄), filtered and evaporated under reduced pressure to afford the title compound as an oil, 2.45 g.

¹H NMR (400 MHz, CDCl₃): δ [ppm] 1.45 (9H, s), 1.75 (2H, d), 2.15 (2H, m), 2.72 (1H, m), 2.80 (1H, m), 3.58–3.72 (4H, m), 3.80 (2H, m), 3.95 (1H, d), 4.10 (1H, d), 7.18 (1H, m), 7.30 (4H, m). LRMS: m/z 333.3 (MH⁺).

PREPARATION 25

9-Allyl-3-thia-9-azabicyclo[3.3.1]nonan-7-one Oxime

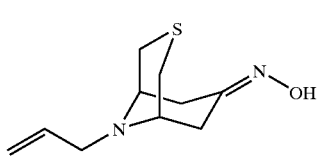

The title compound from preparation 17 (6.4 g, 32.4 mmol), hydroxylamine hydrochloride (2.48 g, 37.7 mmol) and pyridine (3.2 ml, 39 mmol) were heated under reflux in ethanol (140 ml) for 2 hours. The reaction was allowed to cool to room temperature and the solvent removed under reduced pressure. The residue was partitioned between saturated sodium carbonate solution and dichloromethane the layers separated and the aqueous phase extracted with dichloromethane (2×). The combined organic solutions were washed with brine, dried (MgSO$_4$), filtered and evaporated under reduced pressure to afford the title compound as a brown solid, 6.33 g.

$^1$H NMR (400 MHz, CDCl$_3$): δ [ppm] 2.15–2.45 (4H, m), 2.65 (1H, m), 3.1 (1H, d), 3.2–3.4 (6H, m), 5.1–5.3 (2H, m), 5.8 (1H, m), 8.0–8.6 (1H, bs). LRMS: m/z 212.9 (MH$^+$).

PREPARATION 26

8-Benzyl-8-azabicyclo[3.2.1]octan-3-exo-amine

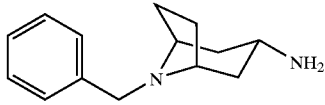

A solution of the title compound from preparation 21 (18.10 g, 79 mmol) in pentanol (500 ml) was heated under reflux with portionwise addition of sodium (22.0 g, 957 mmol) over 2½ hours. The reaction was then heated under reflux for a further 2 hours, then cooled to 0° C. in an ice bath and water added until no more hydrogen gas evolved. The mixture was acidified using 6N hydrochloric acid and the phases separated. The organic layer was extracted with 6N hydrochloric acid (3×), the combined aqueous extracts were basified to pH12 with sodium hydroxide pellets (400 g) and the aqueous solution extracted with ethyl acetate (3×). The combined organic solutions were dried (MgSO$_4$), filtered and evaporated under reduced pressure to afford the title compound, 15.65 g.

$^1$H NMR (400 MHz, CDCl$_3$): δ [ppm] 1.20–1.40 (2H, bm), 1.48 (2H, m), 1.58 (2H, d), 1.64–1.76 (2H, bm), 2.00 (2H, bm), 2.95 (1H, m), 3.19 (2H, bs), 3.57 (2H, s), 7.18–7.26 (1H, m), 7.30 (2H, m), 7.37 (2H, d). LRMS: m/z 217.3 (MH$^+$).

PREPARATION 27 tert-Butyl 3-endo-Amino-8-azabicyclo[3.2.1]octane-8-carboxylate

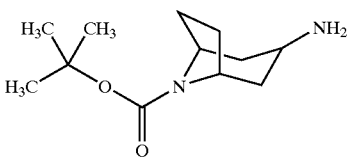

A mixture of the title compound from preparation 22 (7.00 g, 22.1 mmol), ammonium formate (7.00 g, 111 mmol) and 20% w/w palladium hydroxide on carbon (700 mg) in ethanol (200 ml) was heated to 50° C., until gas evolution ceased. The cooled mixture was filtered through Arbocel® and the filtrate evaporated under reduced pressure. The residue was purified by column chromatography on silica gel using an elution gradient of dichloromethane:methanol:0.88 ammonia (98:2:0.25 to 95:5:0.5) to afford the title compound as a colourless oil, 4.70 g.

LRMS: m/z 227.2 (MH$^+$).

PREPARATION 28

9-Benzyl-3-exo-oxa-9-azabicyclo[3.3.1]non-7-yl-amine

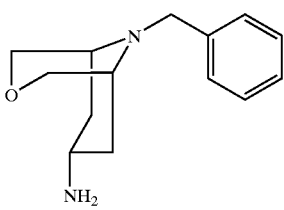

The title compound was obtained (64%) from the title compound from preparation 23, using a similar procedure to that described in preparation 26.

$^1$H NMR (300 MHz, CDCl$_3$): δ [ppm] 1.70 (4H, m), 2.70 (2H, s), 3.70 (3H, m), 3.80–3.95 (6H, m), 7.20–7.40 (5H, m). LRMS: m/z 233.1(MH$^+$).

PREPARATION 29 tert-Butyl 7-endo-amino-3-oxa-9-azabicyclo[3.3.1]nonane-9-carboxylate

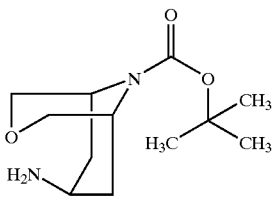

A mixture of the title compound from preparation 24 (2.45 g, 7.7 mmol) and 10% palladium on carbon (300 mg) in ethyl acetate (40 ml) was hydrogenated at 50 psi for 36 hours at 50° C. The cooled reaction was filtered through Arbocel® and the solvent removed under reduced pressure. The residue was purified by column chromatography on silica gel, using an eluant of dichloromethane:methanol:0.88 ammonia (79:20:1) to afford the title compound as a colourless oil, 1.44 g.

$^1$H NMR (400 MHz, CDCl$_3$): δ [ppm] 1.45 (9H, s), 1.55 (2H, m), 2.18–2.30 (2H, m), 3.0 (1H, m), 3.60–3.78 (4H, m), 3.97 (1H, m), 4.10 (1H, m). LRMS: m/z 242.5 (MH$^+$).

PREPARATION 30

9-Allyl-3-thia-9-azabicyclo[3.3.1]non-7-yl-exo-amine

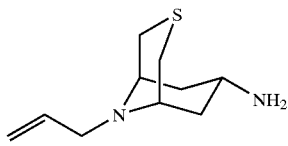

The title compound from preparation 25 (5.33 g, 25.1 mmol) was heated under reflux in pentanol (200 ml) with portionwise addition of sodium (5.8 g, 251.1 mmol) over 1 hour. The reaction was then heated under reflux for a further 2 hours, then cooled to 0° C. in an ice bath and water added until no more hydrogen gas evolved. The mixture was acidified with 6N hydrochloric acid, the layers separated and the organic phase extracted with 6N hydrochloric acid (3×). The combined aqueous extracts were basified to pH12 using sodium hydroxide pellets and the solution extracted with dichloromethane (2×). The combined organic layers were dried (MgSO$_4$), filtered and evaporated under reduced pressure and freeze-dried from water/acetonitrile to afford the title compound as a brown powder, 4.73 g.

$^1$H NMR (400 MHz, CDCl$_3$): δ [ppm] 1.30–1.70 (4H, m), 1.90 (2H, m), 2.10 (2H, d), 3.06–4.42 (6H, m), 4.62 (1H, m), 5.0–5.23 (2H, m), 5.80 (1H, m). LRMS: m/z 199.1 (MH$^+$).

PREPARATION 31

Ethyl exo 3-(2-nitroanilino)-8-azabicyclo[3.2.1]octane-8-carboxylate

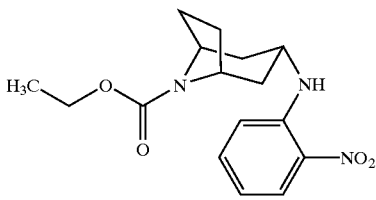

A mixture of the title compound from preparation 11 (12.7 g, 64.1 mmol), potassium carbonate (9.0 g, 65.1 mmol) and 1-fluoro-2-nitrobenzene (7.44 ml, 70.5 mmol) in N,N-dimethylformamide (30 ml) was heated at 150° C. for 2½ hours. The cooled reaction was concentrated under reduced pressure and the residue partitioned between water and ethyl acetate. The phases were separated, the organic layer dried (MgSO$_4$), filtered and evaporated under reduced pressure. The crude product was purified by column chromatography on silica gel using an elution gradient of dichloromethane:methanol (100:0 to 98:2) to afford the title compound as a solid, 16.9 g.

$^1$H-NMR (300 MHz, CDCl$_3$): δ [ppm] 1.32 (3H, t), 1.60–1.80 (4H, m), 2.13 (4H, m), 4.02 (1H, m), 4.19 (2H, q), 4.41 (2H, bs), 6.62 (1H, m), 6.86 (1H, d), 7.42 (1H, m), 7.90 (1H, d), 8.16 (1H, m). LRMS: m/z 320 (MH$^+$).

PREPARATION 32

N-(8-Benzyl-8-azabicyclo[3.2.1]oct-3-yl)-exo-N-(2-nitrophenyl)amine

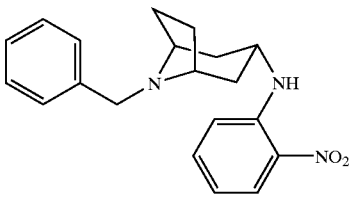

The title compound from preparation 26 (8.47 g, 39 mmol), 1-fluoro-2-nitrobenzene (4.55 ml, 43 mmol) and potassium carbonate (5.50 g, 40 mmol) were heated to 120° C. in N,N-dimethylformamide for 4½ hours. The reaction was allowed to cool to room temperature and concentrated under reduced pressure. The residue was taken up in ethyl acetate and washed with water. The organic layer was dried (MgSO$_4$), filtered and evaporated under reduced pressure. The residue was purified by column chromatography on silica gel, using an eluant of dichloromethane:methanol:0.88 ammonia (98:2:0.25) to afford the title compound as a bright orange/yellow solid, 8.80 g.

$^1$H NMR (400 MHz, CDCl$_3$): δ [ppm] 1.66–1.80 (4H, m), 1.92–2.02 (2H, m), 2.08–2.20 (2H, m), 3.32 (2H, s), 3.60 (2H, s), 3.85 (1H, m), 6.60 (1H, m), 6.87 (1H, d), 7.20–7.28 (1H, m), 7.32 (2H, m), 7.38 (3H, m), 7.97 (1H, bd), 8.16 (1H, d). LRMS: m/z 338.5 (MH$^+$).

PREPARATION 33 tert-Butyl 3-endo-(2-nitroanilino)-8-azabicyclo[3.2.1]octane-8-carboxylate

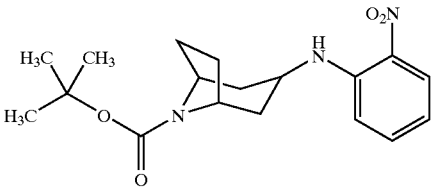

A mixture of the title compound from preparation 27 (4.69 g, 20.7 mmol), 1-fluoro-2-nitrobenzene (3.21 g, 22.7 mmol) and potassium carbonate (3.21 g, 23.3 mmol) were heated for 2 hours in N,N-dimethylformamide (75 ml) at 100° C. The solvent was removed under reduced pressure and the residue partitioned between ethyl acetate and water. The layers were separated and the aqueous phase extracted with ethyl acetate. The organic solutions were dried (MgSO$_4$), filtered and evaporated under reduced pressure to afford the title compound as a bright orange oil, which crystallized on standing, 7.50 g.

$^1$H NMR (400 MHz, CDCl$_3$): δ [ppm] 1.48 (9H, s), 1.80–1.87 (2H, m), 2.00–2.16 (4H, m), 2.16–2.41 (2H, m), 3.87–3.94 (1H, m), 4.14–4.39 (2H, m), 6.60–6.74 (1H, m), 6.69–6.74 (1H, d), 7.39–7.45 (1H, m), 8.16–8.21 (1H, d), 8.68–8.77 (1H, m).

PREPARATION 34

N-[(1R,5S)-3-Benzyl-3-azabicyclo[3.1.0]hex-6-yl]-N-(2-nitrophenyl)amine

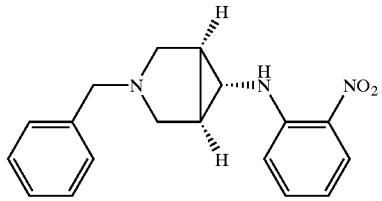

Potassium carbonate (4.59 g, 33.2 mmol), followed by 1-fluoro-2-nitrobenzene (1.87 g, 13.3 mmol) were added to a solution of (1R,5S)-3-benzyl-3-azabicyclo[3.1.0]hex-6-ylamine (WO 9318001), (2.50 g, 13.3 mmol) in N,N-dimethylformamide (40 ml), and the reaction mixture stirred at 130° C. for 18 hours. The cooled mixture was filtered, and the filtrate concentrated under reduced pressure. The residue was partitioned between ethyl acetate and water, the phases separated, and the aqueous layer extracted with ethyl acetate (3×). The combined organic solutions were washed with brine, dried (MgSO$_4$), filtered and evaporated under reduced pressure. The residual brown oil was purified by column chromatography on silica gel using an elution gradient of pentane:ethyl acetate (95:5 to 90:10) to afford the title compound as an orange crystalline foam, 3.11 g.

$^1$H NMR (400 MHz, CDCl$_3$): δ [ppm] 1.64 (2H, s), 2.54 (2H, m), 2.96 (1H, s), 3.18 (2H, m), 3.62 (2H, s), 6.68 (1H, m), 7.19 (1H, m), 7.29 (5H, m), 7.43 (1H, m), 7.96 (1H, bs), 8.16 (1H, m). LRMS: m/z 309.8 (M$^+$).

PREPARATION 35

N-(9-Benzyl-3-oxa-9-azabicyclo[3.3.1]non-7-yl)-N-(2-nitrophenyl)-exo-amine

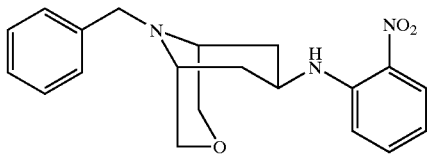

The title compound was obtained (63%) as a bright orange/yellow solid, from the compound of preparation 28, following the procedure described in preparation 32.

$^1$H NMR (400 MHz, CDCl$_3$): δ [ppm] 1.90–2.10 (4H, m), 1.90 (2H, s), 3.82 (2H, d), 3.90 (2H, s), 3.97 (2H, d), 4.90 (1H, m), 6.60 (1H, m), 7.00 (1H, d), 7.30 (1H, m), 7.35 (2H, m), 7.40 (3H, m), 8.00 (1H, d), 8.18 (1H, d). LRMS: m/z 354.1 (MH$^+$).

PREPARATION 36 tert-Butyl 7-endo-(2-nitroanilino)-3-oxa-9-azabicyclo[3.3.1]nonane-9-carboxylate

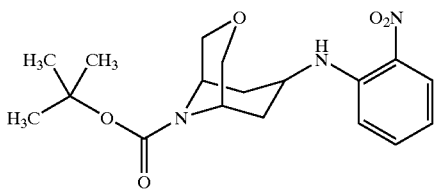

The title compound was obtained as a yellow orange oil (99%), from the title compound of preparation 29, and 1-fluoro-2-nitrobenzene, following the procedure described in preparation 32.

$^1$H NMR (400 MHz, CDCl$_3$): δ [ppm] 1.50 (9H, s), 1.80 (2H, m), 2.38 (2H, m), 3.75 (2H, m), 3.85 (2H, m), 3.95 (1H, m), 4.10 (1H, m), 4.18 (1H, m), 6.60 (1H, m), 6.80 (1H, d), 7.40 (1H, m), 8.18 (1H, d), 9.22 (1H, d). LRMS: m/z 364.1 (MH$^+$).

PREPARATION 37

N-(9-Allyl-3-thia-9-azabicyclo[3.3.1]non-7-yl)-N-(2-nitrophenyl)-exo-amine

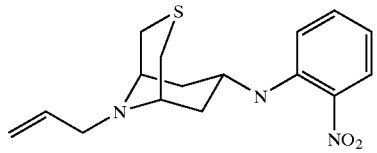

The title compound was obtained as a yellow orange oil (53%), from the title compound of preparation 30, and 1-fluoro-2-nitrobenzene, following the procedure described in preparation 32.

$^1$H NMR (400 MHz, CDCl$_3$): δ [ppm] 1.90 (2H, m), 2.10–2.32 (4H, m), 3.25 (2H, s), 3.40 (4H, m), 5.11–5.3 (2H, m), 5.80 (2H, m), 6.62 (1H, m), 7.0 (1H, d), 7.40 (1H, m), 7.91 (1H, d), 8.15 (1H, d). LRMS: m/z 320.3 (MH$^+$).

PREPARATION 38

Ethyl 3-exo-(2-Aminoanilino)-8-azabicyclo[3.2.1]octane-8-carboxylate

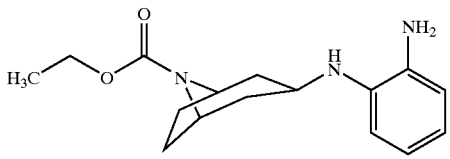

A mixture of the title compound from preparation 31 (16.9 g, 52.9 mmol), and 10% palladium on charcoal (2.0 g) in methanol (50 ml) and ethyl acetate (300 ml), was hydrogenated at 1 atm of hydrogen, and room temperature for 15 hours. The reaction was filtered through Arbocel®, and the filtrate evaporated under reduced pressure to afford the title compound as a dark solid, 14.7 g.

$^1$H-NMR (300 MHz, CDCl$_3$): δ [ppm] 1.30 (3H, t), 1.43–1.63 (2H, m), 1.79 (2H, m), 2.00–2.18 (4H, m), 3.18–3.35 (2H, bs), 3.78 (1H, m), 4.15 (2H, q), 4.39 (2H, bs), 6.65–6.80 (4H, m). LRMS: m/z 290 (MH⁺).

PREPARATION 39

N¹-(8-Benzyl-8-azabicyclo[3.2.1]oct-3-yl)-exo-1,2-benzenediamine

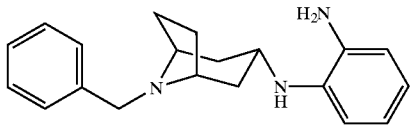

A mixture of the title compound from preparation 32 (8.80 g, 26 mmol) and 10% palladium on carbon (1.0 g) in ethyl acetate (300 ml) and methanol (50 ml) was stirred under 1 atmosphere of hydrogen for 3 hours at room temperature. The reaction mixture was filtered through Arbocel® and the filtrate removed under reduced pressure to afford the title compound as a dark brown oil, 7.23 g.

¹H NMR (400 MHz, CDCl₃): δ [ppm] 1.59 (2H, m), 1.67–1.76 (2H, m), 1.92–2.02 (2H, m), 2.06–2.15 (2H, m), 3.27 (3H, m), 3.52–3.67 (3H, m), 6.60–6.72 (3H, m), 6.78 (1H, m), 7.20–7.28 (1H, m), 7.32 (2H, m), 7.38 (2H, d). LRMS: m/z 308.6 (MH⁺).

PREPARATION 40

N-endo-(2-Aminophenyl)-N-(8-azabicyclo[3.2.1]oct-3-yl)amine

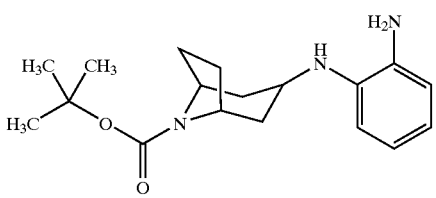

Tin (II) chloride dihydrate (25.0 g, 111 mmol) was added in five equal portions of 5 g to a solution of the title compound from preparation 33 (7.50 g, 21.6 mmol) in ethanol (200 ml) over a period of 25 minutes and the mixture was heated under reflux for 2 hours. The cooled mixture was concentrated under reduced pressure and the residue treated with 6M sodium hydroxide solution until basic. Ethyl acetate was added, the mixture filtered through Celite®, and the layers separated. The organic phase was dried (MgSO₄), filtered and evaporated under reduced pressure to afford the title compound as a colourless oil, 3.10 g.

LRMS: m/z 218.3 (MH⁺).

PREPARATION 41

N-(2-Aminophenyl)-N-(3-benzyl-3-azabicyclo[3.1.0]hex-6-yl)amine

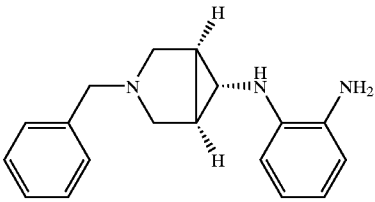

Iron powder (2.44 g, 43.6 mmol) and calcium chloride (269 mg, 2.42 mmol) were added to a solution of the title compound from preparation 34 (1.50 g, 4.85 mmol), and the reaction heated under reflux for 18 hours. The cooled mixture was filtered through Celite®, washing through with ethanol, the filtrate evaporated under reduced pressure, and azeotroped with toluene. The residue was purified by column chromatography on silica gel using dichloromethane:methanol:0.88 ammonia (97.5:2.5:0.25) as eluant to afford the title compound as a dark brown oil, 751 mg.

¹H NMR (400 MHz, CDCl₃): δ [ppm] 1.58 (2H, m), 2.49 (2H, m), 2.81 (1H, s), 3.14 (2H, m), 3.48 (2H, s), 3.60 (2H, s), 6.68 (2H, m), 6.82 (1H, m), 6.95 (1H, m), 7.26 (5H, m). LRMS: m/z 280.8 (MH⁺).

PREPARATION 42

N¹-(9-Benzyl-3-oxa-9-azabicyclo[3.3.1]non-7-yl)-1,2-exo-benzenediamine

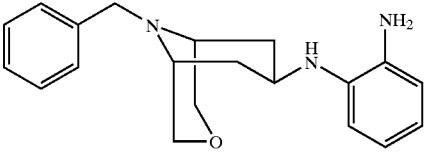

A mixture of the title compound from preparation 35 (4 g, 11 mmol) and 10% palladium on carbon (0.5 g) in ethyl acetate (60 ml) was hydrogenated under 1 atmosphere of hydrogen for 4 hours at room temperature. The reaction was filtered through Arbocel® and the solvent removed under reduced pressure to afford the title compound as a white solid, 2.87 g.

¹H NMR (400 MHz, CDCl₃): δ [ppm] 1.80 (2H, m), 2.08 (2H, m), 2.78 (2H, s), 3.17 (1H, s), 3.30 (2H, s), 3.80 (2H, d), 3.90 (2H, s), 3.95 (2H, d), 4.60 (1H, m), 6.65 (1H, m), 6.70 (1H, m), 6.80 (2H, m), 7.25 (1H, m), 7.30 (2H, m), 7.40 (2H, d). LRMS: m/z 323.7 & 325.3 (MH⁺).

PREPARATION 43 tert-Butyl 7-endo-(2-aminoanilino)-3-oxa-9-azabicyclo[3.3.1]nonane-9-carboxylate

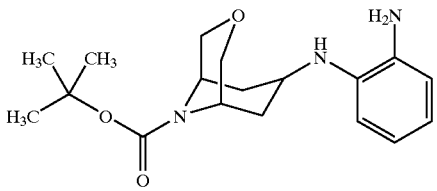

The title compound was obtained as a dark oil (97%) from the title compound from preparation 36, following the procedure described in preparation 42.

$^1$H NMR (400 MHz, CDCl$_3$): δ [ppm] 1.00 (2H, bs), 1.50 (9H, s), 1.60 (1H, s), 1.85 (2H, d), 2.15–2.32 (2H, m), 3.70–3.85 (5H, m), 4.00 (1H, bs), 4.10 (1H, bs), 6.62 (2H, m), 6.70 (1H, m), 6.78 (1H, m). LRMS: m/z 334.1 (MH$^+$).

PREPARATION 44

N$^1$-(9-Allyl-3-thia-9-azabicyclo[3.3.1]non-7-yl)-1,2-exo-benzenediamine

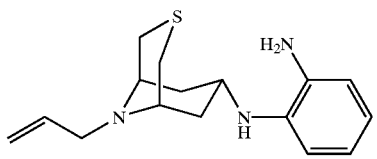

A mixture of the title compound from preparation 37 (3.9 g 12.211 mmol), iron powder (10 g) and glacial acetic acid (10 ml) was heated to reflux in water:ethanol (2:1 150 ml) for 1 hour. The reaction was allowed to cool to room temperature, basified with 1M sodium hydroxide solution and diluted with ethyl acetate. The mixture was filtered, the layers separated and the aqueous phase extracted with ethyl acetate (3×). The combined organic solutions were washed with brine, dried (MgSO$_4$), filtered and evaporated under reduced pressure to afford the title compound as a brown oil, 3.7 g.

$^1$H NMR (400 MHz, CDCl$_3$): δ [ppm] 1.77 (2H, m), 2.10–2.25 (4H, m), 2.45–3.20 (3H, bs), 3.20–3.45 (6H, m), 5.10–5.30 (2H, m), 5.40 (1H, m), 5.80 (1H, m), 6.60–6.85 (4H, m). LRMS: m/z 290.1 (MH$^+$).

PREPARATION 45

Ethyl 3-exo-(2-methyl-1H-benzimidazol-1-yl)-8-azabicyclo[3.2.1]octane-8-carboxylate

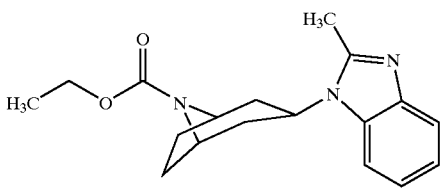

A solution of the the title compound from preparation 38 (14.7 g, 50.8 mmol) in triethylorthoacetate (200 ml) was heated under reflux for 18 hours. The cooled reaction was evaporated under reduced pressure to afford the title compound as a brown oil, that crystallised on standing, 15.9 g.

$^1$H-NMR (300 MHz, CDCl$_3$): δ [ppm] 1.19–1.31 (2H, m), 1.40 (3H, m), 1.82 (4H, m), 2.20 (2H, m), 2.62 (3H, s), 4.31 (2H, m), 4.57 (2H, bs), 4.74 (1H, m), 7.18 (2H, m), 7.49 (1H, m), 7.64 (1H, m). LRMS: m/z 314 (MH$^+$).

PREPARATION 46

1-(8-Benzyl-8-azabicyclo[3.2.1]oct-3-yl)-exo-2-methyl-1H-benzimidazole

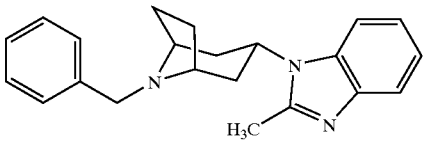

A mixture of the title compound from preparation 39 (17.00 g, 55 mmol) was heated under reflux in triethyl orthoacetate (250 ml) for 16 hours, then cooled. Excess triethyl orthoacetate was evaporated under reduced pressure and the residue and 4-toluenesulphonic acid (3.00 g) were heated under reflux in toluene (250 ml) for 18 hours. The cooled mixture was evaporated under reduced pressure, the residue suspended in dichloromethane, and washed with saturated sodium carbonate solution, water and brine. The organic solution was dried (MgSO$_4$), filtered and evaporated under reduced pressure to afford the title compound, 18.32 g.

$^1$H NMR (400 MHz, CDCl$_3$): δ [ppm] 1.65–1.74 (2H, m), 1.74–1.82 (2H, m), 2.14–2.28 (2H, m), 2.58–2.72 (5H, m), 3.40 (2H, bs), 3.66 (2H, s), 4.56 (1H, m), 7.16–7.32 (3H, m), 7.37 (2H, m), 7.47 (2H, d), 7.66 (2H, m). LRMS: m/z 331.9 (MH$^+$).

PREPARATION 47

1-(3-Benzyl-3-azabicyclo[3.1.0]hex-6-yl)-2-methyl-1H-benzimidazole

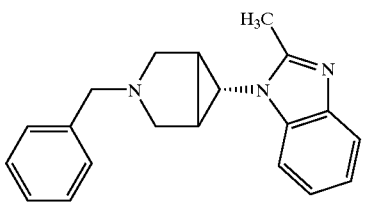

A solution of the title compound from preparation 41 (751 mg, 2.69 mmol) in acetic anhydride (10 ml) was stirred at 130° C. for 18 hours. The cooled solution was basified to pH 8 using saturated aqueous sodium bicarbonate solution, and this mixture extracted with ethyl acetate (3×). The combined organic extracts were washed with brine, dried (MgSO$_4$), filtered and evaporated under reduced pressure. The residual brown oil was purified by column chromatography on silica gel using dichloromethane:methanol:0.88 ammonia (97.5:2.5:0.25) as eluant to afford the title compound as a brown oil, 200 mg.

$^1$H NMR (300 MHz, CDCl$_3$): δ [ppm] 2.02 (2H, s), 2.60 (5H, m), 3.34 (2H, m), 3.59 (1H, s), 3.66 (2H, s), 7.18–7.43 (8H, m), 7.64 (1H, m). LRMS: m/z 304.0 (MH$^+$).

PREPARATION 48 tert-Butyl 3-(3-exo-{4-[(Methylsulphonyl)amino]benzyl}-1,2,4-oxadiazol-5-yl)-8-azabicyclo[3.2.1]octane-8-carboxylate

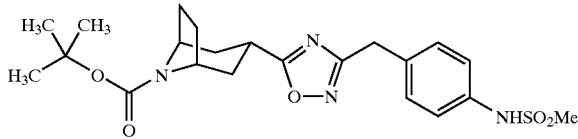

A solution of the title compound from preparation 20 (1.0 g, 3.91 mmol) in dichloromethane (10 ml) was treated with N-ethyldiisopropylamine (815 µl, 4.69 mmol). Bis(tetramethylene)fluoroformamidinium hexafluorophosphate (1.48 g, 4.68 mmol) was added and the solution stirred at room temperature for 1 hour. N-Hydroxy-2-{4-[(methylsulphonyl)amino]phenyl}ethanimidic acid (J.Med.Chem. 1993; 36(11); 1529), (1.14 g, 4.69 mmol) and N-ethyldiisopropylamine (680 µl, 3.91 mmol) were added, the resulting solution was stirred at room temperature for 48 hours, then heated to 50° C. to concentrate the solution. Dioxan (20 ml) was added, the solution was heated to 120° C. for 3 hours, cooled to room temperature, diluted with ethyl acetate and basified with 10% aqueous sodium bicarbonate solution. The layers were separated, the aqueous phase extracted with ethyl acetate, and the combined organic solutions were dried (MgSO$_4$), filtered and evaporated under reduced pressure.

The residue was purified by column chromatography on silica gel, using an eluant of dichloromethane:methanol (98:2) to afford the title compound as an oil, 1.48 g $^1$H NMR (400 MHz, CDCl$_3$): δ [ppm] 1.45 (9H, s), 1.65 (3H, m), 1.75 (3H, m), 1.95–2.10 (6H, m), 3.65 (2H, s), 4.00 (2H, s), 6.90 (1H, bs), 7.20 (2H, d), 7.30 (2H, m).

PREPARATION 49

9-Benzyl-7-(2-methyl-exo-1H-benzimidazol-1-yl)-3-oxa-7-azabicyclo[3.3.1]nonane

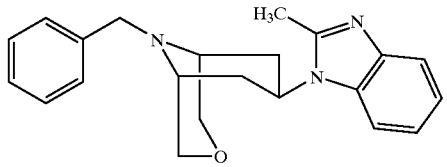

A mixture of the title compound from preparation 42 (2.87 g, 8.9 mmol) in triethyl orthoacetate (20 ml) was heated under reflux for 8 hours. The cooled reaction mixture was evaporated under reduced pressure. The oily residue was purified by column chromatography on silica gel, using ethyl acetate:pentane (20:80) as eluant to afford the title compound as a yellow oil, 1.47 g.

$^1$H NMR (400 MHz, CDCl$_3$): δ [ppm] 1.78 (2H, m), 1.90 (3H, s), 2.05 (2H, m), 2.75 (2H, s), 3.80 (2H, d), 3.90 (2H, s), 3.95 (2H, d), 4.60 (1H, m), 6.60 (2H, m), 6.80 (1H, d), 6.90 (1H, m), 7.23 (1H, m), 7.30 (2H, m), 7.38 (2H, m). LRMS: m/z 348.1 (MH$^+$).

PREPARATION 50 tert-Butyl 7-(2-methyl-endo-1H-benzimidazol-1-yl)-3-oxa-9-azabicyclo[3.3.1]nonane-9-carboxylate

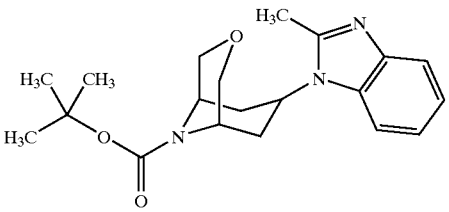

A solution of the title compound from preparation 43 (1.88 g, 5.6 mmol) in triethyl orthoacetate (20 ml) was heated under reflux for 7 hours. The cooled mixture was concentrated under reduced pressure and the residue redissolved in toluene (250 ml). 4-Toluenesulphonic acid (300 mg, 1.57 mmol) was added and the reaction heated under reflux for 2 hours, then cooled. The solvent was evaporated under reduced pressure, the residue suspended in ethyl acetate, and washed with 10% aqueous sodium bicarbonate solution. The organic layer was dried (Na$_2$SO$_4$), filtered and evaporated under reduced pressure to afford the title compound, 1.64 g.

Found: C, 67.00; H, 7.67; N, 11.64%. C$_{20}$H$_{27}$N$_3$O$_3$ requires C, 67.20; H, 7.67; N 11.64%. $^1$H NMR (400 MHz, CDCl$_3$): δ [ppm] 1.30 (9H, s), 2.30 (2H, m), 2.55 (3H, s), 2.60 (2H, m), 3.62–3.80 (4H, m), 4.12 (1H, m), 4.25 (1H, d), 4.40 (1H, d), 7.20 (2H, m), 7.65 (2H, m). LRMS: m/z 358.2 (MH$^+$).

PREPARATION 51

9-Allyl-7-(2-methyl-exo-1H-benzimidazol-1-yl)-3-thia-9-azabicyclo[3.3.1]nonane

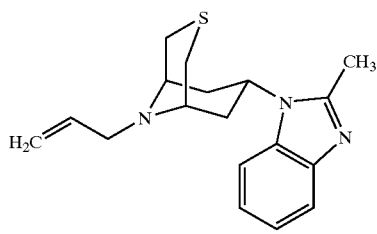

A solution of the title compound from preparation 44 (3.68 g, 12.21 mmol) was heated under reflux in triethyl orthoacetate (20 ml) for 16 hours. Excess triethyl orthoacetate was evaporated under reduced pressure. The resulting oil was purified by column chromatography on silica gel, using an eluant of dichloromethane:methanol (99.5:1). The product was suspended in toluene (80 ml) para-toluenesulfonic acid (catalytic) was added, and the mixture heated at reflux for 3 hours, then cooled and concentrated under reduced pressure. The residue was dissolved in ethyl acetate and washed with aqueous saturated sodium bicarbonate solution, water and brine. The organic layer was dried (MgSO$_4$), filtered and evaporated under reduced pressure to afford the title compound as a tan-coloured solid, 1.25 g.

Found: C, 67.81; H, 7.44; N, 12.86%. C$_{18}$H$_{23}$N$_3$S;0.35H$_2$O requires C, 67.61; H, 7.47; N, 13.14%. $^1$H NMR (400 MHz, CDCl$_3$): δ [ppm] 1.50 (2H, m), 2.25

(2H, d), 2.63 (3H, s), 2.80–2.90 (2H, m ), 3.30–3.60 (6H, m), 5.10–5.40 (2H, m), 5.85 (1H, m), 6.75 (1H, m), 7.20 (2H, m), 7.60 (1H, m), 7.71 (1H, m). LRMS: m/z 314 (M+H⁺).

PREPARATION 52 exo 1-(8-Azabicyclo[3.2.1]oct-3-yl)-2-methyl-1H-benzimidazole

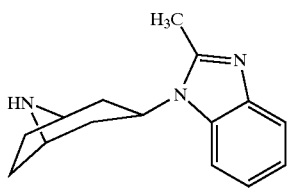

A mixture of the title compound of preparation 45 (1.3 g, 4.15 mmol) in hydrochloric acid (6N, 30 ml) was heated to 120° C. for 20 hours. The cooled reaction mixture was basified with sodium hydroxide solution (15%) and the solution extracted with dichloromethane (×4). The combined organic extracts were dried (MgSO₄), filtered and evaporated under reduced pressure. The crude product was purified by column chromatography on silica gel using dichloromethane:methanol:0.88 ammonia (95:5:0.5) as the eluant to afford the title compound as a solid, 620 mg.

¹H-NMR (300 MHz, CDCl₃): δ [ppm] 1.64–1.98 (6H, m), 2.49 (2H, m), 2.59 (3H, s), 3.66 (2H, m), 4.50 (1H, m), 7.12 (2H, m), 7.51 (1H, m), 7.63 (1H, m). LRMS: m/z 242 (MH⁺).

ALTERNATIVE METHOD

Ammonium formate (2.82 g, 44.8 mmol) was added the title compound from preparation 46 (2.84 g, 8.6 mmol) and palladium hydroxide (2.0 g) in ethanol (60 ml). The mixture was heated under reflux for 1½ hours and the reaction was allowed to cool to room temperature and filtered through Arbocel®. The solvent was evaporated under reduced pressure and the residue purified by column chromatography on silica gel, using an elution gradient of dichloromethane:methanol:0.88 ammonia (98:2:0.25 to 95:5:0.5) to afford the title compound, 1.74 g.

¹H NMR (400 MHz, CDCl₃): δ [ppm] 1.74–1.87 (4H, m), 1.90–2.02 (2H, m), 2.53 (2H, m), 2.63 (3H, s), 3.76 (2H, bm), 4.56 (1H, m), 7.13–7.25 (2H, m), 7.52–7.57 (1H, m), 7.64–7.71 (1H, m). LRMS: m/z 242.1 (MH⁺).

PREPARATION 53 endo 1-(8-Azabicyclo[3.2.1]oct-3-yl)-2-methyl-1H-benzimidazole Dihydrochloride

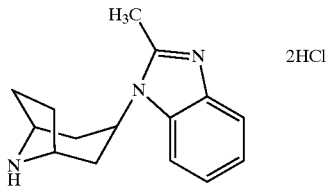

A solution of the title compound from preparation 40 (2.0 g, 9.2 mmol) and triethyl orthoacetate (50 ml) were heated under reflux at 150° C. for 1 hour. The cooled mixture was concentrated under reduced pressure. The residue was dissolved in ethyl acetate and washed with saturated aqueous sodium carbonate solution then water. The organic solution was dried (MgSO₄), filtered and evaporated under reduced pressure. The residue was dissolved in 50 ml of 2.25M methanolic hydrochloric acid and heated under reflux for 24 hours. The solvent was removed under reduced pressure to afford the title compound as an off white solid, 1.05 g.

¹H NMR (400 MHz, D₂O): δ [ppm] 2.20–2.42 (6H, m), 2.71–2.84 (2H, m), 2.80 (3H, s), 4.21–4.27 (2H, m), 4.94–5.06 (1H, m), 7.50–7.55 (2H, m), 7.68–7.74 (1H, m), 7.75 (1H, m).

PREPARATION 54 endo-1-(8-Azabicyclo[3.2.1]oct-3-yl)-1H-benzimidazole

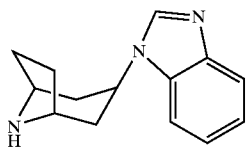

A solution of the title compound from preparation 40 (1.10 g, 5.06 mmol) in 30 ml of triethyl orthoformate was heated under reflux for 3 hours. The solvent was removed under reduced pressure and the residue was heated under reflux for 1 hour in 30 ml of dioxan:concentrated hydrochloric acid (2:1). The solvents were removed under reduced pressure. The residue was basified with saturated sodium carbonate solution and extracted with dichloromethane (×3). The combined organic solutions were dried (MgSO₄), filtered and evaporated under reduced pressure. The residue was purified using column chromatography on silica gel using an eluant of dichloromethane:methanol:0.88 ammonia (98:2:0.25) to afford the title compound as a gum, 540 mg.

LRMS: m/z 228 (MH⁺)

PREPARATION 55

1-(3-Azabicyclo[3.1.0]hex-6-yl)-2-methyl-1H-benzimidazole

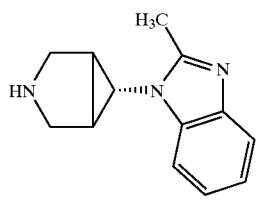

A mixture of the title compound from preparation 47 (200 mg, 0.70 mmol), ammonium formate (1.4 g, 22.2 mmol), and 10% palladium on carbon (90 mg) in methanol (10 ml) was heated under reflux for 2 hours. The cooled reaction mixture was filtered through Celite®, washing through with additional methanol. The filtrate was evaporated under reduced pressure to give a yellow oil. The crude product was purified by column chromatography on silica gel using dichloromethane:methanol:0.88 ammonia (95:5:1) as eluant to afford the title compound, 56 mg.

¹H NMR (400 MHz, CDCl₃): δ [ppm] 2.12 (2H, m), 2.63 (4H, m), 3.02 (1H, m), 3.18 (2H, d), 3.50 (1H, s), 7.22 (2H, m), 7.42 (1H, m), 7.66 (1H, m). LRMS: m/z 214.5 (MH⁺).

PREPARATION 56

N-(4-{[5-exo-(8-Azabicyclo[3.2.1]oct-3-yl)-1.2.4-oxadiazol-3-yl]methyl}phenyl)methanesulphonamide

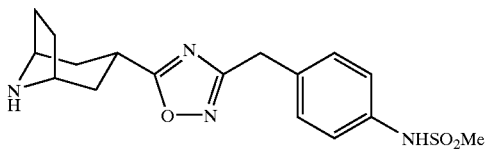

A solution of the title compound from preparation 48 (1.48g, 3.20 mmol) in 4M hydrochloric acid in dioxan (15 ml) was stirred for 2 hours at room temperature. The solvent was evaporated under reduced pressure and the oily residue partitioned between dichloromethane and sodium carbonate solution. The phases were separated and the aqueous layer was extracted with dichloromethane (2×). The combined organic solutions were dried (MgSO$_4$), filtered and evaporated under reduced pressure.

The residue was purified by column chromatography on silica gel, using an elution gradient of dichloromethane:methanol:0.88 ammonia (98:2:0 to 89:10:1) to afford the title compound as a brown solid, 375 mg.

$^1$H NMR (400 MHz, CDCl$_3$): δ [ppm] 1.70 (4H, m), 1.90 (6H, m), 3.00 (3H, s), 3.30 (1H, m), 3.58 (1H, bs), 3.62 (1H, m), 4.00 (2H, s), 7.15 (2H, d), 7.30 (2H, m). LRMS: m/z 363.1 (MH$^+$).

PREPARATION 57

7-(exo-2-Methyl-1H-benzimidazol-1-yl)-3-oxa-9-azabicyclo[3.3.1]nonane

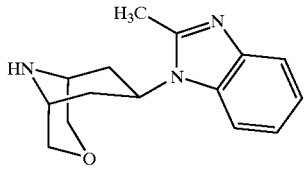

Ammonium formate (1 g, 15.8 mmol) was added to the title compound of preparation 49 (1.12 g, 3.2 mmol) and palladium hydroxide (0.1 g) in ethanol (50 ml), and the mixture heated under reflux for 2 hours. The reaction was allowed to cool to room temperature and filtered through Arbocel®. The solvent was evaporated under reduced pressure and the residue purified by column chromatography on silica gel, using an elution gradient of dichloromethane:methanol:0.88 ammonia (97:3:0 to 89:5:1) to afford the title compound, 651 mg.

Found: C, 667.86; H, 7.79; N, 15.47%. C$_{15}$H$_{19}$N$_2$O; 0.5 H$_2$O requires C, 67.64; H, 7.57; N, 15.78%.

$^1$H NMR (400 MHz, CDCl$_3$): δ [ppm] 2.10 (2H, m), 2.65 (3H, s), 2.80 (2H, m), 3.18 (2H, s), 3.90–4.00 (4H, m), 5.07 (1H, m), 7.18 (2H, m), 7.60 (1H, d), 7.70 (1H, d). LRMS: m/z 258.2 (MH$^+$).

PREPARATION 58

7-endo-(2-Methyl-1H-benzimidazol-1-yl)-3-oxa-9-azabicyclo[3.3.1]nonane

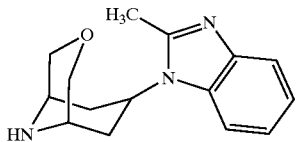

A solution of the title compound from preparation 50 (1.64 g, 4.59 mmol) and 4M hydrochloric acid in dioxan (15 ml) was stirred at room temperature for 1 hour. The solvent was evaporated under reduced pressure and the residue basified to pH 8 with saturated aqueous sodium carbonate solution. The aqueous layer was extracted with dichloromethane (2×). The combined organic solutions were washed with brine, dried (MgSO$_4$), filtered and evaporated under reduced pressure to afford the title compound as a dark solid, 1.08 g.

$^1$H NMR (400MHz, CDCl$_3$): δ [ppm] 2.20 (2H, m), 2.60 (2H, m), 2.65 (3H, s), 3.25 (2H, m), 3.72 (4H, m), 4.70 (1H, m), 7.20 (2H, m), 7.70 (1H, m), 7.75 (1H, m). LRMS: m/z 258.1 (MH$^+$).

PREPARATION 59

7-exo-2-Methyl-1H-benzimidazol-1-yl)-3-thia-9-azabicyclo[3.3.1]nonane

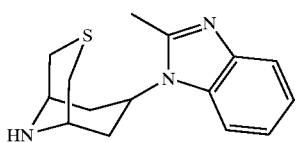

Tris(dibenzylidineacetone)dipalladium (176 mg 0.192 mmol) and 1,4bis(diphenylphosphino)butane (82 mg 0.192 mmol) were stirred for 30 minutes in tetrahydrofuran. A solution of the title compound from preparation 51 (1.2 g 3.80 mmol) and 2-mercaptobenzoic acid (0.70 g 4.6 mmol) in tetrahydrofuran (10 ml) was added and the solution stirred for 16 hours then evaporated under reduced pressure. The red solid was purified by column chromatography on silica gel, using an eluant of dichloromethane:methanol (97:3). The product was dissolved in dichloromethane and washed with saturated sodium bicarbonate solution, water and brine. The organic layer was dried (MgSO$_4$), filtered and evaporated under reduced pressure to afford the title compound as a tan solid, 0.66 g $^1$H NMR (400 MHz, CDCl$_3$): δ [ppm] 2.05 (2H, m), 2.52 (2H, d), 2.63 (3H, s), 2.83 (2H, m), 3.30 (2H, d), 3.60 (2H, s), 6.70 (1H, m), 7.1–7.23 (2H, m), 7.60 (1H, m), 7.70 (1H, m). LRMS: m/z 274.3 (MH$^+$).

PREPARATION 60

1-[(Benzyloxy)carbonyl]-3-azetidinecarboxylic Acid

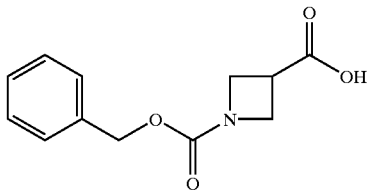

A solution of 3-azetidine carboxylic acid (0.50 g, 4.9 mmol), trimethylsilyl chloride (1.25 ml, 9.8 mmol) and N-ethyldiisopropylamine (2.20 ml, 12.6 mmol) was heated under reflux in dichloromethane (20 ml) for 20 minutes. The reaction mixture was cooled in an ice bath and benzyl chloroformate (0.92 ml, 6.4 mmol) added. The mixture was stirred at room temperature for 72 hours before quenching with saturated aqueous sodium bicarbonate solution. The layers were separated and the aqueous phase was acidified to pH2 with 2N hydrochloric acid and extracted with ethyl acetate (3×). The combined organic extracts were dried (MgSO$_4$), filtered and evaporated under reduced pressure to afford the title compound as a brown oil, 1.01 g.

$^1$H NMR (400 MHz, CDCl$_3$): δ [ppm] 3.44 (1H, m), 4.21 (4H, d), 5.09 (2H, s), 7.28–7.41 (5H, m). LRMS: m/z253.1 (MNH$_4^+$).

PREPARATION 61

1-tert-Butoxycarbonyl)-3-azetidinecarboxylic Acid

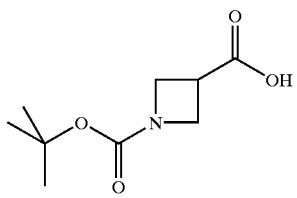

Di-tert-butyl dicarbonate (3.02 g, 13.8 mmol) was added to a suspension of 3-azetidine carboxylic acid (1 g, 10 mmol) and potassium carbonate (1.8 g, 13 mmol) in water (18 ml) and dioxan (18 ml) at 0° C., with stirring and allowed to warm to room temperature. The mixture was stirred for 15 hours and then concentrated under reduced pressure. The residue was acidified to pH 4 by addition of 1M citric acid solution and extracted with dichloromethane (×3). The combined organic extracts were washed with water then brine, dried (MgSO$_4$), filtered and solvent evaporated under reduced pressure to afford the title compound as a white solid, 2.1 g.

$^1$H NMR (400 MHz, CDCl$_3$): δ [ppm] 1.44 (9H, s), 3.38 (1H, m), 4.14 (4H, m). LRMS: m/z 200 (MH$^-$).

PREPARATION 62 tert-Butyl (1S) 3-[exo-3-(2-Methyl-1H-benzimidazol-1-yl)-azabicyclo[3.2.1]oct-yl]-1-phenylpropylcarbamate

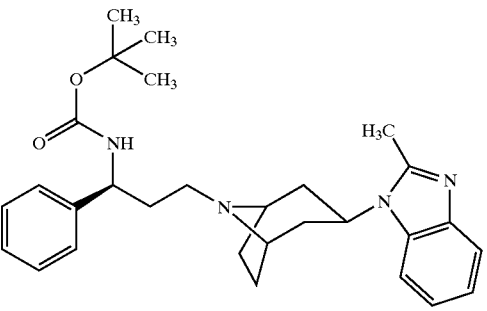

Sodium triacetoxyborohydride (395 mg, 1.86 mmol) and glacial acetic acid (75 mg, 1.25 mmol) were added to a solution of the title compounds of preparations 52 (300 mg, 1.24 mmol) and 7 (341 mg, 1.37 mmol) in dichloromethane (10 ml), and the reaction stirred at room temperature for 18 hours. The mixture was basified with 10% aqueous sodium carbonate solution, and extracted with dichloromethane (2×). The combined organic extracts were washed with brine, dried (MgSO$_4$), filtered and evaporated under reduced pressure to afford the title compound as a white foam, 444 mg.

$^1$H-NMR (400 MHz, CDCl$_3$): δ [ppm] 1.37 (9H, s), 1.72 (4H, m), 1.88 (1H, m), 1.98–2.15 (3H, m), 2.50 (2H, t), 2.62 (5H, m), 3.39 (1H, m), 3.45 (1H, m), 4.55 (1H, m), 4.87 (1H, s), 6.50 (1H, m), 7.20 (2H, m), 7.25 (1H, m), 7.36 (4H, m), 7.58 (1H, m), 7.66 (1H, d). LRMS: m/z 475 (MH$^+$).

PREPARATION 63 tert-Butyl (1S) 3-[endo3-(2-methyl-1H-benzimidazol-1-yl)-8-azabicyclo[3.2.1]oct-yl]-1-phenylpropylcarbamate

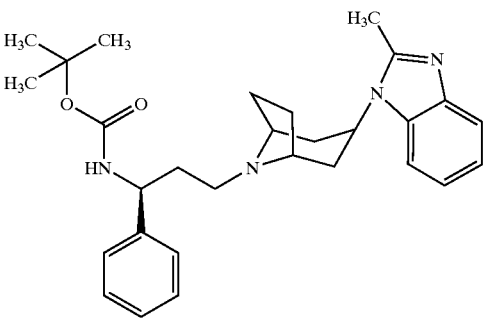

A solution of the title compounds from preparations 7 (480 mg, 1.93 mmol), and 53 (600 mg, 1.91 mmol) and sodium triacetoxyborohydride (600 mg, 2.83 mmol) were stirred together in a 30 ml mixture of glacial acetic acid:dichloromethane (1:9) for 30 minutes at room temperature. The solvents were removed under reduced pressure and the residue basified with 6N NaOH then extracted with dichloromethane (×3). The combined organic extracts were dried (MgSO$_4$), filtered and evaporated under reduced pressure to afford the title compound as a foam, 900 mg. LRMS: m/z 475.1 (MH$^+$).

PREPARATION 64 tert-Butyl (1S)-3-[3-exo-(3-{4-[(methylsulphonyl)amino]benzyl}-1.2.4-oxadiazol-5-yl)-8-azabicyclo[3.2.1]oct-8-yl]-1-phenylpropylcarbamate

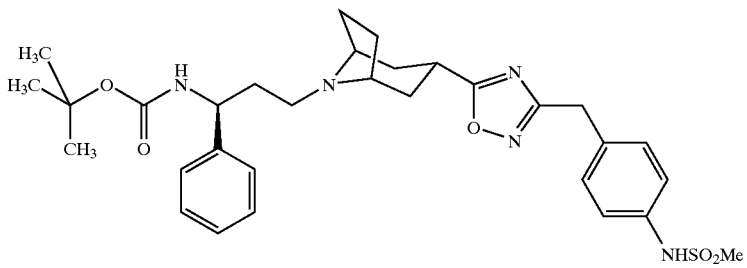

The title compound was prepared from the title compounds from preparations 7 and 56, following a similar procedure to that described in preparation 62.

The crude product was purified by column chromatography on silica gel, using an elution gradient of dichloromethane:methanol (99:1 to 98:2) to afford the title compound as a white foam, 392 mg.

$^1$H NMR (400 MHz, CDCl$_3$): δ [ppm] 1.38 (9H, s), 1.55 (5H, bs), 1.70–2.10 (12H, m), 2.35 (3H, m), 3.00 (3H, s), 3.19 (1H, m), 3.25 (1H, m), 3.37 (1H, m), 4.00 (2H, s), 7.10–7.30 (9H, m).

PREPARATION 65 tert-Butyl (1S)-3-[7-exo-2-methyl-1H-benzimidazol-1-yl)-3-oxa-9-azabicyclo[3.3.1]non-9-yl]-1-phenylpropylcarbamate

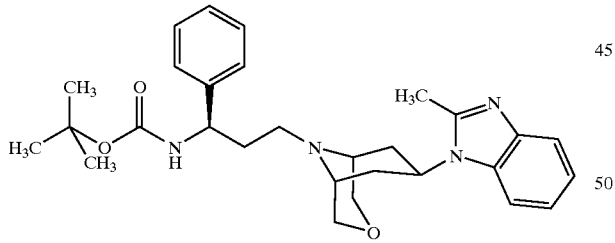

The title compound was obtained as a white solid (90%), from the title compounds of preparations 7 and 57, following the procedure of preparation 64.

Found: C, 69.10; H, 7.91; N, 10.47%. C$_{29}$H$_{38}$N$_4$O$_3$; 0.8H$_2$O requires C, 68.97; H, 7.90; N, 10.37%. $^1$H NMR (400 MHz, CDCl$_3$): δ [ppm] 1.40 (9H, s), 1.78 (2H, m), 1.90–2.08 (2H, m), 2.62 (3H, s), 2.65–2.95 (6H, m), 3.92 (2H, m), 4.05 (2H, m), 4.90 (1H, s), 5.65 (1H, m), 6.15 (1H, d), 7.18 (2H, m), 7.25–7.38 (5H, m), 7.42 (1H, d), 7.70 (1H, d). LRMS: m/z 491.2 (MH$^+$).

PREPARATION 66 tert-Butyl (1S)-3-[7-(exo-2-methyl-1H-benzimidazol-1yl)-3-thia-9-azabicyclo[3.3.1]non-9-yl]-1-phenylpropylcarbamate

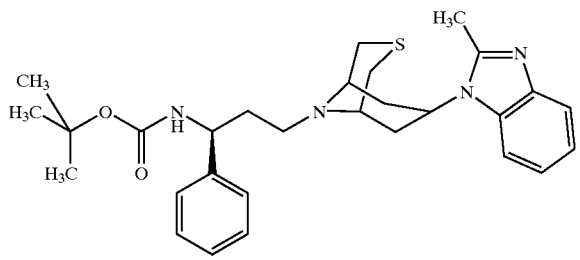

The title compound was obtained as a white solid (77%), from the title compounds of preparations 7 and 59, following the procedure of preparation 64.

$^1$H NMR (400 MHz, CDCl$_3$): δ [ppm] 1.4 (9H, s), 1.80–2.0 (4H, m), 2.36 (2H, t), 2.64 (3H, s), 2.70–2.90 (4H, m), 3.35 (2H, s), 3.45 (2H, t), 4.90 (1H, br s), 6.0 (1H, br s), 6.75 (1H, m), 7.20 (2H, m), 7.25–7.40 (5H, m), 7.55 (1H, d), 7.70 (1H, d). LRMS: m/z 507.1 (MH$^+$).

PREPARATION 67

(1S) 3-[exo3-(2-Methyl-1H-benzimidazol-1-yl)-8-azabicyclo[3.2.1]oct-8-yl]-1-phenylpropylamine

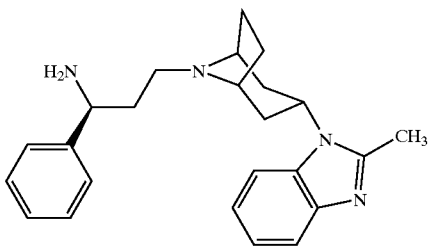

A solution of the title compound from preparation 62 (1.00 g, 2.1 mmol) and trifluoroacetic acid (8 ml) in dichloromethane (20 ml) was stirred for 60 hours at room temperature. The solvent was concentrated under reduced pressure and the residue quenched with aqueous saturated sodium carbonate solution. This aqueous mixture was extracted with dichloromethane (3x) and the combined organic extracts washed with brine, dried (MgSO$_4$), filtered and evaporated under reduced pressure to afford the title compound, 600 mg.

$^1$H NMR (400 MHz, CDCl$_3$): δ [ppm] 1.60–1.84 (6H, m), 1.92 (2H, m), 2.01–2.14 (2H, bm), 2.51 (3H, m), 2.54–2.66 (4H, m), 3.44 (2H, m), 4.17 (1H, m), 4.52 (1H, m), 7.18 (2H, m), 7.22–7.28 (1H, m), 7.31–7.41 (4H, m), 7.47–7.53 (1H, m), 7.64–7.69 (1H, m). LRMS: m/z 375.6 (MH$^+$).

PREPARATION 68

(1S) 3-[endo3-(2-Methyl-1H-benzimidazol-1-yl)-8-azabicyclo[3.2.1]oct-8-yl]-1-phenylpropylamine

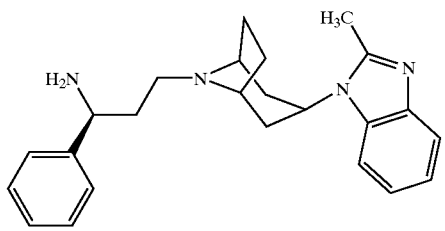

A solution of the title compound from preparation 63 (900 mg, 1.90 mmol) was stirred for 1 hour at 40° C. in a 30 ml mixture of dichloromethane:trifluoroacetic acid (4:1). The solvents were removed under reduced pressure, the residue basified with saturated sodium carbonate solution and extracted with dichloromethane (x3). The combined organic extracts were dried (MgSO$_4$), filtered and evaporated under reduced pressure to afford the title compound as a foam, 330 mg. LRMS: m/z 375.2 (MH$^+$).

PREPARATION 69

(1S)-3-[7-endo-(2-Methyl-1H-benzimidazol-1-yl)-3-oxa-9-azabicyclo[3.3.1]non-9-yl]-1-phenyl-1-propanamine

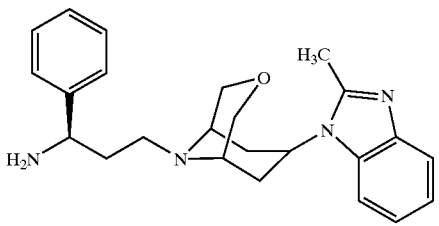

A mixture of the title compounds from preparations 58 (500 mg, 1.94 mmol), and 7 (533 mg, 2.13 mmol), sodium triacetoxyborohydride (618 mg, 2.91 mmol), and glacial acetic acid (115 ml) in dichloromethane (10 ml) was stirred at room temperature for 24 hours. The reaction was diluted with aqueous saturated sodium carbonate solution, and the phases separated. The aqueous layer was extracted with dichloromethane (2x) and the combined organic extracts washed with brine, dried (Na$_2$SO$_4$), filtered and evaporated under reduced pressure. The resulting brown foam was stirred in 4M hydrochloric acid in dioxan (20 ml) for 1 hour. The excess of solvent was evaporated under reduced pressure and the residue was basified with aqueous saturated sodium carbonate solution. The aqueous layer was extracted with dichloromethane (3x). The combined organic solutions were washed with brine, dried (Na$_2$SO$_4$), filtered and evaporated under reduced pressure to afford the title compound as a brown solid, 729 mg.

$^1$H NMR (400 MHz, CDCl$_3$): δ [ppm] 1.90 (2H, m), 2.30 (2H, m), 2.60 (2H, m), 2.64 (3H, s), 2.80 (2H, m), 3.00 (2H, m), 3.40 (2H, d), 3.70 (2H, m), 3.90 (2H, m), 4.07 (1H, t), 4.80 (1H, m), 7.20 (2H, m), 7.25 (1H, m), 7.35 (4H, m), 7.68 (1H, m), 7.78 (1H, m). LRMS: m/z 391.1 (MH$^+$).

PREPARATION 70

(1S)-3-[7-(exo-2-Methyl-1H-benzimidazol-1-yl)-3-oxa-9-azabicyclo[3.3.1]non-9-yl-1-phenyl-1-propanamine Trihydrochloride

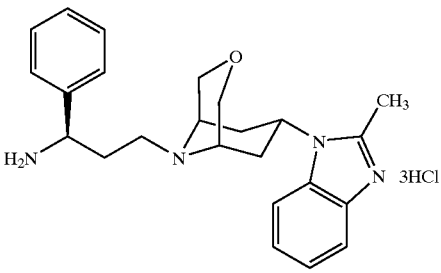

A solution of the title compound from preparation 65 (1.10 g, 2.24 mmol) in 4M hydrochloric acid in dioxan (10 ml) was stirred for 1 hour. The solvent was evaporated under reduced pressure to afford the title compound as a white solid, 1.30 g.

$^1$H NMR (400 MHz, DMSO-d$_6$): δ [ppm] 2.45–2.70 (3H, m), 2.92 (3H, s), 3.40 (4H, m), 3.72 (1H, m), 3.83 (1H, m), 3.95–4.10 (2H, m), 4.30(1H, d), 4.45 (2H, m), 5.82 (1H, m), 7.35–7.55 (5H, m), 7.60 (2H, d), 7.80 (1H, d), 8.80 (2H, bs), 9.10 (1H, d), 12.28 (1H, bs). LRMS: m/z 391.2 (MH$^+$).

PREPARATION 71

Benzyl 3-[({(1S)-3-[exo-(2-methyl-1H-benzimidazol-1-yl)-8-azabicyclo3.2.1]oct-8-yl]-1-phenylpropy}amino)carbonyl]-1-azetidine Carboxylate

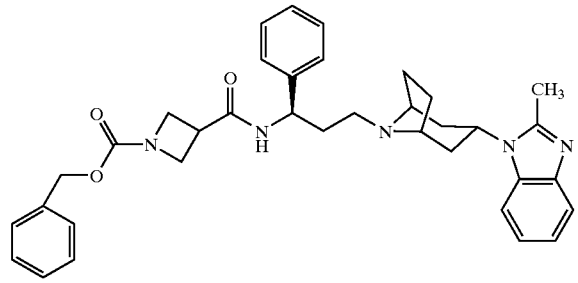

A solution of the title compound from preparation 67 (222 mg, 0.59 mmol) in dichloromethane (5 ml) was added to the title compound from preparation 60 (136 mg, 0.58 mmol), 1-(3-dimethylaminopropyl)-3-ethyl-carbodiimide hydrochloride (136 mg, 0.71 mmol), N-ethyldiisopropylamine (108 μl, 0.62 mmol) and 1-hydroxybenzotriazole hydrate (88 mg, 0.65 mmol) in dichloromethane (5 ml). The reaction mixture was stirred at room temperature for 20 hours. The solvent was evaporated under reduced pressure and the residue taken up in ethyl acetate, washed with water, brine, dried (MgSO$_4$) filtered and evaporated under reduced pressure. The residual pale brown solid was purified by column chromatography on silica gel, using an eluant of dichloromethane:methanol:0.88 ammonia (95:5:0.5) to afford the title compound as a white solid, 279 mg.

$^1$H NMR (400 MHz, CDCl$_3$): δ [ppm] 1.62–1.72 (2H, bm), 1.76 (2H, m), 1.94–2.18 (4H, m), 2.44–2.58 (3H, m), 2.58–2.68 (4H, m), 3.21–3.32 (1H, m), 3.44 (2H, m), 4.08–4.17 (2H, bm), 4.55 (1H, m), 5.08 (2H, s), 5.24 (1H, m), 7.08–7.24 (3H, m), 7.28–7.41 (9H, m), 7.46–7.54 (1H, m), 7.63–7.72 (1H, m). LRMS: m/z 592.6 (MH$^+$).

PREPARATION 72 tert-Butyl1-[({(1S)-3-exo-[3-(2-methyl-1H-benzimidazol-1-yl)-8-azabicyclo[3.2.1]oct-8-yl]-1-phenylpropyl}amino)carbonyl]cyclopentylcarbamate

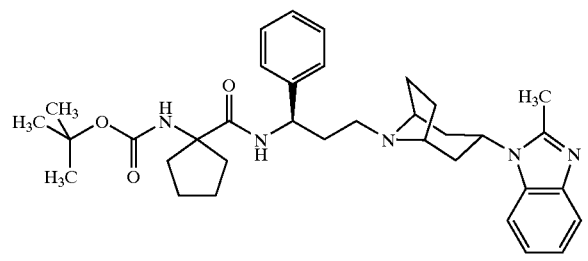

The title compound was obtained as a white solid (85%), from the title compound of preparation 67 and 1-[(tert-butoxycarbonyl)amino]cyclopentanecarboxylic acid (J. Med. Chem. 14; 1971; 904), (61 mg, 0.27 mmol), following the procedure described in preparation 71.

$^1$H NMR (400 MHz, CDCl$_3$): δ [ppm] 1.42 (9H, s), 1.54–1.86 (10H, m), 1.90–2.20 (5H, m), 2.20–2.37 (2H, bm), 2.37–2.64 (7H, m), 3.41 (2H, bs), 4.52 (1H, m), 4.77 (1H, bm), 5.16 (1H, m), 7.14–7.22 (2H, m), 7.30–7.38 (4H, m), 7.42–7.58 (2H, bm), 7.63–7.71 (1H, m). LRMS: m/z 586.1 (MH$^+$).

PREPARATION 73 tert-Butyl (1S)-3-endo-3-(1H-benzimidazol-1-yl)-8-azabicyclo[3.2.1]oct-8-yl]-1-phenylpropylcarbamate

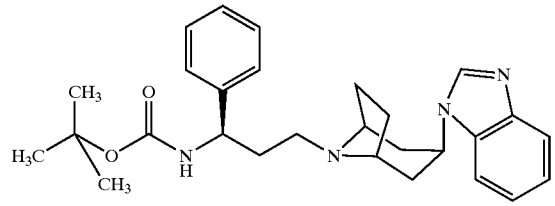

A mixture of the title compounds from preparations 7 (592 mg, 2.37 mmol), and 54 (540 mg, 2.37 mmol) and sodium triacetoxyborohydride (750 mg, 3.54 mmol) were stirred together in a 25 ml mixture of glacial acetic acid-:dichloromethane (1:9) for 30 minutes at room temperature. The solvents were removed under reduced pressure, the residue suspended in saturated sodium carbonate solution and extracted with dichloromethane (×3). The combined organic extracts were dried (MgSO$_4$), filtered and evaporated under reduced pressure. The residue was purified by column chromatography on silica gel using an eluant of dichloromethane:methanol:0.88 ammonia (98:2:0.25) to afford the title compound as a foam, 750 mg.

$^1$H NMR (400 MHz, CDCl$_3$): δ [ppm] 1.35–1.48 (9H, m), 1.60–1.71 (2H, m), 1.87–2.16 (6H, m), 2.29–2.37 (2H, m), 2.69–2.81 (2H, m), 3.32–3.39 (1H, m), 3.42–3.47 (1H, m), 3.68–3.76 (1H, m), 4.69–4.82 (1H, m), 4.82–4.95 (1H, m), 6.63–6.73 (1H, m), 7.23–7.39 (7H, m), 7.39–7.53 (1H, m), 7.77–7.82 (1H, m), 8.05 (1H, s).

PREPARATION 74 tert-Butyl3-[({(1S)-3-endo-[3-(1H-benzimidazol-1-yl)-8-azabicyclo[3.2.1]oct-8-yl]-1-phenylpropyl}amino)carbonyl]-1-azetidinecarboxylate

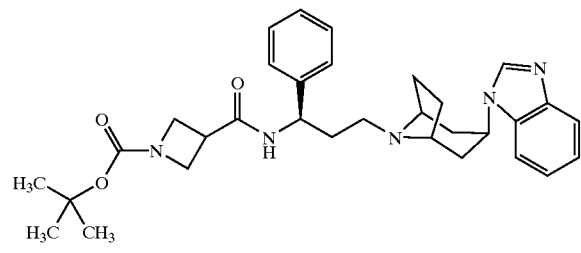

A solution of the title compound from preparation 73 (750 mg, 1.63 mmol) was stirred for 5 hours at room temperature in a mixture of dichloromethane:trifluoroacetc acid (4:1), (20 ml). The solvents were removed under reduced pressure, the residue was basified using saturated sodium hydrogen carbonate solution and extracted with dichloromethane (×3). The combined organic extracts were dried (MgSO$_4$), filtered and evaporated under reduced pressure. The residue was purified by column chromatography on silica gel using an eluant of dichloromethane:methanol:0.88 ammonia (98:2:0.25) to afford the title compound as a foam, 480 mg.

A mixture of this intermediate amine (480 mg, 1.33 mmol), the title compound from preparation 61 (250 mg, 1.33 mmol) and 1-(3-dimethylaminopropyl)-3-ethylcarbodiimide hydrochloride (280 mg, 1.46 mmol) were stirred together for 1 hour at room temperature in dichloromethane (10 ml). The solvent was removed under reduced pressure, the residue dissolved in ethyl acetate and washed with saturated sodium hydrogen carbonate solution and water. The organic solution was dried (MgSO$_4$), filtered and evaporated under reduced pressure. The residue was purified by column chromatography on silica gel using an eluant of dichloromethane:methanol:0.88 ammonia (98:2:0.25) to afford the title compound as a foam, 730 mg.

$^1$H NMR (400 MHz, CDCl$_3$): δ [ppm] 1.42 (9H, s), 1.60–1.69 (2H, m), 1.96–2.10 (6H, m), 2.29–2.35 (2H, m), 2.55–2.74 (2H, m), 3.13–3.26 (1H, m), 3.34–3.40 (2H, m), 4.02–4.18 (4H, m), 4.66–4.76 (1H, m), 5.19–5.26 (1H, m), 7.00–7.13 (1H, bs), 7.23–7.32 (5H, m), 7.32–7.45 (3H, m), 7.77–7.82 (1H, m), 8.06 (1H, s). LRMS: m/z 544.4 (MH$^+$).

PREPARATION 75

N-(8-Benzyl-8-azabicyclo[3.2.1]oct-3-yl)-3-exo-)4-fluorophenyl)propanamide

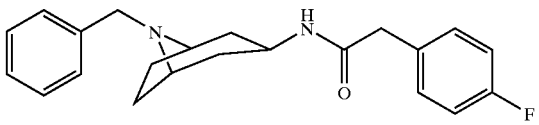

The title compound from preparation 26 (2.0 g, 9.2 mmol) was added to 4-fluorophenylacetic acid (1.42 g, 9.2 mmol) N-ethyidiisopropylamine (1.6 ml, 9.2 mmol), 1-(3-dimethylaminopropyl)-3-ethyl-carbodiimide hydrochloride (1.77 g, 9.2 mmol), and 1-hydroxybenzotriazole hydrate (1.41, 9.2 mmol) in dichloromethane (20 ml). The reaction mixture was stirred at room temperature for 16 hours then saturated aqueous sodium carbonate solution (30 ml) was added. The layers were separated and the aqueous phase was extracted with dichloromethane (2×). The combined organic extracts were washed with water, dried (MgSO$_4$), filtered and evaporated under reduced pressure. The residue was purified by column chromatography on silica gel, using an elution gradient of dichloromethane:methanol:0.88 ammonia (98:2:0 to 95.5:4:0.5) to afford the title compound as a white solid, 1.04 g.

$^1$H NMR (400 MHz, CDCl$_3$): δ [ppm] 1.40 (2H, m), 1.70 (2H, d), 1.75 (2H, m), 2.02 (2H, m), 3.18 (2H, s), 3.50 (4H, s), 4.10 (1H, m), 7.00 (2H, m), 7.15–7.32 (7H, m). LRMS: m/z 353.1 (MH$^+$).

PREPARATION 76 tert-Butyl3-endo-{[2-(4-fluorophenyl)acetyl[amino}-8-azabicyclo[3.2.1]octane-8-carboxylate

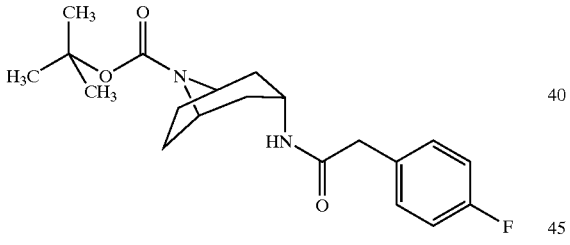

The title compound was obtained (86%) as a white solid, from the title compound of preparation 27 and 4-fluorophenylacetic acid, following a similar procedure to that described in preparation 75.

$^1$H NMR (400 MHz, CDCl$_3$): δ [ppm] 1.10–1.30 (2H, m), 1.38–1.60 (11H, m), 1.83 (2H, m), 2.0–2.30 (2H, bm), 3.56 (2H, s), 4.0–4.20 (3H, m), 5.70 (1H, m), 7.10 (1H, m), 7.20–7.30 (3H, m). LRMS: m/z 385.3 (MH$^+$).

PREPARATION 77

N-8-Azabicyclo[3.2.1]oct-3-yl)-3-exo-(4-fluorophenyl)propanamide

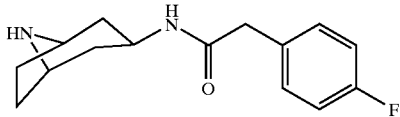

A mixture of the title compound from preparation 75 (2.69 g, 7.63 mmol) and 10% palladium on carbon (0.5 g) in ethyl acetate (30 ml) was hydrogenated at 50 psi at 50° C. for 48 hours. The reaction mixture was filtered through Arbocel® and the filtrate removed under reduced pressure to afford the title compound as a white solid, 1.96 g.

$^1$H NMR (300 MHz, CDCl$_3$): δ [ppm] 1.30 (2H, m), 1.65–1.80 (4H, m), 1.80–2.20 (5H, m), 3.55 (2H, s), 4.15 (1H, m), 5.20 (1H, d), 7.00 (2H, m), 7.20 (2H, m). LRMS: m/z 263.1 (MH$^+$).

PREPARATION 78

N-(8-Azabicyclo[3.2.1]oct-3-yl)-3-endo-(4-fluorophenyl)propanamide Hydrochloride

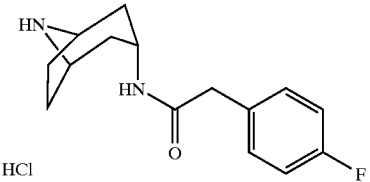

A solution of the title compound from preparation 76 (2.04 g, 5.62 mmol) was stirred in 4M hydrochloric acid solution in dioxan (20 ml). The excess solvent was evaporated under reduced pressure to afford the title compound as a white solid, 1.55 g.

$^1$H NMR (400 MHz, DMSO-d$_6$): δ [ppm] 1.85 (4H, m), 2.1 (4H, m), 3.45 (2H, s), 3.7 (1H, m), 3.85 (2H, bs), 7.1 (2H, m), 7.25 (2H, m), 8.15 (1H, d), 8.85 (1H, bs), 9.1 (1H, bs). LRMS: m/z 262.9 (MH$^+$).

PREPARATION 79 tert-Butyl (1S)-3-(3-endo-{[2-(4-fluorophenyl)acetyl]amino}-8-azabicyclo[3.2.1]oct-8-yl)-1-phenylpropylcarbamate

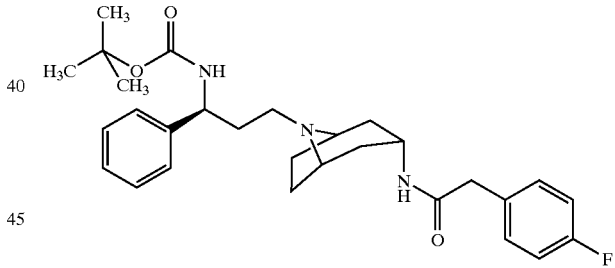

The title compound was obtained as a white solid (68%), from the title compounds of preparations 7 and 78, following a similar procedure to that described in preparation 64.

$^1$H NMR (400 MHz, CDCl$_3$ ): δ [ppm] 1.0–2.0 (18H, m), 2.10–2.30 (4H, m), 3.02 (1H, s), 3.15 (1H, s), 3.50 (1H, s), 4.15 (1H, q), 4.77 (1H, bs), 5.53 (1H, d), 7.04 (2H, m), 7.2–7.4 (7H, m). LRMS: m/z 496.9 (MH$^+$).

PREPARATION 80

N-{8-[(3S)-3-exo-Amino-3-phenylpropyl[-8-azabicyclo[3.2.1]oct-3-yl}-3-(4-fluorophenyl)propanamide Hydrochloride

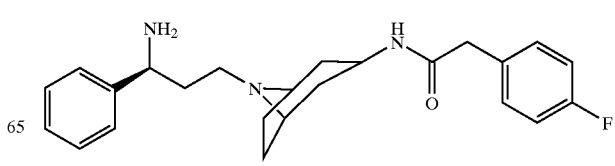

A mixture of the title compounds from preparations 77 (1.96 g, 7.47 mmol) and 7 (2.9 g, 9.58 mmol), sodium triacetoxyborohydride (2.37 g, 11.2 mmol), and glacial acetic acid (0.5 ml) in dichloromethane (30 ml) was stirred at room temperature for 16 hours. The reaction mixture was basified to pH 8 using saturated sodium bicarbonate solution. The phases were separated and the aqueous layer was extracted with dichloromethane (2x). The combined organic extracts were washed with brine, dried (MgSO$_4$), filtered and evaporated under reduced pressure. The residue was purified by column chromatography on silica gel, using an elution gradient of dichloromethane:methanol (98:2 to 95:5) to afford 2.49 g of a white solid.

This intermediate was stirred in 4M hydrochloric acid solution in dioxan (20 ml) at room temperature. The solvent was evaporated under reduced pressure to afford the title compound as a white solid, 2.26 g.

$^1$H NMR (400 MHz, DMSO-d$_6$): δ [ppm] 1.90 (4H, m), 1.98–2.20 (4H, m), 2.40 (2H, m), 2.78 (1H, m), 3.08 (1H, m), 3.80–4.02 (3H, m), 4.40 (1H, m), 7.10 (2H, m), 7.25 (2H, m), 7.42 (2H, m), 7.58 (2H, m), 8.25 (m, 1H), 8.80 (2H, bs), 10.75 (1H, bs). LRMS: m/z 396.1 (MH$^+$).

PREPARATION 81

N-{8-[(3S)-3-endo-Amino-3-phenylpropyl]-8-azabicyclo[3.2.1]oct-3-yl}-3-(4-fluorophenyl)propanamide Hydrochloride

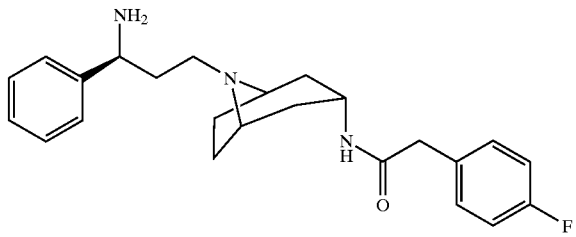

The title compound was obtained as a cream solid (quantitative), from the title compound of preparation 80, following the procedure of preparation 79.

LRMS: m/z (MH$^+$). 396.1 (MH$^+$).

PREPARATION 82

1-(Acetylamino)cylopentanecarboxylic Acid

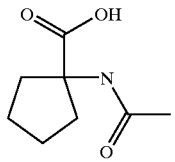

The title compound was prepared according to the method described in Bull. Soc. Chim. Fr. 1965; 2942.

PREPARATION 83

1-Benzyl-3-pyrrolidinecarboxylic Acid

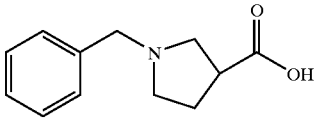

The title compound was prepared according to the method described in J. Org. Chem. 1968; 33; 3637.

PREPARATION 84

8-Benzyl-N-(4-fluoro-2-nitrophenyl)-8-azabicyclo[3.2.1]octan-3-exo-amine

A mixture of the title compound of preparation 26 (7.0 g, 32.4 mmol), 2, 5-difluoronitrobenzene (5.41 g, 34.0 mmol) and potassium carbonate (13.4 g, 0.97 mmol) in dimethylformamide (100 ml) was heated to 100° C. for 12 hours. The cooled mixture was concentrated under reduced pressure, dissolved in dichloromethane (300 ml) and washed with water then brine. The organic layer was dried (MgSO$_4$) and evaporated under reduced pressure. The residue was purified by column chromatography on silica gel, using an eluent of dichloromethane:methanol (98:2:0) to afford the title compound as a orange solid, 7.6 g.

$^1$H NMR (400 MHz, CDCl$_3$): δ [ppm] 1.74 (4H, m); 1.95 (2H, m); 2.15 (2H, m); 3.34 (2H, s); 3.60 (2H, s); 3.8 (1H, m); 6.82 (1H, m); 7.18–7.42 (6H, m); 7.86 (2H, m). LRMS: m/z 356.4 (MH$^+$).

PREPARATION 85

1-(8-Benzyl-8-azabicyclo[3.2.1]oct-3-yl)-4-fluoro-1,2-exo-benzenediamine

The title compound of preparation 84 (7.6 g, 21.41 mmol) and 5% palladium on carbon (0.8 g) in ethanol (50 ml) and tetrahydrofuran (150 ml) were stirred under 1 atmosphere of hydrogen for 24 hours at room temperature. The reaction was filtered through arbocel and the solvent removed under reduced pressure to afford the title compound as a dark red oil, 6.0 g.

$^1$H NMR (400 MHz, CDCl$_3$): δ [ppm] 1.38–1.76 (5H, m); 1.85 (2H, m); 2.06 (2H, m); 3.26 (2H, s); 3.36–3.70 (5H, m); 6.40 (2H, m); 6.60 (1H, m); 7.18–7.40 (5H, m). LRMS: m/z 326.6 (MH$^+$).

PREPARATION 86

1-(8-Benzyl-8-azabicyclo[3.2.1]oct-3-yl)-exo-5-fluoro-1H-benzimidazole

The title compound of preparation 85 (3.0 g, 9.22 mmol) was refluxed in triethyl orthoformate (20 ml) for 16 hours. Excess triethyl orthoformate was evaporated under reduced pressure. The oily residue was taken up in toluene (80 ml) refluxed with catalytic para-toluenesulfonic acid for 3 hours and concentrated under reduced pressure. The crude product was purified by column chromatography on silica gel, using an eluent of dichloromethane:methanol (98:2) to afford the title compound as a light pink solid, 1.91 g.

$^1$H NMR (400 MHz, CDCl$_3$): δ [ppm] 1.8 (2H, q); 1.98 (2H, m); 2.20–2.36 (4H, m); 3.40 (2H, s); 3.63 (2H, s); 4.56 (1H, m); 7.03 (1H, m); 7.20–7.50 (6H, m); 8.03 (1H, s). LRMS: m/z 336.3 (MH$^+$).

PREPARATION 87

1-(8-Azabicyclo[3.2.1]oct-3-yl)-exo-5-fluoro-1H-benzimidazole

The title compound of preparation 86 (1.91 g, 5.71 mmol) in ethanol (80 ml) was treated with ammonium formate (2.75 g, 43.6 mmol) and 20% palladium hydroxide on carbon (500 mg) and the mixture was heated to reflux under nitrogen for 5 hours. The cooled mixture was filtered through arbocel and concentrated under reduced pressure. The mixture was dissolved in dichloromethane (100 ml) and washed with saturated sodium bicarbonate solution then brine, was dried (MgSO$_4$) and concentrated under reduced pressure to afford the title compound as a red oil, 1.23 g.

$^1$H NMR (400 MHz, CDCl$_3$): δ [ppm] 1.77–2.30 (9H, m); 3.72 (2H, s); 4.52 (1H, m); 7.02 (1H, m); 7.34 (1H, m); 7.44 (1H, dd); 7.98 (1H, s). LRMS: m/z 246.0 (MH$^+$).

PREPARATION 88 tert-Butyl (1S)-3-[3-exo-(5-fluoro-1H-benzimidazol-1-yl)-8-azabicyclo[3.2.1]oct-8-yl-]-1-phenylpropylcarbamate The title compound of preparation 88 (1.23 g, 5.03 mmol) was stirred in dichloromethane (10 ml). The title compound of preparation 7 (1.25 g, 5.025 mmol), sodium triacetoxyborohydride (1.60 g, 7.55 mmol) and glacial acetic acid (0.30 ml) were added, and the solution stirred at room temperature for 16 hours. The reaction mixture was basified with saturated sodium bicarbonate. The aqueous layer was extracted with dichloromethane (2×) and the combined organic extracts washed with brine, dried (MgSO$_4$), filtered and evaporated under reduced pressure. The residue was purified by column chromatography on silica gel, using an eluent of dichloromethane:methanol (98:2) to afford 1.505 g of a light pink solid.

$^1$H NMR (400 MHz, CDCl$_3$): δ [ppm] 1.20–1.47 (10H, m); 1.62–1.88 (3H, m); 1.90–2.18 (5H, m); 2.20–2.46 (4H, m); 3.38 (1H, s); 3.60 (1H, s); 4.52 (1H, m); 4.90 (1H, m); 7.0 (2H, m); 7.20–7.50 (5H, m); 7.55 (1H, d); 8.0 (1H, s). LRMS: m/z 479.0 (MH$^+$).

PREPARATION 89 tert-Butyl3-[({(1S)-3-[3-exo-5-fluoro-1H-benzimidazol-1-yl)-8-azabicyclo[3.2.1]oct-8-yl]-1-phenylpropyl}amino)carbonyl]-1-azetidinecarboxylate The title compound of preparation 88 (1.505 g, 3.15 mmol) and 4M hydrochloric acid in dioxane (10 ml) were stirred for 1 hour. The excess of solvent was evaporated under reduced pressure to give a cream solid, which was added to the title compound of preparation 61 (0.695 g, 3.46 mmol), diisopropyl ethylamine (2.2 ml, 12.6 mmol), 1-(3-dimethylaminopropyl)-3-ethyl-carbodiimide hydrochloride (0.663 g, 3.46 mmol), and 1-hydroxybenzotriazole hydrate (0.467 g, 3.46 mmol) in dichloromethane (20 ml). The reaction mixture was stirred at room temperature for 16 hours, concentrated and dissolved in ethyl acetate then washed with 10% sodium carbonate solution. The organic layer was dried (MgSO$_4$), filtered and evaporated under reduced pressure. The residue was purified by column chromatography on silica gel, using an eluent of dichloromethane:methanol (99:4) to afford the title compound as a white powder, 1.182 g.

$^1$H NMR (400 MHz, CDCl$_6$): δ [ppm] 1.4 (10H, m); 1.8 (2H, m); 1.92–2.30 (9H, m); 2.48 (1H, m); 3.15 (1H, m); 3.42 (2H, m); 3.96–4.20 (4H, m); 4.55 (1H, m); 5.20 (1H, q); 7.02 (1H, m); 7.10–7.40 (6H, m); 7.54 (1H, m); 8.0 (1H, s). LRMS: m/z 489.2 (MH$^+$).

EXAMPLE 1

N-{3-[3-exo-(2-Methyl-1H-benzimidazol-1-yl)-8-azabicyclo[3.2.1]oct-8-yl]-1-phenylpropyl}cyclobutanecarboxamide Dihydrochloride

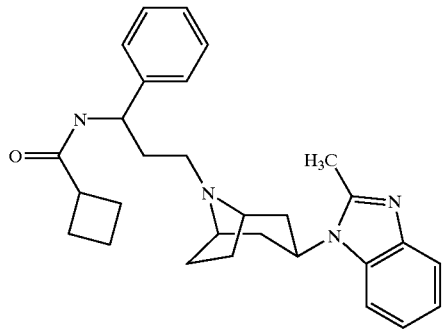

The title compounds of preparation 52 (0.20 g, 0.829 mmol) and preparation 3 (0.174 g, 0.753 mmol) were stirred together with sodium triacetoxyborohydride (0.240 g, 1.13 mmol) and acetic acid (0.05 ml, 0.833 mmol) in dichloromethane (10 ml) under an atmosphere of nitrogen for 24 hours at room temperature. A solution of 10% sodium carbonate was added and the product extracted with dichloromethane. The combined organic extracts were dried (MgSO$_4$) and the solvent evaporated under reduced pressure. The product was purified by chromatography on silica gel using dichloromethane:methanol (98:2) as eluant, then dissolved in diethyl ether saturated with HCl. Evaporation to dryness provided the title compound, 127 mg.

$^1$H-NMR (400 MHz, CDCl$_3$): δ [ppm] 1.66–1.80 (4H, m), 1.85–2.23 (10H, m), 2.25–2.40 (2H, m), 2.50–2.58 (2H, m), 2.65 (3H, s), 3.08 (1H, m), 3.44 (2H, m), 4.58 (1H, m), 5.20 (1H, m), 6.85 (1H, d), 7.22 (2H, m), 7.28–7.40 (5H, m), 7.52 (1H, m), 7.68 (1H, m). LRMS: m/z 457.6 (MH$^+$).

EXAMPLE 2

N-{(1S)-3-[3-exo-(2-Methyl-1H-benzimidazol-1-yl)-azabicyclo[3.2.1]oct-8-yl]-1-phenylpropyl}cyclobutanecarboxamide

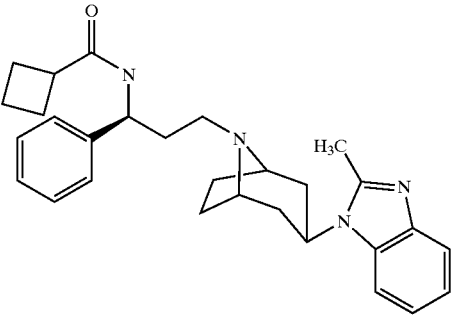

Cycobutane carboxylic acid chloride (224 mg, 1.89 mmol) was added to the title compound of preparation 67 (646 mg, 1.72 mmol) and triethylamine (505 µl, 3.62 mmol)

in dichloromethane (10 ml). The reaction mixture was stirred at room temperature for 3 hours after which time more triethylamine (500 μl, 3.62 mmol) and cyclobutane carboxylic acid chloride (104 mg, 0.876 mmol) were added. Water was added to the mixture, the product was extracted with dichloromethane (2×), the combined organics were washed with brine, dried (MgSO$_4$), filtered and evaporated under reduced pressure. The residue was purified by column chromatography on silica gel, using an elution gradient of dichloromethane:methanol: 0.88 ammonia (98:2:0.5 to 95:4:1) to afford the title compound as a white powder, 196 mg.

Found C, 73.91; H, 8.08; N, 11.82%; C$_{29}$H$_{36}$N$_4$O;1H$_2$O requires C, 73.39; H, 8.07; N, 11.80%; $^1$H-NMR (400 MHz, CDCl$_3$): δ [ppm] 1.60–1.80 (4H, m), 1.90–2.20 (9H, m), 2.25–2.40 (3H, m), 2.50–2.58 (2H, m), 2.55–2.65 (4H, m), 3.08 (1H, m), 3.40 (2H, m), 4.58 (1H, m), 5.20 (1H, m), 6.80 (1H, d), 7.18–7.40 (6H, m), 7.50 (1H, m), 7.65 (1H, m); LRMS: m/z 457.2 (MH$^+$); [α]$_D$ −40.0° (c=0.10, CH$_2$Cl$_2$).

EXAMPLE 3

N-{(1S)-3-[3-endo-(2-Methyl-1H-benzimidazol-1-yl)-8-azabicyclo[3.2.1]oct-8-yl]-1-phenylpropyl}cyclobutanecarboxamide

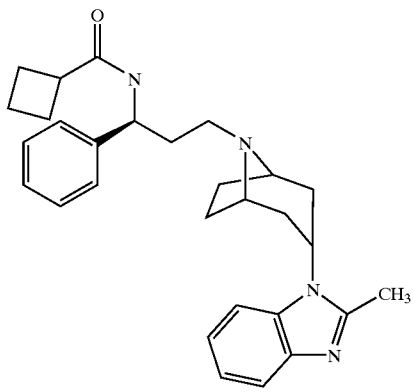

The title compound of preparation 68 (565 mg, 1.51 mmol), cyclobutanecarboxylic acid chloride (207 μl, 1.81 mmol), and triethylamine (464 μl, 3.32 mmol) were stirred in dichloromethane (15 ml) for 18 hours at room temperature. The reaction was diluted with water and extracted with dichloromethane (2×). The combined organic extracts were dried (MgSO$_4$), filtered and evaporated under reduced pressure. The residue was purified by column chromatography on silica gel, using an eluant of dichloromethane:methanol:0.88 ammonia (98:1.5:0.5) to afford the title compound as a white solid, 260 mg.

Found C, 74.13; H, 7.97; N, 11.97%; C$_{29}$H$_{36}$N$_4$O;0.7H$_2$O requires C, 74.23; H, 8.03; N, 11.94%; $^1$H NMR (400 MHz, CDCl$_3$): δ [ppm] 1.70 (2H, m); 1.82–2.00 (3H, m); 2.10–2.20 (4H, m); 2.22–2.35 (4H, m); 2.47 (5H, m); 2.60 (3H, s); 3.00 (1H, m); 3.40 (2H, bs); 4.75 (1H, m); 5.15 (1H, m); 6.30 (1H, d); 7.18 (2H, m); 7.20–7.30 (6H, m); 7.62 (1H, m); LRMS: m/z 457.4 (MH$^+$).

EXAMPLE 4

N-{(1S)-3-[3-exo-(2-Methyl-1H-benzimidazol-1-yl)-8-azabicyclo[3.2.1]oct-8-yl]-1-phenylpropyl}tetrahydro-2H-pyran-4-carboxamide

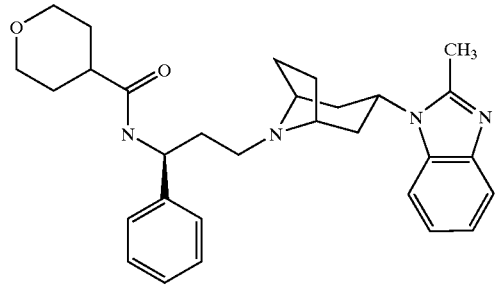

The title compound of preparation 67 (86 mg, 0.23 mmol) in dichloromethane (2.5 ml) was added to tetrahydropyran-4-carboxylic acid (30 mg, 0.23 mmol), 1-(3-dimethylaminopropyl)-3-ethyl-carbodiimide hydrochloride (53 mg, 0.28 mmol), N-diisopropylethylamine (44 μl, 0.25 mmol) and 1-hydroxybenzotriazole hydrate (34 mg, 0.25 mmol) in dichloromethane (2.5 ml). The reaction mixture was stirred for 16 hours at room temperature. The solvent was evaporated under reduced pressure and the residue taken up in ethyl acetate, washed with water, brine, dried (MgSO$_4$) filtered and evaporated under reduced pressure. The residual pale brown solid was purified by column chromatography on silica gel, using an elution gradient of dichloromethane:methanol:0.88 ammonia (98:2:0.25 to 95:5:0.5) to afford the title compound as a white solid, 48 mg.

Found C, 70.59; H, 7.83; N, 10.94%; C$_{30}$H$_{38}$N$_4$O$_2$;1.3H$_2$O requires C, 70.64; H, 8.02; N, 10.98%; $^1$H NMR (400 MHz, CDCl$_3$): δ [ppm] 1.65 (2H, bm), 1.71–1.92 (6H, m), 1.96–2.22 (4H, m), 2.37 (1H, m), 2.46–2.68 (7H, m), 3.39–3.50 (4H, m), 3.98 (2H, m), 4.54 (1H, m), 5.20 (1H, m), 6.79 (1H, m), 7.13–7.21 (2H, m), 7.23–7.30 (1H, m), 7.30–7.40 (4H, m), 7.42–7.54 (1H, m), 7.62–7.72 (1H, m); LRMS: m/z 487.3 (MH$^+$); Melting point [°C.]: 95–96.

EXAMPLES 5–16

The compounds of the following tabulated examples with the general structure:

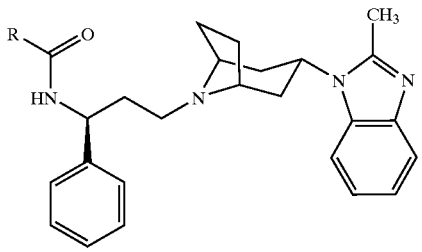

were prepared using a similar method to Example 4 from the title compound of preparation 67 and the corresponding acids.

| Example Number | R | Yield (%) | Characterization Data |
|---|---|---|---|
| 5<br>1-Acetyl-N-{(1S)-3-[3-exo-(2-methyl-1H-benzimidazol-1-yl)-8-azabicyclo[3.2.1]oct-8-yl]-1-phenylpropyl}-3-azetidine carboxamide | | 1 | Found C, 68.66; H, 7.40; N, 13.00% $C_{30}H_{37}N_5O_2$; 1.5$H_2O$ requires C, 68.42; H, 7.66; N, 13.30% $^1$H NMR (400 MHz, CDCl$_3$): δ [ppm] 1.61–1.84(4H, m), 1.84(3H, s), 1.93–2.20(4H, bm), 2.44–2.71(7H, m), 3.24(1H, m), 3.42(2H, bs), 4.04–4.15 (3H, m), 4.42(1H, q), 4.56(1H, m), 5.24 (1H, bm), 7.11–7.21(6H, m), 7.44–7.56 (1H, m), 7.63–7.73(1H, m) LRMS: m/z 500.7 (MH$^+$) |
| 6<br>1-Hydroxy-N-{(1S)-3-[3-exo-(2-methyl-1H-benzimidazol-1-yl)-8-azabicyclo[3.2.1]oct-8-yl]-1-phenylpropyl}cyclopentanecarboxamide | | 9 | Found C, 71.31; H, 7.58; N, 10.87% $C_{30}H_{38}N_4O_2$; 0.7$H_2O$; 0.1$CH_2Cl_2$ requires C, 71.20; H, 7.86; N, 11.03% $^1$H NMR (400 MHz, CDCl$_3$): δ [ppm] 1.47–1.92(10H, m), 1.96–2.14(5H, m), 2.14–2.28(2H, m), 2.50(2H, m), 2.53–2.67(5H, m), 3.41(2H, bs), 4.52 (1H, m), 5.20(1H, m), 7.12–7.23(2H, m), 7.23–7.30(1H, m), 7.30–7.41(4H, m), 7.51–7.60(1H, m), 7.62–7.70(1H, m), 7.82(1H, d). LRMS: m/z 487.2 (MH$^+$) Melting point [° C.]: 90–91 |
| 7<br>2-Methyl-N-{(1S)-3-[3-exo-(2-methyl-1H-benzimidazol-1-yl)-8-azabicyclo[3.2.1]oct-8-yl]-1-phenylpropyl}cyclopropanecarboxamide | | 4 | Found C, 74.17; H, 8.04; N, 11.63% $C_{29}H_{36}N_4O$; 0.75$H_2O$ requires C, 74.09; H, 8.04; N, 11.92% $^1$H NMR (400 MHz, CDCl$_3$): δ [ppm] 0.98–1.26(6H, m), 1.32–1.41(1H, m), 1.62–1.80(4H, m), 1.93–2.18(4H, m), 2.43–2.72(7H, m), 3.38–3.52(2H, m), 4.54(1H, m), 5.20(1H, q), 7.05(1H, bd), 7.11–7.22(2H, m), 7.24–7.30(1H, m), 7.32–7.40(4H, m), 7.47–7.54(1H, m), &.62–7.71(1H, m) LRMS: m/z 457.6 (MH$^+$) Melting point [° C.]: 105–106 |
| 8<br>2-Cyclopropyl-N-{(1S)-3-[3-exo-(2-methyl-1H-benzimidazol-1-yl)-8-azabicyclo[3.2.1]oct-8-yl]-1-phenylpropyl}acetamide | | 3 | Found C, 73.28; H, 7.99; N, 11.77% $C_{29}H_{36}N_4O$; 1$H_2O$ requires C, 73.39; H, 8.07; N, 11.88% $^1$H NMR (400 MHz, CDCl$_3$): δ [ppm] 0.21(2H, m), 0.61(2H, m), 0.97–1.08(1H, m), 1.61–1.80(4H, m), 1.96–2.14(4H, bm), 2.21(2H, m), 2.44–2.68 (7H, m), 3.42(2H, bs), 4.54(1H, m), 5.24 (1H, m), 6.88(1H, d), 7.16–7.22(2H, m), 7.24–7.30(1H, m), 7.32–7.41(4H, m), 7.47–7.56(1H, m), 7.62–7.70(1H, m) LRMS: m/z 456.9 (MH$^+$) Melting point [° C.]: 85–86 |
| 9<br>N-{(1S)-3-[3-exo-(2-methyl-1H-benzimidazol-1-yl)-8-azabicyclo[3.2.1]oct-8-yl]-1-phenylpropyl}tetrahydro-3-furancarboxamide | | 6 | Found C, 70.92; H, 7.73; N, 11.41% $C_{29}H_{36}N_4O_2$; 1$H_2O$ requires C, 70.99; H, 7.81; N, 11.42% $^1$H NMR (400 MHz, CDCl$_3$): δ [ppm] 1.68(2H, bm), 1.73(2H, d), 1.94–2.26(6H, m), 2.48–2.56(3H, m), 2.56–2.68(4H, m), 2.92(1H, bm), 3.43(2H, bs), 3.76–3.84(1H, m), 3.86–4.01(3H, m), 4.56(1H, m), 5.21(1H, m), 7.03–7.12 (1H, bm), 7.13–7.23(2H, m), 7.23–7.40 (5H, m), 7.45–7.54(1H, m), 7.64–7.72 (1H, m) LRMS: m/z 473.6 (MH$^+$) Melting point [° C.]: 93–94 |

| Example Number | R | Yield (%) | Characterization Data |
|---|---|---|---|
| 10<br>3,3,3-Trifluoro-N-{(1S)-3-[3-exo-(2-methyl-1H-benzimidazol-1-yl)-8-azabicyclo[3.2.1]oct-8-yl]-1-phenylpropyl}propanamide | 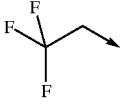 | 2 | Found C, 66.18; H, 6.51; N, 11.33%<br>$C_{27}H_{31}F_3N_4O$; 0.3$H_2O$ requires<br>C, 66.19; H, 6.50; N, 11.43%<br>$^1$H NMR (400 MHz, CDCl$_3$): δ<br>[ppm] 1.67(2H, d), 1.76(2H, d), 2.01 (1H, m), 2.06–2.18(3H, m), 2.47–2.68 (7H, m), 3.10(2H, q), 3.44(2H, bm), 4.54 (1H, m), 5.22–5.31(1H, m), 7.14–7.22 (2H, m), 7.22–7.34(3H, m), 7.34–7.40 (2H, m), 7.43–7.54(2H, m), 7.64–7.72 (1H, m)<br>LRMS: m/z 485.3 (MH$^+$) |
| 11<br>N-{(1S)-3-[3-exo-(2-Methyl-1H-benzimidazol-1-yl)-8-azabicyclo[3.2.1]oct-8-yl]-1-phenylpropyl}tetrahydro-2-furancarboxamide | 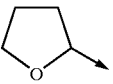 | 3 | Found C, 71.06; H, 7.66; N, 11.08%<br>$C_{29}H_{36}N_4O_2$; 1$H_2O$ requires<br>C, 70.99; H, 7.81; N, 11.42%<br>$^1$H NMR (400 MHz, CDCl$_3$): δ<br>[ppm] 1.58–1.76(4H, bm), 1.79–1.94(2H, m), 1.98–2.16(5H, bm), 2.20–2.35(1H, m), 2.40–2.67(7H, bm), 3.32–3.47(2H, bm), 3.81–4.00(2H, m), 4.26–4.44(1H, m), 4.52(1H, m), 5.13–5.33(1H, m), 7.12–7.23(2H, m), 7.26–7.42(5H, m), 7.47–7.58(1H, m), 7.57–7.71(1H, m)<br>LRMS: m/z 473.0 (MH$^+$) |
| 12<br>1-(Acetylamino)-N-{(1S)-3-exo-(2-methyl-1H-benzimidazol-1-yl)-8-azabicyclo[3.2.1]oct-8-yl]-1-phenylpropyl}cyclopentane carboxamide | 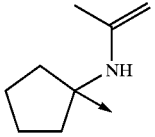 | 0 | Found C, 66.86; H, 7.34; N, 12.21%<br>$C_{32}H_{41}N_5O_2$; 0.7$CH_2Cl_2$ requires<br>C, 66.89; H, 7.28; N, 11.93%<br>$^1$H NMR (400 MHz, CDCl$_3$): δ<br>[ppm] 1.46–1.82(5H, bm), 1.88–2.19 (11H, m), 2.19–2.42(3H, bm), 2.42–2.76 (8H, bm), 3.44(2H, bs), 4.52(1H, m), 5.09(1H, m), 5.72(1H, bs), 7.16–7.23 (2H, m), 7.28–7.40(4H, m), 7.59(1H, bs), 7.63–7.70(1H, m), 7.92(1H, bd)<br>LRMS: m/z 528.6 (MH$^+$) |
| 13<br>N-{(1S)-3-[3-exo-(2-Methyl-1H-benzimidazol-1-yl)-8-azabicyclo[3.2.1]oct-8-yl]-1-phenylpropyl}acetamide (by-product in Example 5) | CH$_3$ → | | Found C, 74.09; H, 7.84; N, 13.10%<br>$C_{26}H_{32}N_4O$; 0.3$H_2O$ requires<br>C, 74.01; H, 7.79; N, 13.28%<br>$^1$H NMR (400 MHz, CDCl$_3$): δ<br>[ppm] 1.64–1.80(4H, m), 1.92–2.18(7H, m), 2.43–2.57(3H, m), 2.60–2.68(4H, m), 3.37–3.52(3H, m), 4.54(1H, m), 5.23 (1H, m), 7.12–7.21(3H, m), 7.30–7.42 (4H, m), 7.50(1H, m), 7.68(1H, m)<br>LRMS: m/z 417.5 (MH$^+$) |
| 14<br>1-Methoxy-N-{(1S)-3-[3-exo-(2-methyl-1H-benzimidazol-1-yl)-8-azabicyclo[3.2.1]oct-8-yl]-1-phenylpropyl}cyclopentane carboxamide | 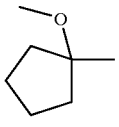 | 6 | Found C, 71.95; H, 8.11; N, 10.77%<br>$C_{31}H_{40}N_4O_2$; 0.9$H_2O$ requires<br>C, 72.03; H, 8.15; N, 10.84%<br>$^1$H NMR (400 MHz, CDCl$_3$): δ<br>[ppm] 1.61–1.80(8H, m), 1.81–1.94(2H, m), 1.94–2.20(7H, m), 2.43–2.67(7H, m), 3.23(3H, s), 3.43(2H, bs), 4.54 and 4.85 (1H, 2 × m), 5.19(1H, m), 7.13–7.22(2H, m), 7.23–7.28(1H, m), 7.29–7.40(4H, m), 7.56–7.64(1H, m), 7.68(1H, m)<br>LRMS: m/z 501.9 (MH$^+$) |
| 15<br>1-Methyl-N-{(1S)-3-[3-exo-(2-methyl-1H-benzimidazol-1-yl)-8-azabicyclo[3.2.1]oct-8-yl]-1-phenylpropyl}-2-oxo-4-pyrrolidine-carboxamide | 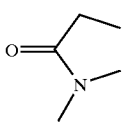 | 5 | Found C, 67.53; H, 7.66; N, 12.99%<br>$C_{30}H_{37}N_5O_2$; 2$H_2O$ requires<br>C, 67.27; H, 7.71; N, 13.07%<br>$^1$H NMR (400 MHz, CDCl$_3$): δ<br>[ppm] 1.64–1.72(2H, m), 1.78(2H, d), 1.95–2.18(4H, m), 2.45–2.78(9H, m), 2.83(3H, s), 3.07(1H, m), 3.40–3.54(3H, m), 3.62–3.76(1H, m), 4.56(1H, m), 5.22 (1H, q), 7.12–7.24(3H, m), 7.31(3H, m), 7.34–7.41(2H, m), 7.48(1H, m), 7.68 (1H, m)<br>LRMS: m/z 500.5 (MH$^+$) |

EXAMPLE 16

1-Amino-N-{(1S)-3-exo-[3-(2-methyl-1H-benzimidazol-1-yl)-8-azabicyclo[3.2.1]oct-8-yl]-1-phenylpropyl}cyclopentanecarboxamide

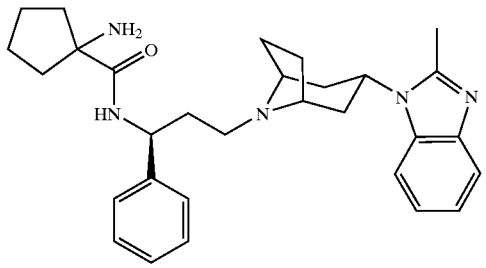

The title compound of preparation 72 (135 mg, 0.23 mmol) and trifluoroacetic acid (2 ml) in dichloromethane (5 ml) were stirred for 16 hours. The solvent was evaporated under reduced pressure and the residue quenched with aqueous saturated sodium carbonate solution. This aqueous solution was extracted with dichloromethane (3×) and the combined organic extracts washed with brine, dried (MgSO$_4$), filtered and evaporated under reduced pressure. The residual pale brown solid was purified by column chromatography on silica gel, using an elution gradient of dichloromethane:methanol:0.88 ammonia (98:2:0.25 to 95:5:0.5) to afford the tide compound as a white solid, 96 mg.

Found C, 71.87; H, 8.26; N, 14.03%; C$_{30}$H$_{39}$N$_5$O;0.9H$_2$O requires C, 71.80; H, 8.19; N, 13.95%; $^1$H NMR (400 MHz, CDCl$_3$): δ [ppm] 1.27–1.89 (11H, m), 1.89–2.18 (5H, m), 2.18–2.35 (2H, m), 2.41–2.53 (2H, m), 2.55–2.66 (5H, m), 3.40 (2H, bs), 4.52 and 4.77 (1H, 2×m), 5.06–5.18 (1H, m), 7.12–7.22 (2H, m), 7.22–7.33 (1H, m), 7.33–7.39 (4H, m), 7.52–7.59 (1H, m), 7.63–7.71 (1H, m), 8.24 and 8.43 (1H, 2×m); LRMS: m/z 486.9 (MH$^+$).

EXAMPLES 17 AND 18

1-Acetyl-N-{(1S)-3-[3-endo-2-methyl-1H-benzimidazol-1-yl)-8-azabicyclo[3.2.1]oct-8-yl]-1-phenylpropyl}-3-azetidinecarboxamide

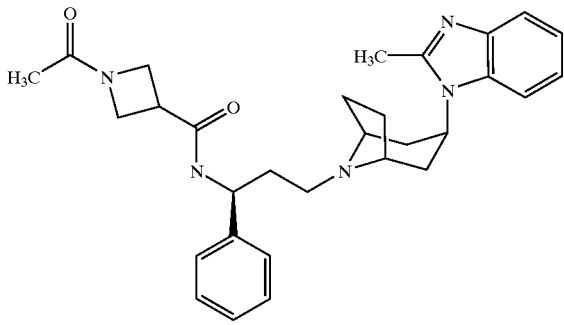

N-{(1S)-3-[3-endo-(2-methyl-1H-benzimidazol-1-yl)-8-azabicyclo[3.2.1]oct-yl]-1-phenylpropyl}acetamide

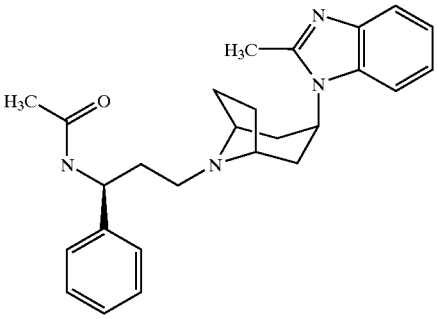

1-(3-Dimethyl aminopropyl)-3-ethylcarbodiimide hydrochloride (100 mg, 0.52 mmol) was added to a solution of the title compound of preparation 68 (150 mg, 0.40 mmol) and 1-acetyl-3-azetidinecarboxylic acid (69 mg, 0.48 mmol) in dichloromethane (10 ml). The reaction mixture was stirred for 3 hours after which time the solution was evaporated to dryness, re-dissolved in ethyl acetate, washed with a saturated aqueous sodium carbonate solution, then water. The organic layer was dried (MgSO$_4$), filtered and evaporated under reduced pressure. The crude product was purified by column chromatography on silica gel using dichloromethane:methanol:0.88 ammonia (95:5:0.5) as eluant to afford the title compound of example 17 as a white foam (75 mg), Found C, 67.96; H, 7.44; N, 13.09%; C$_{30}$H$_{37}$N$_5$O$_2$;1.6H$_2$O requires C, 68.18; H, 7.67; N, 13.25%; $^1$H-NMR (400 MHz, CDCl$_3$): δ [ppm] 1.68–1.80 (2H, m), 1.87 (3H, s), 1.92–2.31 (8H, m), 2.40–2.48 (2H, m), 2.63 (3H, s), 3.10 (1H, m), 3.36–3.47 (2H, m), 4.00–4.22 (3H, m), 4.37–4.46 (1H, m), 4.68–4.80 (1H, m), 5.20 (1H, m), 6.13 (1H, bd), 7.15–7.41 (8H, m), 7.67 (1H, m); LRMS: m/z 500.4 (MH$^+$); and the title compound of example 18, 20 mg. $^1$H-NMR (400 MHz, CDCl$_3$): δ [ppm] 1.71–1.84 (2H, m), 1.96–2.03 (7H, m), 2.05–2.33 (4H, m), 2.40–2.58 (2H, m), 2.63 (3H, m), 3.38–3.42 (2H, m), 4.72 (1H, m), 5.19 (1H, m), 6.34 (1H, d), 7.14–7.40 (8H, m), 7.64 (1H, m); LRMS: m/z 417.2 (MH$^+$).

EXAMPLE 19

N-{(1S)-3-[6-(2-Methyl-1H-benzimidazol-1-yl)-3-azabicyclo[3.1.0]hex-3-yl]-1-phenylpropyl}cyclobutanecarboxamide

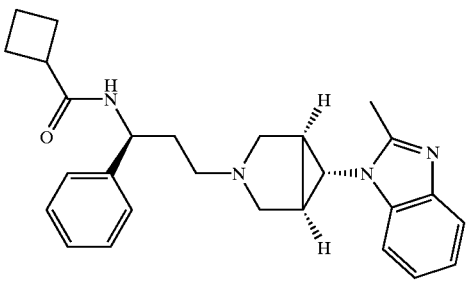

The title compounds of preparation 55 (0.056 g, 0.262 mmol) and preparation 8 (0.091 g, 0.394 mmol) were stirred together with sodium triacetoxyborohydride (0.083 g, 0.394 mmol) and acetic acid (0.015 ml, 0.262 mmol) in dichloromethane (10 ml) under an atmosphere of nitrogen for 4 hours at room temperature. A saturated aqueous solution of sodium bicarbonate was added and the product extracted with dichloromethane. The combined organic extracts were washed with water and brine, dried (MgSO$_4$) and the solvent evaporated under reduced pressure. The product was purified by column chromatography on silica gel using ethyl acetate:methanol:0.88 ammonia (97.5:2.5:0.25) as eluant, then dissolved in acetonitrile/water and freeze-dried to provide the title compound, 50 mg.

Found C, 73.35; H, 7.65; N, 12.51%; C$_{27}$H$_{32}$N$_4$O; 0.75H$_2$O; requires C, 73.36; H, 7.64; N, 12.67%; $^1$H-NMR (400 MHz, CDCl$_6$): δ [ppm]1.80–2.20 (8H, m), 2.20–2.36 (2H, m), 2.40–2.56 (4H, m), 2.63 (3H, s), 2.88–3.00 (1H, m), 3.37–3.42 (3H, m), 5.06 (1H, m), 6.20 (1H, m), 7.18–7.38 (7H, m), 7.40 (1H, m), 7.64 (1H, m); LRMS: m/z 429.4 (MH$^+$); [α]$_D$ −39.4 (c=0.10, CH$_3$OH).

EXAMPLE 20

2-Cyclopropyl-N-{(1S)-3-[3-exo-(3-{4-[(methylsulphonyl)amino]benzyl}-1.2.4-oxadiazol-5-yl)-8-azabicyclo[3.2.1]oct-8-yl]-1-phenylpropyl}acetamide Trifluoroacetate

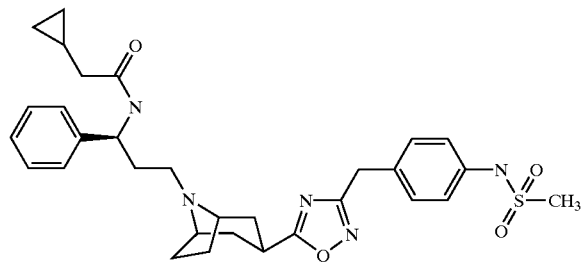

The title compound of preparation 64 (392 mg, 6.58 mmol) and 4M hydrochloric acid in dioxan (10 ml) were stirred for 1 hour and the reaction concentrated under reduced pressure. The residue was partitioned between dichloromethane and aqueous sodium carbonate solution and the aqueous layer was extracted with dichloromethane (2×). The combined organic solutions were washed with brine, dried (MgSO$_4$), filtered and evaporated under reduced pressure. The resulting colorless oil (150 mg, 0.302 mmol), cyclopropane acetic acid (36 mg, 0.363 mmol), and 1-(3-dimethylaminopropyl)-3-ethyl-carbodiimide hydrochloride (70 mg, 0.363 mmol) in dichloromethane (5 ml) were stirred at room temperature for 16 hours. The reaction was basified with 10% aqueous sodium carbonate solution and extracted with dichloromethane. The organic layer was washed with water, dried (MgSO$_4$), filtered and evaporated under reduced pressure. The residue was purified by column chromatography on silica gel, using an elution gradient of dichloromethane:methanol (98:2 to 96:4), then purification by reverse phase preparative HPLC, using an elution gradient of 0.1% trifluoroacetic acid in water:acetonitrile (90:10 to 10:90), to afford the title compound as a white solid, 44 mg.

Found C, 55.09; H, 5.77; N, 9.43%; C$_{31}$H$_{39}$N$_5$O$_4$S; 1.5H$_2$O;1CF$_3$CO$_2$H requires C, 55.14; H, 6.03; N, 9.74%; $^1$H NMR (400 MHz, CDCl$_3$): δ [ppm] 0.18 (2H, m); 0.55 (2H, m); 1.05 (1H, m); 1.62 (2H, m); 1.70–2.10 (11H, bm); 2.18 (2H, d); 2.40 (2H, m); 3.00 (2H, s); 3.23 (2H, m); 3.40 (1H, bs); 4.00 (1H, s); 5.20 (1H, m); 7.10–7.30 (9H, m); 8.40 (1H, bs); LRMS: m/z 578.3 (MH$^+$).

EXAMPLE 21

N-{(1S)-3-[7-exo-(2-Methyl-1H-benzimidazol-1-yl)-3-oxa-9-azabicyclo[3.3.1]non-9-yl]-1-phenylpropy}cyclobutanecarboxamide

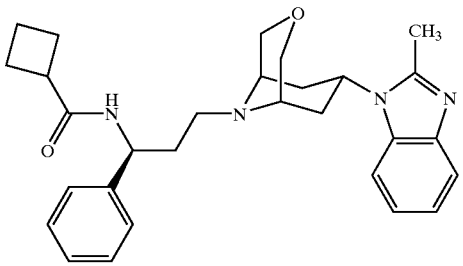

The title compound of preparation 70 (200 mg, 0.4 mmol) in dichloromethane (2.5 ml) was added to cyclobutanecarboxylic acid chloride (57 mg, 0.48 mmol), and N-diisopropylethylamine (313 μl, 1.8 mmol) in dichloromethane (2.5 ml). The reaction mixture was stirred at room temperature for 3 hours, then washed with water and brine. The organic layer was dried (MgSO$_4$), filtered and evaporated under reduced pressure. The residue was purified by column chromatography on silica gel, using an eluant of dichloromethane:methanol (98:2) to afford the title compound as a white powder, 43.2 mg.

Found C, 71.32; H, 7.74; N, 11.31%; C$_{29}$H$_{36}$N$_4$O$_2$;1H$_2$O requires C, 70.99; H, 7.81; N, 11.42%; $^1$H NMR (400 MHz, CDCl$_3$): δ [ppm] 1.75 (2H, m); 1.90 (1H, m); 1.95–2.10 (3H, m); 2.15 (2H, m); 2.30 (2H, m); 2.62 (3H, s); 2.65–2.78 (2H, m); 2.82 (2H, m); 2.92 (2H, d); 3.02 (1H, m); 3.95 (3H, m); 4.02 (1H, t); 5.28 (1H, m); 5.62 (1H, m); 6.50 (1H, d); 7.18 (2H, m); 7.30–7.40 (6H, m); 7.70 (1H, d); LRMS: m/z 473.2 (MH$^+$); [α]$_D$ −31.5 (c=0.54, MeOH).

EXAMPLE 22

2-Cyclopropyl-N-{(1S)-3-[7-exo-(2-methyl-1H-benzimidazol-1-yl)-3-oxa-9-azabicyclo[3.3.1]non-9-yl]-1-phenylpropyl}acetamide

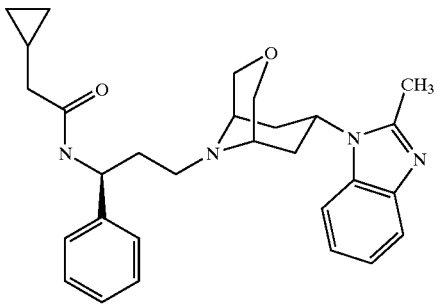

The title compound of preparation 70 (200 mg, 0.4 mmol) in dichloromethane (2.5 ml) was added to cyclopropane acetic acid (48 mg, 0.48 mmol), N-diisopropylethylamine (312 μl, 1.8 mmol), 1-(3-dimethylaminopropyl)-3-ethyl-carbodiimide hydrochloride (77 mg, 0.40 mmol), and hydroxybenzotriazole hydrate (61 mg, 0.40 mmol) in dichloromethane (2.5 ml). The reaction mixture was stirred at room temperature for 16 hours, then washed with 10% aqueous sodium carbonate solution. The organic layer was dried (MgSO$_4$), filtered and evaporated under reduced pressure. The residue was purified by column chromatography on silica gel, using an elution gradient of dichloromethane:methanol (98:2 to 97:3) to afford the title compound as a white powder, 109 mg.

Found C, 71.52; H, 7.81; N, 11.41%; $C_{29}H_{36}N_4O_4$; $0.8H_2O$ requires C, 71.52; H, 7.78; N, 11.50%; $^1H$ NMR (400 MHz, CDCl$_3$): δ [ppm] 0.20 (2H, m); 0.6 (2H, m); 1.00 (1H, m); 1.75 (2H, d); 1.95–2.10 (2H, m); 2.18 (2H, d); 2.62 (3H, s); 2.65–2.90 (5H, m); 2.95 (1H, s); 3.92 (2H, m); 3.95 (1H, s); 4.00 (1H, t); 5.30 (1H, m); 5.62 (1H, m); 6.62 (1H, d); 7.15 (2H, m); 7.30–7.40 (6H, m); 7.65 (1H, d); LRMS: m/z 473.3 (MH$^+$); [α]$_D$ –29 (c=1, MeOH)

EXAMPLE 23

3.3.3-Trifluoro-N-{(1S)-3-[7-exo-(2-methyl-1H-benzimidazol-1-yl)-3-oxa-9-azabicyclo[3.3.1]non-9-yl]-1-phenylpropyl}propanamide

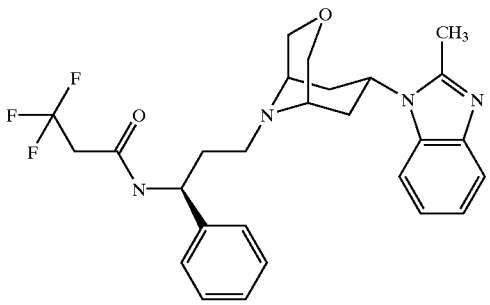

The title compound of preparation 70 (200 mg, 0.4 mmol) in dichloromethane (2.5 ml) was added to 3,3,3-trifluoropropionic acid (62 mg, 0.48mmol), N-diisopropylethylamine (312 μl, 1.8 mmol), 1-(3-dimethylaminopropyt)-3-ethyl-carbodiimide hydrochloride (77 mg, 0.40 mmol), and 1-hydroxybenzotriazole hydrate (61 mg, 0.40 mmol) in dichloromethane (2.5 ml). The reaction mixture was stirred at room temperature for 24 hours, then washed with 10% aqueous sodium carbonate solution. The organic layer was dried (MgSO$_4$), filtered and evaporated under reduced pressure. The residue was purified by column chromatography on silica gel, using an elution gradient of dichloromethane:methanol (98:2 to 97:3) to afford the title compound as a white powder, 146 mg.

Found C, 63.14; H, 6.33; N, 10.89%; $C_{27}H_{31}N_4F_3O_2$; $0.7H_2O$ requires C, 63.19; H, 6.36; N, 10.92%. $^1H$ NMR (400 MHz, CDCl$_3$): δ [ppm] 1.75 (2H, m); 2.08 (2H, m); 2.62 (3H, s); 2.64–2.80 (2H, m); 2.82 (2H, m); 2.92 (2H, s); 3.10 (2H, m); 3.95 (3H, m); 4.05 (1H, m); 5.35 (1H, m); 5.62 (1H, m); 7.10–7.20 (3H, m); 7.30 (3H, m); 7.35 (3H, m); 7.70 (1H, d); LRMS: m/z 501.1 (MH$^+$); [α]$_D$ –30 (c=1, MeOH)

EXAMPLE 24

N-{(1S)-3-[7-endo-(2-Methyl-1H-benzimidazol-1-yl)-3-oxa-9-azabicylo[3.3.1]non-9-yl]-1-phenylpropyl}cyclobutanecarboxamide

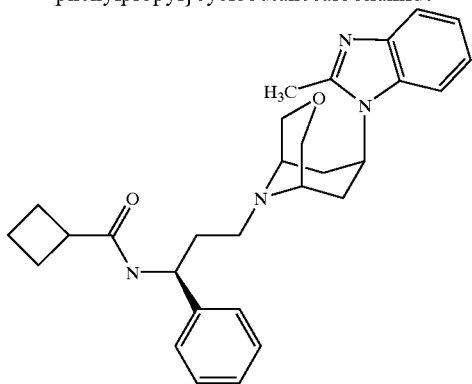

The title compound of preparation 69 (200 mg, 0.51 mmol) in dichloromethane (2.5 ml) was added to cyclobutanecarboxylic acid chloride (57 μl, 0.61 mmol), N-diisopropylethylamine (133 μl, 0.76 mmol), 1-(3-dimethylaminopropyl)-3-ethyl-carbodiimide hydrochloride (99 mg, 0.51 mmol), and 1-hydroxybenzotriazole hydrate (79 mg, 0.51 mmol) in dichloromethane (2.5 ml). The reaction mixture was stirred at room temperature for 16 hours, then basified with 10% aqueous sodium carbonate solution, and the phases separated. The aqueous layer was extracted with dichloromethane (2×). The combined organics were washed with brine, dried (MgSO$_4$), filtered and evaporated under reduced pressure. The residue was purified by column chromatography on silica gel, using an elution gradient of dichloromethane:methanol (98:2 to 96:4) to afford the title compound as a white solid, 133 mg.

Found C, 71.67; H, 7.79; N, 11.46%; $C_{29}H_{36}N_4O_2$; $0.7H_2O$ requires C, 71.78; H, 7.77; N, 11.55%; $^1H$ NMR (400 MHz, CDCl$_3$): δ [ppm] 1.85 (1H, m); 1.95 (3H, m); 2.10 (2H, m); 2.28 (4H, m); 2.58 (2H, t); 2.64 (3H, s); 2.75 (2H, m); 3.00 (3H, m); 3.45 (2H, d); 3.90 (2H, t); 4.85 (1H, m); 5.20 (1H, d); 5.82 (1H, d); 7.20 (2H, m); 7.30 (3H, m); 7.38 (2H, m); 7.70 (1H, m); 7.79 (1H, m); LRMS: m/z 473.7 (MH$^+$); [α]$_D$ –44 (c=2, MeOH).

EXAMPLE 25

2-Cyclopropyl-N-{(1S)-3-[7-endo-(2-methyl-1H-benzimidazol-1-yl)-3-oxa-9-azabicyclo[3.3.1]non-9-yl]-1-phenylpropyl}acetamide

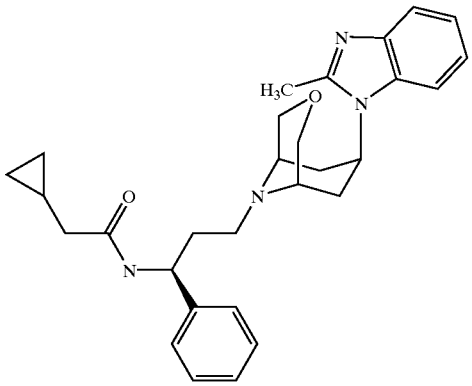

The title compound of preparation 69 (200 mg, 0.51 mmol) in dichloromethane (2.5 ml) was added to cyclopropane acetic acid (58 μl, 0.61 mmol), N-diisopropylethylamine (133 μl, 0.76 mmol), 1-(3-dimethylaminopropyl)-3-ethyl-carbodiimide hydrochloride (99 mg, 0.51 mmol), and 1-hydroxybenzotriazole hydrate (79 mg, 0.51 mmol) in dichloromethane (2.5 ml). The reaction mixture was stirred at room temperature for 16 hours, then basified with saturated aqueous sodium carbonate solution. The phases were separated and the aqueous layer was extracted with dichloromethane (2×). The combined organics were washed with brine, dried (MgSO$_4$), filtered and evaporated under reduced pressure. The residue was purified by column chromatography on silica gel, using an elution gradient of dichloromethane:methanol (98:2 to 96:4) to afford the title compound as a white solid, 209 mg.

Found C, 71.37; H, 7.81; N, 11.44%. $C_{29}H_{36}N_4O_2$;$1H_2O$ requires C, 70.99; H, 7.81; N, 11.42%; $^1H$ NMR (400 MHz, CDCl$_3$): δ [ppm] 0.2 (2H, m); 0.6 (2H, m); 0.95 (1H, m); 2.02 (2H, m); 2.19 (2H, m); 2.32 (2H, m); 2.58 (2H, m); 2.65 (3H, s); 2.78 (2H, m); 2.95 (1H, d); 3.05 (1H, d); 3.42 (2H, d); 3.90 (2H, t); 4.90 (1H, m); 5.27 (1H, m); 6.22 (1H, d);

7.20 (2H, m); 7.30 (3H, m); 7.38 (2H, m); 7.68 (1H, m); 7.78 (1H, m); LRMS: m/z 474.4 (MH$^+$); [α]$_D$ −40 (c=2, MeOH).

EXAMPLE 26
N-{(1S)-3-y[7-exo-(2-Methyl-1H-benzimidazol-1-yl)-3-thia-9-azabicyclo[3.3.1]non-9-yl]-1-phenylpropyl}cyclobutanecarboxamide

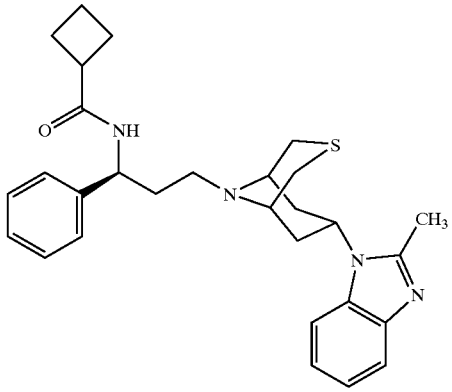

The title compound of preparation 66 (0.936 g, 1.85 mmol) and 4M hydrochloric acid in dioxan (10 ml) were stirred for 1 hour. The excess of solvent was evaporated under reduced pressure to give a cream solid, which was added to cyclobutanecarboxylic acid (0.2 ml, 2.03 mmol), N-diisopropylethylamine (1.6 ml, 9.2 mmol), 1-(3-dimethylaminopropyl)-3-ethyl-carbodiimide hydrochloride (390 mg, 2.03 mmol), and 1-hydroxybenzotriazole hydrate (275 mg, 2.03 mmol) in dichloromethane (5 ml). The reaction mixture was stirred at room temperature for 16 hours, concentrated under reduced pressure and dissolved in ethyl acetate then washed with 10% aqueous sodium carbonate solution The organic layer was dried (MgSO$_4$), filtered and evaporated under reduced pressure. The residue was purified by column chromatography on silica gel, using an eluant of dichloromethane:methanol (99:1) to afford the title compound as a white powder, 656 mg.

Found C, 69.84; H, 7.45; N, 11.17%; C$_{29}$H$_{36}$N$_4$OS; 0.6H$_2$O requires C, 69.77; H, 7.51; N, 11.22%; $^1$H NMR (400 MHz, CDCl$_3$): δ [ppm] 1.80–2.50 (12H, m); 2.63 (3H, s); 2.70–2.95 (4H, m); 3.05 (1H, m); 3.20–3.50 (4H, m); 5.25 (1H, d); 6.35 (1H, d), 6.70 (1H, m); 7.0–7.4 (7H, m); 7.45 (1H, m); 7.70 (1H, m); LRMS: m/z 489.2 (MH$^+$); [α]$_D$ −31.5 (c=1, MeOH).

EXAMPLE 27
2-Cyclopropyl-N-[(1S)-3-(3-endo-{[2-(4-fluorophenyl)acetyl]amino}-8-azabicyclo[3.2.1]oct-8-yl)-1-phenylpropyl]acetamide

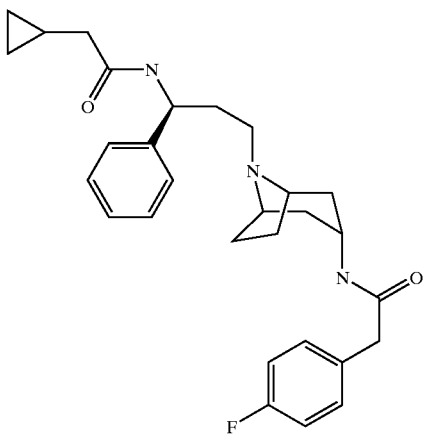

The title compound of preparation 81 (0.2 g, 0.42 mmol) was added to cyclopropane acetic acid (51 mg, 0.52 mmol), N-diisopropylethylamine (0.26 ml, 1.47 mmol), 1-(3-dimethylaminopropyl)-3-ethyl-carbodiimide hydrochloride (82 mg, 0.42 mmol), and 1-hydroxybenzotriazole hydrate (66 mg, 0.42 mmol) in dichloromethane (10 ml). The reaction mixture was stirred at room temperature for 16 hours, then washed with a saturated aqueous sodium carbonate solution. The organic layer was dried (MgSO$_4$), filtered and evaporated under reduced pressure. The residue was purified by column chromatography on silica gel, using an elution gradient of dichloromethane:methanol (98:2 to 97:3) to afford the title compound as a white powder, 40 mg.

Found C, 70.73; H, 7.54; N, 8.47%; C$_{29}$H$_{36}$FN$_3$O$_2$; 0.8H$_2$O, requires C, 70.79; H, 7.54; N, 8.54%. $^1$H NMR (400 MHz, CDCl$_3$): δ [ppm] 0.18 (2H, m); 0.55 (2H, m); 1.0 (1H, m); 1.20 (2H, m); 1.5 (2H, m); 1.6–2.0 (4H, m); 2.0–2.2 (4H, m); 2.2–2.4 (2H, m); 3.1 (1H, s); 3.25 (1H, s); 3.55 (2H, s); 4.1 (1H, m); 5.1 (1H, m); 5.7 (1H, d); 7.0–7.1 (2H, m); 7.2–7.4 (7H, m); 7.8 (1H, d); LRMS: m/z 478.4 (MH$^+$); [α]$_D$ −36.0 (c=1.0, MeOH)

EXAMPLE 28
N-[(1S)-3-(3-{[3-endo-4-Fluorophenyl)propanoyl]amino}-8-azabicyclo[3.2.1]oct-yl)-1-phenylpropyl]cyclobutanecarboxamide The title compound of preparation 81 (0.3 g, 0.640 mmol) was added to cyclobutanecarboxylic acid chloride (0.084 ml, 0.735 mmol) and N-diisopropylethylamine (0.38 ml, 2.18 mmol) in dichloromethane (10 ml). The reaction mixture was stirred at room temperature for 2 hours and basified with saturated aqueous sodium carbonate solution. The phases were separated and the aqueous layer was extracted with dichloromethane (2×). The combined organic solutions were washed with brine, dried (MgSO$_4$), filtered and evaporated under reduced pressure. The residue was purified by column chromatography on silica gel, using an elution gradient of dichloromethane:methanol: 0.88 ammonia (98:2:0 to 95.5:4:0.5) to afford the title compound as a white powder, 80 mg.

Found C, 70.40; H, 7.61; N, 8.12%; C$_{29}$H$_{36}$FN$_3$O$_2$;1H$_2$O requires C, 70.28; H, 7.73; N, 8.48%; $^1$H NMR (400 MHz, CDCl$_3$): δ [ppm] 1.20 (2H, m); 1.55 (2H, m); 1.75–2.40 (14H, m); 3.0 (1H, q); 3.15 (1H, s); 3.25 (1H, s); 3.65 (2H, s); 4.10 (1H, m); 5.10 (1H, m); 5.7 (1H, m); 7.10 (2H, m); 7.15–7.3 (7H, m); 8.9 (1H, s); LRMS: m/z 478.0 (MH$^+$); [α]$_D$ −46.4 (c=1.0, MeOH).

EXAMPLE 29
N-[(1S)-3-(3-{[3-exo-4-Fluorophenyl)propanoyl]amino}-8-azabicyclo[3.2.1]oct-yl)-1-phenylpropyl]cyclobutanecarboxamide

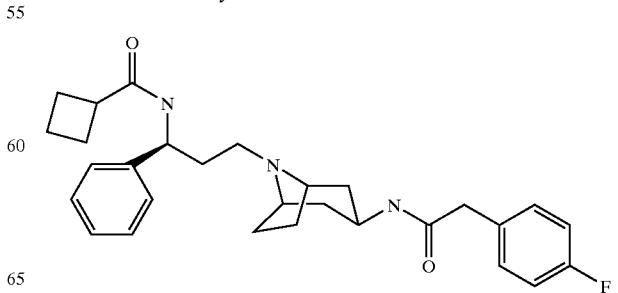

The title compound was obtained as a white powder (30%), from the compound of preparation 80 (0.2 g, 0.42 mmol) and cyclobutanecarboxylic acid, following the procedure described in example 28.

Found C, 71.36; H, 7.64; N, 8.54%; $C_{29}H_{36}N_3O_2;0.6H_2O$ requires C, 71.31; H, 7.68; N, 8.60%; $^1H$ NMR (400 MHz, $CDCl_3$): δ [ppm] 1.22–1.40 (2H, m); 1.65 (2H, m); 1.75–2.35 (14H, m); 2.90 (1H, m); 3.20 (1H, s); 3.25 (1H, s); 3.50 (2H, s); 4.10 (1H, m); 5.10 (2H, m); 7.05 (2H, m); 7.18–7.30 (7H, m); 7.50 (1H, d); LRMS: m/z 478.5 (MH$^+$); $[α]_D$ −20 (c=0.4, MeOH).

EXAMPLE 30

2-Cyclopropyl-N-[(1S)-3-(3-exo-{[2-(4-fluorophenyl)acetyl]amino}-8-azabicyclo[3.2.1]oct-8-yl)-1-phenylpropy]acetamide

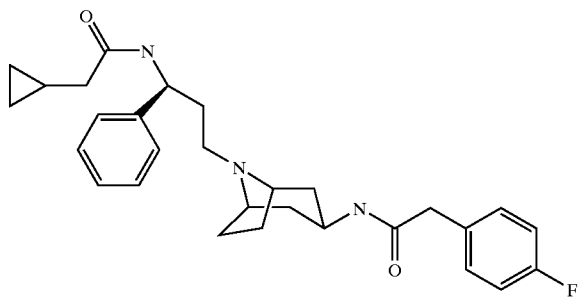

The title compound was obtained as a white powder (20%), from the compound of preparation 80 (0.2 g, 0.42 mmol) and cyclopropane acetic acid (51 mg, 0.52 mmol), following the procedure of example 27.

Found C, 71.06; H, 7.67; N, 8.48%; $C_{29}H_{36}FN_3O_2$; $0.7H_2O$ requires C, 71.05; H, 7.69; N, 8.57%; $^1H$ NMR (400 MHz, $CDCl_3$): δ [ppm] 0.15 (2H, m); 0.58 (2H, m); 0.95 (1H, m); 1.25–1.40 (2H, m); 1.70 (2H, m); 1.75–1.98 (7H, m); 2.10 (2H, m); 2.30 (2H, m); 3.20 (2H, d); 3.45 (2H, s); 4.10 (1H, m); 5.10 (2H, m); 7.00 (2H, m); 7.15–7.35 (7H, m); LRMS: m/z 477.9 (MH$^+$). $[α]_D$ −30 (c=0.4, MeOH).

EXAMPLE 31

N-{(1S)-3-[3-exo-(2-Methyl-1H-benzimidazol-1-yl)-8-azabicyclo[3.2.1]oct-yl-1-phenylpropyl}-3-azetidinecarboxamide

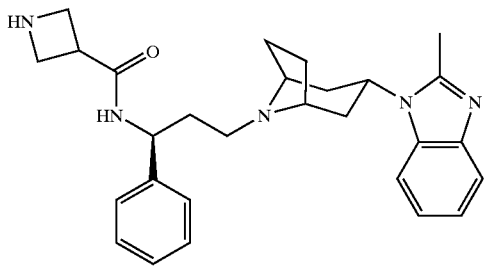

The title compound was obtained from the title compound of preparation 71 as a clear glass in 64% yield using a similar procedure to that described in preparation 52 (alternative method).

Found C, 68.29; H, 7.64; N, 14.01%; $C_{28}H_{35}N_5O;2H_2O$ requires C, 68.13; H, 7.96; N, 14.19%; $^1H$ NMR (400 MHz, $CDCl_3$): δ [ppm] 1.56–1.91 (5H, m), 1.97–2.20 (4H, m), 2.44–2.71 (7H, m), 3.31–3.54 (3H, m), 3.68–3.80 (2H, m), 3.84–3.96 (2H, m), 4.44–4.61 (1H, m), 5.15–5.28 (1H, m), 7.12–7.41 (7H, m), 7.44–7.57 (1H, m), 7.61–7.74 (1H, m); LRMS: m/z 458.7 (MH$^+$).

EXAMPLE 32

N-{(1S)-3-[3-exo-(2-Methyl-1H-benzimidazol-1-yl)-azabicyclo[3.2.1]oct-8-yl]-1-phenylpropyl}-1-propionyl-3-azetidinecarboxamide

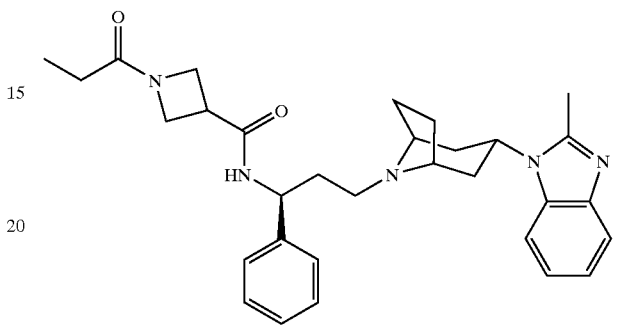

Propionyl chloride (14 μl, 0.16 mmol) was added to a solution of the title compound of example 31 (70 mg, 0.15 mmol) and triethylamine (24 μl, 0.17 mmol) in dichloromethane (6 ml). The reaction mixture was stirred at room temperature for 16 hours. The solvent was evaporated under reduced pressure and the residue taken up in ethyl acetate, washed with brine, dried ($MgSO_4$), filtered and evaporated under reduced pressure. The residue was purified by column chromatography on silica gel, using an elution gradient of dichloromethane:methanol:0.88 ammonia (98:2:0.25 to 90:5:0.5) to afford the title compound as a white solid, 29 mg.

Found C, 67.72; H, 7.85; N, 12.48%; $C_{31}H_{39}N_5O_2;2H_2O$ requires C, 67.73; H, 7.88; N, 17.74%; $^1H$ NMR (400 MHz, $CDCl_3$): δ [ppm] 1.08 (3H, t), 1.76 (2H, d), 1.94–2.18 (7H, bm), 2.44–2.67 (8H, bm), 3.26 (1H, m), 3.44 (2H, bs), 4.05–4.24 (3H, m), 4.41 (1H, m), 4.56 (1H, m), 5.24 (1H, m), 7.15–7.23 (2H, m), 7.28–7.43 (6H, m), 7.48 (1H, m), 7.63–7.71 (1H, d); LRMS: m/z 514.6 (MH$^+$).

EXAMPLE 33

N-{(1S)-3-(3-endo-(2-Methyl-1H-benzimidazol-1-yl)-8-azabicyclo[3.2.1]oct-8-yl]-1-phenylpropyl}tetrahydro-3-furancarboxamide

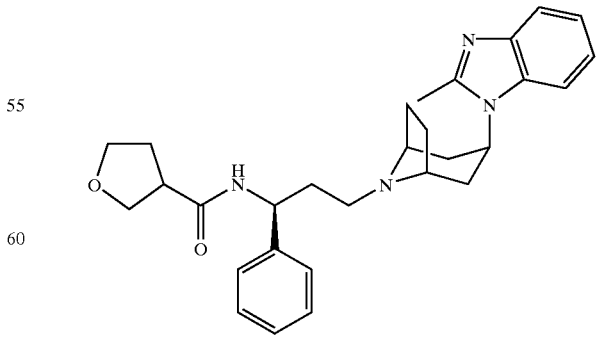

The title compound of preparation 68 (110 mg, 0.29 mmol), tetrahydro-3-furanoic acid (36 mg, 0.31 mmol) and 1-(3-dimethylaminopropyl)-3-ethylcarbodiimide hydrochloride (62 mg, 0.32 mmol) were stirred together for 30 minutes at room temperature in 5 ml of dichloromethane. The solvent was removed under reduced pressure. The residue was dissolved in ethyl acetate and washed with aqueous saturated sodium carbonate solution then water. The organic phase was dried (MgSO$_4$), filtered and evaporated under reduced pressure. The residue was purified using column chromatography on silica gel using an eluant of dichloromethane:methanol:0.88 ammonia (98:2:0.25) to afford the title compound as white foam, 69 mg.

Found C, 71.40; H, 7.82; N, 11.62%; $C_{29}H_{36}N_4O_2$; 0.9H$_2$O requires C, 71.25; H, 7.79; N, 11.46%; $^1$H NMR (400 MHz, CDCl$_3$): δ [ppm] 1.68–1.81 (2H, m), 1.92–2.06 (4H, m), 2.06–2.32 (7H, m), 2.39–2.53 (2H, m), 2.58–2.65 (3H, m), 2.85–2.97 (1H, m), 3.35–3.45 (2H, m), 3.77–3.85 (1H, m), 3.85–3.98 (3H, m), 4.69–4.80 (1H, m), 5.13–5.23 (1H, m), 6.29–6.40 (1H, m), 7.15–7.23 (2H, m), 7.23–7.42 (5H, m), 7.65–7.73 (1H, m); LRMS: m/z 473.0 (MH$^+$).

EXAMPLE 34

N-{(1S)-3-[3]-endo-(2-Methyl-1H-benzimidazol-1-yl)-8-azabicyclo[3.2.1]oct-8-yl]-1-phenylpropy}tetrahydro-2H-pyran-4-carboxamide

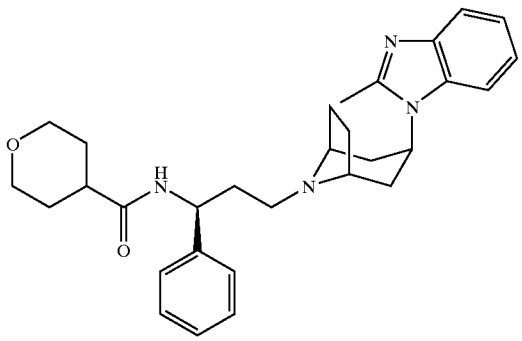

The title compound was obtained from the title compound of preparation 68 and tetrahydro-2H-pyran-4-carboxylic acid in 41% yield using a similar procedure to that described in example 33.

Found C, 71.93; H, 7.96; N, 11.29%; $C_{30}H_{38}N_4O_2$; 0.8H$_2$O requires C, 71.91; H, 7.97; N, 11.18%; $^1$H NMR (400 MHz, CDCl$_3$): δ [ppm] 1.68–1.90 (6H, m), 1.94–2.03 (4H, m), 2.06–2.19 (2H, m), 2.19–2.52 (5H, m), 2.63 (3H, s), 3.32–3.45 (4H, m), 3.98–4.05 (2H, m), 4.68–4.81 (1H, m), 5.13–5.23 (1H, m), 5.92–5–97 (1H, d), 7.13–7.23 (2H, m), 7.26–7.40 (6H, m), 7.65–7.68 (1H, m); LRMS: m/z 487.0 (MH$^+$).

EXAMPLE 35

N-{(1S)-3-[3-endo-(2-Methyl-1H-benzimidazol-1-yl)-8-azabicyclo[3.2.1]oct-yl]-1-phenylpropyl}tetrahydro-2-furancarboxamide

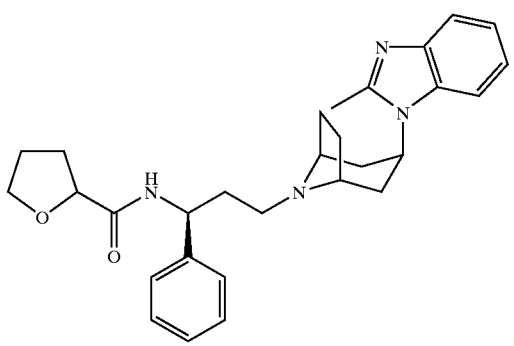

The title compound was prepared in 67% yield from the title compound of preparation 68 and tetrahydro-2-furanoic acid using a similar method to that described in example 33.

Found C, 71.78; H, 7.73; N, 11.63%; $C_{29}H_{36}N_4O_2$; 0.7H$_2$O requires C, 71.78; H, 7.77; N, 11.55%; $^1$H NMR (400 MHz, CDCl$_3$): δ [ppm] 1.68–2.35 (12H, m), 2.39–2.55 (2H, m), 2.58–2.65 (3H, m), 3.32–3.45 (2H, m), 3.84–4.00 (4H, m), 4.32–4.39 and 4.39–4.45 (1H, m), 4.74–4.87 (1H, m), 5.13–5.23 (1H, m), 7.13–7.23 (2H, m), 7.23–7.32 (2H, m), 7.32–7.39 (5H, m), 7.65–7.71 (1H, m); LRMS: m/z 473.0 (MH$^+$).

EXAMPLE 36

1-Acetyl-N-{(1S)-3-[3-endo-1H-benzimidazol-1-yl)-8-azabicyclo[3.2.1]oct-8-yl]-1-phenylpropyl}-3-azetidinecarboxamide

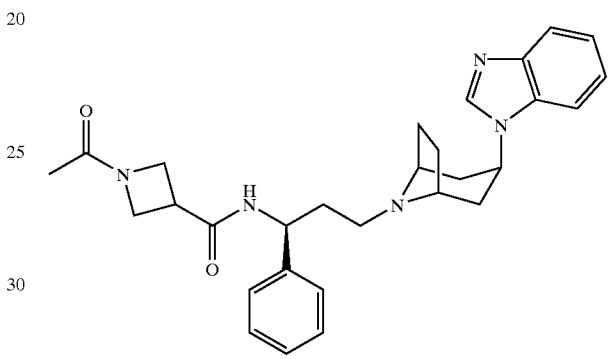

The title compound of preparation 73 (730 mg, 1.34 mmol) was stirred for 8 hours at room temperature in a 10 ml mixture of dichloromethane:trifluoroacetic acid (4:1). The solvents were removed under reduced pressure. The residue was basified with saturated aqueous sodium hydrogen carbonate solution and extracted with dichloromethane (×4). The combined organic layers were dried (MgSO$_4$), filtered and evaporated under reduced pressure to afford a foam, 500 mg.

This intermediate azetidine, (100 mg, 0.23 mmol) and triethylamine (34 μl, 0.25 mmol) were dissolved in dichloromethane (6 ml) at 0° C. and acetyl chloride (17 μl, 0.24 mmol) was added. The solvent was removed under reduced pressure. The residue was basified with saturated aqueous sodium hydrogen carbonate and extracted with dichloromethane. The combined organic layers were dried (MgSO$_4$), filtered and evaporated under reduced pressure. The residue was purified by column chromatography on silica gel using an eluant of dichloromethane:methanol:0.88 ammonia (95:5:0.5) to afford the title compound as a foam, 62 mg.

Found C, 68.31; H, 7.46; N, 13.75%; $C_{29}H_{35}N_5O_2$; 1H$_2$O;0.1CH$_2$Cl$_2$ requires C, 68.25; H, 7.32; N, 13.67%; $^1$H NMR (400 MHz, CDCl$_3$): δ [ppm] 1.60–1.68 (2H, m), 1.84 (3H, s), 1.94–2.10 (6H, m), 2.27–2.39 (2H, m), 2.55–2.74 (2H, m), 3.16–3.29 (1H, m), 3.32–3.42 (2H, m), 4.03–4.24 (3H, m), 4.35–4.45 (1H, m), 4.65–4.76 (1H, m), 5.16–5.27 (1H, m), 6.87–6.94 and 7.00–7.13 (1H, m), 7.23–7.32 (5H, m), 7.32–7.44 (3H, m), 7.76–7.82 (1H, m), 8.03–8.06 (1H, m); LRMS: m/z 486.0 (MH$^+$).

EXAMPLE 37

N-{(1S)-3-[3-endo-(1H-Benzimidazol-1-yl)-8-azabicyclo[3.2.1]oct-8-yl]-1-phenylpropyl}-1-propionyl-3-azetidinecarboxamide

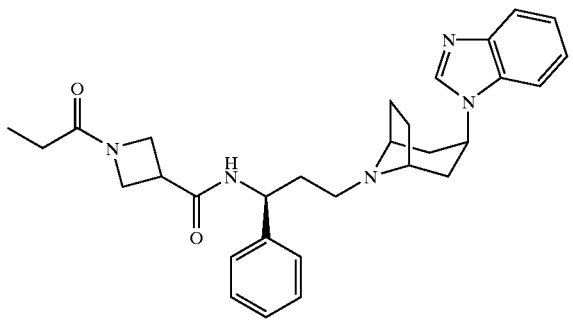

The title compound was prepared from the title compound of preparation 73 and propionyl chloride using a similar procedure to that described in example 36 in 55% yield.

Found C, 70.19; H, 7.62; N, 13.60%; $C_{30}H_{37}N_5O_2$; 0.8$H_2O$ requires C, 70.09; H, 7.57; N, 13.62; $^1$H NMR (400 MHz, CDCl$_3$): δ [ppm] 1.06–1.13 (3H, t), 1.60–1.68 (2H, m), 1.92–2.13 (8H, m), 2.29–2.39 (2H, m), 2.53–2.74 (2H, m), 3.18–3.32 (1H, m), 3.32–3.42 (2H, m), 4.05–4.23 (3H, m), 4.35–4.45 (1H, m), 4.66–4.76 (1H, m), 5.16–5.27 (1H, m), 6.84–6.94 and 7.06–7.13 (1H, m), 7.23–7.32 (5H, m), 7.32–7.44 (3H, m), 7.76–7.82 (1H, m), 8.03–8.06 (1H, m); LRMS: m/z 500.0 (MH$^+$).

EXAMPLE 38

Methyl3-[({(1S)-3-[3-exo-(2-methyl-1H-benzimidazol-1-yl)-8-azabicyclo[3.2.1]oct-8-yl]-1-phenylpropyl}amino)carbonyl]-1-azetidinecarboxytate

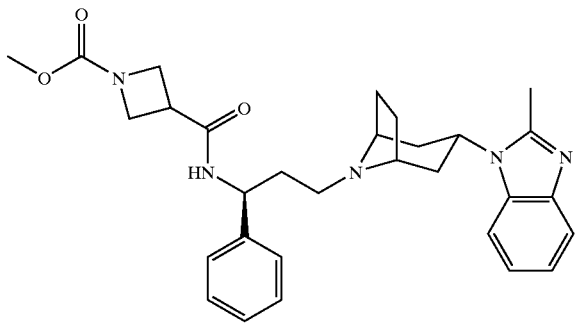

Methyl chloroformate (11 μl, 0.14 mmol) was added to a solution of the title compound of example 31 (64 mg, 0.14 mmol) and triethylamine (21 μl, 0.15 mmol) in dichloromethane (5 ml). The reaction mixture was stirred at room temperature for 3 hours. The solvent was evaporated under reduced pressure and the residue taken up in ethyl acetate, washed with brine, dried (MgSO$_4$), filtered and evaporated under reduced pressure. The residue was purified by column chromatography on silica gel, using an elution gradient of dichloromethane:methanol:0.88 ammonia (98:2:0.25 to 90:5:0.5) to afford the title compound as a white solid, 20 mg. $^1$H NMR (400 MHz, CDCl$_3$): δ [ppm] 1.69 (2H, bm), 1.78 (2H, bd), 1.95–2.18 (4H, m), 2.46–2.70 (8H, m), 3.16 (1H, m), 3.44 (2H, bs), 3.64 (3H, s), 4.06–4.14 (2H, m), 4.14–4.24 (2H, m), 4.57 (1H, m), 5.13 (1H, m), 7.12–7.23 (3H, m), 7.28–7.32 (3H, m), 7.33–7.42 (1H, m), 7.53 (1H, m), 7.68 (1H, m); LRMS: m/z 516.3 (MH$^+$).

EXAMPLE 39

1-Acetyl-N-{(1S)-3-[3-exo-(4-fluoro-1H-benzimidazol-1-yl)-8-azabicyclo[3.2.1]oct-8-yl]-1-phenylpropyl}-3-azetidinecarboxamide

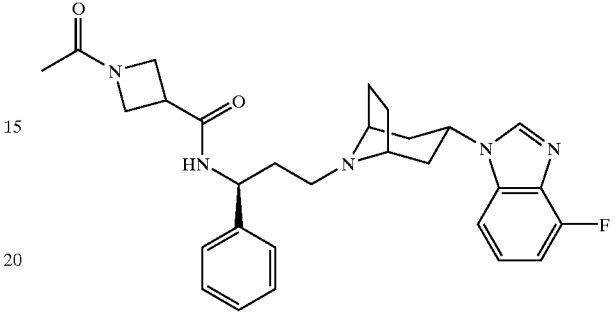

The title compound of preparation 89 (0.591 g, 1.052 mmol) and 4M hydrochloric acid in dioxane (10 ml) were stirred for 1 hour. The excess of solvent was evaporated under reduced pressure to give a cream solid, which was added to glacial acetic acid (0.072 ml, 1.263 mmol), diisopropyl ethylamine (0.75 ml, 4.2 mmol), 1-(3-dimethylaminopropyl)-3-ethyl-carbodiimide hydrochloride (0.242 g, 1.263 mmol), and 1-hydroxybenzotriazole hydrate (0.171 g, 1.263 mmol) in dichloromethane (8 ml). The reaction mixture was stirred at room temperature for 16 hours, concentrated and dissolved in ethyl acetate then washed with 10% sodium carbonate solution. The organic layer was dried (MgSO$_4$), filtered and evaporated under reduced pressure. The residue was purified by column chromatography on silica gel, using an eluent of dichloromethane:methanol (99:4) to afford the title compound as a white powder, 0.160 g.

Found C, 65.28; H, 6.87; N, 13.410%; $C_{29}H_{34}FN_5O_2$. 1.7$H_2O$ requires C, 65.20; H, 7.06; N, 13.11; $^1$H NMR (400 MHz, CDCl$_3$): δ [ppm] 1.75–2.70 (16H, m), 3.24 (1H, m), 3.56 (2H, m), 4.02–4.22 (3H, m), 4.40 (1H, m), 4.58 (1H, m), 5.12 (1H, q), 7.02 (1H, m), 7.10–7.42 (7H, m), 8.0 (1H, s); LRMS: m/z 505 (MH$^+$). [α]$_D$ −59.0° (c=1.0, MeOH).

The following compounds have been prepared using methods similar to those described above:

N-{(1S)-3-[3-endo-(2-Methyl-1H-benzimidazol-1-yl)-8-azabicyclo[3.2.1]oct-8-yl]-1-phenylpropyl}-1-propionyl-3-azetidinecarboxamide

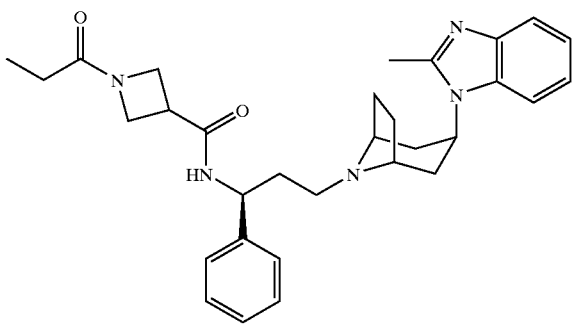

131

1-Acetyl-N-{(1S)-3-[3-endo-(2-methyl-1H-benzimidazol-1-yl)-8-azabicycol[3.2.1]oct-8-yl]-1-phenylpropyl}-2-azetidinecarboxamide

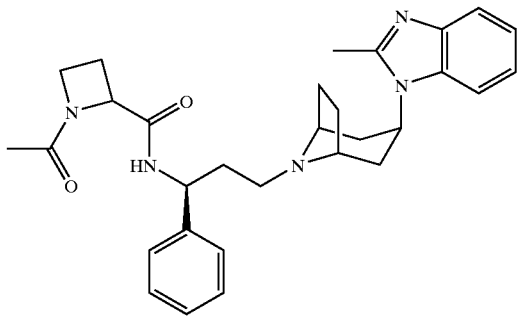

[Acetyl(methyl)amino]-N-{(1S)-3-[3-endo-(2-methyl-1H-benzimidazol-1-yl)-8-azabicyclo[3.2.1]oct-8-yl]-1-phenylpropyl}acetamide

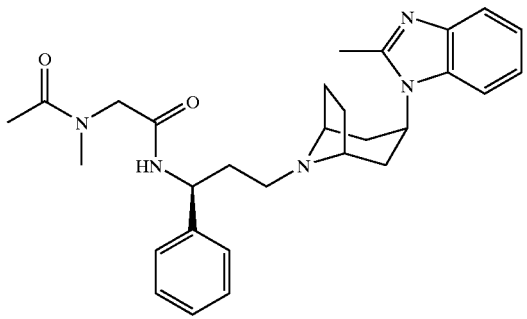

[Acetyl(methyl)amino]-N-{(1S)-3-[3-endo-(2-methyl-1H-benzimidazol-1-yl)-8-azabicyclo[3.2.1]oct-8-yl]-1-phenylpropyl}propanamide

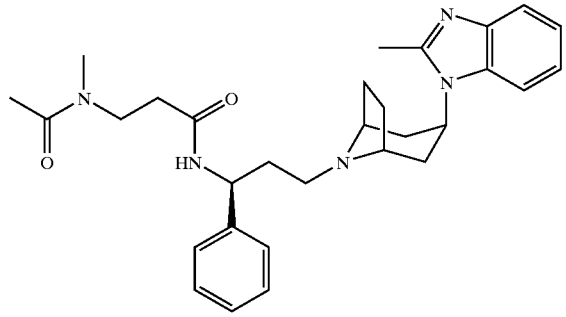

2-Methoxy-N-{(1S)-3-[3-endo-(2-methyl-1H-benzimidazol-1-yl)-8-azabicyclo[3.2.1]oct-8-yl]-1-phenylpropyl}acetamide

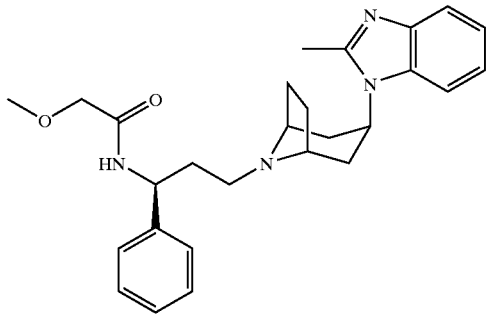

132

3-Methoxy-N-{(1S)-3-[3-endo-(2-methyl-1H-benzimidazol-1-yl)-8-azabicyclo[3.2.1]oct-8-yl]-1-phenylpropyl}propanamide

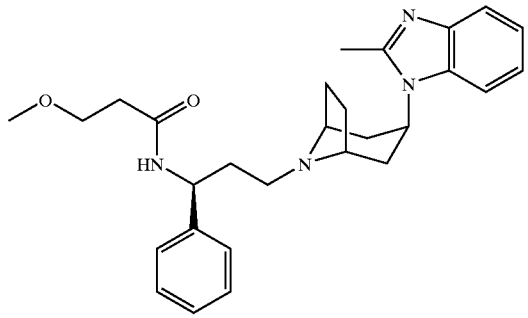

1-Acetyl-N-{(1S)-3-[3-endo-(2-methyl-1H-benzimidazol-1-yl)-8-azabicyclo[3.2.1]oct-8-yl]-1-phenylpropyl}-3-pyrrolidinecarboxamide

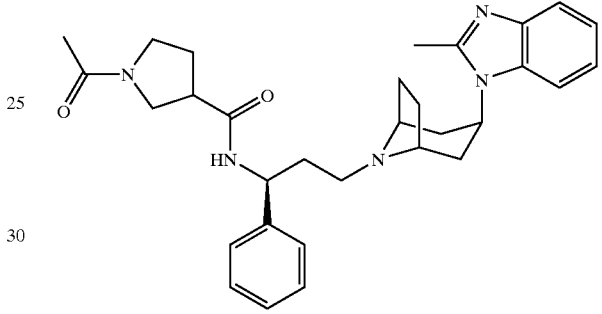

1-Methyl-N-{(1S)-3-[3-endo-(2-methyl-1H-benzimidazol-1-yl)-8-azabicyclo[3.2.1]oct-8-yl]-1-phenylpropyl}-2-oxo-4-pyrrolidinecarboxamide

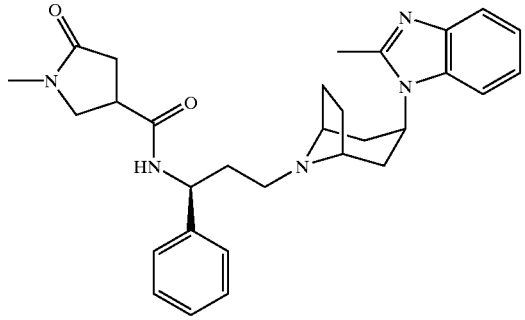

1-Acetyl-N-{(1S)-3-[3-exo-(2-ethyl-1H-benzimidazol-1-yl)-8-azabicyclo[3.2.1]oct-8-yl]-1-phenylpropyl}-3-azetidinearboxamide

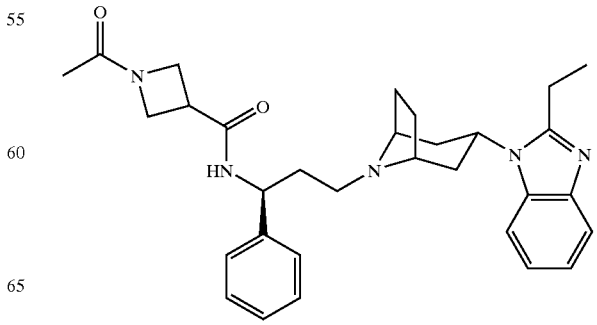

133

N-{(1S)-3-[3-exo-(2-Ethyl-1H-benzimidazol-1-yl)-
8-azabicyclo[3.2.1]oct-8-yl]-1-phenylpropyl}-1-
propionyl-3-azetidinecarboxamide

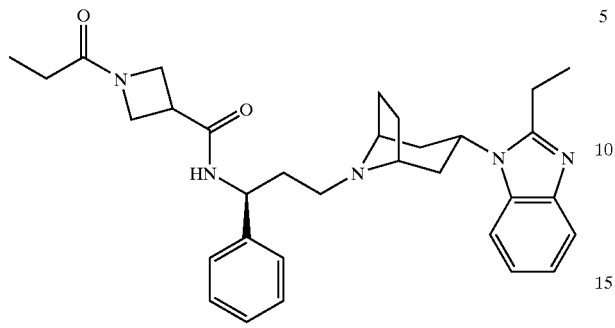

1-Acetyl-N-((1S)-1-phenyl-3-{3-exo-[2-
(trifluoromethyl)-1H-benzimidazol-1-yl]8-
azabicyclo[3.2.1]oct-8-yl}propyl)-3-
azetidinecarboxamide

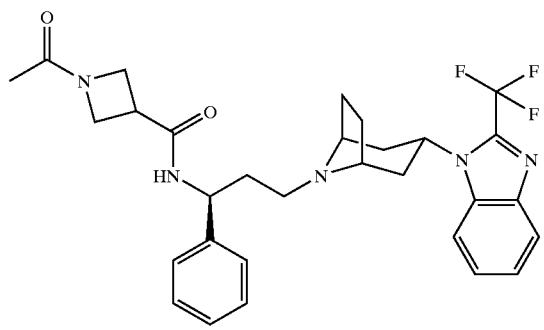

N-((1S)-1-Phenyl-3-{3-exo-[2-(trifuoromethyl)-1H-
benzimidazol-1-yl]-8-azabicyclo[3.2.1]oct-8-
yl}propyl)-1-propionyl-3-azetidinecarboxamide

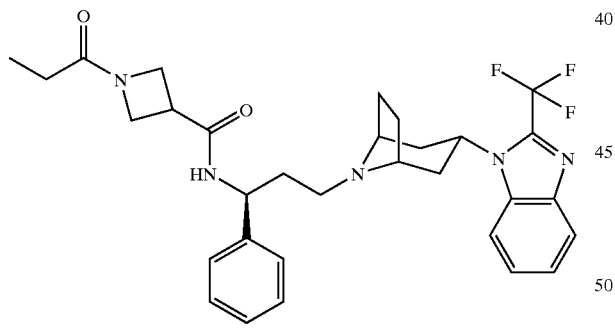

N-((1S)-1-Phenyl-3-{3-exo-[2-(trifluoromethyl)-1H-
benzimidazol-1-yl]8-azabicyclo[3.2.1]oct-8-
yl}propyl)acetamide

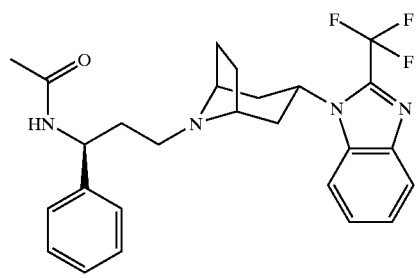

134

2-[Acetyl(methyl)amino]-N-((1S)-1-phenyl-3-{3-
exo-[2-(trifluoromethyl)-1H-benzimidazol-1-yl]-8-
azabicyclo[3.2.1]oct-8-yl}propyl)acetamide

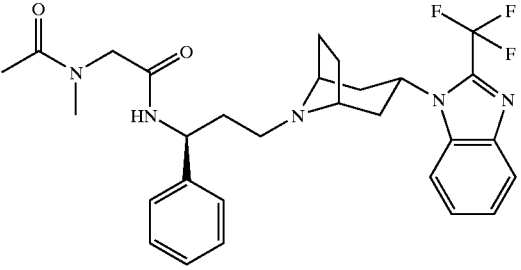

1-Acetyl-N-{(1S)-3-[3-exo-1H-benzimidazol-1-yl)-
azabicyclo[3.2.1]oct-8-yl]-1-phenylpropyl}-3-
azetidinecarboxamide

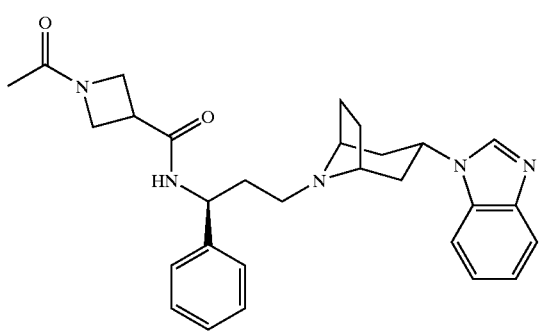

N-{(1S)-3-[3-exo-(1H-Benzimidazol-1-yl)-
azabicyclo[3.2.1]oct-8-yl]-phenylpropyl}-1-
propionyl-3-azetidinecarboxamide

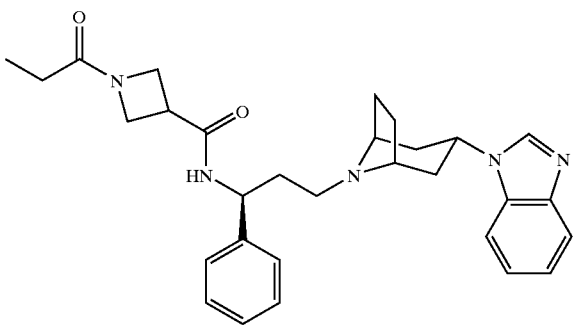

1-Acetyl-N-{(1S)-3-[3-exo-(5-fluoro-1H-
benzimidazol-1-yl)-8-azabicyclo[3.2.1]oct-8-yl]-1-
phenylpropyl}-3-azetidinecarboxamide

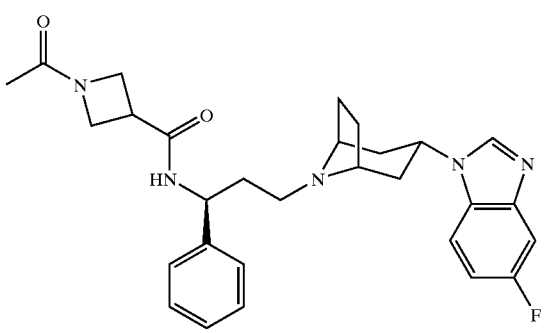

135

N-{(1S)-3-[3-exo-(5-Fluoro-1H-benzimidazol-1-yl)-
8-azabicycol[3.2.1]oct-1-yl]-1-phenylpropyl}-1-
propionyl-3-azetidinecarboxamide

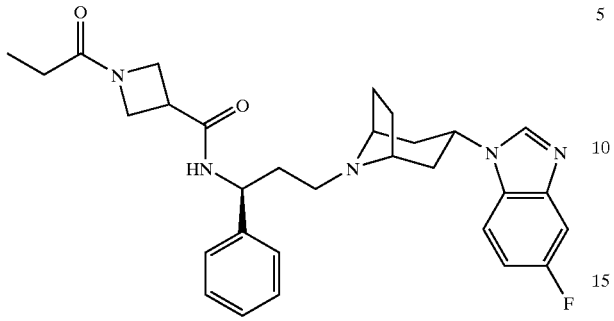

1-Acetyl-N-{(1S)-3-[3-exo-(5-fluoro-2-methyl-1H-
benzimidazol-1-yl)-8-azabicyclo[3.2.1]oct-8-yl]-1-
phenylpropyl}-3-azetidinecarboxamide

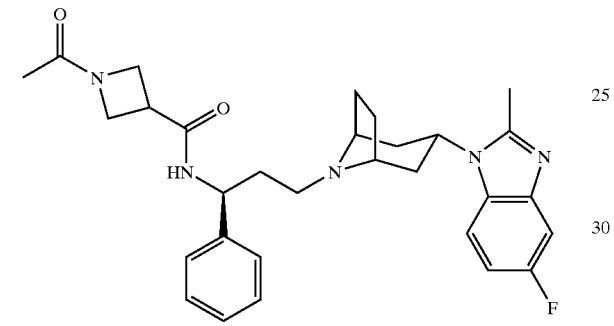

N-{(1S)-3-[3-exo-(5-Fluoro-2-methyl-1H-
benzimidazol-1-yl)-8-azabicyclo[3.2.1]oct-8-yl]-1-
phenydpropyl}-1-propionyl-3-azetidinecarboxamide

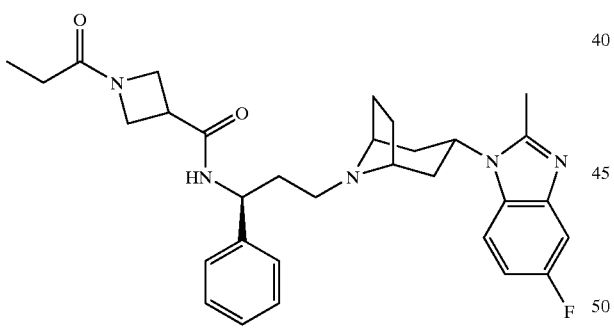

1-Methyl-N-{(1S)-3-[3-exo-(2-methyl-1H-
benzimidazol-1-yl)-azabicyclo[3.2.1]oct-8-yl]-1-
phenylpropyl}-3-azetidinecarboxamide

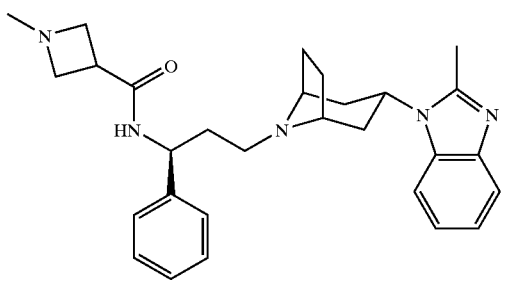

136

(2S)-1-Acetyl-N-{(1S)-3-[3-exo-(2-methyl-1H-
benzimidazol-1-yl)-8-azabicyclo[3.2.1]oct-8-yl]-1-
phenylpropyl}-2-azetidinecarboxamide

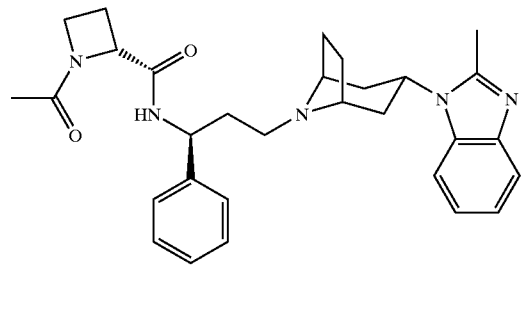

(2R)-1-Acetyl-N-{(1S)-3-[3-exo-(2-methyl-1H-
benzimidazol-1-yl)-8-azabicyclo[3.2.1]oct-8-yl]-1-
phenylpropyl}-2-azetidinecarboxamide

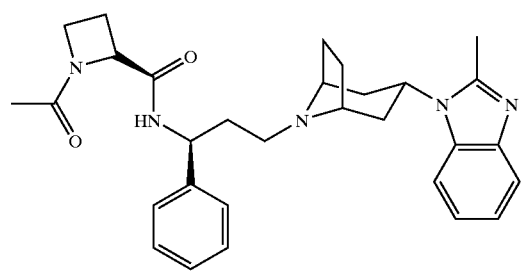

[Acetyl(methyl)amino]-N-{(1S)-3-[3-exo-(2-methyl-
1H-benzimidazol-1-yl)-8-azabicyclo[3.2.1]oct-8-yl]-
1-phenylpropyl}acetamide

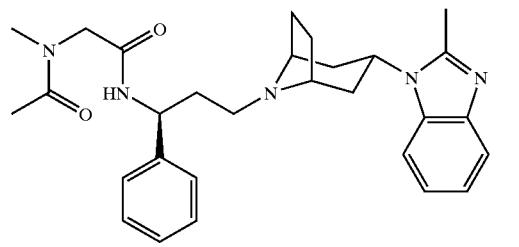

[Acetyl(methyl)amino]-N-{(1S)-3-[3-exo-(2-methyl-
1H-benzimidazol-1-yl)-8-azabicyclo[3.2.1]oct-8-yl]-
1-phenylpropyl}propanamide

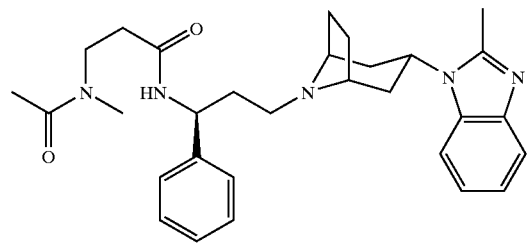

| 137 | 138 |
|---|---|
| 1-Acetyl-N-{(1S)-3-[3-exo-(2-methyl-1H-benzimidazol-1-yl)-8-azabicyclo[3.2.1]oct-8-yl]-1-phenylpropyl}-3-pyrrolidinecarboxamide | 1-Acetyl-N-{(1S)-3-[3-exo-(4-fluoro-2-methyl-1H-benzimidazol-1-yl)-8-azabicyclo[3.2.1oct-8-yl]-1-phenylpropyl}-3-azetidinecarboxamide |

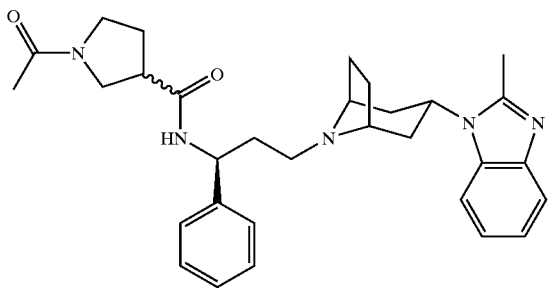

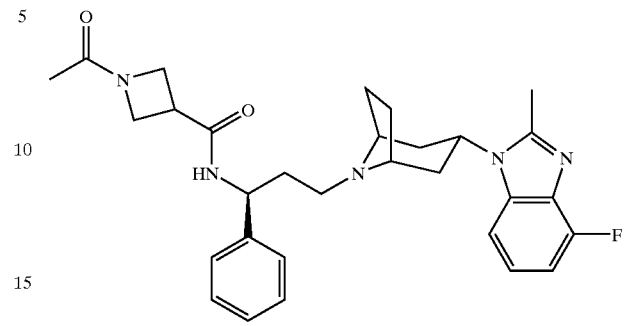

{(1S)-3-[3-exo-(2-Methyl-1H-benzimidazol-1-yl)-8-azabicyclo[3.2.1]oct-8-yl]-1-phenylpropyl}-1(trifluoromethyl)cyclopropanecarboxamide N-{(1S)-3-[3-exo-(4-Fluoro-2-methyl-1H-benzimidazol-1-yl)-8-azabicyclo[3.2.1]oct-8-yl]-1-phenylpropyl}-3-azetidinecarboxamide

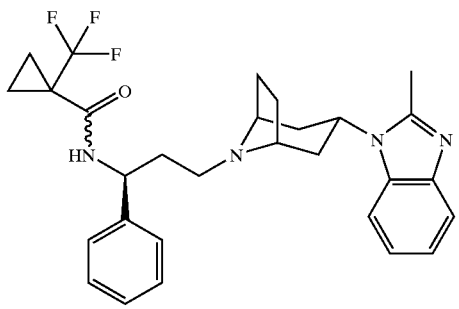

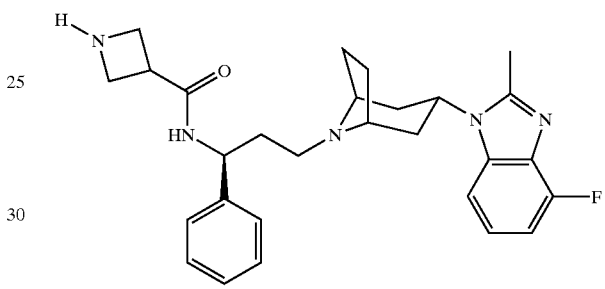

2-Methoxy-N{(1S)-3-[3-exo-(2-methyl-1H-benzimidazol-1-yl)-8-azabicyclo[3.2.1]oct-8-yl]-1-phenylpropyl}acetamide 1-Methyl-N-{(1S)-3-[3-exo-(4-fluoro-2-methyl-1H-benzimidazol-1-yl)-8-azabicyclo[3.2.1]oct-8-yl]-1-phenylpropyl}-3-azetidinecarboxamide

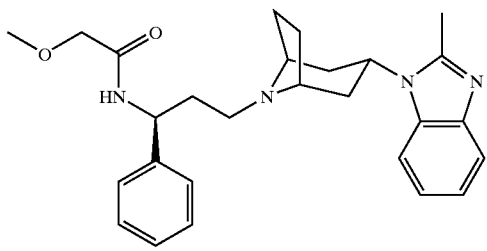

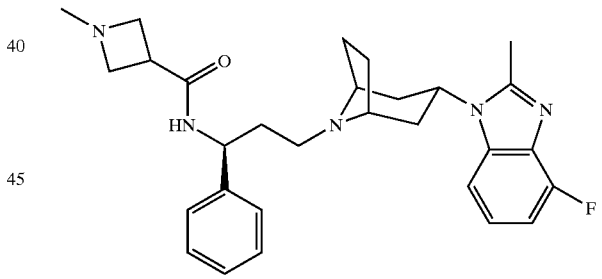

3-Methoxy-N{(1S)-3-[3exo-(2-methyl-1H-benzimidazol-1-yl)-8-azabicyclo[3.2.1]oct-8-yl]-1-phenylpropyl}propanamide N-{(1S)-3-[3-exo-(4-Fluoro-2-methyl-1H-benzimidazol-1-yl)-8-azabicyclo[3.2.1]oct-8-yl]-1-phenylpropyl}-3-azetidinecarboxamide

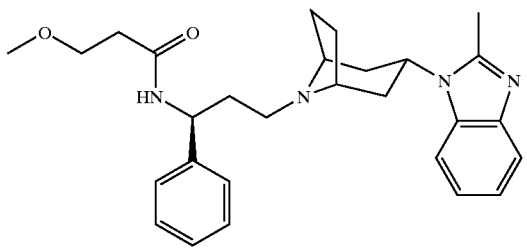

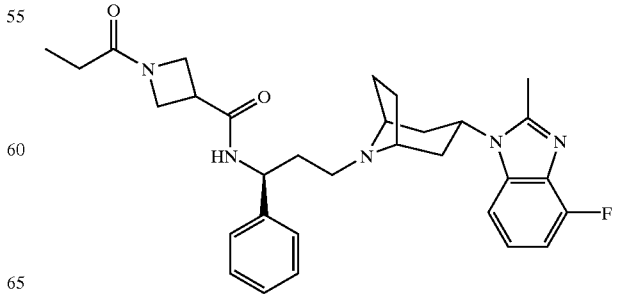

139

2-Methoxy-N-{(1S)-3-[3-exo-(4-fluoro-2-methyl-1H-benzimidazol-1-yl)-8-azabicyclo[3.2.1]oct-8-yl]-1-phenylpropyl}acetamide

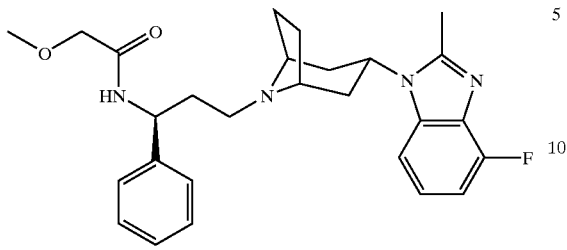

N-{(1S)-3-[3-exo-(4-Fluoro-2-methyl-1H-benzimidazol-1-yl)-8-azabicyclo[3.2.1]oct-8]-yl-1-phenylpropyl}acetamide

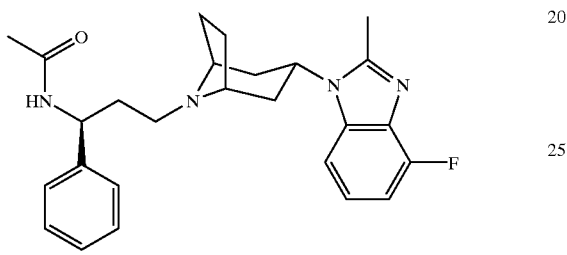

2-Methyl-N-{(1S)-3-[3-exo-(4-fluoro-2-methyl-1H-benzimidazol-1-yl)-8-azabicyclo[3.2.1]oct-8-yl]-8]-yl-1-phenylpropyl}acetamide

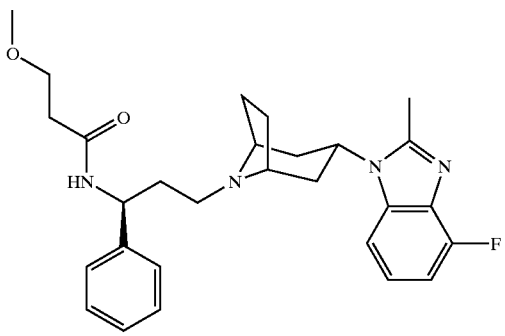

2-[Acetyl(methyl)amino]-N-{(1S)-3-[3-exo-(4-fluoro-2-methyl-1H-benzimidazol-1-yl)-8-azabicyclo[3.2.1]oct-8-yl]-1-phenylpropyl}acetamide

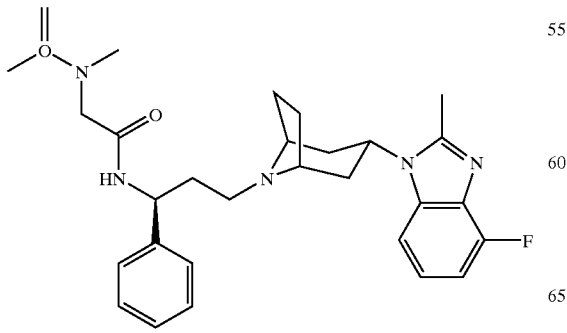

140

2-[Acetyl(methyl)amino]-N-{(1S)-3-[3-exo-(4-fluoro-2-methyl-1H-benzimidazol-1-yl)-8-azabicyclo[3.2.1]oct-8-yl]-1-phenylpropyl}acetamide

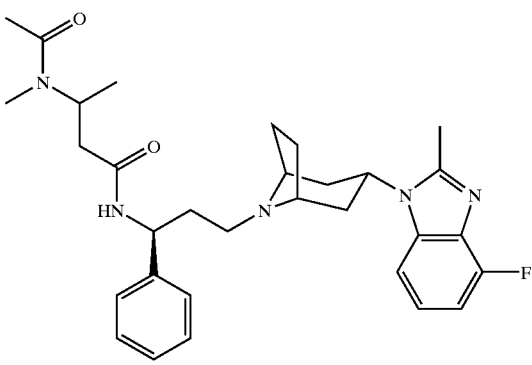

N-{(1S)-3-[3-exo-(4-Fluoro-2-methyl-1H-benzimidazol-1-yl)-8-azabicyclo[3.2.1]oct-8]-yl-1-phenylpropyl}-3-methyl-3-oxetanecarboxamide

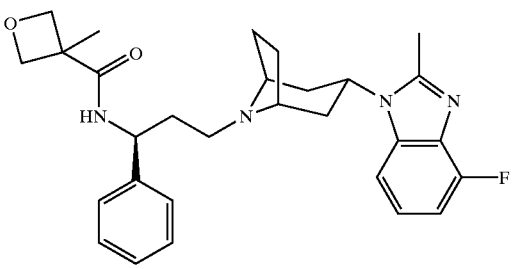

3-Ethyl-N-{(1S)-3-[3-exo-(4-fluoro-2-methyl-1H-benzimidazol-1-yl)-8-azabicyclo[3.2.1]oct-8-yl]-1-phenylpropyl}-3-oxetanecarboxamide

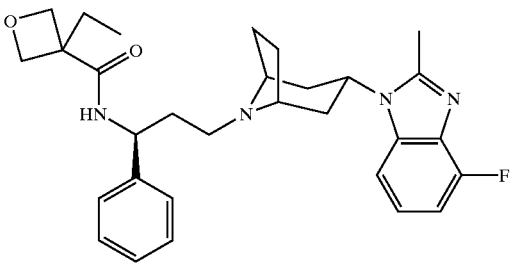

N-{(1S)-3-[3-exo-(4-Fluoro-2-methyl-1H-benzimidazol-1-yl)-8-azabicyclo[3.2.1]oct-8]-yl-1-phenylpropyl}-3-oxetanecarboxamide

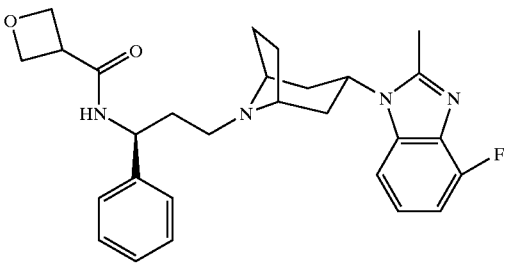

141

3-Ethyl-N-{(1S)-3-[3-exo-(4-fluoro-1H-benzimidazol-1-yl)-8-azabicyclo[3.2.1]oct-8]-yl-1-phenylpropyl}-3-oxetanecarboxamide

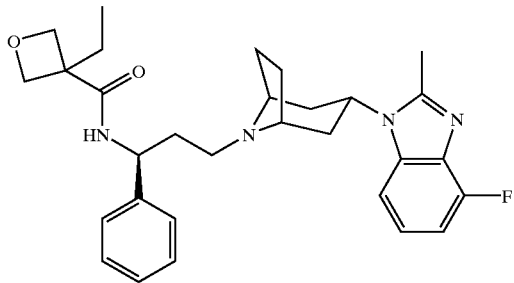

N-{(1S)-3-[3-exo-(4-Fluoro-2-methyl-1H-benzimidazol-1-yl)-8-azabicyclo[3.2.1]oct-8-yl]-1-phenylpropyl}-3-methyl-3-oxetanecarboxamide

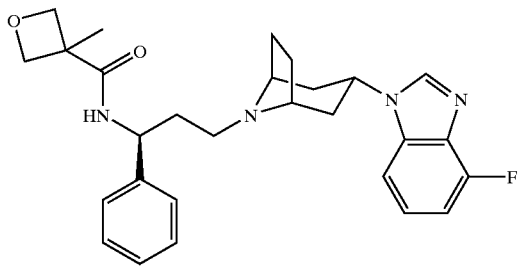

N-{(1S)-3-[3-exo-(4-Fluoro-1H-benzimidazol-1-yl)-8-azabicyclo[3.2.1]oct-8-yl]-1-phenylpropyl}-3-oxetanecarboxamide

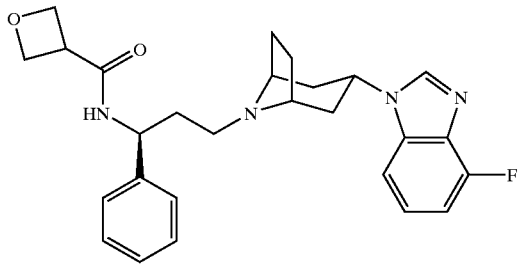

N-{(1S)-3-[3-exo-(4-Fluoro-1H-benzimidazol-1-yl)-8-azabicyclo[3.2.1]oct-8-yl]-1-phenylpropyl}-3-azetidinecarboxamide

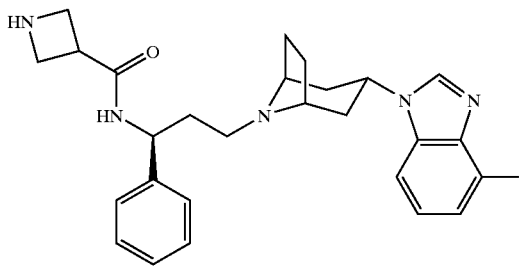

142

N-{(1S)-3-[3-exo-(4-Fluoro-1H-benzimidazol-1-yl)-8-azabicyclo[3.2.1]oct-8-yl]-1-phenylpropyl}-1-methyl-3-azetidinecarboxamide

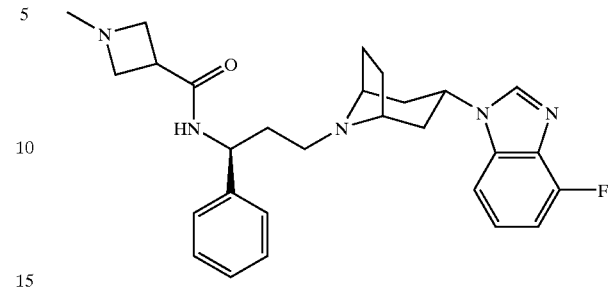

N-{(1S)-3-[3-exo-(4-Fluoro-1H-benzimidazol-1-yl)-8-azabicyclo[3.2.1]oct-8-yl]-1-phenylpropyl}-1-propionyl-3-azetidinecarboxamide

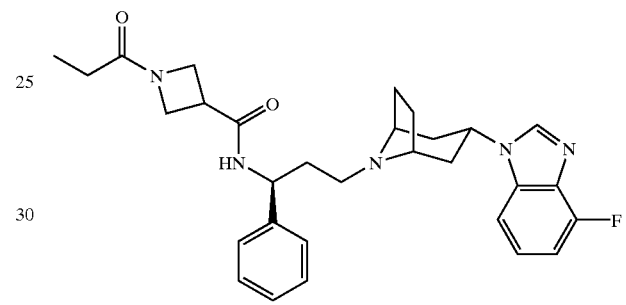

N-{(1S)-3-[3-exo-(4-Fluoro-1H-benzimidazol-1-yl)-8-azabicyclo[3.2.1]oct-8-yl]-1-phenylpropyl}-2-methoxyacetamide

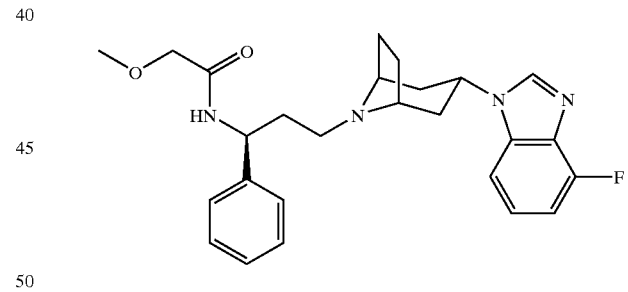

N-{(1S)-3-[3-exo-(4-Fluoro-1H-benzimidazol-1-yl)-8-azabicyclo[3.2.1]oct-8-yl]-1-phenylpropyl}acetamide

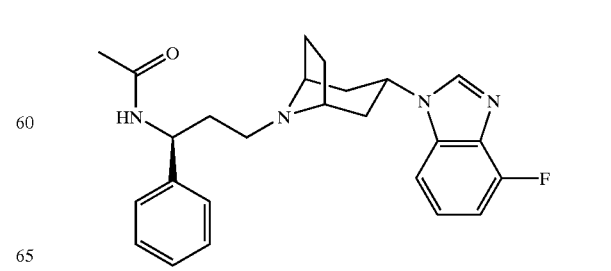

N-{(1S)-3-[3-exo-(4-Fluoro-1H-benzimidazol-1-yl)-8-azabicyclo[3.2.1]oct-8-yl]-1-phenylpropyl}-3-methoxypropanamide

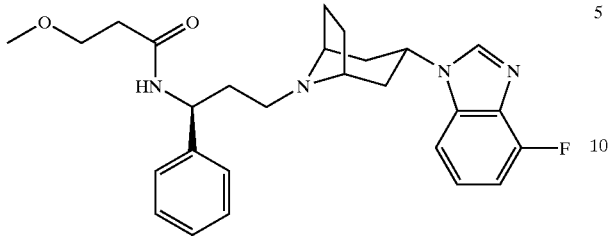

2-[Acetyl(methyl)amino]-N-{(1S)-3-[3-exo-(4-fluoro-1H-benzimidazol-1-yl)-8-azabicyclo[3.2.1]oct-8-yl]-1-phenylpropyl}acetamide

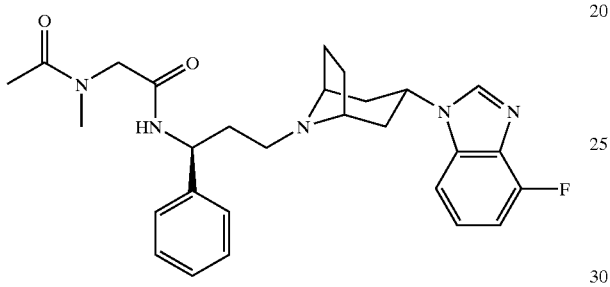

3-[Acetyl(methyl)amino]-N-{(1S)-3-[3-exo-(4-fluoro-1H-benzimidazol-1-yl)-8-azabicyclo[3.2.1]oct-8-yl]-1-phenylpropyl}propanamide

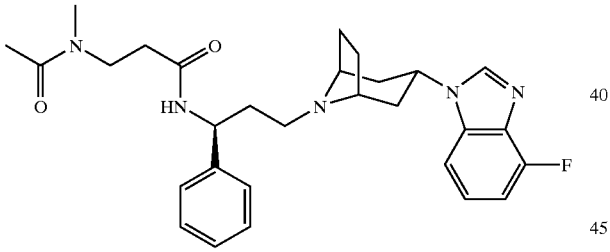

What is claimed is:

1. A compound of the formula

[Region α]-[Region β]-[Region γ]-[Region δ]  (I)

or a pharmaceutically acceptable salt thereof, wherein [Region α] is a moiety of the formula

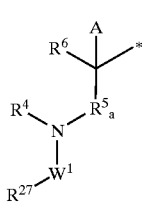

(2.0.0)

wherein the symbol "*" indicates the point of attachment of the moiety of the formula (2.0.0) to Region β;

$R^4$ is H or $C_1$–$C_2$ alkyl;

$R^6$ is H, $C_1$–$C_2$ alkyl, $C_1$–$C_2$ alkoxy, —CN, —OH, or —CONH$_2$;

A is phenyl optionally substituted by up to 4 substituents independently selected from fluoro, chloro, —CO$_2$R$^4$, —OH, —CN, —CONR$^4_a$R$^4_b$, —NR$^4_a$R$^4_b$, —NR$^4_a$COR$^4_b$, —NR$^4_a$CO$_2$R$^4_b$, —NR$^4_a$S(O)$_p$R$^4_b$, —S(O)$_p$NR$^4_a$R$^4_b$, $C_1$–$C_4$ alkyl, $C_1$–$C_4$ alkoxy, $C_1$–$C_2$ alkoxycarbonyl, $C_1$–$C_2$ alkylcarbonyl and $C_1$–$C_2$ alkylcarbonyloxy, said $C_1$–$C_4$ alkyl and $C_1$–$C_4$ alkoxy being optionally substituted by up to 3 substituents independently selected from fluoro and chloro;

p is 0, 1 or 2;

$R^4_a$ and $R^4_b$ are each independently H or $C_1$–$C_2$ alkyl;

$R^5_a$ is a direct bond, —CO— or —SO$_2$—;

$W^1$ is (i) a direct bond, or (ii) in the case where $R^5_a$ is —CO— or —SO$_2$—, $C_1$–$C_3$ alkylene optionally substituted by up to 2 substituents $R^{23}$, or (iii) a moiety independently selected from formulas (2.0.6) through (2.0.16) inclusive;

 (2.0.6)

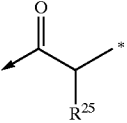 (2.0.7)

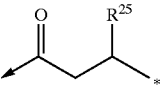 (2.0.8)

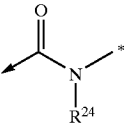 (2.0.9)

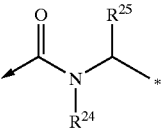 (2.0.10)

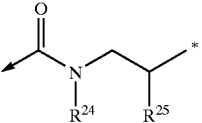 (2.0.11)

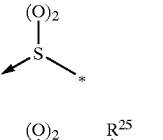 (2.0.12)

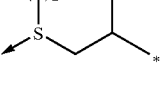 (2.0.13)

-continued (2.0.14)
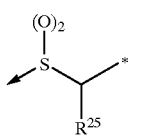

(2.0.15)
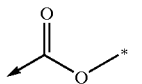

(2.0.16)
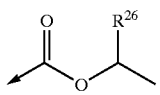

wherein the symbol '→' indicates the point of attachment of the moiety $W_1$ to the nitrogen atom in partial formula (2.0.0) and the symbol '*' indicates the point of attachment of the moiety $W^1$ to the other, remaining portions of partial formula (2.0.0);

$R^{23}$ is fluoro, chloro, —$CO_2R^4$, —OH, —CN, $C_2$–$C_4$ alkoxy, $C_3$–$C_7$ cycloalkyl or phenyl, said $C_1$–$C_4$ alkoxy, $C_3$–$C_7$ cycloalkyl and phenyl being optionally substituted by up to two substituents $R^{11}$;

$R^{11}$ is fluoro, chloro, —$CO_2R^4$, —OH, —CN, —$CONR^4{}_aR^4{}_b$, —$NR^4{}_aR^4{}_b$, —$NR^4{}_aCOR^4{}_b$, —$NR^4{}_aCO_2R^4{}_b$, —$NR^4{}_aS(O)_pR^4{}_b$, —$S(O)_pNR^4{}_aR^4{}_b$, $C_1$–$C_4$ alkyl including dimethyl, $C_1$–$C_4$ alkoxy, $C_1$–$C_2$ alkoxycarbonyl, $C_1$–$C_2$ alkylcarbonyl or $C_1$–$C_2$ alkylcarbonyloxy, said $C_1$–$C_4$ alkyl and $C_1$–$C_4$ alkoxy each being optionally substituted by up to 3 substituents independently selected from fluoro and chloro;

$R^{24}$ is H or $C_1$–$C_4$ alkyl;

$R^{25}$ and $R^{26}$ are each independently —OH, $C_1$–$C_2$ alkyl or $C_1$–$C_2$ alkoxy, said $C_1$–$C_2$ alkyl being optionally substituted by up to 3 substituents selected from fluoro and —OH;

$R^{27}$ is
(i) $C_2$–$C_6$ alkyl, $C_2$–$C_6$ alkenyl or $C_2$–$C_6$ alkynyl, each optionally substituted by up to 3 substituents $R^{28}$; or
(ii) —$(CH_2)_n$—$(C_3$–$C_7$ cycloalkyl) wherein
(a) said $C_3$–$C_7$ cycloalkyl is optionally substituted by up to 3 substituents $R^{28}$,
(b) n is 0, 1 or 2,
(c) in the event that n is 0, the α-carbon of said $C_3$–$C_7$ cycloalkyl is optionally substituted by one substituent selected from $C_1$–$C_4$ alkyl and phenyl wherein said $C_1$–$C_4$ alkyl and phenyl are optionally substituted by 1 or 2 substituents selected from —$CH_3$, —$OCH_3$, —OH or —$NH_2$, and
(d) in the event that n is 1 or 2, the resulting methylene or ethylene is optionally substituted by 1 substituent selected from fluoro, —$NH_2$, —$N(CH_3)_2$, —OH, —$OCH_3$, $C_1$–$C_4$ alkyl or phenyl, said $C_1$–$C_4$ alkyl and phenyl being optionally substituted by 1 or 2 substituents selected from —$CH_3$, —$OCH_3$, —OH and —$NH_2$; or
(iii) phenyl, furyl, tetrahydrofuranyl, tetrahydropyranyl, oxetanyl, thienyl, pyrrolyl, pyrrolidinyl, oxazolyl, isoxazolyl, thiazolyl, isothiazolyl, imidazolyl, pyrazolyl, oxadiazolyl, thiadiazolyl, triazolyl, pyridyl, pyrazinyl, pyridazinyl, piperazinyl, pyrimidinyl, pyranyl, azetidinyl, morpholinyl, thiomorpholino, indolyl, indolinyl, benzo[b]furanyl, 2,3-dihydrobenzofuranyl, benzothienyl, 1H-indazolyl, benzimidazolyl, benzoxazolyl, benzisoxazolyl, benzthiazolyl, quinolinyl, isoquinolinyl, phthalazinyl, quinazolinyl or quinoxalinyl, each optionally substituted
(a) on any one or more carbon atoms by up to 3 substituents $R^{28}$, or
(b) on any one or more nitrogen atoms that is not a point of attachment of said heterocyclic moiety by up to 3 substituents $R^{13}{}_b$, or
(c) on any sulphur atom that is not a point of attachment of said heterocyclic moiety by up to 2 oxygen atoms;

$R^{28}$ is phenyl, fluoro, chloro, oxo, —OH, $C_1$–$C_2$ alkyl, $C_1$–$C_3$ alkoxy, —$CO_2R^{29}$, —$CO(C_1$–$C_4)$alkyl, —$SO_2(C_1$–$C_4)$alkyl, —$CONR^{29}R^{30}$, —$NR^{29}R^{30}$, —$NR^{29}COR^{30}$, —$NR^{29}CO_2R^{30}$, —$NR^{29}S(O)_pR^{30}$ or —$SO_2NR^{29}R^{30}$;

$R^{29}$ and $R^{30}$ are each independently H or $C_1$–$C_4$ alkyl optionally substituted by up to 3 substituents selected from fluoro and chloro;

$R^{13}{}_b$ is H, $C_1$–$C_4$ alkyl, $C_2$–$C_4$ alkenyl, $C_1$–$C_2$ alkoxy, $C_3$–$C_7$ cycloalkyl, —$CO(C_1$–$C_4)$ alkyl, —$SO_2(C_1$–$C_4)$ alkyl or phenyl wherein said $C_1$–$C_4$ alkyl, $C_2$–$C_4$ alkenyl, $C_1$–$C_2$ alkoxy, $C_3$–$C_7$ cycloalkyl and phenyl are optionally substituted by up to 2 substituents $R^{11}$;

[Region β] is an alkyl bridging element of partial Formula (3.0.0):

(3.0.0)
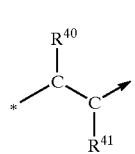

wherein:

"*" is a symbol which represents the point of attachment of the moiety of partial Formula (3.0.0) to $R_{egion}$ α;

"→" is a symbol which represents the point of attachment of the moiety of partial Formula (3.0.0) to $R_{egion}$ γ;

$R^{40}$ and $R^{41}$ are independently selected from the group consisting of hydrogen; ($C_1$–$C_2$) alkyl including dimethyl; hydroxy; and ($C_1$–$C_3$) alkoxy;

[$R_{egion}$ γ] is an aza-bicyclic moiety of partial Formula (4.2.0):

(4.2.0)
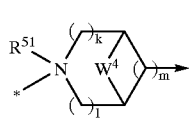

wherein

"*" is a symbol which represents the point of attachment of the moiety of partial Formula (4.2.0) to $R_{egion}$ β;

"→" is a symbol representing a covalent bond from any of the carbon atoms of the moiety of partial Formula (4.2.0) to $R_{egion}$ δ;

$W^4$ is a direct bond; or is a member independently selected from the group consisting of partial Formulas (4.2.1) through (4.2.6):

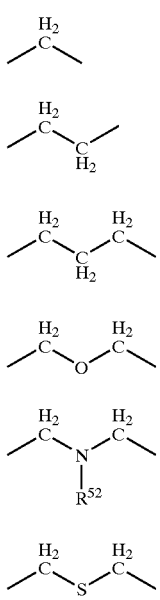

(4.2.1)
(4.2.2)
(4.2.3)
(4.2.4)
(4.2.5)
(4.2.6)

where:
- $R^{52}$ is a member selected from the group consisting of hydrogen; phenyl; $(C_1-C_4)$alkyl substituted by 0 or 1 substituent independently selected from $(C_1-C_2)$ alkoxy and $—CO_2R^4$; $(C_3-C_6)$cycloalkyl; $—CO_2R^4$; $→O$; $C(=O)$ $(C_1-C_3)$alkyl; $—C(=O)NR^4_aR^4_b$; $—S(=O)$ $(C_1-C_4)$alkyl; and $(C_1-C_2)$alkylcarbonyl; where $R^4$, $R^4_a$, and $R^4_b$; are as defined above, but selected on an independent basis;
- $R^{51}$ is absent or is a member selected from the group consisting of $(C_1-C_4)$alkyl substituted by 0 or 1 substituent independently selected from $(C_1-C_2)$ alkoxy and $—CO_2R^4$ where $R^4$ is as defined above; and $→O$; it being understood that in the case where substituent $R^{51}$ is present, the nitrogen atom is in quaternary form; and
- k, l and m are each an integer selected from 0, 1, 2, and 3;

$[R_{egion} \delta]$ is a member selected from the group consisting of:

A. a two-nitrogen-atom-containing five-membered heterocyclic moiety of partial Formulas (5.0.0) through (5.0.10):

(5.0.0)

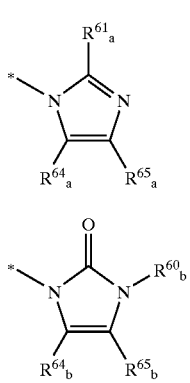

(5.0.1)

(5.0.2)
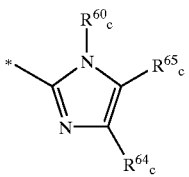

(5.0.3)
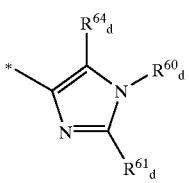

(5.0.4)
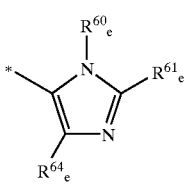

(5.0.5)
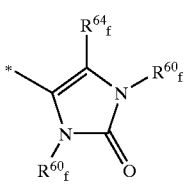

(5.0.6)
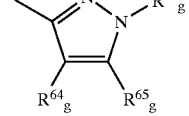

(5.0.7)
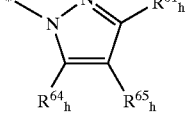

(5.0.8)
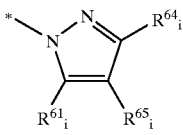

(5.0.9)
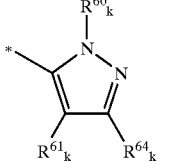

(5.0.10)
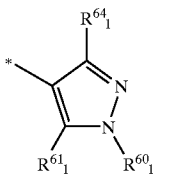

wherein: the symbol: "*" indicates the point of attachment of each of the moieties of partial Formulas (5.0.0) through (5.0.10), inclusive, to $R_{egion} \gamma$;

$R^{60}{}_b$ through $R^{60}{}_g$, inclusive, $R^{60}{}_k$, and $R^{60}{}_l$ are each a member selected from the group consisting of hydrogen; —$CO_2R^4$; —$C(=O)NR^4{}_aR^4{}_b$; —$S(=O)_p$ $NR^4{}_aR^4{}_b$; where: $R^4$; $R^4{}_a$; and $R^4{}_b$ are as defined above but selected on an independent basis; →O; $(C_1-C_2)$ alkylcarbonyl; —$(C_1-C_4)$alkyl; —$(CH_2)_n$—$(C_3-C_7)$ cycloalkyl; —$(C_2-C_3)$alkenyl; —$(CH_2)_n$-(phenyl); and —$(CH_2)_n$-$(HET_1)$, where n is an integer independently selected from 0, 1, and 2; wherein said $(C_1-C_4)$alkyl, alkenyl, cycloalkyl, phenyl and $HET_1$ (heterocyclyl) groups are independently substituted with 0 to 3 substituents $R^{66}$, where:

$HET_1$ is a heterocyclyl group selected from the group consisting of thienyl; oxazolyl; isoxazolyl; thiazolyl; isothiazolyl; pyrazolyl; oxadiazolyl; thiadiazolyl; triazolyl; pyridyl; pyrazinyl; pyridazinyl; pyrimidinyl; thiomorpholino; and morpholinyl; where:

$R^{66}$ is a member selected from the group consisting of —F; —Cl; —OH; cyano; —$C(=O)OR_{68}$; —$C(=O)NR^{68}R^{69}$; —$NR^{68}R^{69}$; —$NR^{68}C(=O)$ $R^{69}$; —$NR^{68}C(=O)OR^{69}$; —$NR^{68}S(=O)_2R^{69}$; —$S(=O)_2NR^{68}R^{69}$; $(C_1-C_4)$alkyl including dimethyl, and $(C_1-C_4)$alkoxy wherein said alkyl and alkoxy are each independently substituted with 0 to 3 substituents independently selected from F and Cl; $(C_1-C_2)$alkoxycarbonyl; $(C_1-C_2)$ alkylcarbonyl; and $(C_1-C_2)$alkylcarbonyloxy, where:

$R^{68}$ and $R^{69}$ are each a member selected from the group consisting of hydrogen; and $(C_1-C_2)$ alkyl; and where said:

$R^{61}{}_a$; $R^{61}{}_d$; $R^{61}{}_e$; and $R^{61}{}_h$ through $R^{61}{}_l$ inclusive; $R^{64}{}_a$ through $R^{64}{}_f$ inclusive; $R^{65}{}_a$ through $R^{65}{}_c$ inclusive; and $R^{65}{}_g$ through $R^{65}{}_i$ inclusive are each a member selected from the group consisting of hydrogen; —OH; —$CF_3$; cyano; —$(C_1-C_3)$alkoxy; —$C(=O)OR^4$; —$C(=O)NR^4{}_aR^4{}_b$; —$NR^4{}_aR^4{}_b$; —$NR^4{}_aC(=O)R^4{}_b$; —$NR^4{}_aC(=O)OR^4{}_b$; —$NR^4{}_aS(=O)_pR^4{}_b$; —$S(=O)_p$ $NR^4{}_aR^4{}_b$; where: $R^4$; $R^4{}_a$; and $R^4{}_b$ are as defined further above but selected on an independent basis; —$(C_1-C_4)$alkyl; —$(CH_2)_n$-$(C_3-C_7)$cycloalkyl; —$(C_2-C_3)$alkenyl; —$(CH_2)_n$-(phenyl); and —$(CH_2)_n$-$(HET_1)$, where n is an integer selected from 0, 1, and 2; wherein said $(C_1-C_4)$alkyl, alkenyl, cycloalkyl, phenyl, and $HET_1$(heterocyclyl) groups where $HET_1$ (heterocyclyl) groups is as defined above, are independently substituted with 0 to 3 substituents $R^{66}$ where: $R^{66}$ is as defined above, or:

$R^{64}{}_a$ through $R^{64}{}_c$ inclusive; $R^{64}{}_g$ through $R^{64}{}_i$ inclusive; $R^{65}{}_a$ through $R^{65}{}_c$ inclusive; and $R^{65}{}_g$ through $R^{65}{}_i$ inclusive may be taken together in their same subscript denominated pairs along with the remaining portions of the moieties of partial Formulas (5.0.0) through (5.0.2), and (5.0.6) through (5.0.8), to form a fused bicyclic ring system comprising a member independently selected from the group consisting of benzimidazolyl; purinyl, i.e., imidazopyrimidinyl; and imidazopyridinyl; wherein said fused bicyclic ring system is independently substituted with 0 to 3 substituents $R^{66}$, where $R^{66}$ has the same meaning as set out further above, except that it is independently selected therefrom;

B. a (substituted)-amide, carbamate, or urea moiety selected from the group consisting of:

1, alkyl-, cycloalkyl-, and alkenyl-(substituted)-amide, carbamate, or urea moieties of partial Formula (5.1.0):

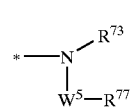

(5.1.0)

wherein: the symbol "*" as defined above;

$R^{73}$ is a member selected from the group consisting of hydrogen and $(C_1-C_2)$alkyl;

$W^5$ is selected from the group consisting the moieties of partial Formulas (5.1.1) through (5.1.12):

(5.1.1)

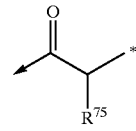

(5.1.2)

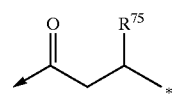

(5.1.3)

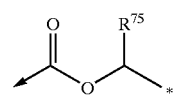

(5.1.4)

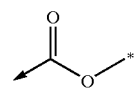

(5.1.5)

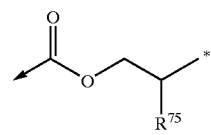

(5.1.6)

(5.1.7)

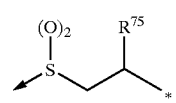

(5.1.8)

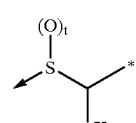

(5.1.9)

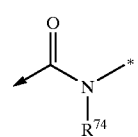

(5.1.10)

-continued (5.1.11)

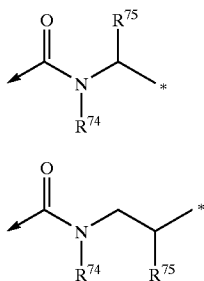

(5.1.12)

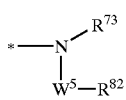

wherein: the symbol: "→" indicates the point of attachment of the moiety $W^5$ represented by partial Formulas (5.1.1) through (5.1.12), inclusive, to the nitrogen atom in partial Formula (5.1.0), and the symbol: "*" indicates the point of attachment of the moiety $W^5$ to $R^{77}$ as defined further below;

$R^{74}$ and $R^{75}$ are each selected from the group consisting of hydrogen; $(C_1-C_2)$alkyl substituted by 0 or 1 substituent independently selected from OH; and $(C_1-C_2)$alkoxy; and $R^{77}$ is a member selected from the group consisting of $(C_1-C_6)$alkyl; $(C_2-C_6)$alkenyl; and —$(CH_2)_n$-$(C_3-C_7)$cycloalkyl, where n is an integer selected from 0, 1, and 2; and wherein said alkyl, alkenyl, and cycloalkyl groups comprising $R^{77}$ are substituted with 0 to 3 substituents $R^{78}$, where:

$R^{78}$ is a member selected from the group consisting of oxo; —OH; —$(C_1-C_2)$alkyl; —$(C_1-C_3)$alkoxy; —$CF_3$; —$C(=O)OR^{79}$; —$C(=O)NR^{79}R^{80}$; —$NR^{79}R^{80}$; —$NR^{79}C(=O)R^{80}$; —$NR^{79}C(=O)OR^{80}$; —$NR^{79}S(=O)_2R^{80}$; and —$S(=O)_2NR^{79}R^{80}$, where:

$R^{79}$ and $R^{80}$ are each a member independently selected from the group consisting of hydrogen; and $(C_1-C_4)$alkyl; and 2. aryl and heterocyclyl-(substituted)-amide, carbamate, or urea moieties of partial Formula (5.2.0):

(5.2.0)

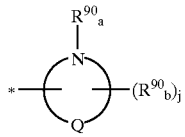

wherein: the symbol: "*"; $R^{73}$; and $W^5$ have the same meanings as under the definitions of partial Formula (5.1.0) above, except that they are independently selected therefrom; and under $W^5$ the symbols: "→" and "*" are as defined under partial Formula (5.1.0); and $R^{82}$ is a member selected from the group consisting of phenyl; cinnolinyl; furyl; thienyl; pyrrolyl; oxazolyl; isoxazolyl; thiazolyl; isothiazolyl; imidazolyl; imidazolinyl; pyrazolyl; pyrazolinyl; oxadiazolyl; thiadiazolyl; triazolyl; pyridyl; pyrazinyl; pyridazinyl; pyrimidinyl; thiomorpholino; indolyl; isoindolyl; indolinyl; benzo[b]furanyl; 2;3-dihydrobenzofuranyl; benzo[b]thiophenyl; 1H-indazolyl; benzimidazolyl; benzthiazolyl; quinolinyl; isoquinolinyl; phthalazinyl; quinazolinyl; quinoxalinyl; wherein:
the aryl or heterocyclyl moiety is substituted by 0 to 3 substituents $R^{78}$ where $R^{78}$ is as defined above, but selected on an independent basis; or C. a (substituted)-heterocyclyl moiety independently selected from the group consisting of:

1. a heterocyclyl moiety of partial Formula (5.3.0):

(5.3.0)

wherein: the symbol: "*" indicates the point of attachment of partial Formula (5.3.0) to $R_{egion}$ γ; Q is N, O or S and partial Formula (5.3.0) represents:

a. a monocyclic heterocyclic group containing a total of 5- members of which one said member is nitrogen and a second said member is selected from O and S where said S may optionally be in the sulfonate form, wherein said heterocyclic group is selected from the group consisting of oxazolyl; isoxazolyl; thiazolyl; and iso-thiazolyl; or b. a monocyclic heterocyclic group containing a total of 5- members of which two said members are nitrogen and a third or fourth said member is independently selected from N, O, and S where said S may optionally be in the sulfonate form, —$S(=O)_2$; wherein said heterocyclic group is independently selected from the group consisting of triazolyl; tetrazolyl; oxadiazolyl; and thiadiazolyl; and $R^{90}{}_a$ and $R^{90}{}_b$ are each a member independently selected from the group consisting of hydrogen, —$(C_1-C_2)$alkylcarbonyl; —$(C_1-C_4)$alkyl; —$(CH_2)_n$-$(C_3-C_7)$cycloalkyl; —$(C_2-C_3)$alkenyl; —$(CH_2)_n$-(phenyl); and —$(CH_2)_n$-($HET_2$), where n is an integer independently selected from 0, 1, and 2; wherein said $(C_1-C_4)$alkyl, alkenyl, cycloalkyl, phenyl, and $HET_2$ groups are independently substituted with 0 to 3 substituents $R^{91}$, where:

j is 0, 1 or 2;

$HET_2$ is a heterocyclyl group selected from the group consisting of thienyl; oxazolyl; isoxazolyl; thiazolyl; isothiazolyl; pyrazolyl; oxadiazolyl; thiadiazolyl; triazolyl; pyridyl; pyrazinyl; pyridazinyl; pyrimidinyl; thiomorpholino; and morpholinyl; where:

$R^{91}$ is selected from the group consisting of —F; —Cl; —$CO_2R^4$; —OH; —CN; —$CONR^{93}R^{94}$; —$NR^{93}R^{94}$; $C(=O)(C_1-C_4)$alkyl; —$NR^{93}C(=O)R^{94}$; —$NR^{93}C(=O)OR^{94}$; —$NR^{93}S(=O)R^{94}$; —$S(=O)NR^{93}R^{94}$; $(C_1-C_4)$alkyl including dimethyl, and $(C_1-C_4)$alkoxy wherein said alkyl and alkoxy are each independently substituted with 0 to 3 substituents independently selected from F and Cl; $(C_1-C_2)$alkoxycarbonyl; $(C_1-C_2)$alkylcarbonyl; and $(C_1-C_2)$alkylcarbonyloxy; wherein:

$R^{93}$ and $R^{94}$ are each a member independently selected from the group consisting of hydrogen; and $(C_1-C_2)$alkyl; and 2. a heterocyclyl moiety of partial Formula (5.4.0):

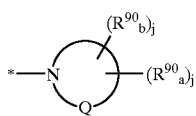

(5.4.0)

wherein: $R^{90a}$, $R^{90b}$ and j have the same meanings as set out above and Q is N, O or S.

2. A compound of the formula (I), as claimed in claimed in claim 1, in which $R^6$ is hydrogen.

3. A compound of the formula (I), as claimed in claims 1, in which A is phenyl.

4. A compound of the formula (I), as clamed in claim 1, in which $R^5_a$ is a direct bond.

5. A compound of the formula (I), as claimed in claim 1, in which $W^1$ is —CO—.

6. A compound of the formula (I), as claimed in claim 1, in which $R^{27}$ is (i) methyl, ethyl, isopropyl, tert-butyl or allyl, each optionally substituted by one substituent selected from fluoro, chloro, —OH, —CF$_3$, —CH$_3$, —OCH$_3$, —CN, —NH$_2$, —NHCH$_3$, —N(CH$_3$)$_2$, —NHCOCH$_3$ and —NCH$_3$(COCH$_3$), or (ii) cyclopropyl, cyclobutyl, cyclopentyl, cyclohexyl, cyclopropylmethyl, cyclobutylethyl, cyclopentylpropmethyl or cyclopentylmethyl, each optionally substituted as defined in claim 1 or (iii) tetrahydropyranyl, oxetanyl, azetidinyl or tetrahydrofuranyl optionally substituted by up to 3 $R^{28}$.

7. A compound of the formula (I), as claimed in claim 1, in which Region α is selected from the moieties of formulas (2.0.30) through (2.0.36) inclusive, formulas (2.1.3) through (2.1.10) inclusive or formulas (2.2.3) through (2.2.14) inclusive:

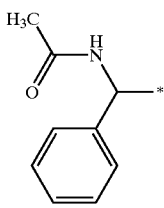

(2.0.30)

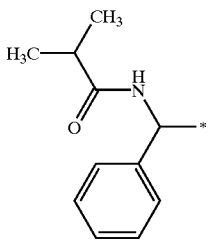

(2.0.31)

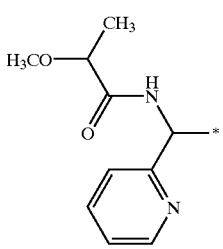

(2.0.32)

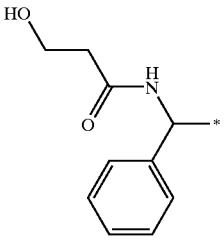

(2.0.33)

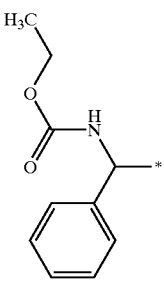

(2.0.34)

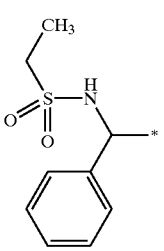

(2.0.35)

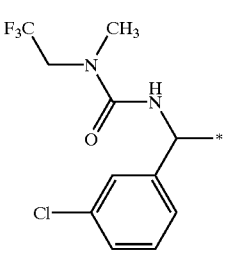

(2.0.36)

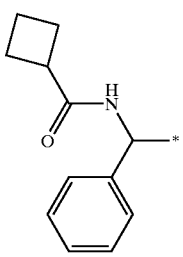

(2.1.3)

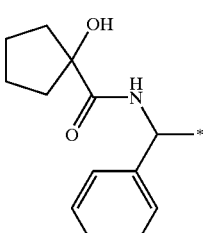

(2.1.4)

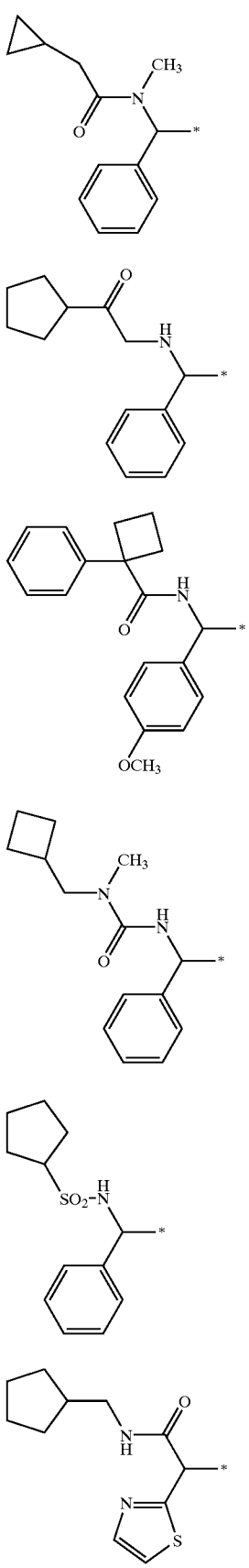
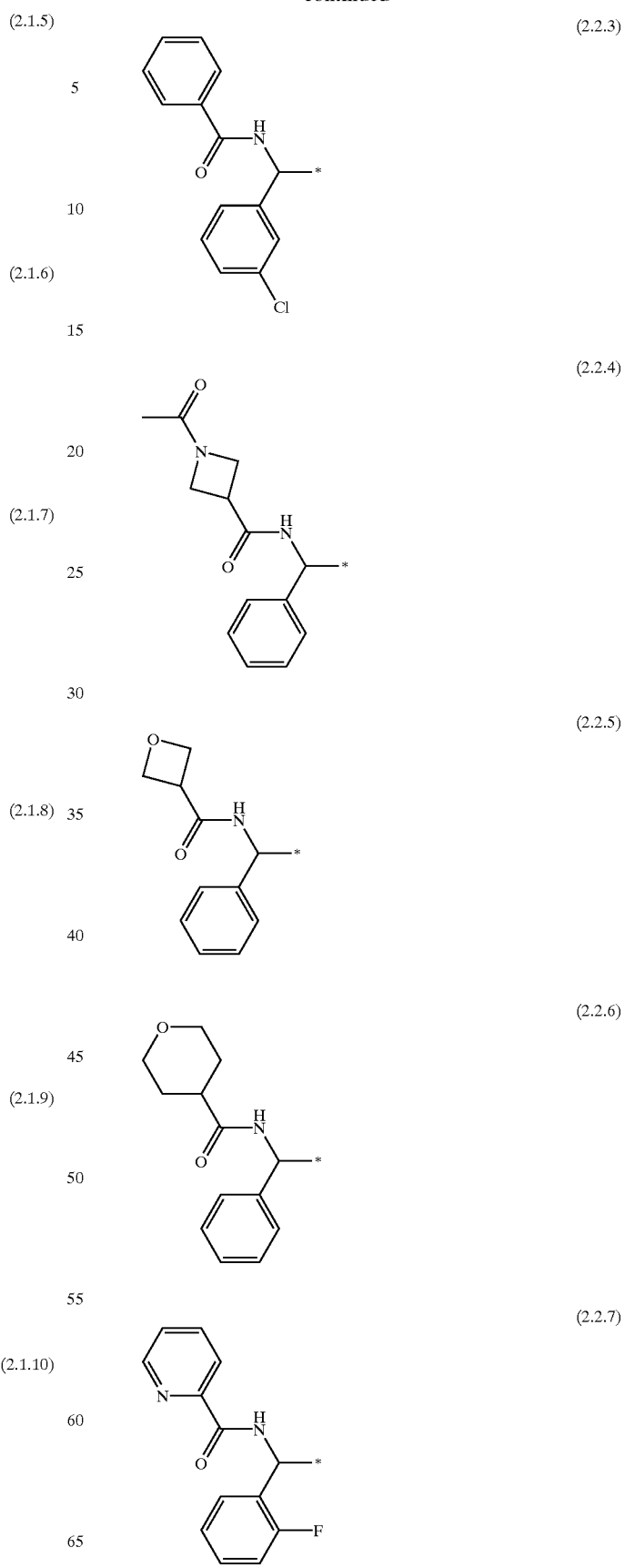

(2.2.8) 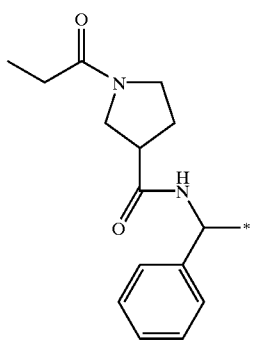

(2.2.9) 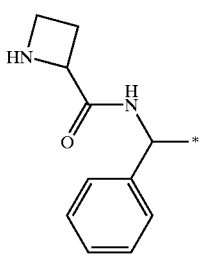

(2.2.10) 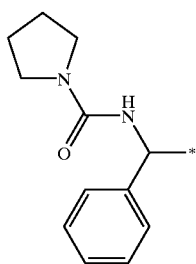

(2.2.11) 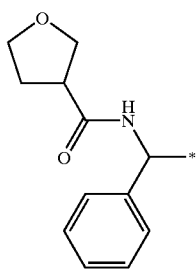

(2.2.12) 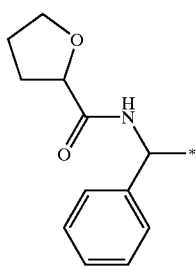

(2.2.13) 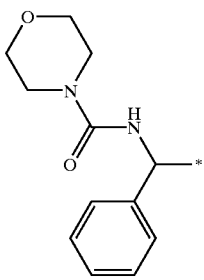

(2.2.14) 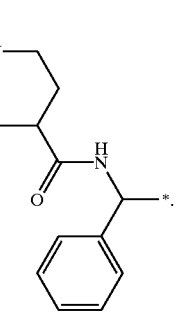

8. A compound of the formula (I), as claimed in claim 1, which $R^{40}$ and $R^{41}$ are H.

9. A compound of the formula (I), as claimed in claim 1, in which Region γ comprises two carbon atoms between the point of attachment to Region δ and the nitrogen atom point of attachment of the moiety of formula (4.2.0) to Region β.

10. A compound of the formula (I), as claimed in claim 1, in which $R^{52}$ is hydrogen.

11. A compound of the formula (I), as claimed in claim 1, in which $R^{51}$ is absent.

12. A compound of the formula (I), as claimed in claim 1, in which Region δ is selected from the moieties of formulas (5.0.15) through (5.0.30) inclusive, formulas (5.0.35) through (5.0.47) inclusive, formulas (5.1.15) through (5.1.22) inclusive, formulas (5.2.1) through (5.2.10) inclusive, formulas (5.3.15) through (5.3.26) inclusive or formulas (5.4.10) through (5.4.17) inclusive:

(5.0.15) 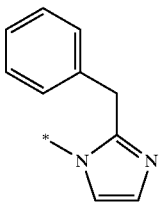

(5.0.16) 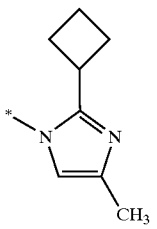

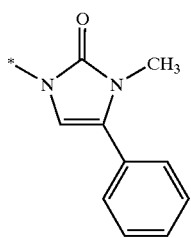 (5.0.17)
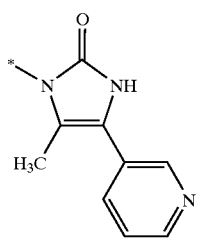 (5.0.18)
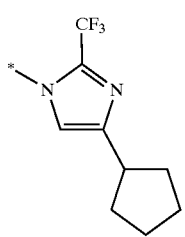 (5.0.19)
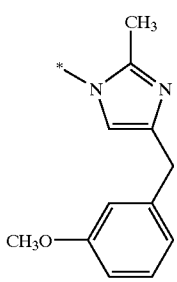 (5.0.20)
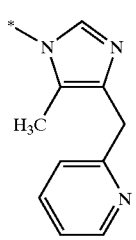 (5.0.21)
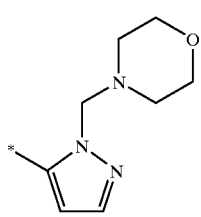 (5.0.22)
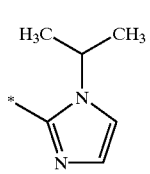 (5.0.23)
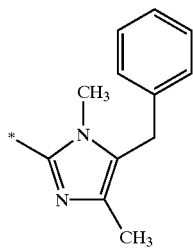 (5.0.24)
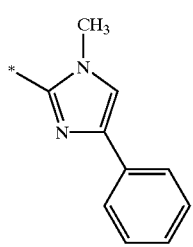 (5.0.25)
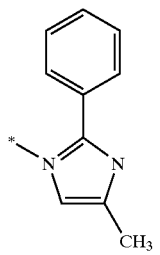 (5.0.26)
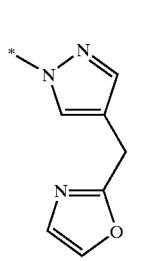 (5.0.27)
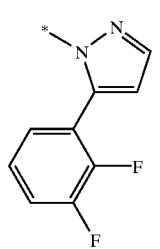 (5.0.28)
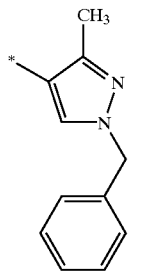 (5.0.29)

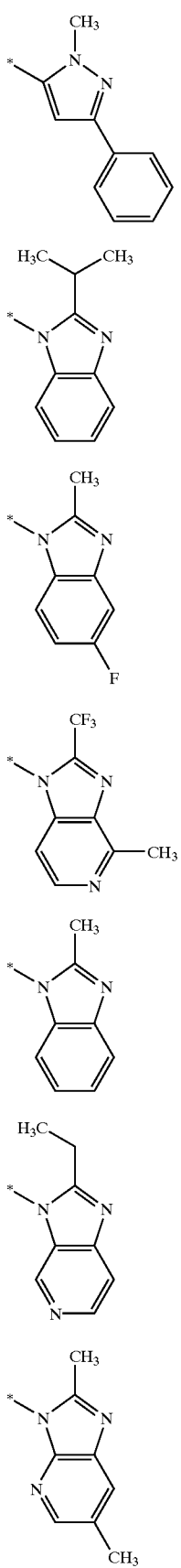
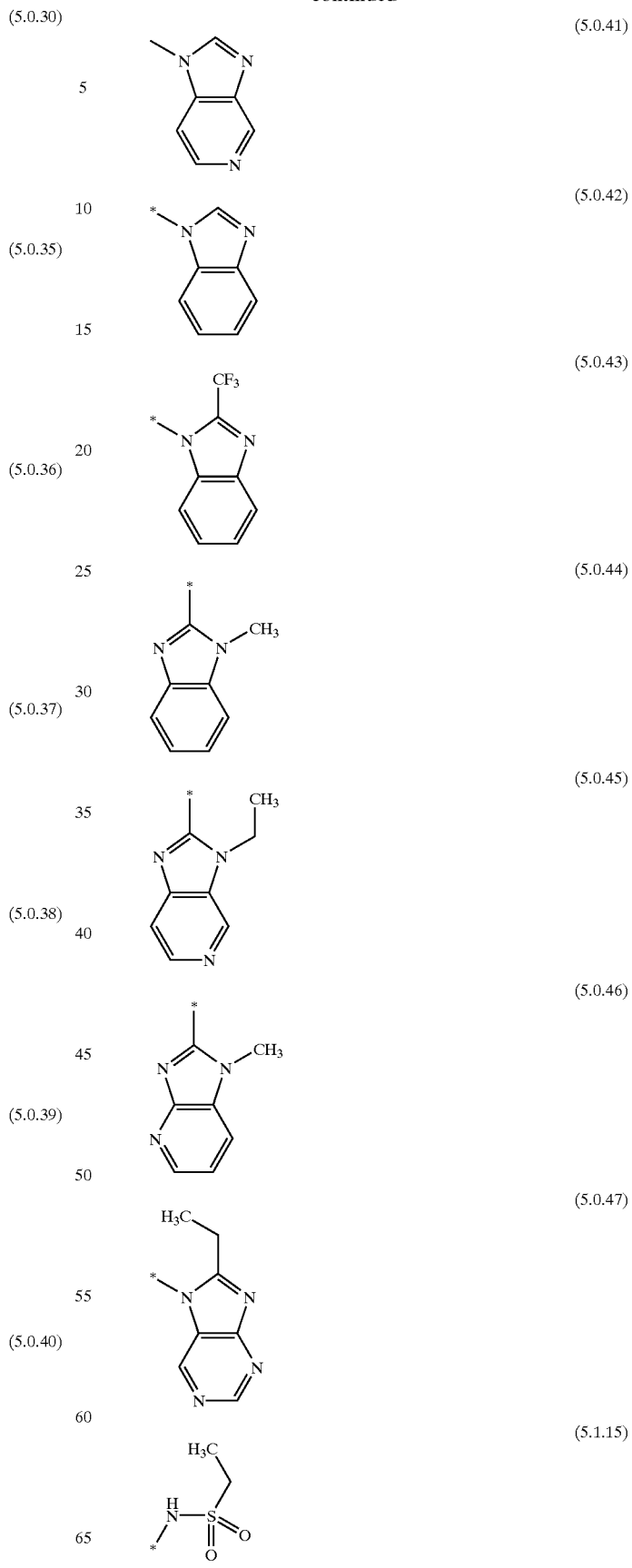

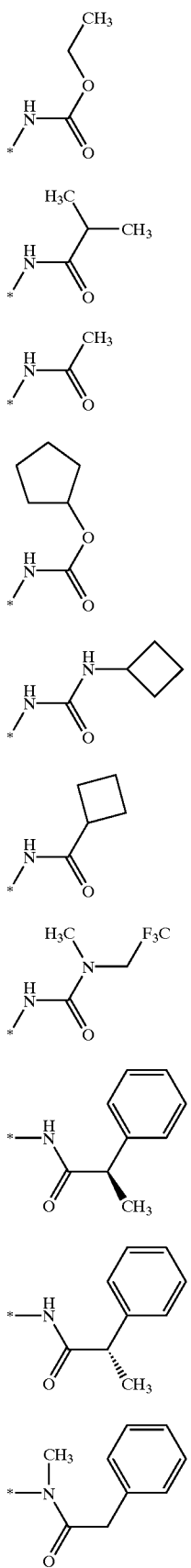
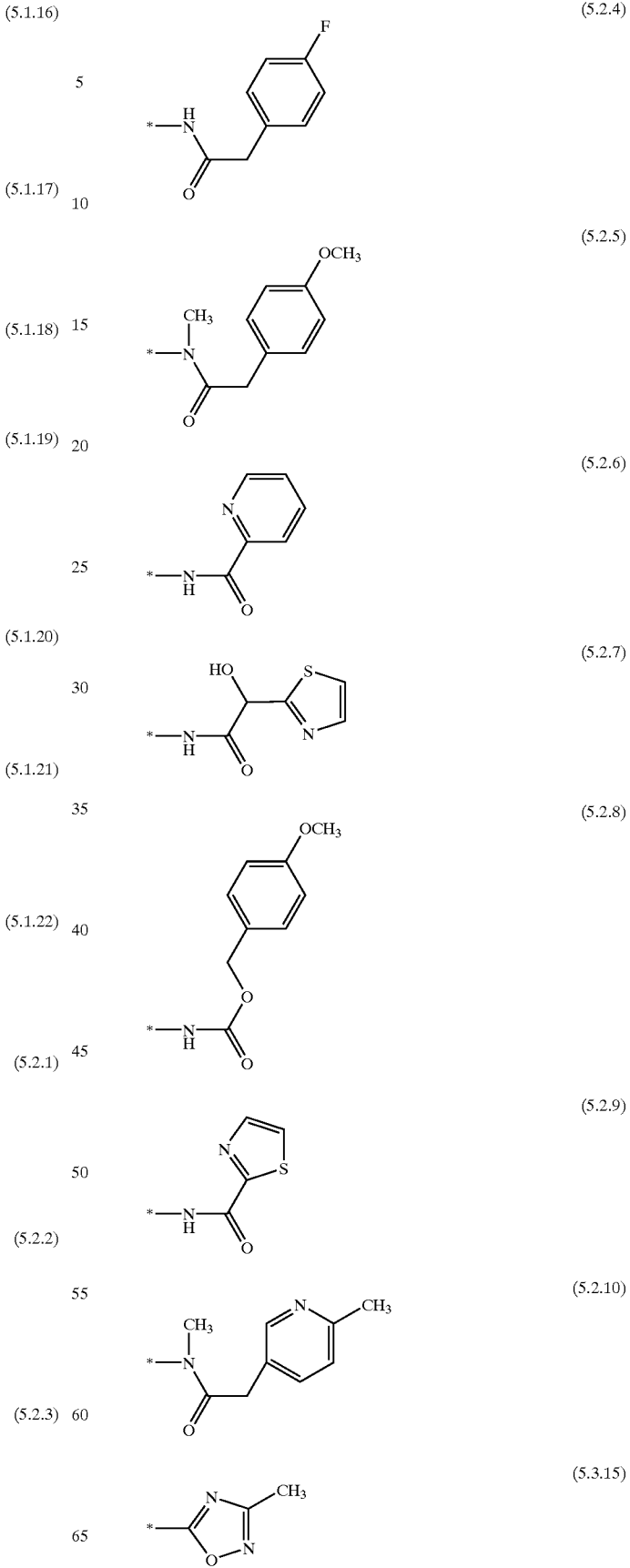

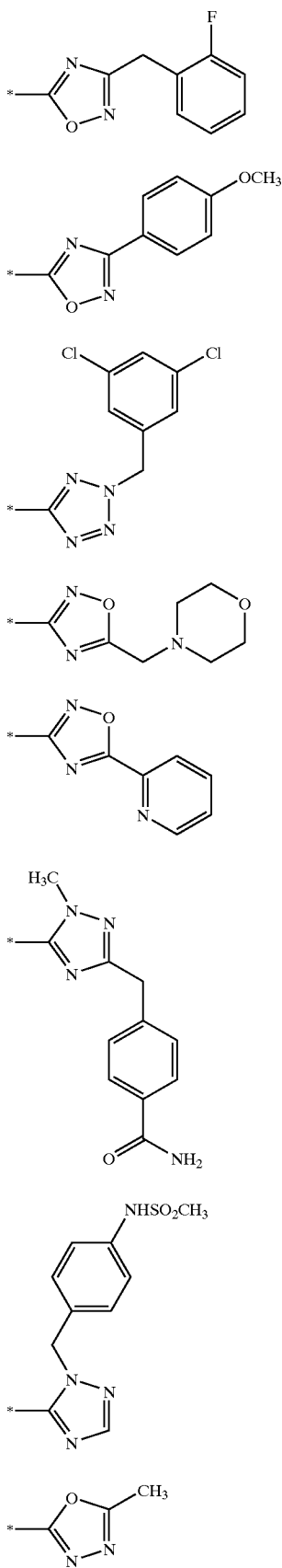

-continued (5.4.16)

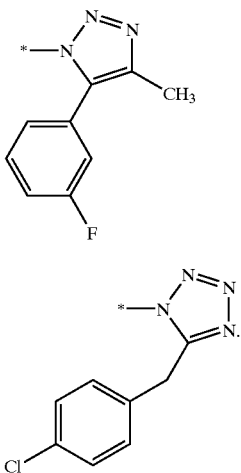

(5.4.17)

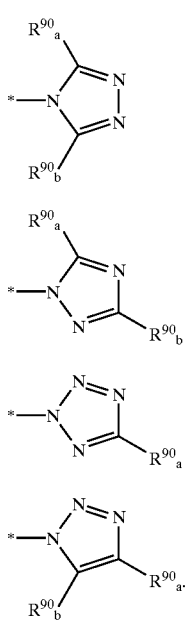

13. A compound of the formula (I), as claimed in claim 1, wherein region δ is selected from the moieties of formulas (5.4.5) through (5.4.8)

(5.4.5)

$R^{90}_a$–N–N–$R^{90}_b$ (triazole)

(5.4.6)

$R^{90}_a$–N–N=N–$R^{90}_b$ (5.4.7)

N=N–N–$R^{90}_a$ (5.4.8)

N=N–N–$R^{90}_a$/$R^{90}_b$

14. A compound of the formula (I), as claimed in claim 1, which is selected from N-{3-[3-exo-(2-Methyl-1H-benzimidazol-1-yl)-8-azabicyclo[3.2.1]oct-8-yl]-1-phenylpropyl}cyclobutanecarboxamide N-{(1S)-3-[3-exo-(2-Methyl-1H-benzimidazol-1-yl)-8-azabicyclo[3.2.1]oct-8-yl]-1-phenylpropyl}cyclobutanecarboxamide N-{(1S)-3-[3-endo-(2-Methyl-1H-benzimidazol-1-yl)-8-azabicyclo[3.2.1]oct-8-yl]-1-phenylpropyl}cyclobutanecarboxamide N-{(1S)-3-[3-exo-(2-Methyl-1H-benzimidazol-1-yl)-8-azabicyclo[3.2.1]oct-8-yl]-1-phenylpropyl}tetrahydro-2H-pyran-4-carboxamide 1-Acetyl-N-{(1S)-3-[3-exo-(2-methyl-1H-benzimidazol-1-yl)-8-azabicyclo[3.2.1]oct-8-yl]-1-phenylpropyl}3-azetidine carboxamide 1-Hydroxy-N-{(1S)-3-[3-exo-(2-methyl-1H-benzimidazol-1-yl)-8-azabicyclo[3.2.1]oct-8-yl]-1-phenylpropyl}cyclopentanecarboxamide 2-Methyl-N-{(1S)-3-[3-exo-(2-methyl-1H-benzimidazol-1-yl)-8-azabicyclo[3.2.1]oct-8-yl]-1-phenylpropyl}cyclopropanecarboxamide 2-Cyclopropyl-N-{1S)-3-[3-exo-(2-methyl-1H-benzimidazol-1-yl)-8-azabicyclo [3.2.1]oct-8-yl]-1-phenylpropyl}acetamide N-{(1S)-3-[3-exo-(2-methyl-1H-benzimidazol-1-yl)-8-azabicyclo[3.2.1]oct-8-yl]-1-phenylpropyl}tetrahydro-3-furancarboxamide 3,3,3-Trifluoro-N-{(1S)-3-[3-exo-(2-methyl-1H-benzimidazol-1-yl)-8-azabicyclo[3.2.1]oct-8-yl]-1-phenylpropyl}propanamide N-{(1S)-3-[3-exo-(2-Methyl-1H-benzimidazol-1-yl)-8-azabicyclo[3.2.1]oct-8-yl]-1-phenylpropyl}tetrahydro-2-furancarboxamide 1-(Acetylamino)-N-{(1S)-3-[3-exo-(2-methyl-1H-benzimidazol-1-yl)-8-azabicyclo[3.2.1]oct-8-yl]-1-phenylpropyl}cyclopentanecarboxamide N-{(1S)-3-[3-exo-(2-Methyl-1H-benzimidazol-1-yl)-8-azabicyclo[3.2.1]oct-8-yl]-1-phenylpropyl}acetamide 1-Methoxy-N-{(1S)-3-[3-exo-(2-methyl-1H-benzimidazol-1-yl)-8-azabicyclo[3.2.1]oct-8-yl]-1-phenylpropyl}cyclopentanecarboxamide 1-Amino-N-{(1S)-3-[3-exo-(2-methyl-1H-benzimidazol-1-yl)-8-azabicyclo[3.2.1]oct-8-yl]-1-phenylpropyl}cyclopentanecarboxamide 1-Methyl-N-{(1S)-3-[3-exo-(2-methyl-1H-benzimidazol-1-yl)-8-azabicyclo[3.2.1]oct-8-yl]-1-phenylpropyl}-2-oxo-4-pyrrolidinecarboxamide 1-Acetyl-N-{(1S)-3-[3-endo-(2-methyl-1H-benzimidazol-1-yl)-8-azabicyclo[3.2.1]oct-8-yl]-1-phenylpropyl)3-azetidinecarboxamide N-{(1S)-3-[3-endo-(2-Methyl-1H-benzimidazol-1-yl)-8-azabicyclo[3.2.1]oct-8-yl]-1-phenylpropyl}acetamide N-{(1S)-3-[6-(2-Methyl-1H-benzimidazol-1-yl)-3-azabicyclo[3.1.0]hex-3-yl]-1-phenylpropyl}cyclobutanecarboxamide 2-Cyclopropyl-N-{(1S)-3-[3-exo-(3-{4-[(methylsulfonyl)amino]benzyl}-1,2,4-oxadiazol-5-yl)-8-azabicyclo[3.2.1]oct-8-yl]-1-phenylpropyl}acet- amide N-{(1S)-3-[7-exo-(2-Methyl-1H-benzimidazol-1-yl)-3-oxa-9-azabicyclo[3.3.1]non-9-yl]-1-phenylpropyl}cyclobutanecarboxamide 2-Cyclopropyl-N-{(1S)-3-[7-exo-(2-methyl-1H-benzimidazol-1-yl)-3-oxa-9-azabicyclo[3.3.1]non-9-yl]-1-phenylpropyl}acetamide 3,3,3-Trifluoro-N-{(1S)-3-[7-exo-(2-methyl-1H-benzimidazol-1-yl)-3-oxa-9-azabicyclo[3.3.1]non-9-yl]-1-phenylpropyl}propanamide N-{(1S)-3-[7-endo-(2-Methyl-1H-benzimidazol-1-yl)-3-oxa-9-azabicyclo[3.3.1]non-9-yl]-1-phenylpropyl}cyclobutanecarboxamide 2-Cyclopropyl-N-{(1S)-3-[7-endo-(2-methyl-1H-benzimidazol-1-yl)-3-oxa-9-azabicyclo[3.3.1]non-9-yl]-1-phenylpropyl}acetamide N-{(1S)-3-[7-exo-(2-Methyl-1H-benzimidazol-1-yl)-3-thia-9-azabicyclo[3.3.1]non-9-yl]-1-phenylpropyl}cyclobutanecarboxamide 2-Cyclopropyl-N-[(1S)-3-(3-endo-{[2-(4-fluorophenyl)acetyl]amino}-8-azabicyclo[3.2.1]oct-8-yl)-1-phenylpropyl]acetamide N-[(1S)-3-(3-{[3-endo-(4-Fluorophenyl)ppropanoyl]
amino}-8-azabicyclo[3.2.1]oct-8-yl)-1-phenylpropyl]
cyclobutanecarboxamide N-[(1S)-3-(3-{[3-exo-(4-Fluorophenyl)prpropanoyl]
amino}-8-azabicyclo[3.2.1]oct-8-yl)-1-phenylpropyl]
cyclobutanecarboxamide 2-Cyclopropyl-N-[(1S)-3-(3-exo-{[2-(4-fluorophenyl)
acetyl]amino}-8-azabicyclo[3.2.1]oct-8-yl)-1-
phenylpropyl]acetamide N-{(1S)-3-[3-exo-(2-Methyl-1H-benzimidazol-1-yl)-8-
azabicyclo[3.2.1]oct-8-yl]-1-phenylpropyl)}1-
propionyl-3-azetidinecarboxamide N-{(1S)-3-[3-endo-(2-Methyl-1H-benzimidazol-1-yl)-8-
azabicyclo[3.2.1]oct-8-yl]-1-phenylpropyl}tetrahydro-
3-furancarboxamide N-{(1S)-3-[3-endo-(2-Methyl-1H-benzimidazol-1-yl)-8-
azabicyclo[3.2.1]oct-8-yl]-1-phenylpropyl}tetrahydro-
2H-pyran4-carboxamide N-{(1S)-3-[3-endo-(2-Methyl-1H-benzimidazol-1-yl)-8-
azabicyclo[3.2.1]oct-8-yl]-1-phenylpropyl}tetrahydro-
2-furancarboxamide 1-Acetyl-N-{(1S)-3-[3-endo-(1H-benzimidazol-1-yl)-8-
azabicyclo[3.2.1]oct-8-yl]-1-phenylpropyl}-3-
azetidinecarboxamide N-{(1S)-3-[3-endo-(1H-Benzimidazol-1-yl)-8-
azabicyclo[3.2.1]oct-8-yl]-1-phenylpropyl}-1-
propionyl-3-azetidinecarboxamide Methyl 3-[({(1S)-3-[3-exo-(2-methyl-1H-benzimidazol-
1-yl)-8-azabicyclo[3.2.1]oct-8-yl]-1-phenylpropyl}-
amino)carbonyl]-1-azetidinecarboxylate N-{(1S)-3-[3-endo-(2-Methyl-1H-benzimidazol-1-yl)-8-
azabicyclo[3.2.1]oct-8-yl]-1-phenylpropyl}-1-
propionyl-3-azetidinecarboxamide 1-Acetyl-N-{(1S)-
3-[3-endo-(2-methyl-1H-benzimidazol-1-yl)-8-
azabicyclo[3.2.1]oct-8-yl]-1-phenylpropyl}-2-
azetidinecarboxamide 2-[Acetyl(methyl)amino]-N-{(1S)-3-[3-endo-(2-methyl-
1H-benzimidazol-1-yl)-8-azabicyclo[3.2.1]oct-8-yl]-1-
phenylpropyl}acetamide 3-[Acetyl(methyl)amino]-N-{(1S)-3-[3-endo-(2-methyl-
1H-benzimidazol-1-yl)-8-azabicyclo[3.2.1]oct-8-yl]-1-
phenylpropyl}propanamide 2-Methoxy-N-{(1S)-3-[3-endo-(2-methyl-1H-
benzimidazol-1-yl)-8-azabicyclo[3.2.1]oct-8-yl]-1-
phenylpropyl}acetamide 3-Methoxy-N-{(1S)-3-[3-endo-(2-methyl-1H-
benzimidazol-1-yl)-8-azabicyclo[3.2.1]oct-8-yl]-1-
phenylpropyl}propanamide 1-Acetyl-N-{(1S)-3-[3-endo-(2-methyl-1H-
benzimidazol-1-yl)-8-azabicyclo[3.2.1]oct-8-yl]-1-
phenylpropyl}-3-pyrrolidinecarboxamide 1-Methyl-N-{(1S)-3-[3-endo-(2-methyl-1H-
benzimidazol-1-yl)-8-azabicyclo[3.2.1]oct-8-yl]-1-
phenylpropyl}-2-oxo-4-pyrrolidinecarboxamide 1-Acetyl-N-{(1S)-3-[3-exo-(2-ethyl-1H-benzimidazol-1-
yl)-8-azabicyclo[3.2.1]oct-8-yl]-1-phenylpropyl}-3-
azetidinecarboxamide N-{(1S)-3-[3-exo-(2-Ethyl-1H-benzimidazol-1-yl)-8-
azabicyclo[3.2.1]oct-8-yl]-1-phenylpropyl}-1-
propionyl-3-azetidinecarboxamide 1-Acetyl-N-((1S)-1-phenyl-3-{3-exo-[2-(trifluoro-
methyl)-1H-benzimidazol-1-yl]-8-azabicyclo[3.2.1]
oct-8-yl}propyl)-3-azetidinecarboxamide N-((1S)-1-Phenyl-3-{3-exo-[2-(trifluoromethyl)-1H-
benzimidazol-1-yl]-8-azabicyclo[3.2.1]oct-8-
yl}propyl)-1-propionyl-3-azetidinecarboxamide N-((1S)-1-Phenyl-3-{3-exo[2-(trifluoromethyl)-1H-
benzimidazol-1-yl]-8-azabicyclo[3.2.1]oct-8-
yl}propyl)acetamide 2-[Acetyl(methyl)amino]-N-((1S)-1-phenyl-3-{3-exo-[2-
(trifluoromethyl)-1H-benzimidazol-1-yl]-8-azabicyclo
[3.2.1]oct-8-yl}propyl)acetamide 1-Acetyl-N-{(1S)-3-[3-exo-(1H-benzimidazol-1-yl)-8-
azabicyclo[3.2.1]oct-8-yl]-1-phenylpropyl}-3-
azetidinecarboxamide N(1S)-3-[3-exo-(1H-Benzimidazol-1-yl)-8-azabicyclo
[3.2.1]oct-8-yl]-1-phenylpropyl}-1-propionyl-3-
azetidinecarboxamide 1-acetyl-N(1S)-3-[3-exo-(5-fluoro-1H-benzimidazol-1-
yl)-8-azabicyclo[3.2.1]oct-8-yl]-1-phenylpropyl)3-
azetidinecarboxamide N-{(1S)-3-[3-exo-(5-Fluoro-1H-benzimidazol-1-yl)-8-
azabicyclo[3.2.1]oct-8-yl]-1-phenylpropyl}-1-
propionyl-3-azetidinecarboxamide 1-Acetyl-N-{(1S)-3-[3-exo-(5-fluoro-2-methyl-1H-
benzimidazol-1-yl)-8-azabicyclo[3.2.1]oct-8-yl]-1-
phenylpropyl}3-azetidinecarboxamide N-{(1S)-3-[3-exo-(5-Fluoro-2-methyl-1H-benzimidazol-
1-yl)-8-azabicyclo[3.2.1]oct-8-yl]-1-phenylpropyl}-1-
propionyl-3-azetidinecarboxamide N-{(1S)-3-[3-exo-(2-methyl-1H-benzimidazol-1-yl)-8-
azabicyclo[3.2.1]oct-8-yl]-1-phenylpropyl}-3-
azetidinecarboxamide 1-methyl-N-{(1S)-3-[3-exo-(2-methyl-1H-benzimidazol-
1-yl)-8-azabicyclo[3.2.1]oct-8-yl]-1-phenylpropyl}-3-
azetidinecarboxamide (2S)-1-acetyl-N-{(1S)-3-[3-exo-(2-methyl-1H-
benzimidazol-1-yl)-8-azabicyclo[3.2.1]oct-8-yl]-1-
phenylpropyl}-2-azetidinecarboxamide (2R)-1-acetyl-N-{(1S)-3-[3-exo-(2-methyl-1H-
benzimidazol-1-yl)-8-azabicyclo[3.2.1]oct-8-yl]-1-
phenylpropyl}-2-azetidinecarboxamide 2-[acetyl(methyl)amino]-N-{(1S)-3-[3-exo-(2-methyl-
1H-benzimidazol-1-yl)-8-azabicyclo[3.2.1]oct-8-yl]-1-
phenylpropyl}acetamide 3-[acetyl(methyl)amino]-N-{(1S)-3-[3-exo-(2-methyl-
1H-benzimidazol-1-yl)-8-azabicyclo[3.2.1]oct-8-yl]-1-
phenylpropyl}propanamide 1-acetyl-N-{(1S)-3-[3-exo-(2-methyl-1H-benzimidazol-
1-yl)-8-azabicyclo[3.2.1]oct-8-yl]-1-phenylpropyl}-3-
pyrrolidinecarboxamide N-{(1S)-3-[3-exo-(2-methyl-1H-benzimidazol-1-yl)-8-
azabicyclo[3.2.1]oct-8-yl]-1-phenylpropyl}-1-
(trifluoromethyl)cyclopropanecarboxamide 2-methoxy-N-{(1S)-3-[3-exo-(2-methyl-1H-
benzimidazol-1-yl)-8-azabicyclo[3.2.1]oct-8-yl]-1-
phenylpropyl}acetamide 3-methoxy-N-{(1S)-3-[3-exo-(2-methyl-1H-
benzimidazol-1-yl)-8-azabicyclo[3.2.1]oct-8-yl]-1-
phenylpropyl}propanamide 1-Acetyl-N-{(1S)-3-[3-exo-(4-fluoro-2-methyl-1H-
benzimidazol-1-yl)-8-azabicyclo[3.2.1]oct-8-yl]-1-
phenylpropyl}-3-azetidinecarboxamide N-{(1S)-3-[3-exo-(4-Fluoro-2-methyl-1H-benzimidazol-
1-yl)-8-azabicyclo[3.2.1]oct-8-yl]-1-phenylpropyl}-3-
azetidinecarboxamide 1-Methyl-N-{(1S)-3-[3-exo-(4-fluoro-2-methyl-1H-
benzimidazol-1-yl)-8-azabicyclo[3.2.1]oct-8-yl]-1-
phenylpropyl}-3-azetidinecarboxamide N-{(1S)-3-[3-exo-(4-Fluoro-2-methyl-1H-benzimidazol-1-yl)-8-azabicyclo[3.2.1]oct-8-yl]-1-phenylpropyl}-1-propionyl-3-azetidinecarboxamide 2-Methoxy-N-{(1S)-3-[3-exo-(4-Fluoro-2-methyl-1H-benzimidazol-1-yl)-8-azabicyclo[3.2.1]oct-8-yl]-1-phenylpropyl}acetamide N-{(1S)-3-[3-exo-(4-Fluoro-2-Methyl-1H-benzimidazol-1-yl)-8-azabicyclo[3.2.1]oct-8-yl]-1-phenylpropyl}-acetamide 3-Methoxy-N-{(1S)-3-[3-exo-(4-fluoro-2-methyl-1H-benzimidazol-1-yl)-8-azabicyclo[3.2.1]oct-8-yl]-1-phenylpropyl}propanamide 2-[Acetyl(methyl)amino]-N-{(1S)-3-[3-exo-(4-fluoro-2-methyl-1H-benzimidazol-1-yl)-8-azabicyclo[3.2.1]oct-8-yl]-1-phenylpropyl}acetamide 3-[Acetyl(methyl)amino]-N-{(1S)-3-[3-exo-(4-fluoro-2-methyl-1H-benzimidazol-1-yl)-8-azabicyclo[3.2.1]oct-8-yl]-1-phenylpropyl}propanamide N-{(1S)-3-[3-exo-(4-fluoro-2-methyl-1H-benzimidazol-1-yl)-8-azabicyclo[3.2.1]oct-8-yl]-1-phenylpropyl}-3-methyl-3-oxetanecarboxamide 3-Ethyl-N-{(1S)-3-[3-exo-(4-fluoro-2-methyl-1H-benzimidazol-1-yl)-8-azabicyclo[3.2.1]oct-8-yl]-1-phenylpropyl}-3-oxetanecarboxamide N-{(1S)-3-[3-exo-(4-Fluoro-2-methyl-1H-benzimidazol-1-yl)-8-azabicyclo[3.2.1]oct-8-yl]-1-phenylpropyl}-3-oxetanecarboxamide 3-Ethyl-N-{(1S)-3-[3-exo-(4-fluoro-1H-benzimidazol-1-yl)-8-azabicyclo[3.2.1]oct-8-yl]-1-phenylpropyl}-3-oxetanecarboxamide N-{(1S)-3-[3-exo-(4-Fluoro-1H-benzimidazol-1-yl)-8-azabicyclo[3.2.1]oct-8-yl]-1-phenylpropyl}-3-methyl-3-oxetanecarboxamide N-{(1S)-3-[3-exo-(4-Fluoro-1H-benzimidazol-1-yl)-8-azabicyclo[3.2.1]oct-8-yl]-1-phenylpropyl}-3-oxetanecarboxamide N-{(1S)-3-[3-exo-(4-Fluoro-1H-benzimidazol-1-yl)-8-azabicyclo[3.2.1]oct-8-yl]-1-phenylpropyl}-3-azetidinecarboxamide N-{(1S)-3-[3-exo-(4-Fluoro-1H-benzimidazol-1-yl)-8-azabicyclo[3.2.1]oct-8-yl]-1-phenylpropyl}-1-methyl-3-azetidinecarboxamide 1-Acetyl-N-{(1S)-3-[3-exo-(4-fluoro-1H-benzimidazol-1-yl)-8-azabicyclo[3.2.1]oct-8-yl]-1-phenylpropyl}-3-azetidinecarboxamide N-{(1S)-3-[3-exo-(4-Fluoro-1H-benzimidazol-1-yl)-8-azabicyclo[3.2.1]oct-8-yl]-1-phenylpropyl}-1-propionyl-3-azetidinecarboxamide N-{(1S)-3-[3-exo-(4-Fluoro-1H-benzimidazol-1-yl)-8-azabicyclo[3.2.1]oct-8-yl]-1-phenylpropyl}-2-methoxyacetamide N-{(1S)-3-[3-exo-(4-Fluoro-1H-benzimidazol-1-yl)-8-azabicyclo[3.2.1]oct-8-yl]-1-phenylpropyl}acetamide N{-1S)-3-[3-exo-(4-fluoro-1H-benzimidazol-1-yl)-8-azabicyclo[3.2.1]oct-8-yl]-1-phenylpropyl}-3-methoxypropanamide 2-[Acetyl(methyl)amino]-N-{(1S)-3-[3-exo-(4-fluoro-1H-benzimidazol-1-yl)-8-azabicyclo[3.2.1]oct-8-yl]-1-phenylpropyl}acetamide 3-[Acetyl(methyl)amino]-N-{(1S)-3-[3-exo-(4-fluoro-1H-benzimidazol-1-yl)-8-azabicyclo[3.2.1]oct-8-yl]-1-phenylpropyl}propanamide and the pharmaceutically acceptable salts thereof.

15. The compound of claim 1 wherein group Y has the structure

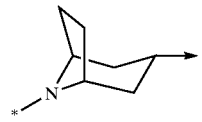

16. A compound of the formula

[Region α]-[Region β]-[Region γ]-[Region δ]   (I)

or a pharmaceutically acceptable salt thereof, wherein [Region α] is a moiety of the formula

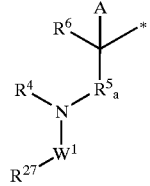

(2.0.0)

wherein the symbol '*' indicates the point of attachment of the moiety of the formula (2.0.0) to Region β;

$R^4$ is H or $C_1$–$C_2$ alkyl;

$R^6$ is H, $C_1$–$C_2$ alkyl, $C_1$–$C_2$ alkoxy, —CN, —OH, or —CONH$_2$;

A is phenyl optionally substituted by up to 4 substituents independently selected from fluoro, chloro, —CO$_2$R$^4$, —OH, —CN, —CONR$^4_a$R$^4_b$, —NR$^4_a$R$^4_b$, —NR$^4_a$COR$^4_b$, —NR$^4_a$CO$_2$R$^4_b$, —NR$^4_a$S(O)$_p$R$^4_b$, —S(O)$_p$NR$^4_a$R$^4_b$, $C_1$–$C_4$ alkyl, $C_1$–$C_4$ alkoxy, $C_1$–$C_2$ alkoxycarbonyl, $C_1$–$C_2$ alkylcarbonyl and $C_1$–$C_2$ alkylcarbonyloxy, said $C_1$–$C_4$ alkyl and $C_1$–$C_4$ alkoxy being optionally substituted by up to 3 substituents independently selected from fluoro and chloro;

p is 0, 1 or 2;

$R^4_a$ and $R^4_b$ are each independently H or $C_1$–$C_2$ alkyl;

$R^5_a$ is a direct bond, —CO— or —SO$_2$—;

$W^1$ is
 (i) a direct bond, or
 (ii) in the case where $R^5_a$ is —CO— or —SO$_2$—, $C_1$–$C_3$ alkylene optionally substituted by up to 2 substituents $R^{23}$, or
 (iii) a moiety independently selected from formulas (2.0.6) through (2.0.16) inclusive;

(2.0.6)

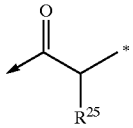

(2.0.7)

-continued (2.0.8)
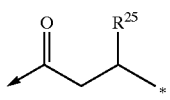

(2.0.9)
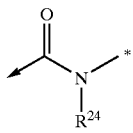

(2.0.10)
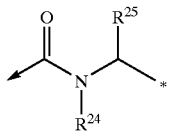

(2.0.11)
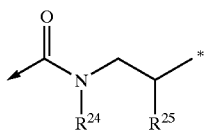

(2.0.12)

(2.0.13)
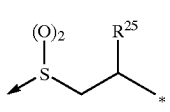

(2.0.14)
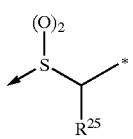

(2.0.15)
(2.0.16)
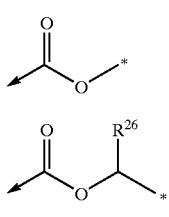

wherein the symbol '→' indicates the point of attachment of the moiety $W^1$ to the nitrogen atom in partial formula (2.0.0) and the symbol '*' indicates the point of attachment of the moiety $W^1$ to the other, remaining portions of partial formula (2.0.0);

$R^{23}$ is fluoro, chloro, —$CO_2R^4$, —OH, —CN, $C_1$–$C_4$ alkoxy, $C_3$–$C_7$ cycloalkyl or phenyl, said $C_1$–$C_4$ alkoxy, $C_3$–$C_7$ cycloalkyl and phenyl being optionally substituted by up to two substituents $R^{11}$;

$R^{11}$ is fluoro, chloro, —$CO_2R^4$, —OH, —CN, —$CONR^4_aR^4_b$, —$NR^4_aR^4_b$, —$NR^4_aCOR^4_b$, $NR^4_aCO_2R^4_b$, —$NR^4_aS(O)_pR^4_b$, —$S(O)_pNR^4_aR^4_b$, $C_1$–$C_4$ alkyl including dimethyl, $C_1$–$C_4$ alkoxy, $C_1$–$C_2$ alkoxycarbonyl, $C_1$–$C_2$ alkylcarbonyl or $C_1$–$C_2$ alkylcarbonyloxy, said $C_1$–$C_4$ alkyl and $C_1$–$C_4$ alkoxy each being optionally substituted by up to 3 substituents independently selected from fluoro and chloro;

$R^{24}$ is H or $C_1$–$C_4$ alkyl;

$R^{25}$ and $R^{26}$ are each independently —OH, $C_1$–$C_2$ alkyl or $C_1$–$C_2$ alkoxy, said $C_1$–$C_2$ alkyl being optionally substituted by up to 3 substituents selected from fluoro and —OH;

$R^{27}$ is
(i) $C_1$–$C_6$ alkyl, $C_2$–$C_6$ alkenyl or $C_2$–$C_6$ alkynyl, each optionally substituted by up to 3 substituents $R^{28}$; or
(ii) —$(CH_2)_n$-($C_3$–$C_7$ cycloalkyl) wherein
 (a) said $C_3$–$C_7$ cycloalkyl is optionally substituted by up to 3 substituents $R^{28}$,
 (b) n is 0, 1 or 2,
 (c) in the event that n is 0, the α-carbon of said $C_3$–$C_7$ cycloalkyl is optionally substituted by one substituent selected from $C_1$–$C_4$ alkyl and phenyl wherein said $C_1$–$C_4$ alkyl and phenyl are optionally substituted by 1 or 2 substituents selected from —$CH_3$, —$OCH_3$, —OH or —$NH_2$, and
 (d) in the event that n is 1 or 2, the resulting methylene or ethylene is optionally substituted by 1 substituent selected from fluoro, —$NH_2$, —$N(CH_3)_2$, —OH, —$OCH_3$, $C_1$–$C_4$ alkyl or phenyl, said $C_1$–$C_4$ alkyl and phenyl being optionally substituted by 1 or 2 substituents selected from —$CH_3$, —$OCH_3$, —OH and —$NH_2$; or
(iii) phenyl, furyl, tetrahydrofuranyl, tetrahydropyranyl, oxetanyl, thienyl, pyrrolyl, pyrrolidinyl, oxazolyl, isoxazolyl, thiazolyl, isothiazolyl, imidazolyl, pyrazolyl, oxadiazolyl, thiadiazolyl, triazolyl, pyridyl, pyrazinyl, pyridazinyl, piperazinyl, pyrimidinyl, pyranyl, azetidinyl, morpholinyl, thiomorpholino, indolyl, indolinyl, benzo[b]furanyl, 2,3-dihydrobenzofuranyl, benzothienyl, 1H-indazolyl, benzimidazolyl, benzoxazolyl, benzisoxazolyl, benzthiazolyl, quinolinyl, isoquinolinyl, phthalazinyl, quinazolinyl or quinoxalinyl, each optionally substituted
 (a) on any one or more carbon atoms by up to 3 substituents $R^{28}$, or
 (b) on any one or more nitrogen atoms that is not a point of attachment of said heterocyclic moiety by up to 3 substituents $R^{13}_b$, or
 (c) on any sulphur atom that is not a point of attachment of said heterocyclic moiety by up to 2 oxygen atoms;

$R^{28}$ is phenyl, fluoro, chloro, oxo, —OH, $C_1$–$C_2$ alkyl, $C_1$–$C_3$ alkoxy, —$CO_2R^{29}$, —$CO(C_1$–$C_4)$alkyl, —$SO_2(C_1$–$C_4)$alkyl, —$CONR^{29}R^{30}$, —$NR^{29}R^{30}$, —$NR^{29}COR^{30}$, —$NR^{29}CO_2R^{30}$, —$NR^{29}S(O)_pR^{30}$ or —$SO_2NR^{29}R^{30}$;

$R^{29}$ and $R^{30}$ are each independently H or $C_1$–$C_4$ alkyl optionally substituted by up to 3 substituents selected from fluoro and chloro;

$R^{13}_b$ is H, $C_1$–$C_4$ alkyl, $C_2$–$C_4$ alkenyl, $C_1$–$C_2$ alkoxy, $C_3$–$C_7$ cycloalkyl, —$CO(C_1$–$C_4)$alkyl, —$SO_2(C_1$–$C_4)$ alkyl or phenyl wherein said $C_1$–$C_4$ alkyl, $C_2$–$C_4$ alkenyl, $C_1$–$C_2$ alkoxy, $C_3$–$C_7$ cycloalkyl and phenyl are optionally substituted by up to 2 substituents $R^{11}$;

[$R_{egion}$ β] is an alkyl bridging element of partial Formula (3.0.0):

(3.0.0)
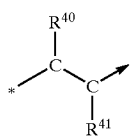

wherein:
"*" is a symbol which represents the point of attachment of the moiety of partial Formula (3.0.0) to $R_{egion}$ α;
"→" is a symbol which represents the point of attachment of the moiety of partial Formula (3.0.0) to $R_{egion}$ γ;

$R^{40}$ and $R^{41}$ are independently selected from the group consisting of hydrogen; $(C_1-C_2)$alkyl including dimethyl; hydroxy; and $(C_1-C_3)$alkoxy;

[$R_{egion}$ γ] is an aza-bicyclic moiety of partial Formula (4.2.0):

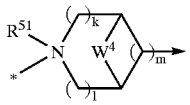

(4.2.0)

wherein

"*" is a symbol which represents the point of attachment of the moiety of partial Formula (4.2.0) to $R_{egion}$ β;

"→" is a symbol representing a covalent bond from any of the carbon atoms of the moiety of partial Formula (4.2.0) to $R_{egion}$ δ;

$W^4$ is a direct bond; or is a member independently selected from the group consisting of partial Formulas (4.2.1) through (4.2.6):

(4.2.1)

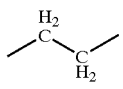

(4.2.2)

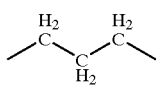

(4.2.3)

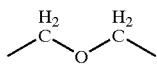

(4.2.4)

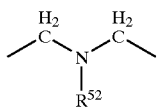

(4.2.5)

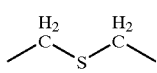

(4.2.6)

where:

$R^{52}$ is a member selected from the group consisting of hydrogen; phenyl; $(C_1-C_4)$alkyl substituted by 0 or 1 substituent independently selected from $(C_1-C_2)$ alkoxy and —$CO_2R^4$; $(C_3-C_6)$cycloalkyl; —$CO_2R^4$; →O; C(=O)$(C_1-C_3)$alkyl; —C(=O)$NR^4_aR^4_b$; —S(=O)$(C_1-C_4)$alkyl; and $(C_1-C_2)$alkylcarbonyl; where $R^4$, $R^4_a$, and $R^4_b$; are as defined above, but selected on an independent basis;

$R^{51}$ is absent or is a member selected from the group consisting of $(C_1-C_4)$alkyl substituted by 0 or 1 substituent independently selected from $(C_1-C_2)$ alkoxy and —$CO_2R^4$ where $R^4$ is as defined above; and →O; it being understood that in the case where substituent $R^{51}$ is present, the nitrogen atom is in quaternary form; and k, l and m are each an integer selected from 0, 1, 2, and 3;

[$R_{egion}$ δ] is a member selected from the group consisting of:

A. a two-nitrogen-atom-containing five-membered heterocyclic moiety of partial Formulas (5.0.0) through (5.0.10):

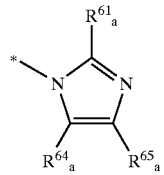

(5.0.0)

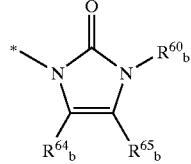

(5.0.1)

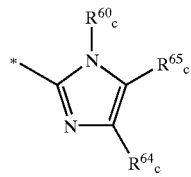

(5.0.2)

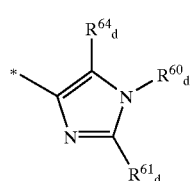

(5.0.3)

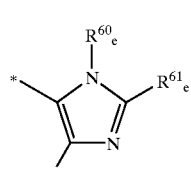

(5.0.4)

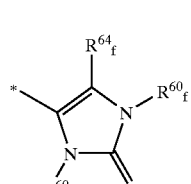

(5.0.5)

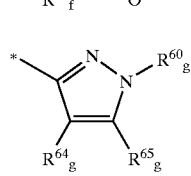

(5.0.6)

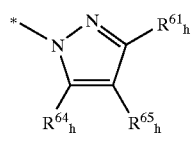

(5.0.7)

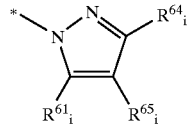

(5.0.8)

-continued

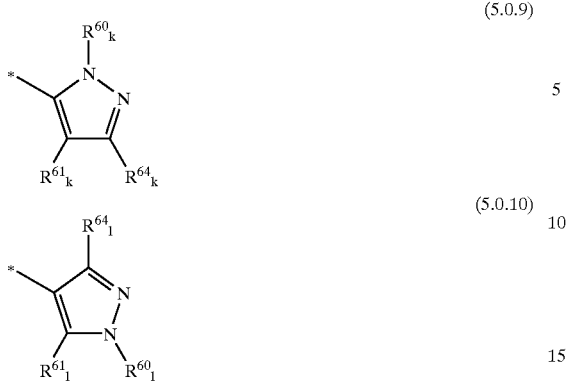

wherein: the symbol: "*" indicates the point of attachment of each of the moieties of partial Formulas (5.0.0) through (5.0.10), inclusive, to $R_{egion}$ γ;

$R^{60}{}_b$ through $R^{60}{}_g$, inclusive, $R^{60}{}_k$, and $R^{60}{}_l$ are each a member selected from the group consisting of hydrogen; —$CO_2R^4$; —$C(=O)NR^4{}_aR^4{}_b$; —$S(=O)_p$ $NR^4{}_aR^4{}_b$; where: $R^4$; $R^4{}_a$; and $R^4{}_b$ are as defined above but selected on an independent basis; →O; ($C_1$–$C_2$) alkylcarbonyl; —($C_1$–$C_4$)alkyl; —$(CH_2)_n$-($C_3$–$C_7$) cycloalkyl; —($C_2$–$C_3$)alkenyl; —$(CH_2)_n$-(phenyl); and —$(CH_2)_n$-($HET_1$), where n is an integer independently selected from 0, 1, and 2; wherein said ($C_1$–$C_4$)alkyl, alkenyl, cycloalkyl, phenyl and $HET_1$ (heterocyclyl) groups are independently substituted with 0 to 3 substituents $R^{66}$, where:

$HET_1$ is a heterocyclyl group selected from the group consisting of thienyl; oxazolyl; isoxazolyl; thiazolyl; isothiazolyl; pyrazolyl; oxadiazolyl; thiadiazolyl; triazolyl; pyridyl; pyrazinyl; pyridazinyl; pyrimidinyl; thiomorpholino; and morpholinyl; where:

$R^{66}$ is a member selected from the group consisting of —F; —Cl; —OH; cyano; —$C(=O)OR^{68}$; —$C(=O)NR^{68}R^{69}$; —$NR^{68}R^{69}$; —$NR^{68}C(=O)$ $R^{69}$; —$NR^{68}C(=O)OR^{69}$; —$NR^{68}S(=O)_2R^{69}$; —$S(=O)_2NR^{68}R^{69}$; ($C_1$–$C_4$)alkyl including dimethyl, and ($C_1$–$C_4$)alkoxy wherein said alkyl and alkoxy are each independently substituted with 0 to 3 substituents independently selected from F and Cl; ($C_1$–$C_2$)alkoxycarbonyl; ($C_1$–$C_2$) alkylcarbonyl; and ($C_1$–$C_2$)alkylcarbonyloxy, where:

$R^{68}$ and $R^{69}$ are each a member selected from the group consisting of hydrogen; and ($C_1$–$C_2$) alkyl; and where said:

$R^{61}{}_a$; $R^{61}{}_d$; $R^{61}{}_e$; and $R^{61}{}_h$ through $R^{61}{}_l$ inclusive; $R^{64}{}_a$ through $R^{64}{}_l$ inclusive; $R^{65}{}_a$ through $R^{65}{}_c$ inclusive; and $R^{65}{}_g$ through $R^{65}{}_l$ inclusive are each a member selected from the group consisting of hydrogen; —OH; —$CF_3$; cyano; —($C_1$–$C_3$)alkoxy; —$C(=O)OR^4$; —$C(=O)$ $NR^4{}_aR^4{}_b$; —$NR^4{}_aR^4{}_b$; —$NR^4{}_aC(=O)R^4{}_b$; —$NR^4{}_aC(=O)OR^4{}_b$; —$NR^4{}_aS(=O)_pR^4{}_b$; —$S(=O)_pNR^4{}_aR^4{}_b$; where: $R^4$; $R^4{}_a$; and $R^4{}_b$ are as defined further above but selected on an independent basis; —($C_1$–$C_4$)alkyl; —$(CH_2)_n$-($C_3$–$C_7$)cycloalkyl; —($C_2$–$C_3$)alkenyl; —$(CH_2)_n$-(phenyl); and —$(CH_2)_n$-($HET_1$), where n is an integer selected from 0, 1, and 2; wherein said ($C_1$–$C_4$)alkyl, alkenyl, cycloalkyl, phenyl, and $HET_1$(heterocyclyl) groups where $HET_1$(heterocyclyl) groups is as defined above, are independently substituted with 0 to 3 substituents $R^{66}$ where:

$R^{66}$ is as defined above, or:

$R^{64}{}_a$ through $R^{64}{}_c$ inclusive; $R^{64}{}_g$ through $R^{64}{}_l$ inclusive; $R^{65}{}_a$ through $R^{65}{}_c$ inclusive; and $R^{65}{}_g$ through $R^{65}{}_l$ inclusive may be taken together in their same subscript denominated pairs along with the remaining portions of the moieties of partial Formulas (5.0.0) through (5.0.2), and (5.0.6) through (5.0.8), to form a fused bicyclic ring system comprising a member independently selected from the group consisting of benzimidazolyl; purinyl, i.e., imidazopyrimidinyl; and imidazopyridinyl; wherein said fused bicyclic ring system is independently substituted with 0 to 3 substituents $R^{66}$, where $R^{66}$ has the same meaning as set out further above, except that it is independently selected therefrom;

B. a (substituted)-amide, carbamate, or urea moiety selected from the group consisting of:

1. alkyl-, cycloalkyl-, and alkenyl-(substituted)-amide, carbamate, or urea moieties of partial Formula (5.1.0):

wherein: the symbol "*" is as defined above;

$R^{73}$ is a member selected from the group consisting of hydrogen and ($C_1$–$C_2$)alkyl;

$W^5$ is selected from the group consisting the moieties of partial Formulas (5.1.1) through (5.1.12):

-continued

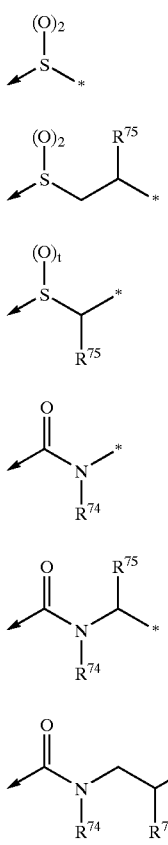

(5.1.7)

(5.1.8)

(5.1.9)

(5.1.10)

(5.1.11)

(5.1.12)

wherein: the symbol: "→" indicates the point of attachment of the moiety $W^5$ represented by partial Formulas (5.1.1) through (5.1.12), inclusive, to the nitrogen atom in partial Formula (5.1.0), and the symbol: "*" indicates the point of attachment of the moiety $W^5$ to $R^{77}$ as defined further below;

$R^{74}$ and $R^{75}$ are each selected from the group consisting of hydrogen; $(C_1-C_2)$alkyl substituted by 0 or 1 substituent independently selected from OH; and $(C_1-C_2)$alkoxy; and $R^{77}$ is a member selected from the group consisting of $(C_1-C_6)$alkyl; $(C_2-C_6)$alkenyl; and —$(CH_2)_n$-$(C_3-C_7)$cycloalkyl, where n is an integer selected from 0, 1, and 2; and wherein said alkyl, alkenyl, and cycloalkyl groups comprising $R^{77}$ are substituted with 0 to 3 substituents $R^{78}$, where:

$R^{78}$ is a member selected from the group consisting of oxo; —OH; —$(C_1-C_2)$alkyl; —$(C_1-C_3)$alkoxy; —$CF_3$; —$C(=O)OR^{79}$; —$C(=O)NR^{79}R^{80}$; —$NR^{79}R^{80}$; —$NR^{79}C(=O)R^{80}$; —$NR^{79}C(=O)OR^{80}$; —$NR^{79}S(=O)_2R^{80}$; and —$S(=O)_2NR^{79}R^{80}$, where:

$R^{79}$ and $R^{80}$ are each a member independently selected from the group consisting of hydrogen; and $(C_1-C_4)$alkyl; and 2. aryl and heterocyclyl-(substituted)-amide, carbamate, or urea moieties of partial Formula (5.2.0):

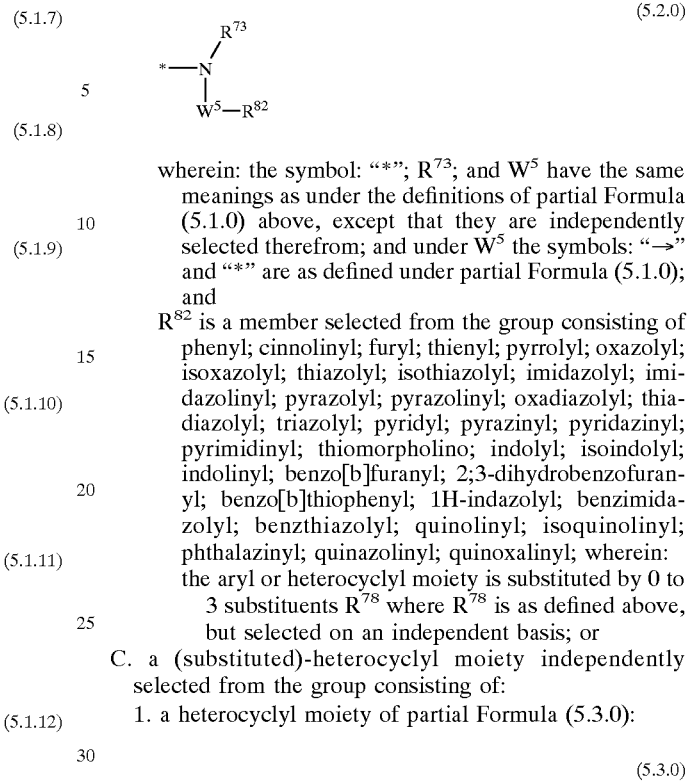

(5.2.0)

wherein: the symbol: "*"; $R^{73}$; and $W^5$ have the same meanings as under the definitions of partial Formula (5.1.0) above, except that they are independently selected therefrom; and under $W^5$ the symbols: "→" and "*" are as defined under partial Formula (5.1.0); and $R^{82}$ is a member selected from the group consisting of phenyl; cinnolinyl; furyl; thienyl; pyrrolyl; oxazolyl; isoxazolyl; thiazolyl; isothiazolyl; imidazolyl; imidazolinyl; pyrazolyl; pyrazolinyl; oxadiazolyl; thiadiazolyl; triazolyl; pyridyl; pyrazinyl; pyridazinyl; pyrimidinyl; thiomorpholino; indolyl; isoindolyl; indolinyl; benzo[b]furanyl; 2;3-dihydrobenzofuranyl; benzo[b]thiophenyl; 1H-indazolyl; benzimidazolyl; benzthiazolyl; quinolinyl; isoquinolinyl; phthalazinyl; quinazolinyl; quinoxalinyl; wherein: the aryl or heterocyclyl moiety is substituted by 0 to 3 substituents $R^{78}$ where $R^{78}$ is as defined above, but selected on an independent basis; or C. a (substituted)-heterocyclyl moiety independently selected from the group consisting of:

1. a heterocyclyl moiety of partial Formula (5.3.0):

(5.3.0)

wherein: the symbol: "*" indicates the point of attachment of partial Formula (5.3.0) to $R_{egion}\gamma$; Q is N, O or S and partial Formula (5.3.0) represents:

a. a monocyclic heterocyclic group containing a total of 5- members of which one said member is nitrogen and a second said member is selected from 0 and S where said S may optionally be in the sulfonate form, wherein said heterocyclic group is selected from the group consisting of oxazolyl; isoxazolyl; thiazolyl; and iso-thiazolyl; or b. a monocyclic heterocyclic group containing a total of 5- members of which two said members are nitrogen and a third or fourth said member is independently selected from N, O, and S where said S may optionally be in the sulfonate form, —$S(=O)_2$; wherein said heterocyclic group is independently selected from the group consisting of triazolyl; tetrazolyl; oxadiazolyl; and thiadiazolyl; and $R^{90}_a$ and $R^{90}_b$ are each a member independently selected from the group consisting of hydrogen, —$(C_1-C_2)$alkylcarbonyl; —$(C_1-C_4)$alkyl; —$(CH_2)_n$-$(C_3-C_7)$cycloalkyl; —$(C_2-C_3)$alkenyl; —$(CH_2)_n$-(phenyl); and —$(CH_2)_n$-$(HET_2)$, where n is an integer independently selected from 0, 1, and 2; wherein said $(C_1-C_4)$alkyl, alkenyl, cycloalkyl, phenyl, and $HET_2$ groups are independently substituted with 0 to 3 substituents $R^{91}$, where:

j is 0, 1 or 2;

HET$_2$ is a heterocyclyl group selected from the group consisting of thienyl; oxazolyl; isoxazolyl; thiazolyl; isothiazolyl; pyrazolyl; oxadiazolyl; thiadiazolyl; triazolyl; pyridyl; pyrazinyl; pyridazinyl; pyrimidinyl; thiomorpholino; and morpholinyl; where:

R$^{91}$ is selected from the group consisting of —F; —Cl; —CO$_2$R$^4$; —OH; —CN; —CONR$^{93}$R$^{94}$; —NR$^{93}$R$^{94}$; C(=O)(C$_1$–C$_4$)alkyl; —NR$^{93}$C(=O)R$^{94}$; —NR$^{93}$C(=O)OR$^{94}$; —NR$^{93}$S(=O)R$^{94}$; —S(=O)NR$^{93}$R$^{94}$; (C$_1$–C$_4$)alkyl including dimethyl, and (C$_1$–C$_4$)alkoxy wherein said alkyl and alkoxy are each independently substituted with 0 to 3 substituents independently selected from F and Cl; (C$_1$–C$_2$)alkoxycarbonyl; (C$_1$–C$_2$)alkylcarbonyl; and (C$_1$–C$_2$)alkylcarbonyloxy; wherein:

R$^{93}$ and R$^{94}$ are each a member independently selected from the group consisting of hydrogen; and (C$_1$–C$_2$)alkyl.

17. A pharmaceutical composition comprising a compound of claim 1 or a pharmaceutically acceptable salt thereof together with a pharmaceutically acceptable excipient, diluent or carrier.

18. A pharmaceutical composition for treating or preventing infection by human immunodeficiency virus (HIV) comprising an amount of a compound as claimed in claim 1 which is therapeutically effective to treat or prevent said infection by HIV, together with a pharmaceutically acceptable carrier therefor.

19. A method of treating a disease ameliorated by CCR5 chemokine receptor antagonism in an individual comprising administering an effective amount of a compound of claim 1.

20. A method of treating or preventing infection by human immunodeficiency virus (HIV) in a patient, comprising administering to said patient an amount of a compound of claim 1 which is therapeutically effective to treat or prevent said infection by HIV.

21. A method of treating or preventing a respiratory disease comprising administering an effective amount of a compound of claim 1, wherein said disease is selected from the group consisting of adult respiratory distress syndrome, bronchitis, chronic bronchitis, chronic obstructive pulmonary disease, cystic fibrosis, asthma, emphysema, rhinitis and chronic sinusitis.

* * * * *